US011946103B2

(12) United States Patent
Graham et al.

(10) Patent No.: US 11,946,103 B2
(45) Date of Patent: Apr. 2, 2024

(54) CLEAVABLE DISULFIDE LINKERS AND USES THEREOF

(71) Applicant: Singular Genomics Systems, Inc, San Diego, CA (US)

(72) Inventors: Ronald Graham, Carlsbad, CA (US); Megha Cila, San Dliego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

(21) Appl. No.: 18/449,601

(22) Filed: Aug. 14, 2023

(65) Prior Publication Data

US 2023/0407389 A1 Dec. 21, 2023

Related U.S. Application Data

(63) Continuation of application No. PCT/US2022/052357, filed on Dec. 9, 2022.

(60) Provisional application No. 63/311,607, filed on Feb. 18, 2022, provisional application No. 63/301,775, filed on Jan. 21, 2022, provisional application No. 63/288,369, filed on Dec. 10, 2021.

(51) Int. Cl.
| | |
|---|---|
| *C12Q 1/68* | (2018.01) |
| *C07H 19/10* | (2006.01) |
| *C07H 19/20* | (2006.01) |
| *C12Q 1/6874* | (2018.01) |
| *C12Q 1/6876* | (2018.01) |
| *C12Q 1/6806* | (2018.01) |

(52) U.S. Cl.
CPC ........... *C12Q 1/6874* (2013.01); *C07H 19/10* (2013.01); *C07H 19/20* (2013.01); *C12Q 1/6876* (2013.01); *C12Q 1/6806* (2013.01)

(58) Field of Classification Search
CPC .. C12Q 1/6874; C12Q 1/6876; C12Q 1/6806; C12Q 1/6869; C07H 19/10; C07H 19/20
See application file for complete search history.

(56) References Cited

U.S. PATENT DOCUMENTS

| | | | |
|---|---|---|---|
| 5,872,244 | A | 2/1999 | Hiatt et al. |
| 6,214,987 | B1 | 4/2001 | Hiatt et al. |
| 6,664,079 | B2 | 12/2003 | Ju et al. |
| 10,738,072 | B1 | 8/2020 | Graham et al. |
| 10,822,653 | B1 | 11/2020 | Graham et al. |
| 11,174,281 | B1 | 11/2021 | Graham et al. |
| 2002/0064782 | A1 | 5/2002 | Shinoki et al. |
| 2011/0014611 | A1 | 1/2011 | Ju et al. |
| 2012/0156671 | A1 | 6/2012 | Liu et al. |
| 2013/0264207 | A1 | 10/2013 | Ju et al. |
| 2016/0108382 | A1 | 4/2016 | Efcavitch et al. |
| 2016/0355541 | A1 | 12/2016 | Jain et al. |
| 2017/0137869 | A1 | 5/2017 | Marma et al. |
| 2017/0166961 | A1 | 6/2017 | Liu et al. |
| 2018/0274024 | A1 | 9/2018 | Ju et al. |
| 2018/0274025 | A1 | 9/2018 | Marma et al. |
| 2019/0077726 | A1 | 3/2019 | Graham et al. |
| 2020/0283467 | A1 | 9/2020 | Liu et al. |
| 2022/0127299 | A1 | 10/2022 | Graham et al. |
| 2023/0002436 | A1 | 1/2023 | Graham et al. |
| 2023/0028359 | A1 | 1/2023 | Graham et al. |
| 2023/0203083 | A1 | 6/2023 | Graham et al. |

FOREIGN PATENT DOCUMENTS

| | | |
|---|---|---|
| EP | 3870593 A1 | 9/2021 |
| EP | 3908286 A1 | 11/2021 |
| EP | 4117682 A1 | 1/2023 |
| WO | WO-2017/058953 A1 | 4/2017 |
| WO | WO-2017/079498 A2 | 5/2017 |
| WO | WO-2017/176679 A1 | 10/2017 |
| WO | WO-2020/069424 A1 | 4/2020 |
| WO | WO-2020/086834 A1 | 4/2020 |
| WO | WO-2020/146397 A1 | 7/2020 |
| WO | WO-2021/216998 A1 | 10/2021 |

OTHER PUBLICATIONS

Bentley, D. R. et al. (Nov. 6, 2008). "Accurate whole human genome sequencing using reversible terminator chemistry," *Nature* 456(7218): 53-59.

Chen, F. et al. (Feb. 2013, e-published Jan. 23, 2013). "The history and advances of reversible terminators used in new generations of sequencing technology," *Genomics, proteomics & bioinformatics* 11(1): 34-40.

Extended European Search Report dated Oct. 19, 2019, for EP Patent Application No. 19875948.2, 15 pages.

Extended European Search Report dated Sep. 8, 2022, for EP Patent Application No. 20738590.7, 10 pages.

Guillier, F. et al. (Jun. 1, 2000, e-published May 6, 2000). "Linkers and cleavage strategies in solid-phase organic synthesis and combinatorial chemistry," *Chemical Reviews* 100(6): 2091-2158.

Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," *PNAS USA* 105(27): 9145-9150.

Hutter, D. et al. (Nov. 2010, e-published Dec. 1, 2010). "Labeled nucleoside triphosphates with reversibly terminating aminoalkoxyl groups," *Nucleosides Nucleotides Nucleic Acids* 29(11): 879-895.

International Search Report and Written Opinion dated Jan. 7, 2020, for PCT application PCT/US2019/057842, filed Oct. 24, 2019, 14 pages.

International Search Report and Written Opinion dated Apr. 2, 2020, for PCT application PCT/US2020/012595, filed Jan. 7, 2020, 6 pages.

(Continued)

*Primary Examiner* — Jezia Riley

(74) *Attorney, Agent, or Firm* — Mintz, Levin, Cohn, Ferris, Glovsky, Popeo, P.C.; Zachary L. Terranova

(57) ABSTRACT

Disclosed herein, inter alia, are methods and cleavable compounds that minimize byproduct formation following cleavage.

20 Claims, 2 Drawing Sheets

(56) References Cited

OTHER PUBLICATIONS

International Search Report and Written Opinion dated Sep. 8, 2021, for PCT application PCT/US2021/028839, filed Apr. 21, 2021, 6 pages.

International Search Report and Written Opinion dated Jun. 13, 2023, for PCT application PCT/US2022/052357, filed Dec. 9, 2022, 12 pages.

Ju, J. et al. (Dec. 26, 2006). "Four-color DNA sequencing by synthesis using cleavable fluorescent nucleotide reversible terminators," *PNAS USA* 103(52): 19635-19640.

Ruparel, H. et al. (Apr. 26, 2005, e-published Apr. 13, 2005). "Design and synthesis of a 3'-O-allyl photocleavable fluorescent nucleotide as a reversible terminator for DNA sequencing by synthesis," *PNAS USA* 102(17): 5932-5937.

Wu, J. et al. (Oct. 16, 2007, e-published Oct. 8, 2007). "3'-O-modified nucleotides as reversible terminators for pyrosequencing," *PNAS USA* 104(42): 16462-16467.

CLEAVABLE DISULFIDE LINKERS AND USES THEREOF

CROSS-REFERENCES TO RELATED APPLICATIONS

This application is a continuation of PCT Application PCT/US2022/052357, filed Dec. 9, 2022, which claims the benefit of U.S. Provisional Application No. 63/288,369, filed Dec. 10, 2021, U.S. Provisional Application No. 63/301,775, filed Jan. 21, 2022, and U.S. Provisional Application No. 63/311,607, filed Feb. 18, 2022, each of which are incorporated herein by reference in their entirety and for all purposes.

BACKGROUND

DNA sequencing is a fundamental tool in biological and medical research; it is an essential technology for the paradigm of personalized precision medicine. Among various new DNA sequencing methods, sequencing by synthesis (SBS) is the leading method for realizing the goal of the $1,000 genome. Accordingly, there is a need for modified nucleotides and nucleosides that are effectively recognized as substrates by DNA polymerases, that are efficiently and accurately incorporated into growing DNA chains during SBS. Disclosed herein, inter alia, are solutions to these and other problems in the art.

BRIEF SUMMARY

In an aspect is provided a compound having the formula:

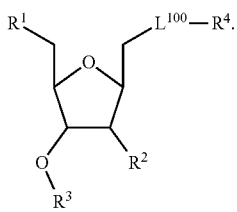

(I)

is a divalent nucleobase. $R^1$ is a 5'-nucleoside protecting group, monophosphate moiety, polyphosphate moiety, or nucleic acid moiety. $R^2$ and $R^3$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety. $R^4$ is a detectable moiety. $L^{100}$ is a divalent linker including

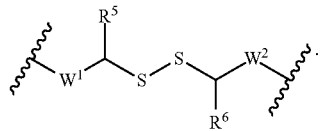

$R^5$ and $R^6$ are independently —CN, —OH, —NH$_2$, —COOH, —CONH$_2$, —NO$_2$, —SO$_3$H, —SO$_4$H, —SO$_2$NH$_2$, —NHNH$_2$, —ONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $W^1$ and $W^2$ are independently —O—, —NH—, —Si—, or —PH—.

In an aspect is provided a method for sequencing a nucleic acid, including (i) incorporating in series with a nucleic acid polymerase (e.g., within a reaction vessel) one of four different compounds into a primer to create an extension strand, wherein the primer is hybridized to the nucleic acid and wherein each of the four different compounds comprises a unique detectable label; (ii) detecting the unique detectable label of each incorporated compound, so as to thereby identify each incorporated compound in the extension strand, thereby sequencing the nucleic acid; wherein each of the four different compounds is independently a compound as described herein, including embodiments.

In an aspect is provided a method of incorporating a compound into a primer, the method comprising combining a polymerase, a primer hybridized to nucleic acid template and the compound within a reaction vessel and allowing the polymerase to incorporate the compound into the primer thereby forming an extended primer, wherein the compound is a compound as described herein, including embodiments.

BRIEF DESCRIPTION OF THE DRAWINGS

FIG. 1B provides an embodiment of the cleavable linkers described herein, where the linkers yield thioketones following cleavage, and a terminal hydroxyl moiety.

DETAILED DESCRIPTION

Figure 1A:
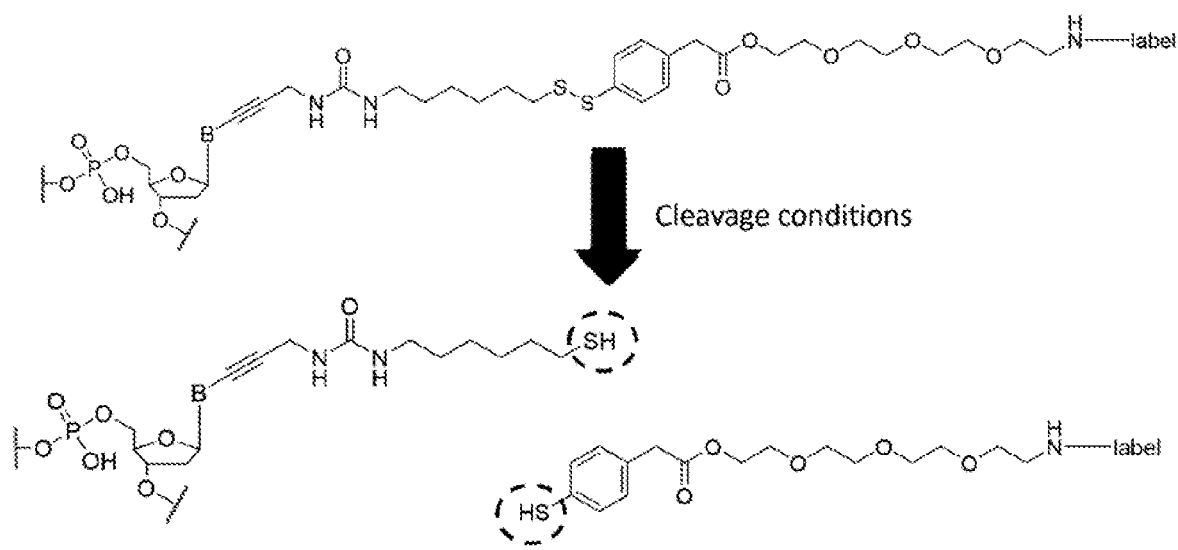
FIGS. 1A-1B. Typical modified nucleotides that have a linear disulfide moiety result in one or more reactive thiols (highlighted with dashed circle) in FIG. 1A. These reactive thiols have downstream complications. For example, a free thiol can serve as a reducing agent and prematurely remove the reversible terminator and or the linker in a labeled modified nucleotide. The thiol can also interact with functional groups present on the label and modulate the detectability of the label (e.g., change the fluorescence emission profile of a fluorophore). Additionally, the remainder of the linker connected to the label may react with the surrounding environment (e.g., the surface of the flowcell) and cause an increase in background signal.

The aspects and embodiments described herein relate to cleavable linkers and methods of use thereof.

I. Definitions

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkenyl includes one or more double bonds. An alkynyl includes one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the alkylene is polyunsaturated. An alkenylene includes one or more double bonds. An alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—

CH₂—S(O)₂—CH₃, —CH=CH—O—CH₃, —Si(CH₃)₃, —CH₂—CH=N—OCH₃, —CH=CH—N(CH₃)—CH₃, —O—CH₃, —O—CH₂—CH₃, and —CN. Up to two or three heteroatoms may be consecutive, such as, for example, —CH₂—NH—OCH₃ and —CH₂—O—Si(CH₃)₃. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—. As described above, heteroalkyl groups, as used herein, include those groups that are attached to the remainder of the molecule through a heteroatom, such as —C(O)R', —C(O)NR', —NR'R", —OR', —SR', and/or —SO₂R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. A heteroalkenylene includes one or more double bonds. A heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. In embodiments, a bicyclic or multicyclic cycloalkyl ring system refers to multiple rings fused together or multiple spirocyclic rings wherein at least one of the fused or spirocyclic rings is a cycloalkyl ring and wherein the multiple rings are attached to the parent molecular moiety through any carbon atom contained within a cycloalkyl ring of the multiple rings.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, a bicyclic or multicyclic cycloalkenyl ring system refers to multiple rings fused together or multiple spirocyclic rings wherein at least one of the fused or spirocyclic rings is a cycloalkenyl ring and wherein the multiple rings are attached to the parent molecular moiety through any carbon atom contained within a cycloalkenyl ring of the multiple rings.

In embodiments, the term "heterocycloalkyl" means a monocyclic, bicyclic, or a multicyclic heterocycloalkyl ring system. In embodiments, heterocycloalkyl groups are fully saturated. In embodiments, a bicyclic or multicyclic heterocycloalkyl ring system refers to multiple rings fused together or multiple spirocyclic rings wherein at least one of the fused or spirocyclic rings is a heterocycloalkyl ring and wherein the multiple rings are attached to the parent molecular moiety through any atom contained within a heterocycloalkyl ring of the multiple rings.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. In embodiments, a bicyclic or multicyclic cycloalkyl ring system refers to multiple rings fused together or multiple spirocyclic rings wherein at least one of the fused or spirocyclic rings is a cycloalkyl ring and wherein the multiple rings are attached to the parent molecular moiety through any carbon atom contained within a cycloalkyl ring of the multiple rings.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, a bicyclic or multicyclic cycloalkenyl ring system refers to multiple rings fused together or multiple spirocyclic rings wherein at least one of the fused or spirocyclic rings is a cycloalkenyl ring and wherein the multiple rings are attached to the parent molecular moiety through any carbon atom contained within a cycloalkenyl ring of the multiple rings.

In embodiments, the term "heterocycloalkyl" means a monocyclic, bicyclic, or multicyclic heterocycloalkyl ring system. In embodiments, the term "heterocycloalkyl" means a monocyclic, bicyclic, or a multicyclic heterocycloalkyl ring system. In embodiments, heterocycloalkyl groups are fully saturated. A bicyclic or multicyclic heterocycloalkyl ring system refers to multiple rings fused together wherein at least one of the fused rings is a heterocycloalkyl ring and wherein the multiple rings are attached to the parent molecular moiety through any atom contained within a heterocycloalkyl ring of the multiple rings.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring and wherein the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom (s) are optionally quaternized. Thus, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol " ⁓ " denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

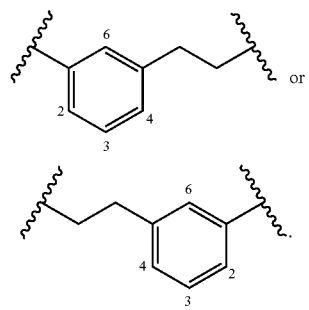

An alkylarylene moiety may be substituted (e.g., with a substituent group) on the alkylene moiety or the arylene linker (e.g., at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$, —SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R'''' groups when more than one of these groups is present.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —S(O)$_2$—, —S(O)$_2$NR'—, or a single bond, and r is an integer from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers from 0 to 3, and X is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound (e.g., nucleotide analogue) is a chemical species set forth in the Examples section, claims, embodiments, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure. The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," "analogue" or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent," "detectable compound," "detectable label," or "detectable moiety" is a substance (e.g., element), molecule, or composition detectable by spectroscopic, photochemical, biochemical, immunochemical, chemical, magnetic resonance imaging, or other physical means. For example, detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g., fluorescent dyes), modified oligonucleotides (e.g., moieties described in PCT/US2015/022063, which is incorporated herein by reference), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monocrystalline iron oxide nanoparticles, monocrystalline iron oxide, nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. In embodiments, a detectable moiety is a moiety (e.g., monovalent form) of a detectable agent.

The terms "fluorophore" or "fluorescent agent" or "fluorescent dye" are used interchangeably and refer to a substance, compound, agent (e.g., a detectable agent), or composition (e.g., compound) that can absorb light at one or more wavelengths and re-emit light at one or more longer wavelengths, relative to the one or more wavelengths of absorbed light. Examples of fluorophores that may be included in the compounds and compositions described herein include fluorescent proteins, xanthene derivatives (e.g., fluorescein, rhodamine, Oregon green, eosin, or Texas red), cyanine and derivatives (e.g., cyanine, indocarbocyanine, oxacarbocyanine, thiacarbocyanine, or merocyanine), napththalene derivatives (e.g., dansyl or prodan derivatives), coumarin and derivatives, oxadiazole derivatives (e.g., pyridyloxazole, nitrobenzoxadiazole or benzoxadiazole), anthracene derivatives (e.g., anthraquinones, DRAQ5, DRAQ7, or CyTRAK Orange), pyrene derivatives (e.g., cascade blue and derivatives), oxazine derivatives (e.g., Nile red, Nile blue, cresyl violet, or oxazine 170), acridine derivatives (e.g., proflavin, acridine orange, acridine yellow), arylmethine derivatives (e.g., auramine, crystal violet, or malachite green), tetrapyrrole derivatives (e.g., porphin, phthalocyanine, bilirubin), CF Dye™, DRAQ™, CyTRAK™, BODIPY™, Alexa Fluor™, DyLight Fluor™, Atto™, Tracy™, FluoProbes™, Abberior Dyes™, DY™ dyes, MegaStokes Dyes™, Sulfo Cy™, Seta™ dyes, SeTau™ dyes, Square Dyes™, Quasar™ dyes, Cal Fluor™ dyes, SureLight Dyes™, PerCP™, Phycobilisomes™ APC™, APCXL™, RPE™, and/or BPE™. A fluorescent moiety is a radical of a fluorescent agent. The emission from the fluorophores can be detected by any number of methods, including but not limited to, fluorescence spectroscopy, fluorescence microscopy, fluorimeters, fluorescent plate readers, infrared scanner analysis, laser scanning confocal microscopy, automated confocal nanoscanning, laser spectrophotometers, fluorescent-activated cell sorters (FACS), image-based analyzers and fluorescent scanners (e.g., gel/membrane scanners). In embodiments, the fluorophore is an aromatic (e.g., polyaromatic) moiety having a conjugated π-electron system. In embodiments, the fluorophore is a fluorescent dye moiety, that is, a monovalent fluorophore.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Examples of detectable agents include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent moiety or fluorescent dye moiety.

In embodiments, the detectable moiety is a moiety of a derivative of one of the detectable moieties described immediately above, wherein the derivative differs from one of the detectable moieties immediately above by a modification resulting from the conjugation of the detectable moiety to a compound described herein.

In embodiments, the detectable label is a fluorescent dye. In embodiments, the detectable label is a fluorescent dye capable of exchanging energy with another fluorescent dye (e.g., fluorescence resonance energy transfer (FRET) chromophores).

The term "cyanine" or "cyanine moiety" as described herein refers to a detectable moiety containing two nitrogen groups separated by a polymethine chain. In embodiments, the cyanine moiety has 3 methine structures (i.e., cyanine 3 or Cy3). In embodiments, the cyanine moiety has 5 methine structures (i.e., cyanine 5 or Cy5). In embodiments, the cyanine moiety has 7 methine structures (i.e., cyanine 7 or Cy7).

Descriptions of compounds (e.g., nucleotide analogues) of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

As used herein, the term "salt" refers to acid or base salts of the compounds described herein. Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. In embodiments, compounds may be presented with a positive charge, and it is understood an appropriate counter-ion (e.g., chloride ion, fluoride ion, or acetate ion) may also be present, though not explicitly shown. Likewise, for compounds having a negative charge

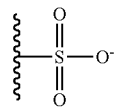

it is understood an appropriate counter-ion (e.g., a proton, sodium ion, potassium ion, or ammonium ion) may also be present, though not explicitly shown. The protonation state of the compound (e.g., a compound described herein) depends on the local environment (i.e., the pH of the environment), therefore, in embodiments, the compound may be described as having a moiety in a protonated state

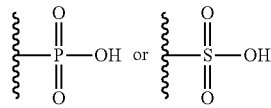

or an ionic state

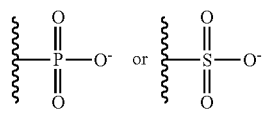

and it is understood these are interchangeable. In embodiments, the counter-ion is represented by the symbol M (e.g., $M^+$ or $M^-$).

The neutral forms of the compounds are preferably regenerated by contacting the salt with a base or acid and isolating the parent compound in the conventional manner. The parent form of the compound may differ from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Hybridize" shall mean the annealing of one single-stranded nucleic acid (such as a primer) to another nucleic acid based on the well-understood principle of sequence complementarity. In an embodiment, the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. Those skilled in the art understand how to estimate and adjust the stringency of hybridization conditions such that sequences having at least a desired level of complementarity will stably hybridize, while those having lower complementarity will not. As used herein, the term "stringent condition" refers to condition(s) under which a polynucleotide probe or primer will hybridize preferentially to its target sequence, and to a lesser extent to, or not at all to, other sequences. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which comprises a double-stranded portion of nucleic acid.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated, however, that the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The term "streptavidin" refers to a tetrameric protein (including homologs, isoforms, and functional fragments thereof) capable of binding biotin. The term includes any recombinant or naturally-occurring form of streptavidin variants thereof that maintain streptavidin activity (e.g., within at least 30%, 40%, 50%, 60%, 70%, 80%, 90%, 95%, or 100% activity compared to wildtype streptavidin).

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. Nucleic acids and polynucleotides are polymers of any length, including longer lengths, e.g., 200, 300, 500, 1000, 2000, 3000, 5000, 7000, 10,000, etc. In certain embodiments the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see, Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. A residue of a nucleic acid, as referred to herein, is a monomer of the nucleic acid (e.g., a nucleotide). The term "nucleoside" refers, in the usual and customary sense, to a glycosylamine including a nucleobase and a five-carbon sugar (ribose or deoxyribose). Non-limiting examples of nucleosides include cytidine, uridine, adenosine, guanosine, thymidine and inosine. Nucleosides may be modified at the base and/or the sugar. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g., polynucleotides contemplated herein include any types of RNA, e.g., mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like. A "nucleic acid moiety" as used herein is a monovalent form of a nucleic acid. In embodiments, the nucleic acid moiety is attached to the 3' or 5' position of a nucleotide or nucleoside.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s). In the context of selective sequencing, "target polynucleotide(s)" refers to the subset of polynucleotide(s) to be sequenced from within a starting population of polynucleotides.

"Nucleotide," as used herein, refers to a nucleoside-5'-phosphate (e.g., polyphosphate) compound, or a structural analog thereof, which can be incorporated (e.g., partially incorporated as a nucleoside-5'-monophosphate or derivative thereof) by a nucleic acid polymerase to extend a growing nucleic acid chain (such as a primer). Nucleotides may comprise bases such as adenine (A), cytosine (C), guanine (G), thymine (T), uracil (U), or analogues thereof, and may comprise 1, 2, 3, 4, 5, 6, 7, 8, or more phosphates in the phosphate group. Nucleotides may be modified at one or more of the base, sugar, or phosphate group. A nucleotide may have a label or tag attached (a "labeled nucleotide" or "tagged nucleotide"). In an embodiment, the nucleotide is a deoxyribonucleotide. In another embodiment, the nucleotide is a ribonucleotide. In embodiments, nucleotides comprise 3 phosphate groups (e.g., a triphosphate group).

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphorothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g., phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

In embodiments, "nucleotide analogue," "nucleotide analog," or "nucleotide derivative" shall mean an analogue of adenine (A), cytosine (C), guanine (G), thymine (T), or uracil (U) (that is, an analogue or derivative of a nucleotide comprising the base A, G, C, T or U), comprising a phosphate group, which may be recognized by DNA or RNA polymerase (whichever is applicable) and may be incorporated into a strand of DNA or RNA (whichever is appropriate). Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the —OH group at the 3'-position of deoxyribose. Nucleotide analogues and DNA polymerase-based DNA sequencing are also described in U.S. Pat. No. 6,664,079, which is incorporated herein by reference in its entirety for all purposes.

The terms "bioconjugate group," "bioconjugate reactive moiety," and "bioconjugate reactive group" refer to a chemical moiety which participates in a reaction to form a bioconjugate linker (e.g., covalent linker). Additional examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
| --- | --- | --- |
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |

-continued

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
| --- | --- | --- |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or streptavidin to form a avidin-biotin complex or streptavidin-biotin complex.

The term "monophosphate" is used in accordance with its ordinary meaning in the arts and refers to a moiety having the formula:

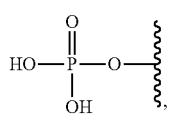

or ionized forms thereof. The term "polyphosphate" refers to at least two phosphate groups, having the formula:

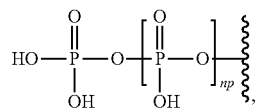

or ionized forms thereof, wherein np is an integer of 1 or greater. In embodiments, np is an integer from 1 to 5. In embodiments, np is an integer from 1 to 2. In embodiments, np is 2. The term "diphosphate" is used in accordance with its ordinary meaning in the arts and refers to a moiety having the formula:

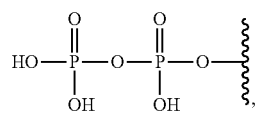 [SMILES: *OP(=O)(O)OP(=O)(O)O]

or ionized forms thereof. The term "triphosphate" is used in accordance with its ordinary meaning in the arts and refers to a moiety having the formula:

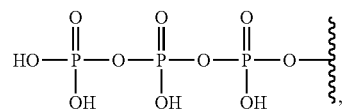 [SMILES: *OP(=O)(O)OP(=O)(O)OP(=O)(O)O]

or ionized forms thereof. In embodiments, a polyphosphate is a diphosphate. In embodiments, a polyphosphate is a triphosphate.

The term "nucleobase" or "base" as used herein refers to a purine or pyrimidine compound, or a derivative thereof, that may be a constituent of nucleic acid (i.e., DNA or RNA, or a derivative thereof). In embodiments, the nucleobase is a divalent purine or pyrimidine, or derivative thereof. In embodiments, the nucleobase is a monovalent purine or pyrimidine, or derivative thereof. In embodiments, the base is a derivative of a naturally occurring DNA or RNA base (e.g., a base analogue). In embodiments the base is a hybridizing base. In embodiments the base hybridizes to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base includes cytosine or a derivative thereof (e.g., cytosine analogue), guanine or a derivative thereof (e.g., guanine analogue), adenine or a derivative thereof (e.g., adenine analogue), thymine or a derivative thereof (e.g., thymine analogue), uracil or a derivative thereof (e.g., uracil analogue), hypoxanthine or a derivative thereof (e.g., hypoxanthine analogue), xanthine or a derivative thereof (e.g., xanthine analogue), 7-methylguanine or a derivative thereof (e.g., 7-methylguanine analogue), deaza-adenine or a derivative thereof (e.g., deaza-adenine analogue), deaza-guanine or a derivative thereof (e.g., deaza-guanine), deaza-hypoxanthine or a derivative thereof (e.g., 5,6-dihydrouracil or a derivative thereof (e.g., 5,6-dihydrouracil analogue), 5-methylcytosine or a derivative thereof (e.g., 5-methylcytosine analogue), or 5-hydroxymethylcytosine or a derivative thereof (e.g., 5-hydroxymethylcytosine analogue) moieties. In embodiments, the base is adenine, guanine, uracil, cytosine, thymine, hypoxanthine, xanthine, theobromine, caffeine, uric acid, or isoguanine, which may be optionally substituted or modified. In embodiments, the base is adenine, guanine, hypoxanthine, xanthine, theobromine, caffeine, uric acid, or isoguanine, which may be optionally substituted or modified.

As used herein, the term "complementary" or "substantially complementary" refers to the hybridization, base pairing, or the formation of a duplex between nucleotides or nucleic acids. For example, complementarity exists between the two strands of a double-stranded DNA molecule or between an oligonucleotide primer and a primer binding site on a single-stranded nucleic acid when a nucleotide (e.g., RNA or DNA) or a sequence of nucleotides is capable of base pairing with a respective cognate nucleotide or cognate sequence of nucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with the nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin or loop structure, with or without an overhang) or portions of separate polynucleotides. In embodiments, one or both sequences in a pair of complementary sequences form portions of longer polynucleotides, which may or may not include additional regions of complementarity.

The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

The term "anchor moiety" as used herein refers to a chemical moiety capable of interacting (e.g., covalently or non-covalently) with a second, optionally different, chemical moiety (e.g., complementary anchor moiety binder). In embodiments, the anchor moiety is a bioconjugate reactive group capable of interacting (e.g., covalently) with a complementary bioconjugate reactive group (e.g., complementary anchor moiety reactive group, complementary anchor moiety binder). In embodiments, an anchor moiety is a click chemistry reactant moiety. In embodiments, the anchor moiety (an "affinity anchor moiety") is capable of non-covalently interacting with a second chemical moiety (e.g., complementary affinity anchor moiety binder). Non-limiting examples of an anchor moiety include biotin, azide, trans-cyclooctene (TCO) (Blackman, M. L., et al., *J. Am. Chem. Soc.*, 2008, 130, 13518-13519; Debets, M. F., et al. *Org. Biomol. Chem.*, 2013, 11, 6439-6455) and phenyl boric acid (PBA) (Bergseid M., et al., *BioTechniques*, 2000, 29, 1126-1133). In embodiments, an affinity anchor moiety (e.g., biotin moiety) interacts non-covalently with a complementary affinity anchor moiety binder (e.g., streptavidin moiety). In embodiments, an anchor moiety (e.g., azide moiety, trans-cyclooctene (TCO) moiety, phenyl boric acid (PBA) moiety) covalently binds a complementary anchor moiety binder (e.g., dibenzocyclooctyne (DBCO) moiety (Jewett J. C. and Bertozzi C. R. *J. Am. Chem. Soc.*, 2010, 132, 3688-3690), tetrazine (TZ) moiety, salicylhydroxamic acid (SHA) moiety).

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. In embodiments, a cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). In embodiments, a cleavable linker is a self-immolative linker, a trivalent linker, or a linker capable of dendritic amplification of signal, or a self-immolative dendrimer containing linker (e.g., all as described in US 2007/0009980, US 2006/0003383, and US 2009/0047699, which are incorporated by reference in their entirety for any purpose). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is sodium dithionite ($Na_2S_2O_4$), weak acid, hydrazine ($N_2H_4$), Pd(0), or light-irradiation (e.g., ultraviolet radiation). In embodiments, cleaving includes removing. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include a modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or Formamidopyrimidine DNA Glycosylase (Fpg). In embodiments, the scissile linkage site includes a sequence-specific nicking site having a nucleotide sequence that is recognized and nicked by a nicking endonuclease enzyme or a uracil DNA glycosylase. The term "self-immolative" referring to a linker is used in accordance with its well understood meaning in Chemistry and Biology as used in US 2007/0009980, US 2006/0003383, and US 2009/0047699, which are incorporated by reference in their entirety for any purpose. In embodiments "self-immolative" referring to a linker refers to a linker that is capable of additional cleavage following initial cleavage by an external stimuli. The term dendrimer is used in accordance with its well understood meaning in Chemistry. In embodiments, the term "self-immolative dendrimer" is used as described in US 2007/0009980, US 2006/0003383, and US 2009/0047699, which are incorporated by reference in their entirety for any purpose and in embodiments refers to a dendrimer that is capable of releasing all of its tail units through a self-immolative fragmentation following initial cleavage by an external stimulus.

A "photocleavable linker" (e.g., including or consisting of an o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of a reducing agent (e.g., tris(3-hydroxypropyl)phosphine). In embodiments, the cleavable linker is a dialkylketal linker (Binaulda S., et al., Chem. Commun., 2013, 49, 2082-2102; Shenoi R. A., et al., J. Am. Chem. Soc., 2012, 134, 14945-14957), an azo linker (Rathod, K. M., et al., Chem. Sci. Tran., 2013, 2, 25-28; Leriche G., et al., Eur. J. Org. Chem., 2010, 23, 4360-64), an allyl linker, a cyanoethyl linker, a 1-(4,4-dimethyl-2,6-dioxocyclohex-1-ylidene)ethyl linker, or a nitrobenzyl linker.

The term "orthogonally cleavable linker" or "orthogonal cleavable linker" as used herein refer to a cleavable linker that is cleaved by a first cleaving agent (e.g., enzyme, nucleophilic/basic reagent, reducing agent, photo-irradiation, electrophilic/acidic reagent, organometallic and metal reagent, oxidizing reagent) in a mixture of two or more different cleaving agents and is not cleaved by any other different cleaving agent in the mixture of two or more cleaving agents. For example, two different cleavable linkers are both orthogonal cleavable linkers when a mixture of the two different cleavable linkers are reacted with two different cleaving agents and each cleavable linker is cleaved by only one of the cleaving agents and not the other cleaving agent and the agent that cleaves each cleavable linker is different. In embodiments, an orthogonally is a cleavable linker that following cleavage the two separated entities (e.g., fluorescent dye, bioconjugate reactive group) do not further react and form a new orthogonally cleavable linker.

The term "orthogonal detectable label" or "orthogonal detectable moiety" as used herein refer to a detectable label (e.g., fluorescent dye or detectable dye) that is capable of being detected and identified (e.g., by use of a detection means (e.g., emission wavelength, physical characteristic measurement)) in a mixture or a panel (collection of separate samples) of two or more different detectable labels. For example, two different detectable labels that are fluorescent dyes are both orthogonal detectable labels when a panel of the two different fluorescent dyes is subjected to a wavelength of light that is absorbed by one fluorescent dye but not the other and results in emission of light from the fluorescent dye that absorbed the light but not the other fluorescent dye. Orthogonal detectable labels may be separately identified by different absorbance or emission intensities of the orthogonal detectable labels compared to each other and not only be the absolute presence of absence of a signal. An example of a set of four orthogonal detectable labels is the set of Rox-Labeled Tetrazine, Alexa488-Labeled SHA, Cy5-Labeled Streptavidin, and R6G-Labeled Dibenzocyclooctyne.

The term "polymerase-compatible cleavable moiety" or "reversible terminator" as used herein refers to a cleavable moiety which does not interfere with a function of a polymerase (e.g., DNA polymerase, modified DNA polymerase, in incorporating the nucleotide, to which the polymerase-compatible cleavable moiety is attached, to the 3' end of the newly formed nucleotide strand). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible cleavable moiety does not decrease the function of a polymerase relative to the absence of the polymerase-compatible cleavable moiety. In embodiments, the polymerase-compatible cleavable moiety does not negatively affect DNA polymerase recognition. In embodiments, the polymerase-compatible cleavable moiety does not negatively affect (e.g., limit) the read length of the DNA polymerase. Additional examples of a polymerase-compatible cleavable moiety may be found in U.S. Pat. Nos. 6,664,079; 6,214,987; 5,872,244; Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218):53-59; or Hutter D. et al. (2010) *Nucleosides Nucleotides & Nucleic Acids* 29:879-895, which are incorporated herein by reference in their entirety for all purposes. In embodiments, a polymerase-compatible cleavable moiety includes an azido moiety or a dithiol linking moiety. In embodiments, the polymerase-compatible cleavable moiety is —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N$_3$. In embodiments, the polymerase-compatible cleavable moiety includes an ester (O—C(O)R$^{Z1}$ wherein R$^{Z1}$ is any alkyl or aryl group which can include a formate, benzoyl formate, acetate, substituted acetate, propionate, and other esters as described in Green, T. W. (Protective Groups in Organic Chemistry, Wiley & Sons, New York, 1981)). In embodiments, the polymerase-compatible cleavable moiety includes an ether (O—R$^{ZZ}$ wherein R$^{ZZ}$ can be substituted or unsubstituted alkyl such as methyl, substituted methyl, ethyl, substituted ethyl, allyl, substituted benzyl, silyl, or any other ether used to transiently protect hydroxyls and similar groups). In embodiments, the polymerase-compatible cleavable moiety includes an O—CH$_2$ (OC$_2$H$_5$)$_M$CH$_3$ wherein M is an integer from 1-10. In embodiments, the polymerase-compatible cleavable moiety includes a phosphate, phosphoramidate, phosphoramide, toluic acid ester, benzoic ester, acetic acid ester, or ethoxyethyl ether. In embodiments, the polymerase-compatible cleavable moiety comprises a disulfide moiety. In embodiments, a polymerase-compatible cleavable moiety is a cleavable moiety on a nucleotide, nucleobase, nucleoside, or nucleic acid that does not interfere with a function of a polymerase (e.g., DNA polymerase, modified DNA polymerase).

The term "allyl" as described herein refers to an unsubstituted methylene attached to a vinyl group (i.e., —CH=CH$_2$), having the formula

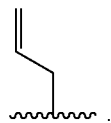

An "allyl linker" refers to a divalent unsubstituted methylene attached to a vinyl group, having the formula

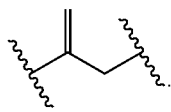 [SMILES: *CC(*)=C]

The term "polymerase-compatible moiety" as used herein refers a moiety which does not interfere with the function of a polymerase (e.g., DNA polymerase, modified DNA polymerase) in incorporating the nucleotide to which the polymerase-compatible moiety is attached to the 3' end of the newly formed nucleotide strand. The polymerase-compatible moiety does, however, interfere with the polymerase function by preventing the addition of another nucleotide to the 3' oxygen of the nucleotide to which the polymerase-compatible moiety is attached. Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments, the polymerase-compatible moiety does not decrease the function of a polymerase relative to the absence of the polymerase-compatible moiety. In embodiments, the polymerase-compatible moiety does not negatively affect DNA polymerase recognition. In embodiments, the polymerase-compatible moiety does not negatively affect (e.g., limit) the read length of the DNA polymerase. Additional examples of a polymerase-compatible moiety may be found in U.S. Pat. No. 6,664,079, Ju J. et al. (2006) *Proc Nat Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible moiety includes hydrogen, —N$_3$, —CN, or halogen. In embodiments, a polymerase-compatible moiety is a moiety on a nucleotide, nucleobase, nucleoside, or nucleic acid that does not interfere with the function of a polymerase (e.g., DNA polymerase, modified DNA polymerase).

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g. Terminator γ, 9° N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044).

As used herein, the term "thermophilic nucleic acid polymerase" refers to a family of DNA polymerases (e.g., 9° N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. PNAS. 1996; 93(11):5281-5285). A thermophilic nucleic acid polymerase is a member of the family B DNA polymerases. Site-directed mutagenesis of the 3'-5' exo motif I (Asp-Ile-Glu or DIE) to AIA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase including its high strand displacement activity. The sequence AIA (D141A, E143A) was chosen for reducing exonuclease. Subsequent mutagenesis of key amino acids results in an increased ability of the enzyme to incorporate dideoxynucleotides, ribonucleotides and acyclonucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Therminator III DNA Polymerase with D141A/E143A/L408S/Y409A/P410V mutations, NEB Therminator IX DNA polymerase), or γ-phosphate labeled nucleotides (e.g., Terminator γ: D141A/E143A/W355A/L408W/R460A/Q461S/K464E/D480V/R484W/A485L). Typically, these enzymes do not have 5'-3' exonuclease activity. Additional information about thermophilic nucleic acid polymerases may be found in (Southworth M W, et al. PNAS. 1996; 93(11):5281-5285; Bergen K, et al. ChemBioChem. 2013; 14(9):1058-1062; Kumar S, et al. Scientific Reports. 2012; 2:684; Fuller C W, et al. 2016; 113(19):5233-5238; Guo J, et al. Proceedings of the National Academy of Sciences of the United States of America. 2008; 105(27): 9145-9150), which are incorporated herein in their entirety for all purposes.

As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

As used herein, the terms "polynucleotide primer" and "primer" refers to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

"Polymerase," as used herein, refers to any natural or non-naturally occurring enzyme or other catalyst that is capable of catalyzing a polymerization reaction, such as the polymerization of nucleotide monomers to form a nucleic acid polymer. Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, E. Coli DNA polymerase I, Bacteriophage T4 DNA polymerase, Sequenase, Taq DNA polymerase, DNA polymerase from Bacillus stearothermophilus, Bst 2.0 DNA polymerase, 9° N polymerase, 9° N polymerase (exo-) A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Terminator™ II DNA Polymerase, Terminator™ III DNA Polymerase, or Terminator™ IX DNA Polymerase. In embodiments, the polymerase is a protein polymerase.

The phrase "stringent hybridization conditions" refers to conditions under which a primer will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

The term "polymer" refers to a molecule including repeating subunits (e.g., polymerized monomers). For example, polymeric molecules may be based upon polyethylene glycol (PEG), tetraethylene glycol (TEG), polyvinylpyrrolidone (PVP), poly(xylene), or poly(p-xylylene). The term "polymerizable monomer" is used in accordance with its meaning in the art of polymer chemistry and refers to a compound that may covalently bind chemically to other monomer molecules (such as other polymerizable monomers that are the same or different) to form a polymer.

"Solid substrate" shall mean any suitable medium present in the solid phase to which a nucleic acid or an agent may be affixed. Non-limiting examples include chips, beads and columns. The solid substrate can be non-porous or porous. Exemplary solid substrates include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides, etc.), nylon, ceramics, resins, Zeonor, silica or silica-based materials including silicon and modified silicon, carbon, metals, inorganic glasses, optical fiber bundles, and polymers. In embodiments, the solid substrate for have at least one surface located within a flow cell. The solid substrate, or regions thereof, can be substantially flat. The solid substrate can have surface features such as wells, pits, channels, ridges, raised regions, pegs, posts or the like. The term solid substrate is encompassing of a substrate (e.g., a flow cell) having a surface comprising a polymer coating covalently attached thereto. In embodiments, the solid substrate is a flow cell. The term "flowcell" or "flow cell" as used herein refers to a chamber including a solid surface across which one or more fluid reagents can be flowed. Examples of flowcells and related fluidic systems and detection platforms that can be readily used in the methods of the present disclosure are described, for example, in Bentley et al., Nature 456:53-59 (2008).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., *Current Protocols in Molecular Biology*, ed. Ausubel, et al., supra.

Where a range of values is provided herein, it is understood that each intervening value, to the tenth of the unit (if appropriate) of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

While various embodiments of the invention are shown and described herein, it will be understood by those skilled in the art that such embodiments are provided by way of example only. Numerous variations, changes, and substitutes may occur to those skilled in the art without departing from the invention. It should be understood that various alternatives to the embodiments of the invention described herein may be employed.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In embodiments the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts). In embodiments, the protecting group is a nucleoside protecting group. In embodiments, the protecting group is a 5'-O-nucleoside protecting group.

The term "5'-nucleoside protecting group" as used herein refers to a moiety covalently bound to a heteroatom (e.g., O) on the 5' position of sugar to prevent reactivity of the heteroatom during one or more chemical reactions performed prior to removal of the protecting group. Typically a protecting group is bound to a heteroatom (e.g., O) during a part of a multipart synthesis wherein it is not desired to have the heteroatom react (e.g., during a chemical reduction) with the reagent. Following protection the protecting group may be removed by any appropriate means (e.g., by modulating the pH). Non-limiting examples of 5'-O-nucleoside protecting groups include silyl ethers (e.g., tert-butyl-diphenylsilyl (TBDPS), or primary and secondary tert-butyldimethylsilyl (TBDMS)) or trityl (e.g., 4,4'-dimethoxytrityl (DMT)). In embodiments, $R^1$ includes a protecting group found in *Green's Protective Groups in Organic Chemistry*, Wiley, Fourth edition, 2007, Peter G. M. Wuts and Theodora W. Greene, and *Current Protocols in Nucleic Acid Chemistry* (2000) 2.3.1-2.3.34, John Wiley & Sons, Inc. which is incorporated herein by reference in its entirety for all purposes.

The term "deprotect" or "deprotecting" is used in accordance with its ordinary meaning in organic chemistry and refers a process or chemical reaction that remove a protecting group, which is covalently bound to a heteroatom, heterocycloalkyl, or heteroaryl, to recover reactivity of the heteroatom, heterocycloalkyl, or heteroaryl for subsequent chemical reactions or metabolic pathway. The "deprotecting agent" or "deprotecting reagent" is used in accordance with its ordinary meaning in organic chemistry and refers to a molecule used for deprotecting. In embodiments, the deprotecting agent is an acid or a base. In embodiments, the deprotecting agent includes alpha-hydroxy amines (amino alcohol), primary amines and secondary amines. In embodiments, the deprotecting agent is ammonium salt (e.g., ammonium hydroxide, ammonium hydrogen sulfate, ceric ammonium nitrate, or ammonium fluoride). In embodiments, the deprotecting agent is concentrated ammonium hydroxide. The terms "5'-nucleoside protecting group" and "5'-O-nucleoside protecting group" are used interchangeably herein.

The term "reaction vessel" is used in accordance with its ordinary meaning in chemistry or chemical engineering, and refers to a container having an inner volume in which a reaction takes place. In embodiments, the reaction vessel may be designed to provide suitable reaction conditions such as reaction volume, reaction temperature or pressure, and stirring or agitation, which may be adjusted to ensure that the reaction proceeds with a desired, sufficient or highest efficiency for producing a product from the chemical reaction. In embodiments, the reaction vessel is a container for liquid, gas or solid. In embodiments, the reaction vessel may include an inlet, an outlet, a reservoir and the like. In embodiments, the reaction vessel is connected to a pump (e.g., vacuum pump), a controller (e.g., CPU), or a monitoring device (e.g., UV detector or spectrophotometer). In embodiments, the reaction vessel is a flow cell. In embodiments, the reaction vessel is within a sequencing device.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —CH$_3$). Likewise, for a linker variable (e.g., L$^1$, L$^2$, or L$^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., packaging, buffers, written instructions for performing a method, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

As used herein, the terms "sequencing", "sequence determination", "determining a nucleotide sequence", and the like include determination of a partial or complete sequence information, including the identification, ordering, or locations of the nucleotides that comprise the polynucleotide being sequenced, and inclusive of the physical processes for generating such sequence information. That is, the term includes sequence comparisons, consensus sequence determination, contig assembly, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. In some embodiments, a sequencing process described herein comprises contacting a template and an annealed primer with a suitable polymerase under conditions suitable for polymerase extension and/or sequencing. The sequencing methods are preferably carried out with the target polynucleotide arrayed on a solid substrate. Multiple target polynucleotides can be immobilized on the solid support through linker molecules, or can be attached to particles, e.g., microspheres, which can also be attached to a solid substrate. In embodiments, the solid substrate is in the form of a chip, a bead, a well, a capillary tube, a slide, a wafer, a filter, a fiber, a porous media, or a column. In embodiments, the solid substrate is gold, quartz, silica, plastic, glass, diamond, silver, metal, or polypropylene. In embodiments, the solid substrate is porous.

As used herein, the term "extension" or "elongation" is used in accordance with its plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) polynucleotide strand.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode sequence and a template nucleotide sequence. In embodiments, a sequencing read includes reading a template nucleotide sequence. In embodiments, a sequencing read includes reading a barcode and not a template nucleotide sequence.

II. Compounds, Compositions & Kits

In an aspect is provided a compound having the formula:

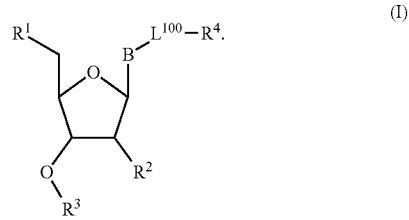

(I)

is a divalent nucleobase. R$^1$ is a 5'-nucleoside protecting group, monophosphate moiety, polyphosphate moiety, nucleic acid moiety, hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OC₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R² is hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety. R³ is hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety. $R^4$ is a detectable moiety. $L^{100}$ is a divalent linker including

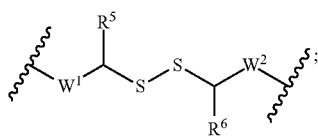

wherein $R^5$ is halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ is halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $W^1$ is —O—, —NH—, —Si—, or —PH—. $W^2$ is O—, —NH—, —Si—, or —PH—.

In an aspect is provided a compound having the formula:

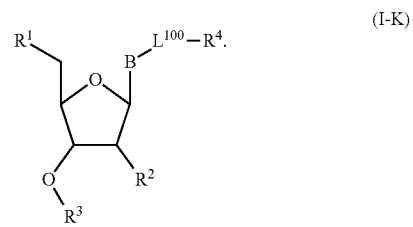

B is a divalent nucleobase. $R^1$ is a 5'-nucleoside protecting group, monophosphate moiety, polyphosphate moiety, nucleic acid moiety, hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety. $R^3$ is hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety. $R^4$ is a detectable moiety. $L^{100}$ is a divalent linker including

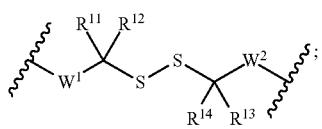

wherein $R^1$, $R^{12}$, $R^{13}$, and $R^{14}$ are independently selected from hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein at least one $R^{11}$, $R^{12}$, $R^{13}$, and $R^{14}$ is not hydrogen. $R^{11}$ and $R^{12}$ may optionally be joined to form a substituted or unsubstituted cycloalkyl, substituted or unsubstituted heterocycloalkyl, substituted or unsubstituted aryl, or substituted or unsubstituted heteroaryl. $R^{13}$ and $R^{14}$ may optionally be joined to form a substituted or unsubstituted cycloalkyl, substituted or unsubstituted heterocycloalkyl, substituted or unsubstituted aryl, or substituted or unsubstituted heteroaryl. $W^1$ is —O—, —NH—, —Si—, or —PH—. $W^2$ is O—, —NH—, —Si—, or —PH—.

In an aspect is provided a compound having the formula

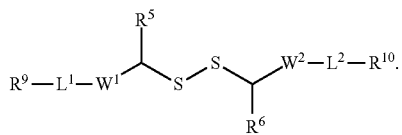
(II)

$R^9$ and $R^{10}$ are independently a protein, bioconjugate reactive moiety, nucleic acid, or a detectable moiety. $L^1$ and $L^2$ are independently a divalent linker. $R^5$ and $R^6$ are independently —CN, —OH, —NH$_2$, —COOH, —CONH$_2$, —NO$_2$, —SO$_3$H, —SO$_4$H, —SO$_2$NH$_2$, —NHNH$_2$, —ONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $W^1$ and $W^2$ are independently —O—, —NH—, —Si—, or —PH—. In embodiments, $L^1$ has the formula -$L^{101}$-$L^{102}$-$L^{103}$-. $L^{101}$, $L^{102}$, and $L^{103}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^2$ has the formula -$L^{201}$-$L^{202}$-$L^{203}$-. $L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In an aspect is provided a compound having the formula

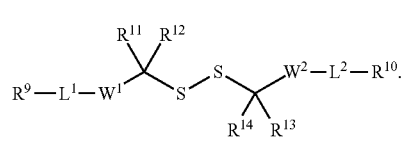
(II-AK)

$R^9$ and $R^{10}$ are independently a protein, bioconjugate reactive moiety, nucleotide, therapeutic moiety, nucleic acid, or a detectable moiety. $L^1$ and $L^2$ are independently a divalent linker. $R^{11}$, $R^{12}$, $R^{13}$, and $R^{14}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein at least one $R^{11}$, $R^{12}$, $R^{13}$, and $R^{14}$ is not hydrogen. $W^1$ and $W^2$ are independently —O—, —NH—, —Si—, or —PH—. In embodiments, $L^1$ has the formula -$L^{101}$-$L^{102}$-$L^{103}$-. $L^{101}$, $L^{102}$, and $L^{103}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^2$ has the formula -$L^{201}$-$L^{202}$-$L^{203}$-. $L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, the compounds of Formula I are referred to as nucleotides, modified nucleotides, or nucleotide analogues. In embodiments, the compounds of Formula I include a nucleotide portion and a 3'-O-reversible terminator. For example, the nucleotide portion is

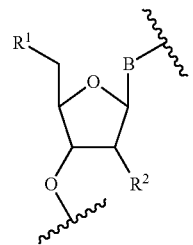

iand the 3'-O-reversible terminator portion is $R^3$, as described herein.

In embodiments, $R^1$ is —OH, a 5'-O-nucleoside protecting group, monophosphate moiety, polyphosphate moiety, or nucleic acid moiety. In embodiments, $R^1$ is a triphosphate moiety. In embodiments, $R^1$ is —OH. In embodiments, $R^1$ is a 5'-O-nucleoside protecting group. In embodiments, $R^1$ is a nucleic acid moiety. In embodiments, $R^1$ is independently a monophosphate moiety or a derivative thereof (e.g., including a phosphoramidate moiety, phosphorothioate moiety, phosphorodithioate moiety, or O-methylphosphoroamidite moiety), polyphosphate moiety or derivative thereof (e.g., including a phosphoramidate, phosphorothioate, phosphorodithioate, or O-methylphosphoroamidite), or nucleic acid moiety or derivative thereof (e.g., including a phosphoramidate, phosphorothioate, phosphorodithioate, or O-methylphosphoroamidite). In embodiments, $R^1$ is a 5'-nucleoside protecting group. In embodiments, $R^1$ is a 5'-O-nucleoside protecting group. In embodiments, the 5'-nucleoside protecting group is a protecting group attached to the 5' carbon of the nucleoside. In embodiments, the 5'-O-nucleoside protecting group is a protecting group attached to the hydroxyl group of the 5' carbon of the nucleoside.

In embodiments, $R^1$ is hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-O-nucleoside protecting group, monophosphate moiety, polyphosphate moiety, or nucleic acid moiety. In embodiments, $R^1$ is a monophosphate moiety including a phosphodiester derivative. In embodiments, $R^1$ is a polyphosphate moiety including a phosphodiester derivative. In embodiments, $R^1$ is a nucleic acid moiety including a phosphodiester derivative. In embodiments, $R^1$ is a phosphoramidate moiety. In embodiments, $R^1$ is a polyphosphate moiety including a phosphoramidate. In embodiments, $R^1$ is a nucleic acid moiety including a phosphoramidate. In embodiments, $R^1$ is a phosphorothioate moiety. In embodiments, $R^1$ is a polyphosphate moiety including a phosphorothioate. In embodiments, $R^1$ is a nucleic acid moiety including a phosphorothioate. In embodiments, $R^1$ is a phosphorodithioate moiety. In embodiments, $R^1$ is a polyphosphate moiety including a phosphorodithioate. In embodiments, $R^1$ is a nucleic acid moiety including a phosphorodithioate. In embodiments, $R^1$ is an O-methylphosphoroamidite moiety. In embodiments, $R^1$ is a polyphosphate moiety including an O-methylphosphoroamidite. In embodiments, $R^1$ is a nucleic acid moiety including an O-methylphosphoroamidite. In embodiments, $R^1$ is a nucleic acid moiety including a nucleotide analog. In embodiments, $R^1$ is a nucleic acid moiety including a plurality of optionally different nucleotide analogs.

In embodiments, $R^1$ is a monophosphate moiety. In embodiments, $R^1$ is a polyphosphate moiety. In embodiments, $R^1$ is a nucleic acid moiety. In embodiments, $R^1$ has the formula:

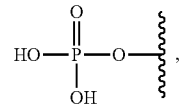

or ionized forms thereof. In embodiments, $R^1$ has the formula

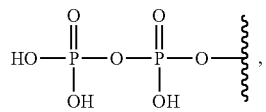

or ionized forms thereof. In embodiments, $R^1$ has the formula

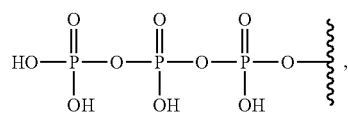

or ionized forms thereof. In embodiments, $R^1$ has the formula:

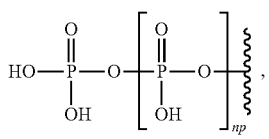

or ionized forms thereof, wherein np is an integer of 1 or greater. In embodiments, np is an integer from 1 to 5. In embodiments, np is 1. In embodiments, np is 2.

In embodiments, $R^1$ is a nucleic acid moiety. In embodiments, $R^1$ has the formula:

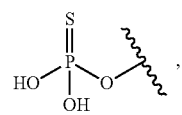

or ionized forms thereof. In embodiments, $R^1$ has the formula

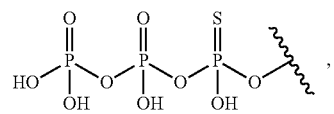

or ionized forms thereof. In embodiments, $R^1$ is —OH.

In embodiments, $R^1$ is a 5'-O-nucleoside protecting group, for example a 5'-O-nucleoside protecting group known in the art include those described in Seliger H. Curr. Protoc Nucleic Acid Chem. 2001; Chapter 2 or K. Seio et al, Nucleic Acids Research Supplement 2, 27-28 (2002); both of which are incorporated by reference for all purposes. Non-limiting examples of 5'-O-nucleoside protecting groups include 2,2,2-Trichloroethyl carbonate (Troc), 2-Methoxyethoxymethyl ether (MEM), 2-Naphthylmethyl ether (Nap), 4-Methoxybenzyl ether (PMB), Acetate (Ac), Benzoate (Bz), Benzyl ether (Bn), Benzyloxymethyl acetal (BOM), Ethoxyethyl acetal (EE), Methoxymethyl acetal (MOM), Methoxypropyl acetal (MOP), Methyl ether, Tetrahydropyranyl acetal (THP), Triethylsilyl ether (TES), Triisopropylsilyl ether (TIPS), Trimethylsilyl ether (TMS), tert-Butyldimethylsilyl ether (TBS, TBDMS), or tert-Butyldiphenylsilyl ether (TBDPS). In embodiments, $R^1$ is

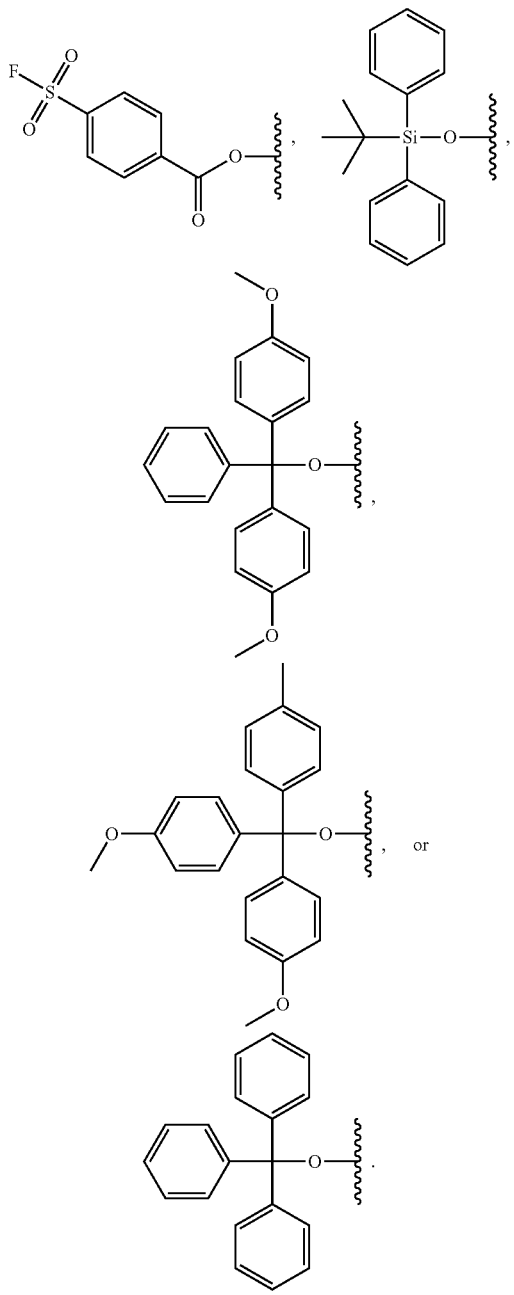

In embodiments, $R^1$ is hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_2NH_2$, $-NHNH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted (e.g., substituted with a substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkyl (e.g., 2 to 8, 2 to 6, 4 to 6, 2 to 3, or 4 to 5 membered), substituted (e.g., substituted with a substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkyl (e.g., 3 to 8, 3 to 6, 4 to 6, 4 to 5, or 5 to 6 membered), substituted (e.g., substituted with a substituent group, size-limited substituent group, or lower substituent group) or unsubstituted aryl (e.g., $C_6$-$C_{10}$ or phenyl), or substituted (e.g., substituted with a substituent group, size-limited substituent group, or lower substituent group) or unsubstituted heteroaryl (e.g., 5 to 10 membered, 5 to 9 membered, or 5 to 6 membered), or a 5'-O-nucleoside protecting group; or $R^1$ is a monophosphate moiety, polyphosphate moiety, or nucleic acid moiety. In embodiments, $R^1$ is hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_2NH_2$, $-NHNH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted (e.g., substituted with a substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkyl (e.g., 2 to 8, 2 to 6, 4 to 6, 2 to 3, or 4 to 5 membered), substituted (e.g., substituted with a substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkyl (e.g., 3 to 8, 3 to 6, 4 to 6, 4 to 5, or 5 to 6 membered), substituted (e.g., substituted with a substituent group, size-limited substituent group, or lower substituent group) or unsubstituted aryl (e.g., $C_6$-$C_{10}$ or phenyl), or substituted (e.g., substituted with a substituent group, size-limited substituent group, or lower substituent group) or unsubstituted heteroaryl (e.g., 5 to 10 membered, 5 to 9 membered, or 5 to 6 membered). In embodiments, $R^1$ is a 5'-O-nucleoside protecting group. In embodiments, $R^1$ is a monophosphate moiety, polyphosphate moiety, or nucleic acid moiety. In embodiments, $R^1$ is a monophosphate moiety. In embodiments, $R^1$ is a polyphosphate moiety. In embodiments, $R^1$ is a nucleic acid moiety. In embodiments, $R^1$ is hydrogen. In embodiments, $R^1$ is a triphosphate moiety. In embodiments, $R^1$ is $-OH$.

In embodiments, a substituted $R^1$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group. In embodiments, when $R^1$ is substituted, it is substituted with 1 to 10 substituent groups. In embodiments, when $R^1$ is substituted, it is substituted with 1 to 10 size-limited substituent groups. In embodiments, when $R^1$ is substituted, it is substituted with 1 to 10 lower substituent groups. In embodiments, when $R^1$ is substituted, it is substituted with 1 to 5 substituent groups. In embodiments, when $R^1$ is substituted, it is substituted with 1 to 5 size-limited substituent groups. In embodiments, when $R^1$ is substituted, it is substituted with 1 to 5 lower substituent groups. In embodiments, when $R^1$ is substituted, it is substituted with a substituent group. In embodiments, when $R^1$ is substituted, it is substituted with a size-limited substituent group. In embodiments, when $R^1$ is substituted, it is substituted with a lower substituent group.

In embodiments, $R^1$ is —OH, a 5'-O-nucleoside protecting group, monophosphate moiety, polyphosphate moiety, or nucleic acid moiety. In embodiments, $R^1$ is a triphosphate moiety. In embodiments, $R^1$ is a triphosphate moiety.

In embodiments, $R^2$ is hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety. In embodiments, $R^2$ is hydrogen. In embodiments, $R^2$ is —OH. In embodiments, $R^2$ is an —O-polymerase-compatible cleavable moiety, wherein the —O— is attached to the 2' position of the ribose sugar of a nucleotide and a polymerase-compatible cleavable moiety is as described herein.

In embodiments, $R^2$ is hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{2A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2A}$-substituted or unsubstituted heteroalkyl (e.g., 2 to 20, 8 to 20, 2 to 10, 2 to 8, 2 to 6, or 2 to 4 membered), $R^{2A}$-substituted or unsubstituted cycloalkyl (e.g., $C_3$-$C_8$, $C_3$-$C_6$, or $C_5$-$C_6$), $R^{2A}$-substituted or unsubstituted heterocycloalkyl (e.g., 3 to 8, 3 to 6, or 5 to 6 membered), $R^{2A}$-substituted or unsubstituted aryl (e.g., $C_6$-$C_{10}$, $C_{10}$, or phenyl), or $R^{2A}$-substituted or unsubstituted heteroaryl (e.g., 5 to 10, 5 to 9, or 5 to 6 membered). In embodiments, $R^2$ is hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered); or a polymerase-compatible cleavable moiety.

$R^{2A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NH$_4$NH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —NH$_3^+$, —SO$_3^-$, —OPO$_3$H$^-$, —SCN, —ONO$_2$, $R^{2B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2B}$-substituted or unsubstituted heteroalkyl (e.g., 2 to 20, 8 to 20, 2 to 10, 2 to 8, 2 to 6, or 2 to 4 membered), $R^{2B}$-substituted or unsubstituted cycloalkyl (e.g., $C_3$-$C_8$, $C_3$-$C_6$, or $C_5$-$C_6$), $R^{2B}$-substituted or unsubstituted heterocycloalkyl (e.g., 3 to 8, 3 to 6, or 5 to 6 membered), $R^{2B}$-substituted or unsubstituted aryl (e.g., $C_6$-$C_{10}$, $C_{10}$, or phenyl), or $R^{2B}$-substituted or unsubstituted heteroaryl (e.g., 5 to 10, 5 to 9, or 5 to 6 membered), or a polymerase-compatible cleavable moiety. In embodiments, $R^{2A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —NH$_3^+$, —SO$_3^-$, —OPO$_3$H$^-$, —SCN, —ONO$_2$, $R^{2B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2B}$-substituted or unsubstituted heteroalkyl (e.g., 2 to 20, 8 to 20, 2 to 10, 2 to 8, 2 to 6, or 2 to 4 membered), $R^{2B}$-substituted or unsubstituted cycloalkyl (e.g., $C_3$-$C_8$, $C_3$-$C_6$, or $C_5$-$C_6$), $R^{2B}$-substituted or unsubstituted heterocycloalkyl (e.g., 3 to 8, 3 to 6, or 5 to 6 membered), $R^{2B}$-substituted or unsubstituted aryl (e.g., $C_6$-$C_{10}$, $C_{10}$, or phenyl), or $R^{2B}$-substituted or unsubstituted heteroaryl (e.g., 5 to 10, 5 to 9, or 5 to 6 membered). In embodiments, $R^{2A}$ is independently a polymerase-compatible cleavable moiety.

$R^{2B}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NH$_4$NH$_2$, —NHC(O)NH$_2$, —NHSO$_2$H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, —NH₃⁺, —SO₃⁻, —OPO₃H⁻, —SCN, —ONO₂, $R^{2C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2C}$-substituted or unsubstituted heteroalkyl (e.g., 2 to 20, 8 to 20, 2 to 10, 2 to 8, 2 to 6, or 2 to 4 membered), $R^{2C}$-substituted or unsubstituted cycloalkyl (e.g., $C_3$-$C_8$, $C_3$-$C_6$, or $C_5$-$C_6$), $R^{2C}$-substituted or unsubstituted heterocycloalkyl (e.g., 3 to 8, 3 to 6, or 5 to 6 membered), $R^{2C}$-substituted or unsubstituted aryl (e.g., $C_6$-$C_{10}$, $C_{10}$, or phenyl), or $R^{2C}$-substituted or unsubstituted heteroaryl (e.g., 5 to 10, 5 to 9, or 5 to 6 membered).

$R^{2C}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NH₄NH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, —NH₃⁺, —SO₃⁻, —OPO₃H⁻, —SCN, —ONO₂, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^2$ is hydrogen. In embodiments, $R^2$ is —OH. In embodiments, $R^2$ is —O-polymerase-compatible cleavable moiety. In embodiments, the -polymerase-compatible cleavable moiety is:

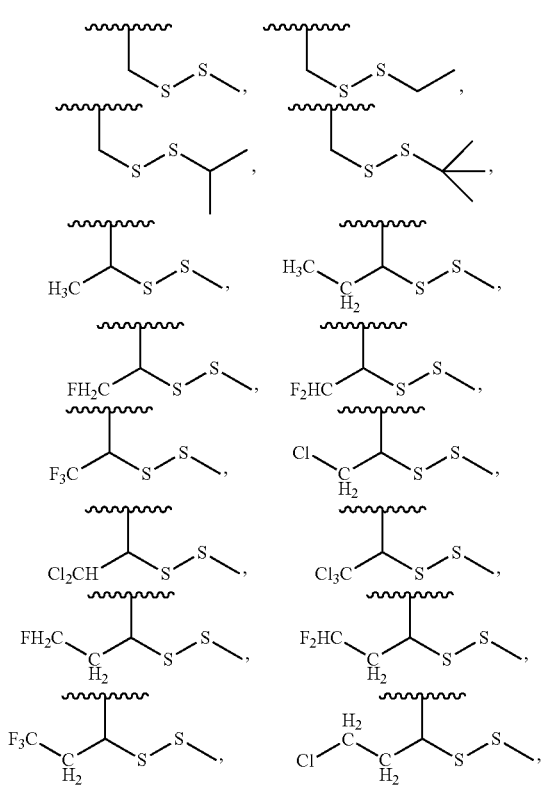

-continued

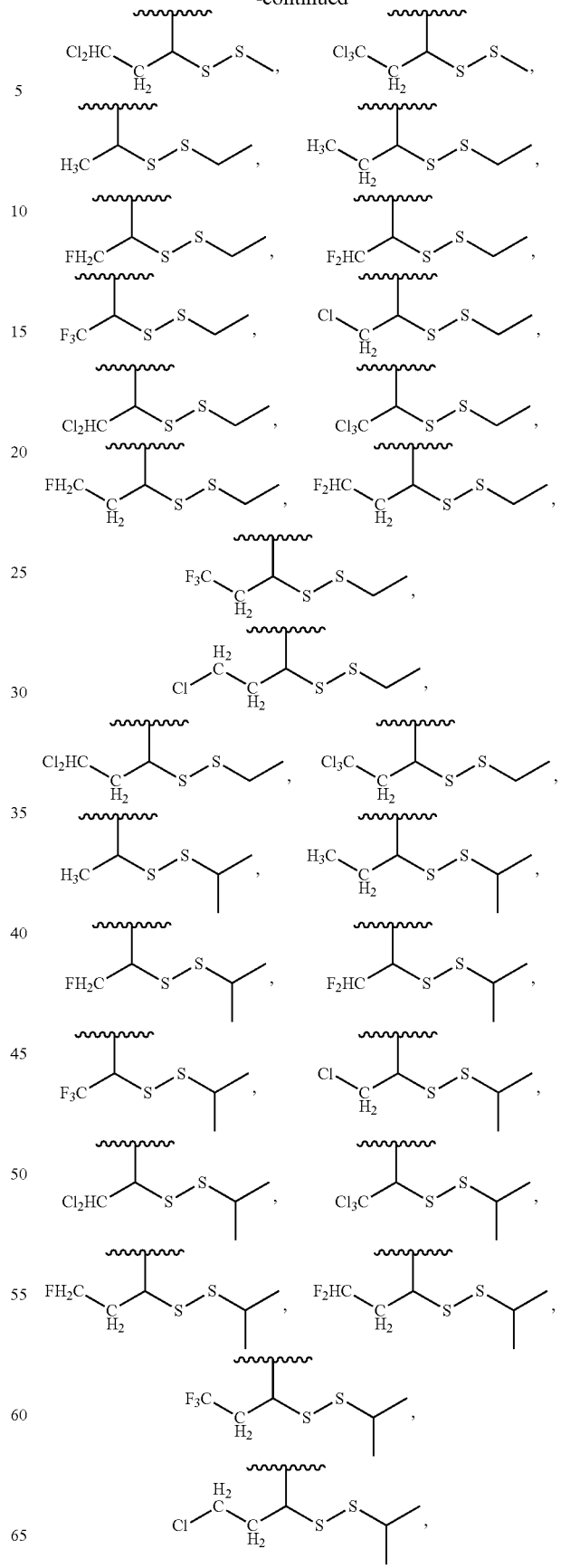

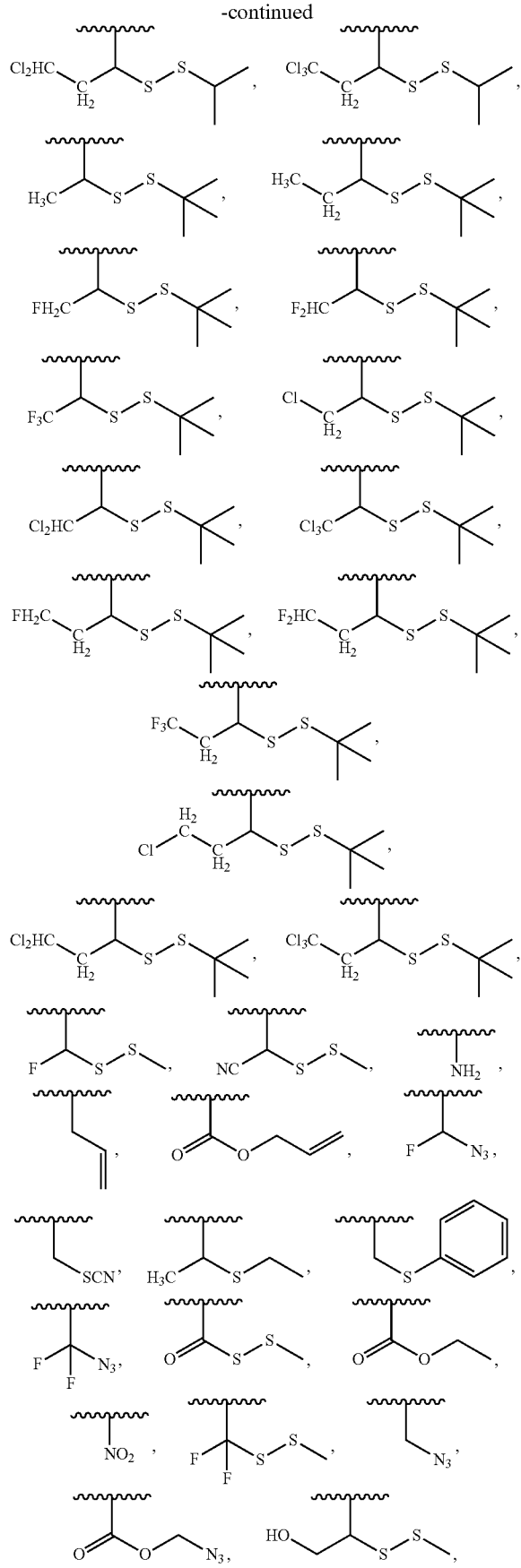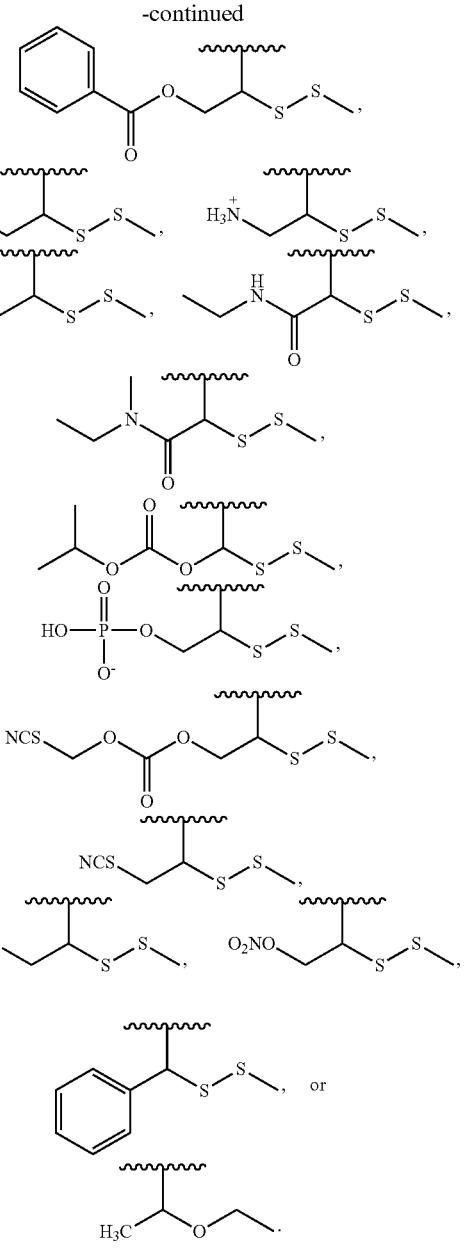
In embodiments the -polymerase-compatible cleavable moiety is:
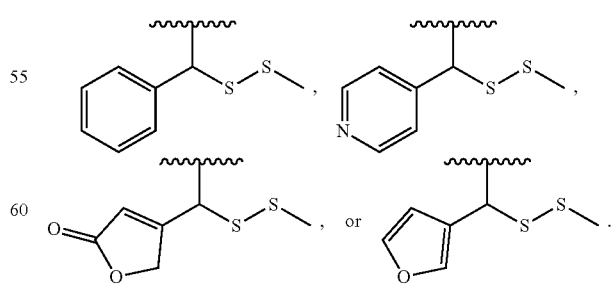
In embodiments, $R^2$ is H. In embodiments, $R^2$ is —OH.
In embodiments, $R^3$ is hydrogen, halogen, —$CCl_3$, —$CBr_3$, —$CF_3$, —$CI_3$, —$CHCl_2$, —$CHBr_2$, —$CHF_2$, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, SF₅, substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), substituted or unsubstituted heteroaryl (e.g., 5 to 10, 5 to 9, or 5 to 6 membered), or a polymerase-compatible cleavable moiety.

In embodiments, a substituted $R^3$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group.

In embodiments, B is a divalent nucleobase. In embodiments, B is

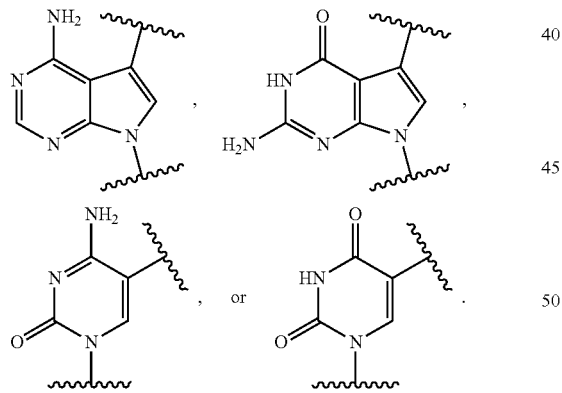

In embodiments, B is

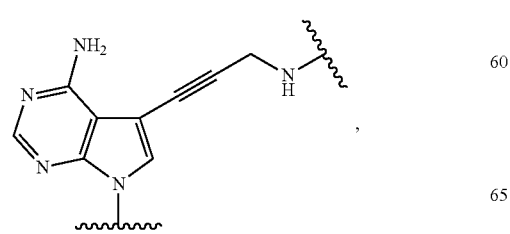

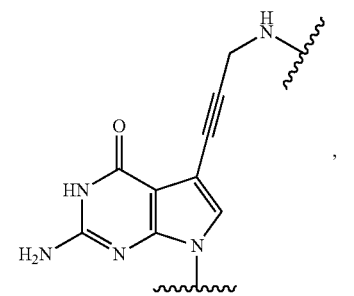

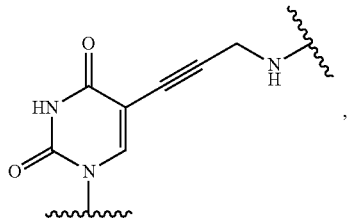

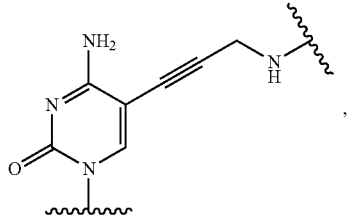

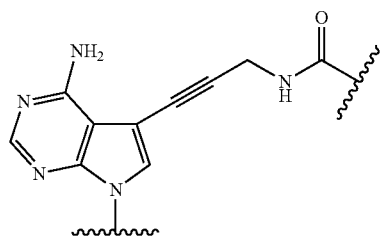

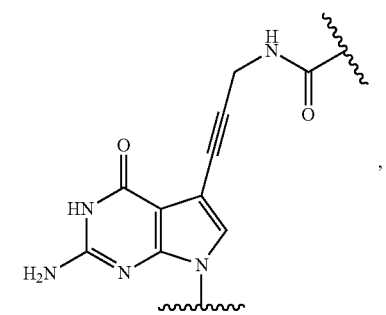

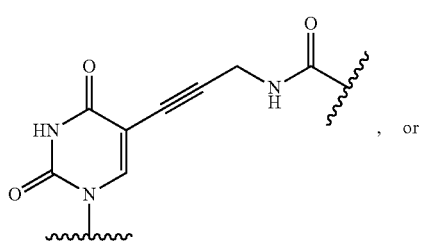

, or

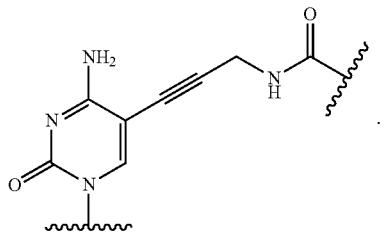

In embodiments, B is a cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

In embodiments, B is

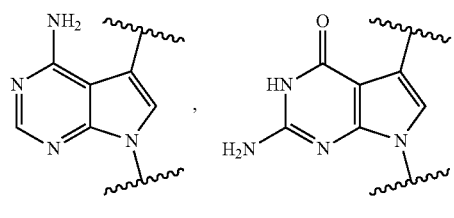

In embodiments, B

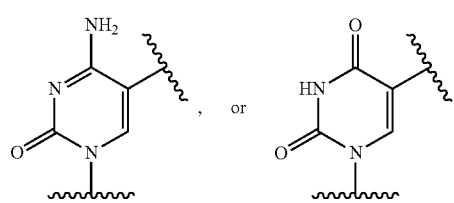

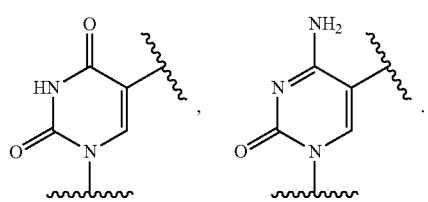

In embodiments, B is

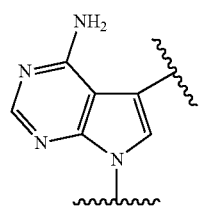

In embodiments, B is

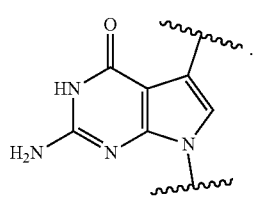 [SMILES: *c1cn(*)c2nc(N)[nH]c(=O)c12]

In embodiments, B is

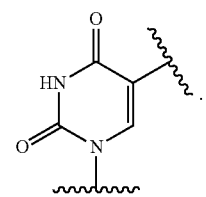 [SMILES: *c1cn(*)c(=O)[nH]c1=O]

In embodiments, B is

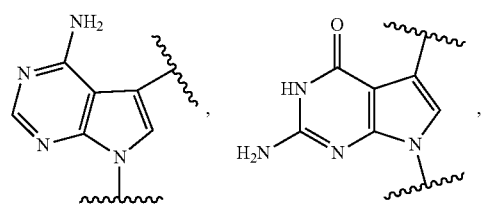

In embodiments, B is

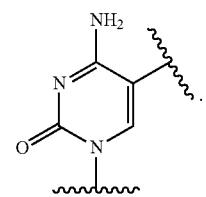 [SMILES: *c1cn(*)c(=O)nc1N]

In embodiments, B is

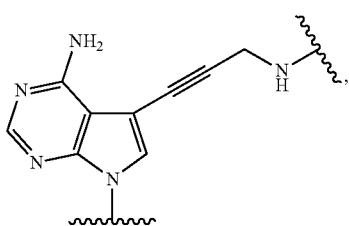

-continued

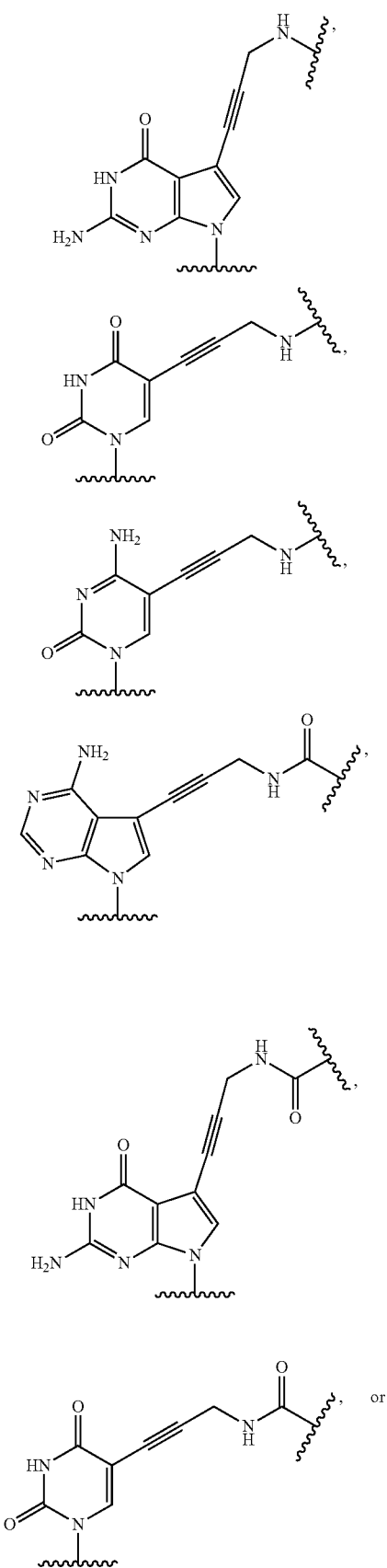

-continued

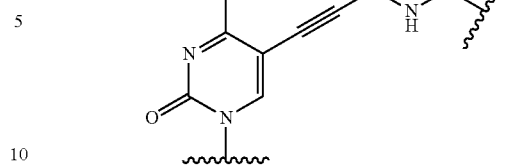

In embodiments, B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof. In embodiments, B is a divalent cytosine or a derivative thereof. In embodiments, B is a divalent guanine or a derivative thereof. In embodiments, B is a divalent adenine or a derivative thereof. In embodiments, B is a divalent thymine or a derivative thereof. In embodiments, B is a divalent uracil or a derivative thereof. In embodiments, B is a divalent hypoxanthine or a derivative thereof. In embodiments, B is a divalent xanthine or a derivative thereof. In embodiments, B is a divalent 7-methylguanine or a derivative thereof. In embodiments, B is a divalent 5,6-dihydrouracil or a derivative thereof. In embodiments, B is a divalent 5-methylcytosine or a derivative thereof. In embodiments, B is a divalent 5-hydroxymethylcytosine or a derivative thereof. In embodiments, B is a divalent cytosine. In embodiments, B is a divalent guanine. In embodiments, B is a divalent adenine. In embodiments, B is a divalent thymine. In embodiments, B is a divalent uracil. In embodiments, B is a divalent hypoxanthine. In embodiments, B is a divalent xanthine. In embodiments, B is a divalent 7-methylguanine. In embodiments, B is a divalent 5,6-dihydrouracil. In embodiments, B is a divalent 5-methylcytosine. In embodiments, B is a divalent 5-hydroxymethylcytosine.

In embodiments, the compound is

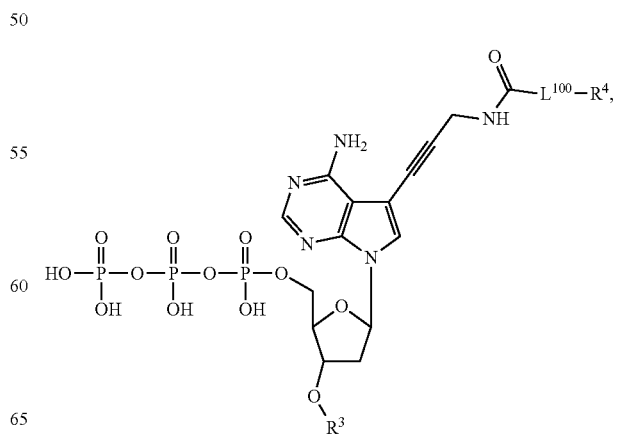

-continued
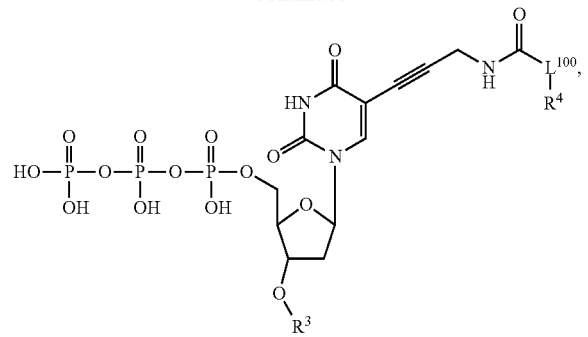
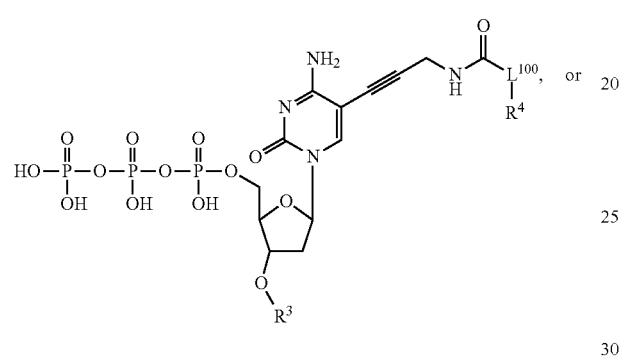
wherein, $L^{100}$ is a cleavable linker including
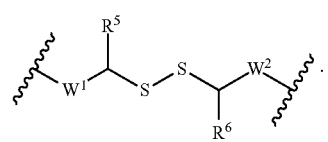
In embodiments, $L^{100}$ includes
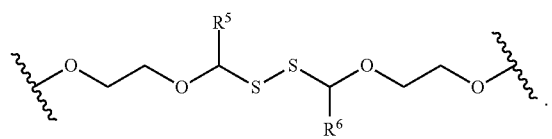
In embodiments, the compound is
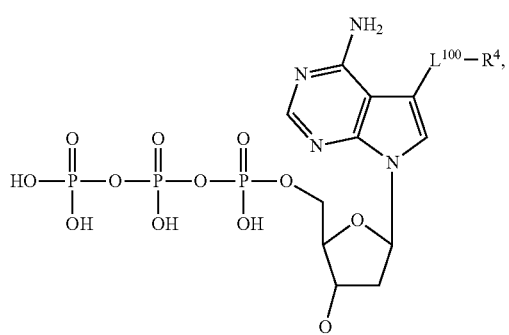
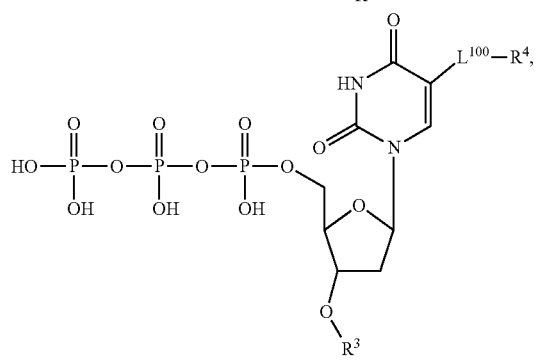
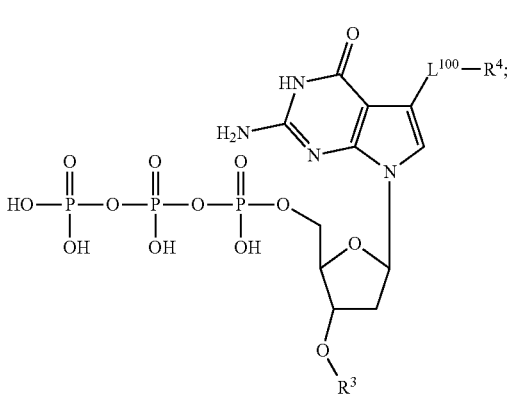

wherein $L^{100}$ has the formula:

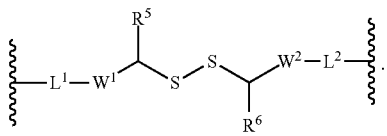

In embodiments, $L^1$ has the formula -$L^{101}$-$L^{102}$-$L^{103}$-. $L^{101}$, $L^{102}$, and $L^{103}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ has the formula -$L^{201}$-$L^{202}$-$L^{203}$-; and $L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{101}$ is a substituted or unsubstituted alkenylene, or substituted or unsubstituted heteroalkenylene. In embodiments, $L^{101}$ is a substituted or unsubstituted alkynylene, or substituted or unsubstituted heteroalkynylene.

In embodiments, the compound is:

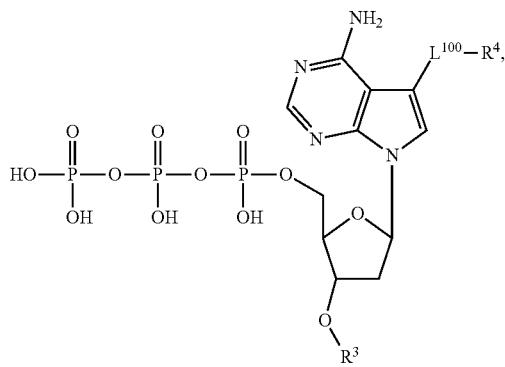

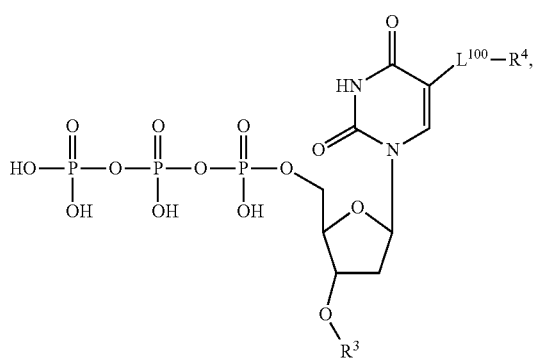

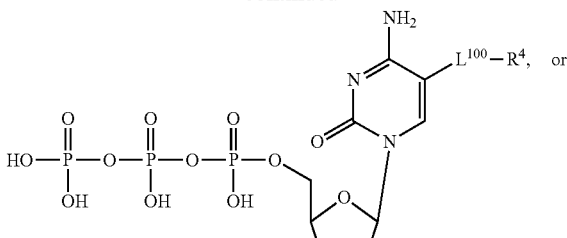

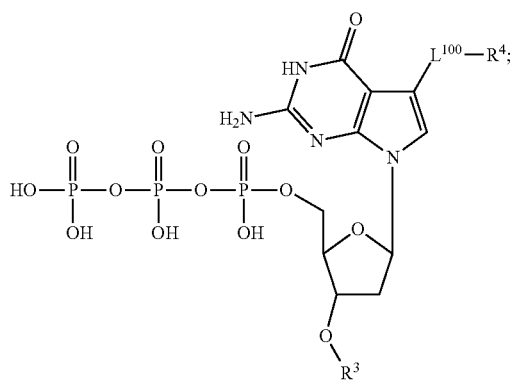

wherein $L^{100}$ has the formula:

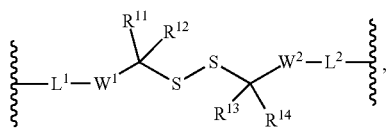

wherein $L^1$ has the formula -$L^{101}$-$L^{102}$-$L^{103}$-; $L^{101}$, $L^{102}$, and $L^{103}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^2$ has the formula -$L^{201}$-$L^{202}$-$L^{203}$-; and $L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{100}$ is

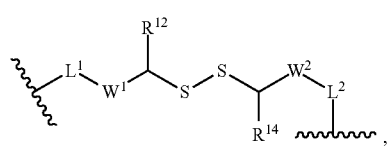

wherein $L^1$, $W^1$, $R^{12}$, $R^{14}$, $W^2$, and $L^2$ are as described herein. In embodiments, $L^{100}$ is

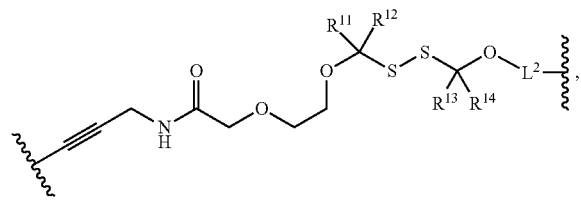

wherein $R^{11}$, $R^{12}$, $R^{13}$, $R^{14}$, and $L^2$ are as described herein.

In embodiments, $W^1$ or $W^2$ are independently —O— or —NH—. In embodiments, $W^1$ or $W^2$ are —O—. In embodiments, $W^1$ is —O—. In embodiments, $W^1$ is —NH—. In embodiments, $W^1$ is —Si—. In embodiments, $W^1$ is —PH—. In embodiments, $W^2$ is —O—. In embodiments, $W^2$ is —NH—. In embodiments, $W^2$ is —Si—. In embodiments, $W^2$ is —PH—.

In embodiments, $L^{100}$ includes

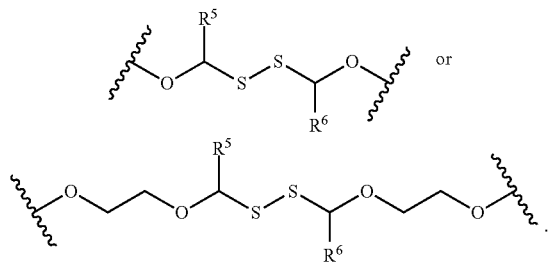

In embodiments, $L^{100}$ includes

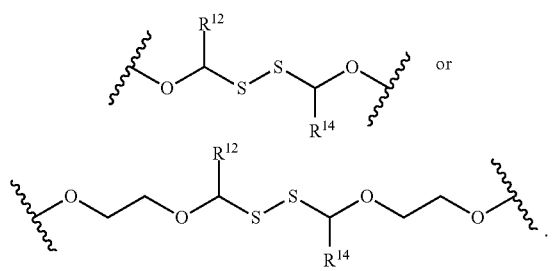

In embodiments, $R^5$ is halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, or —SF$_5$. In embodiments, $R^5$ is —CN, —OH, —NH$_2$, —COOH, —CONH$_2$, —NO$_2$, —SO$_3$H, —SO$_4$H, —SO$_2$NH$_2$, —NHNH$_2$, or —ONH$_2$. In embodiments, $R^5$ is substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered). In embodiments, $R^5$ is $R^{5A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{5A}$-substituted or unsubstituted heteroalkyl (e.g., 2 to 20, 8 to 20, 2 to 10, 2 to 8, 2 to 6, or 2 to 4 membered), $R^{5A}$-substituted or unsubstituted cycloalkyl (e.g., $C_3$-$C_8$, $C_3$-$C_6$, or $C_5$-$C_6$), $R^{5A}$-substituted or unsubstituted heterocycloalkyl (e.g., 3 to 8, 3 to 6, or 5 to 6 membered), $R^{5A}$-substituted or unsubstituted aryl (e.g., $C_6$-$C_{10}$, $C_{10}$, or phenyl), or $R^{5A}$-substituted or unsubstituted heteroaryl (e.g., 5 to 10, 5 to 9, or 5 to 6 membered).

$R^{5A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NH—NH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —NH$_3^+$, —SO$_3^-$, —OPO$_3$H$^-$, —SCN, —ONO$_2$, $R^{5B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{5B}$-substituted or unsubstituted heteroalkyl (e.g., 2 to 20, 8 to 20, 2 to 10, 2 to 8, 2 to 6, or 2 to 4 membered), $R^{5B}$-substituted or unsubstituted cycloalkyl (e.g., $C_3$-$C_8$, $C_3$-$C_6$, or $C_5$-$C_6$), $R^{5B}$-substituted or unsubstituted heterocycloalkyl (e.g., 3 to 8, 3 to 6, or 5 to 6 membered), $R^{5B}$-substituted or unsubstituted aryl (e.g., $C_6$-$C_{10}$, $C_{10}$, or phenyl), or $R^{5B}$-substituted or unsubstituted heteroaryl (e.g., 5 to 10, 5 to 9, or 5 to 6 membered). In embodiments, $R^{5A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_5$Cl, —OCH$_5$Br, —OCH$_2$I, —OCH$_2$F, —N$_3$, —SF$_5$, —NH$_3^+$, —SO$_3^-$, —OPO$_3$H$^-$, —SCN, —ONO$_2$, $R^{5B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{5B}$-substituted or unsubstituted heteroalkyl (e.g., 2 to 20, 8 to 20, 2 to 10, 2 to 8, 2 to 6, or 2 to 4 membered), $R^{5B}$-substituted or unsubstituted cycloalkyl (e.g., $C_3$-$C_8$, $C_3$-$C_6$, or $C_5$-$C_6$), $R^{5B}$-substituted or unsubstituted heterocycloalkyl (e.g., 3 to 8, 3 to 6, or 5 to 6 membered), $R^{5B}$-substituted or unsubstituted aryl (e.g., $C_6$-$C_{10}$, $C_{10}$, or phenyl), or $R^{5B}$-substituted or unsubstituted heteroaryl (e.g., 5 to 10, 5 to 9, or 5 to 6 membered).

$R^{5B}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NH—NH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_5$Cl, —OCH$_2$Br, —OCH$_2$I, —OCH$_2$F, —N$_3$, —SF$_5$, —NH$_3^+$, —SO$_3^-$, —OPO$_3$H$^-$, —SCN, —ONO$_2$, $R^{5C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{5C}$-substituted or unsubstituted heteroalkyl (e.g., 2 to 20, 8 to 20, 2 to 10, 2 to 8, 2 to 6, or 2 to 4 membered), $R^{5C}$-substituted or unsubstituted cycloalkyl (e.g., $C_3$-$C_8$, $C_3$-$C_6$, or $C_5$-$C_6$), $R^{5C}$-substituted or unsubstituted heterocycloalkyl (e.g., 3 to 8, 3 to 6, or 5 to 6 membered), $R^{5C}$-substituted or unsubstituted aryl (e.g., $C_6$-$C_{10}$, $C_{10}$, or phenyl), or $R^{5C}$-substituted or unsubstituted heteroaryl (e.g., 5 to 10, 5 to 9, or 5 to 6 membered).

$R^{5C}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NH_4NH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^5$ is substituted or unsubstituted $C_1$-$C_6$ alkyl. In embodiments, $R^5$ is substituted or unsubstituted $C_1$-$C_6$ alkyl. In embodiments, $R^5$ is substituted or unsubstituted $C_1$ alkyl. In embodiments, $R^5$ is substituted or unsubstituted $C_2$ alkyl. In embodiments, $R^5$ is substituted or unsubstituted $C_3$ alkyl. In embodiments, $R^5$ is substituted or unsubstituted $C_4$ alkyl. In embodiments, $R^5$ is substituted or unsubstituted $C_5$ alkyl. In embodiments, $R^5$ is substituted or unsubstituted $C_6$ alkyl. In embodiments, $R^5$ is substituted $C_1$ alkyl. In embodiments, $R^5$ is substituted $C_2$ alkyl. In embodiments, $R^5$ is substituted $C_3$ alkyl. In embodiments, $R^5$ is substituted $C_4$ alkyl. In embodiments, $R^5$ is substituted $C_5$ alkyl. In embodiments, $R^5$ is substituted $C_6$ alkyl. In embodiments, $R^5$ is unsubstituted $C_1$ alkyl. In embodiments, $R^5$ is unsubstituted $C_2$ alkyl. In embodiments, $R^5$ is unsubstituted $C_3$ alkyl. In embodiments, $R^5$ is unsubstituted $C_4$ alkyl. In embodiments, $R^5$ is unsubstituted $C_5$ alkyl. In embodiments, $R^5$ is unsubstituted $C_6$ alkyl.

In embodiments, $R^5$ is substituted or unsubstituted 2 to 8 membered heteroalkyl. In embodiments, $R^5$ is substituted or unsubstituted 2 to 6 membered heteroalkyl. In embodiments, $R^5$ is substituted or unsubstituted 2 to 4 membered heteroalkyl. In embodiments, $R^5$ is substituted 2 to 8 membered heteroalkyl. In embodiments, $R^5$ is substituted 2 to 6 membered heteroalkyl. In embodiments, $R^5$ is substituted 2 to 4 membered heteroalkyl. In embodiments, $R^5$ is unsubstituted 2 to 8 membered heteroalkyl. In embodiments, $R^5$ is unsubstituted 2 to 6 membered heteroalkyl. In embodiments, $R^5$ is unsubstituted 2 to 4 membered heteroalkyl.

In embodiments, $R^5$ is substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^5$ is substituted or unsubstituted cycloalkyl (e.g., $C_3$-$C_8$, $C_3$-$C_6$, $C_4$-$C_6$, or $C_5$-$C_6$). In embodiments, $R^5$ is substituted cycloalkyl (e.g., $C_3$-$C_8$, $C_3$-$C_6$, $C_4$-$C_6$, or $C_5$-$C_6$). In embodiments, $R^5$ is an unsubstituted cycloalkyl (e.g., $C_3$-$C_8$, $C_3$-$C_6$, $C_4$-$C_6$, or $C_5$-$C_6$). In embodiments, $R^5$ is substituted or unsubstituted heterocycloalkyl (e.g., 3 to 8 membered, 3 to 6 membered, 4 to 6 membered, 4 to 5 membered, or 5 to 6 membered). In embodiments, $R^5$ is substituted heterocycloalkyl (e.g., 3 to 8 membered, 3 to 6 membered, 4 to 6 membered, 4 to 5 membered, or 5 to 6 membered). In embodiments, $R^5$ is an unsubstituted heterocycloalkyl (e.g., 3 to 8 membered, 3 to 6 membered, 4 to 6 membered, 4 to 5 membered, or 5 to 6 membered).

In embodiments, $R^5$ is substituted or unsubstituted aryl (e.g., $C_6$-$C_{10}$, $C_{10}$, or phenyl). In embodiments, $R^5$ is substituted aryl (e.g., $C_6$-$C_{10}$, $C_{10}$, or phenyl). In embodiments, $R^5$ is unsubstituted aryl (e.g., $C_6$-$C_{10}$, $C_{10}$, or phenyl). In embodiments, $R^5$ is unsubstituted phenyl. In embodiments, $R^5$ is substituted or unsubstituted heteroaryl (e.g., 5 to 10, 5 to 9, or 5 to 6 membered). In embodiments, $R^5$ is substituted heteroaryl (e.g., 5 to 10, 5 to 9, or 5 to 6 membered). In embodiments, $R^5$ is unsubstituted heteroaryl (e.g., 5 to 10, 5 to 9, or 5 to 6 membered). In embodiments, $R^5$ is a substituted or unsubstituted 5 membered heteroaryl. In embodiments, $R^5$ is a substituted or unsubstituted 6 membered heteroaryl. In embodiments, $R^5$ is a substituted or unsubstituted 5 membered heteroaryl. In embodiments, $R^5$ is an unsubstituted 5 membered heteroaryl. In embodiments, $R^5$ is an unsubstituted 6 membered heteroaryl. In embodiments, $R^5$ is an unsubstituted 7 membered heteroaryl.

In embodiments, $R^5$ is unsubstituted alkyl, —CN, —OH, —$NH_2$, —COOH, —$CONH_2$, —$NO_2$, —$SO_3H$, —$SO_4H$, —$SO_2NH_2$, —$NHNH_2$, —$ONH_2$, substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ is unsubstituted alkyl, substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^5$ is

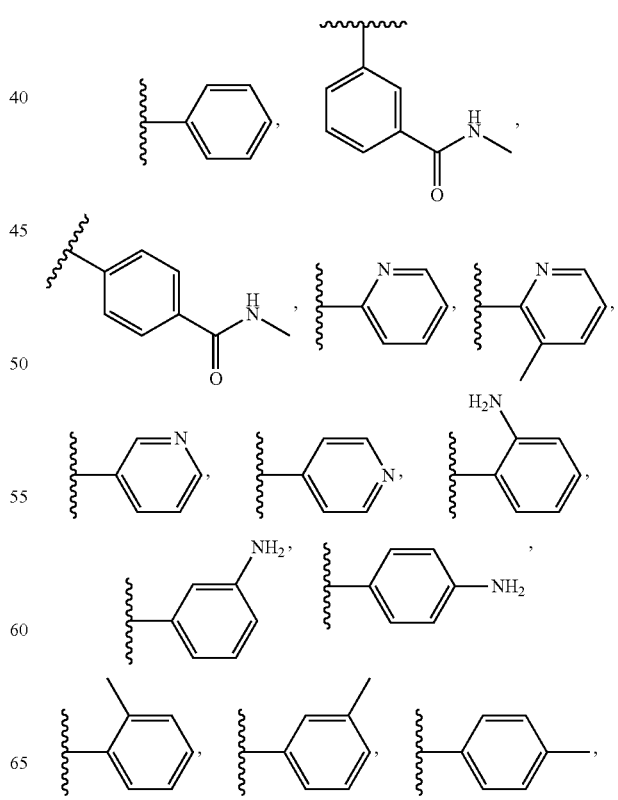

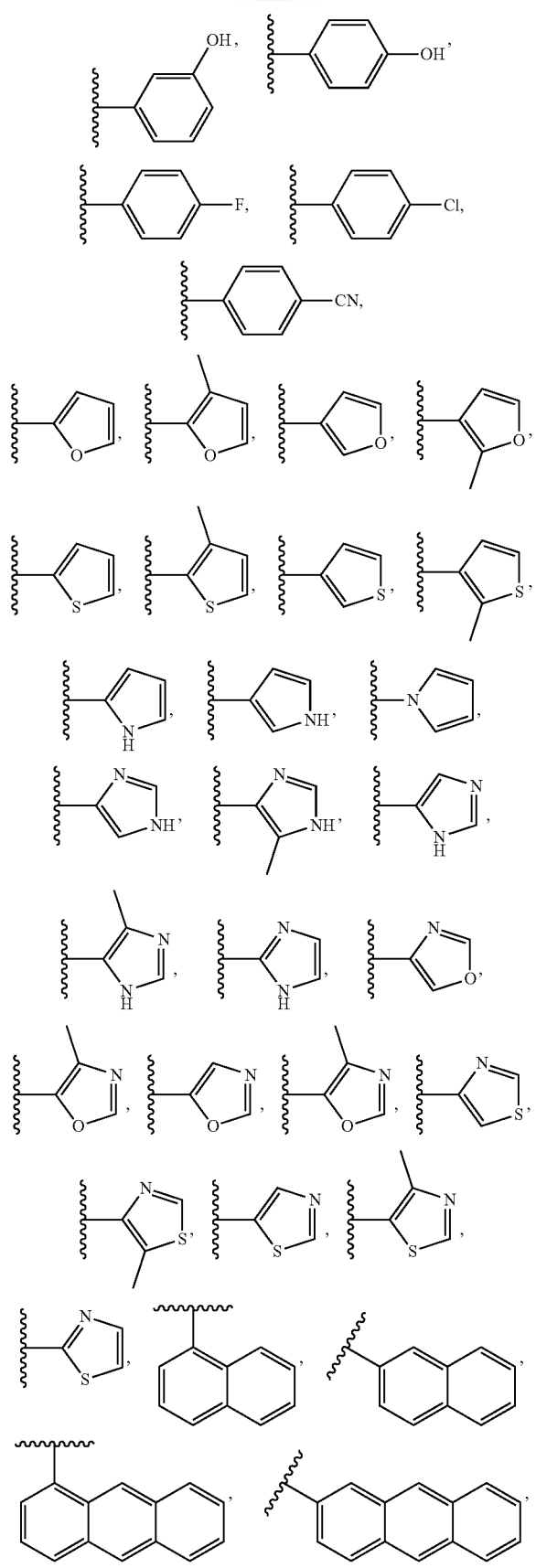
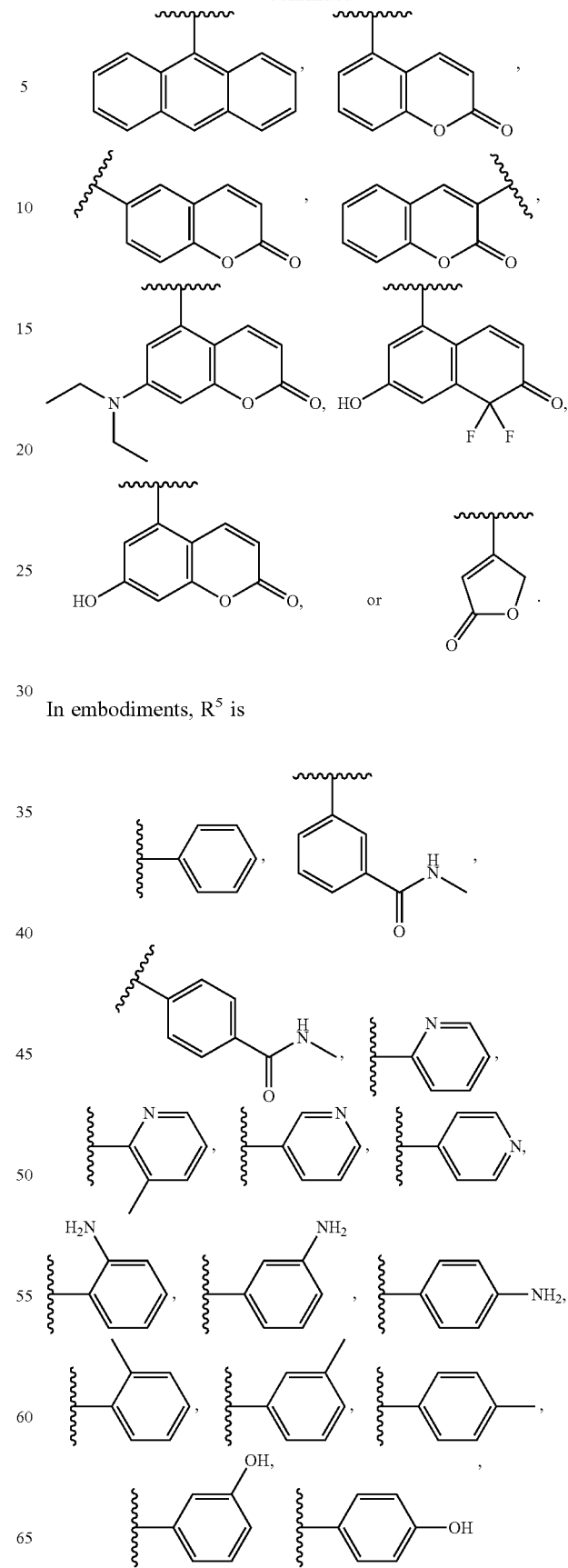
In embodiments, $R^5$ is

-continued
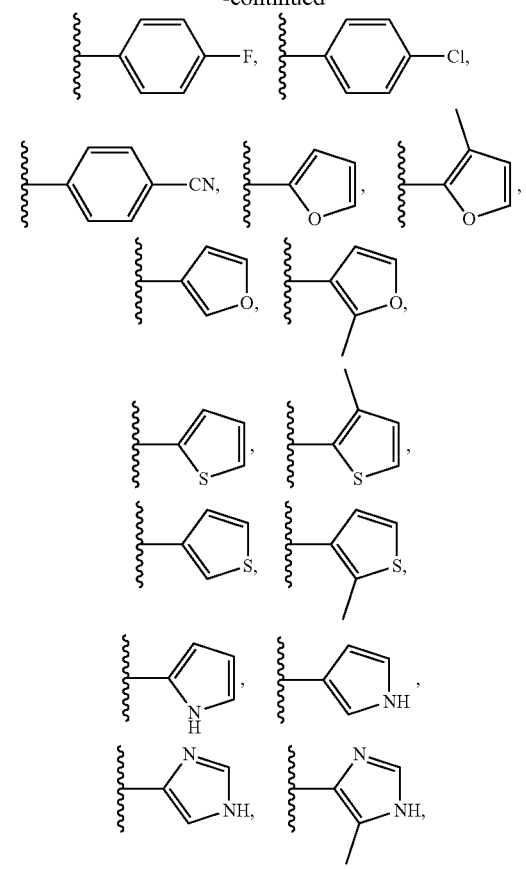
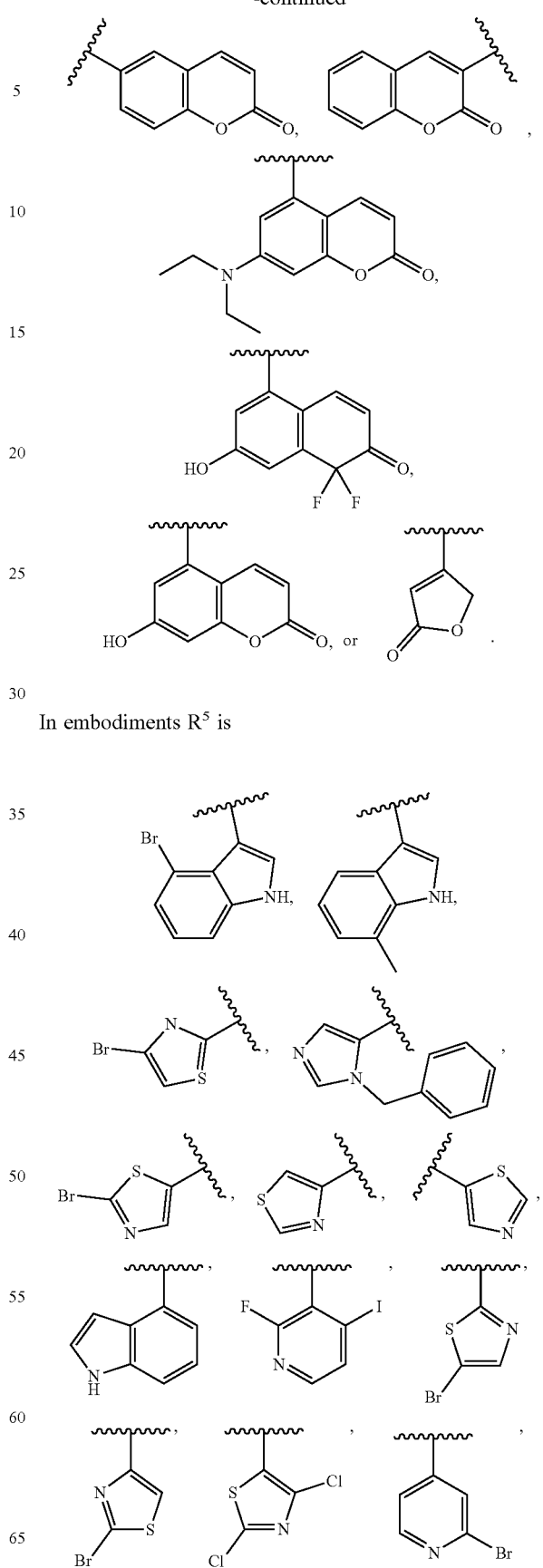
In embodiments $R^5$ is

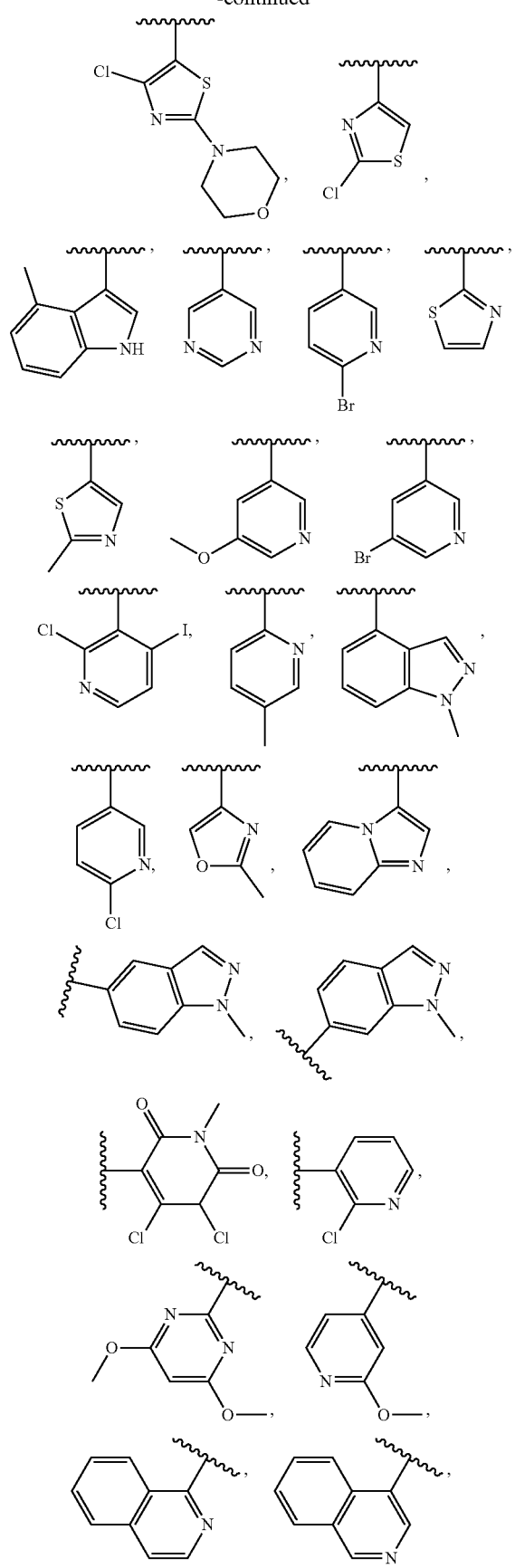
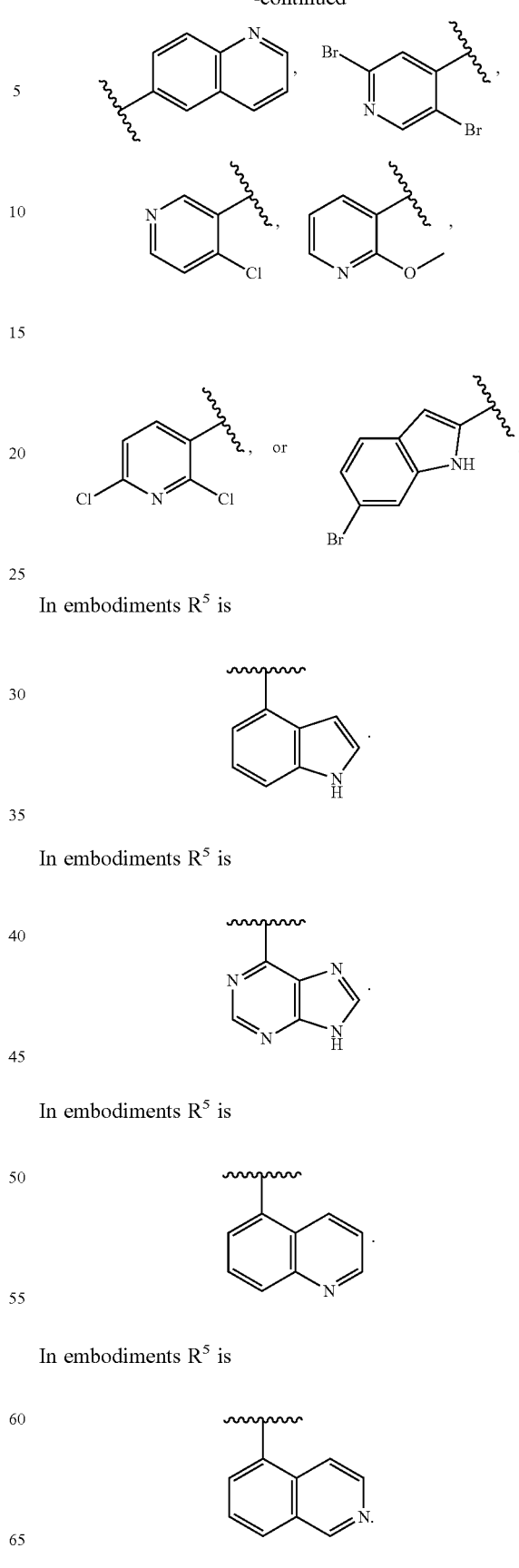
In embodiments $R^5$ is
In embodiments $R^5$ is
In embodiments $R^5$ is
In embodiments $R^5$ is In embodiments R⁵ is
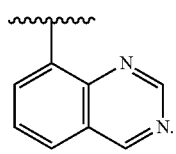
In embodiments R⁵ is
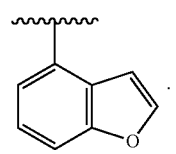 [SMILES: *c1cccc2occc12]
In embodiments R⁵ is
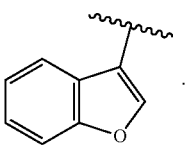 [SMILES: *c1coc2ccccc12]
In embodiments, R⁵ is
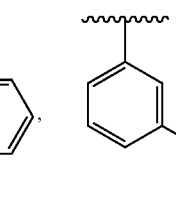
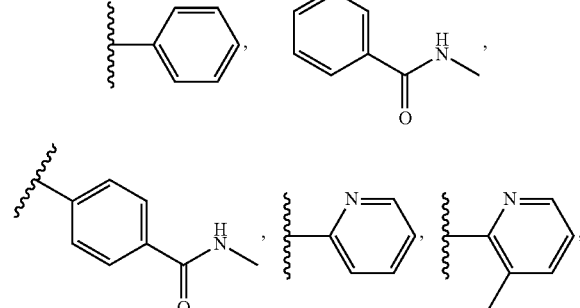
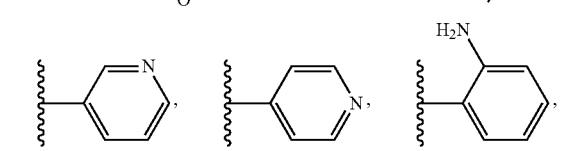
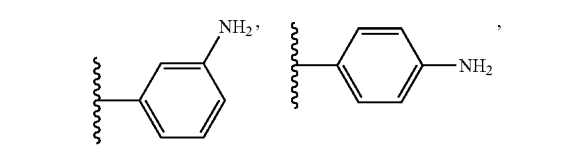
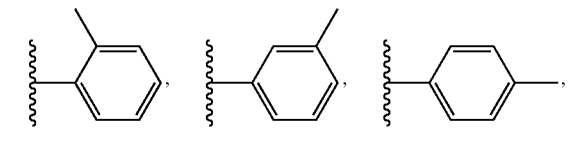
-continued
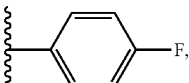
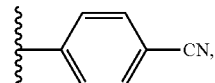
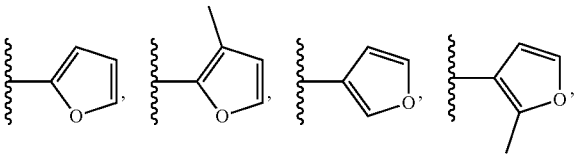
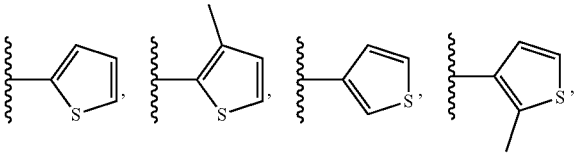
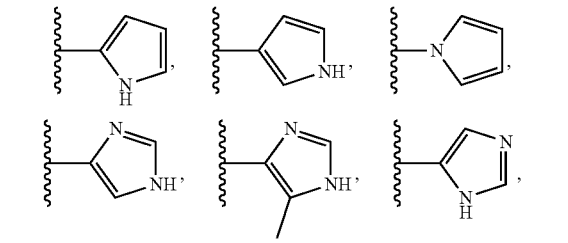
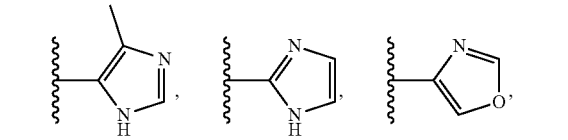
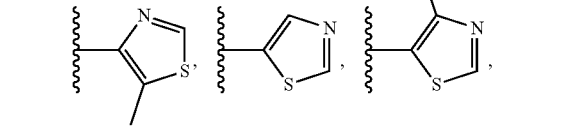
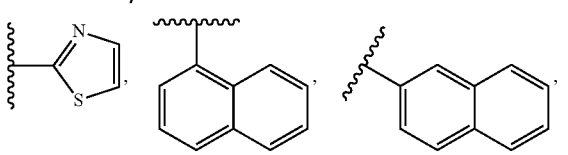
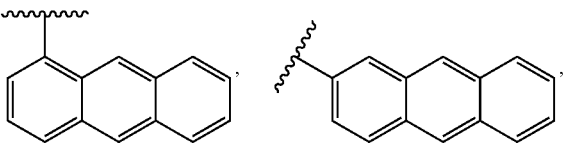
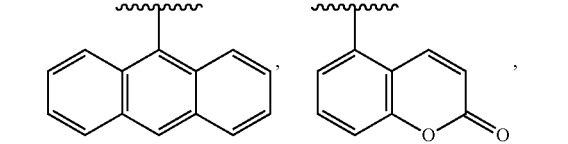

-continued

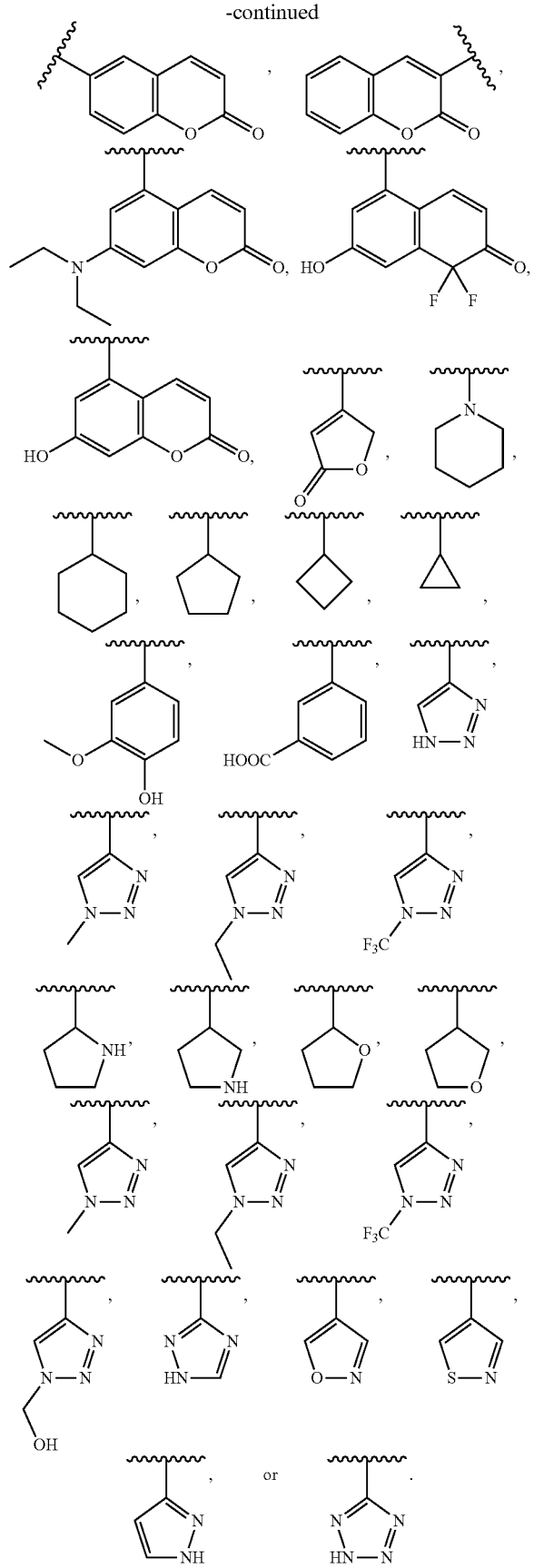

In embodiments, $R^6$ is halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, or —SF$_5$. In embodiments, $R^6$ is —CN, —OH, —NH$_2$, —COOH, —CONH$_2$, —NO$_2$, —SO$_3$H, —SO$_4$H, —SO$_2$NH$_2$, —NHNH$_2$, or —ONH$_2$. In embodiments, $R^6$ is substituted or unsubstituted alkyl (e.g., C$_1$-C$_{20}$, C$_{10}$-C$_{20}$, C$_1$-C$_8$, C$_1$-C$_6$, or C$_1$-C$_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., C$_3$-C$_8$, C$_3$-C$_6$, or C$_5$-C$_6$), substituted or unsubstituted heterocycloalkyl (e.g., 3 to 8, 3 to 6, or 5 to 6 membered), substituted or unsubstituted aryl (e.g., C$_6$-C$_{10}$, C$_{10}$, or phenyl), or substituted or unsubstituted heteroaryl (e.g., 5 to 10, 5 to 9, or 5 to 6 membered). In embodiments, $R^6$ is $R^{6A}$-substituted or unsubstituted alkyl (e.g., C$_1$-C$_{20}$, C$_{10}$-C$_{20}$, C$_1$-C$_8$, C$_1$-C$_6$, or C$_1$-C$_4$), $R^{6A}$-substituted or unsubstituted heteroalkyl (e.g., 2 to 20, 8 to 20, 2 to 10, 2 to 8, 2 to 6, or 2 to 4 membered), $R^{6A}$-substituted or unsubstituted cycloalkyl (e.g., C$_3$-C$_8$, C$_3$-C$_6$, or C$_5$-C$_6$), $R^{6A}$-substituted or unsubstituted heterocycloalkyl (e.g., 3 to 8, 3 to 6, or 5 to 6 membered), $R^{6A}$-substituted or unsubstituted aryl (e.g., C$_6$-C$_{10}$, C$_{10}$, or phenyl), or $R^{6A}$-substituted or unsubstituted heteroaryl (e.g., 5 to 10, 5 to 9, or 5 to 6 membered).

$R^{6A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —NH$_3^+$, —SO$_3^-$, —OPO$_3$H$^-$, —SCN, —ONO$_2$, $R^{6B}$-substituted or unsubstituted alkyl (e.g., C$_1$-C$_{20}$, C$_{10}$-C$_{20}$, C$_1$-C$_8$, C$_1$-C$_6$, or C$_1$-C$_4$), $R^{6B}$-substituted or unsubstituted heteroalkyl (e.g., 2 to 20, 8 to 20, 2 to 10, 2 to 8, 2 to 6, or 2 to 4 membered), $R^{6B}$-substituted or unsubstituted cycloalkyl (e.g., C$_3$-C$_8$, C$_3$-C$_6$, or C$_5$-C$_6$), $R^{6B}$-substituted or unsubstituted heterocycloalkyl (e.g., 3 to 8, 3 to 6, or 5 to 6 membered), $R^{6B}$-substituted or unsubstituted aryl (e.g., C$_6$-C$_{10}$, C$_{10}$, or phenyl), or $R^{6B}$-substituted or unsubstituted heteroaryl (e.g., 5 to 10, 5 to 9, or 5 to 6 membered). In embodiments, $R^{6A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_5{}_{C}$l, —OCH$_5{}_{B}$r, —OCH$_2$I, —OCH$_2$F, —N$_3$, —SF$_5$, —NH$_3^+$, —SO$_3^-$, —OPO$_3$H$^-$, —SCN, —ONO$_2$, $R^{6B}$-substituted or unsubstituted alkyl (e.g., C$_1$-C$_{20}$, C$_{10}$-C$_{20}$, C$_1$-C$_8$, C$_1$-C$_6$, or C$_1$-C$_4$), $R^{6B}$-substituted or unsubstituted heteroalkyl (e.g., 2 to 20, 8 to 20, 2 to 10, 2 to 8, 2 to 6, or 2 to 4 membered), $R^{6B}$-substituted or unsubstituted cycloalkyl (e.g., C$_3$-C$_8$, C$_3$-C$_6$, or C$_5$-C$_6$), $R^{6B}$-substituted or unsubstituted heterocycloalkyl (e.g., 3 to 8, 3 to 6, or 5 to 6 membered), $R^{6B}$-substituted or unsubstituted aryl (e.g., $C_6$-$C_{10}$, $C_{10}$, or phenyl), or $R^{6B}$-substituted or unsubstituted heteroaryl (e.g., 5 to 10, 5 to 9, or 5 to 6 membered).

$R^{6B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_5Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{6C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{6C}$-substituted or unsubstituted heteroalkyl (e.g., 2 to 20, 8 to 20, 2 to 10, 2 to 8, 2 to 6, or 2 to 4 membered), $R^{6C}$-substituted or unsubstituted cycloalkyl (e.g., $C_3$-$C_8$, $C_3$-$C_6$, or $C_5$-$C_6$), $R^{6C}$-substituted or unsubstituted heterocycloalkyl (e.g., 3 to 8, 3 to 6, or 5 to 6 membered), $R^{6C}$-substituted or unsubstituted aryl (e.g., $C_6$-$C_{10}$, $C_{10}$, or phenyl), or $R^{6C}$-substituted or unsubstituted heteroaryl (e.g., 5 to 10, 5 to 9, or 5 to 6 membered).

$R^{6C}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_5Cl$, —$CH_{5B}r$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_5Cl$, —$OCH_{5B}r$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^6$ is substituted or unsubstituted $C_1$-$C_6$ alkyl. In embodiments, $R^6$ is substituted or unsubstituted $C_1$-$C_6$ alkyl. In embodiments, $R^6$ is substituted or unsubstituted $C_1$ alkyl. In embodiments, $R^6$ is substituted or unsubstituted $C_2$ alkyl. In embodiments, $R^6$ is substituted or unsubstituted $C_3$ alkyl. In embodiments, $R^6$ is substituted or unsubstituted $C_4$ alkyl. In embodiments, $R^6$ is substituted or unsubstituted $C_5$ alkyl. In embodiments, $R^6$ is substituted or unsubstituted $C_6$ alkyl. In embodiments, $R^6$ is substituted $C_1$ alkyl. In embodiments, $R^6$ is substituted $C_2$ alkyl. In embodiments, $R^6$ is substituted $C_3$ alkyl. In embodiments, $R^6$ is substituted $C_4$ alkyl. In embodiments, $R^6$ is substituted $C_5$ alkyl. In embodiments, $R^6$ is substituted $C_6$ alkyl. In embodiments, $R^6$ is unsubstituted $C_1$ alkyl. In embodiments, $R^6$ is unsubstituted $C_2$ alkyl. In embodiments, $R^6$ is unsubstituted $C_3$ alkyl. In embodiments, $R^6$ is unsubstituted $C_4$ alkyl. In embodiments, $R^6$ is unsubstituted $C_5$ alkyl. In embodiments, $R^6$ is unsubstituted $C_6$ alkyl.

In embodiments, $R^6$ is substituted or unsubstituted 2 to 8 membered heteroalkyl. In embodiments, $R^6$ is substituted or unsubstituted 2 to 6 membered heteroalkyl. In embodiments, $R^6$ is substituted or unsubstituted 2 to 4 membered heteroalkyl. In embodiments, $R^6$ is substituted 2 to 8 membered heteroalkyl. In embodiments, $R^6$ is substituted 2 to 6 membered heteroalkyl. In embodiments, $R^6$ is substituted 2 to 4 membered heteroalkyl. In embodiments, $R^6$ is unsubstituted 2 to 8 membered heteroalkyl. In embodiments, $R^6$ is unsubstituted 2 to 6 membered heteroalkyl. In embodiments, $R^6$ is unsubstituted 2 to 4 membered heteroalkyl.

In embodiments, $R^6$ is substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^6$ is substituted or unsubstituted cycloalkyl (e.g., $C_3$-$C_8$, $C_3$-$C_6$, $C_4$-$C_6$, or $C_5$-$C_6$). In embodiments, $R^6$ is substituted cycloalkyl (e.g., $C_3$-$C_8$, $C_3$-$C_6$, $C_4$-$C_6$, or $C_5$-$C_6$). In embodiments, $R^6$ is an unsubstituted cycloalkyl (e.g., $C_3$-$C_8$, $C_3$-$C_6$, $C_4$-$C_6$, or $C_5$-$C_6$). In embodiments, $R^6$ is substituted or unsubstituted heterocycloalkyl (e.g., 3 to 8 membered, 3 to 6 membered, 4 to 6 membered, 4 to 5 membered, or 5 to 6 membered). In embodiments, $R^6$ is substituted heterocycloalkyl (e.g., 3 to 8 membered, 3 to 6 membered, 4 to 6 membered, 4 to 5 membered, or 5 to 6 membered). In embodiments, $R^6$ is an unsubstituted heterocycloalkyl (e.g., 3 to 8 membered, 3 to 6 membered, 4 to 6 membered, 4 to 5 membered, or 5 to 6 membered).

In embodiments, $R^6$ is substituted or unsubstituted aryl (e.g., $C_6$-$C_{10}$, $C_{10}$, or phenyl). In embodiments, $R^6$ is substituted aryl (e.g., $C_6$-$C_{10}$, $C_{10}$, or phenyl). In embodiments, $R^6$ is unsubstituted aryl (e.g., $C_6$-$C_{10}$, $C_{10}$, or phenyl). In embodiments, $R^6$ is unsubstituted phenyl. In embodiments, $R^6$ is substituted or unsubstituted heteroaryl (e.g., 5 to 10, 5 to 9, or 5 to 6 membered). In embodiments, $R^6$ is substituted heteroaryl (e.g., 5 to 10, 5 to 9, or 5 to 6 membered). In embodiments, $R^6$ is unsubstituted heteroaryl (e.g., 5 to 10, 5 to 9, or 5 to 6 membered). In embodiments, $R^6$ is a substituted or unsubstituted 5 membered heteroaryl. In embodiments, $R^6$ is a substituted or unsubstituted 6 membered heteroaryl. In embodiments, $R^6$ is a substituted or unsubstituted 5 membered heteroaryl. In embodiments, $R^6$ is an unsubstituted 5 membered heteroaryl. In embodiments, $R^6$ is an unsubstituted 6 membered heteroaryl. In embodiments, $R^6$ is an unsubstituted 7 membered heteroaryl.

In embodiments, R is unsubstituted alkyl, —CN, —OH, —$NH_2$, —COOH, —$CONH_2$, —$NO_2$, —$SO_3H$, —$SO_4H$, —$SO_2NH_2$, —$NHNH_2$, —$ONH_2$, substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^6$ is unsubstituted alkyl, substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments $R^6$ is

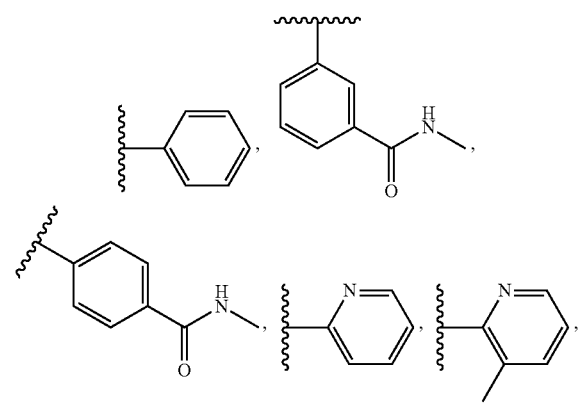

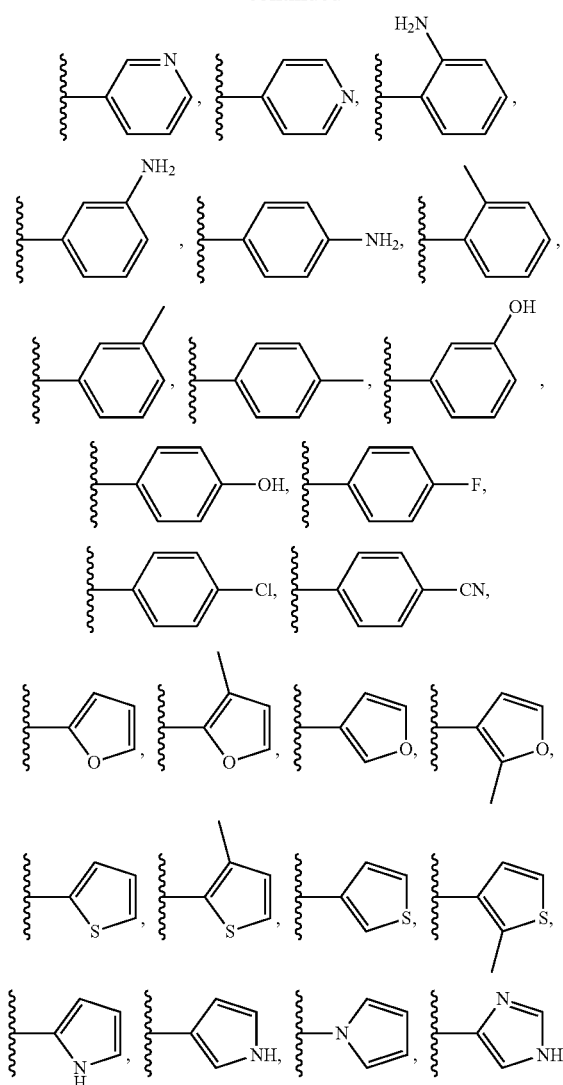
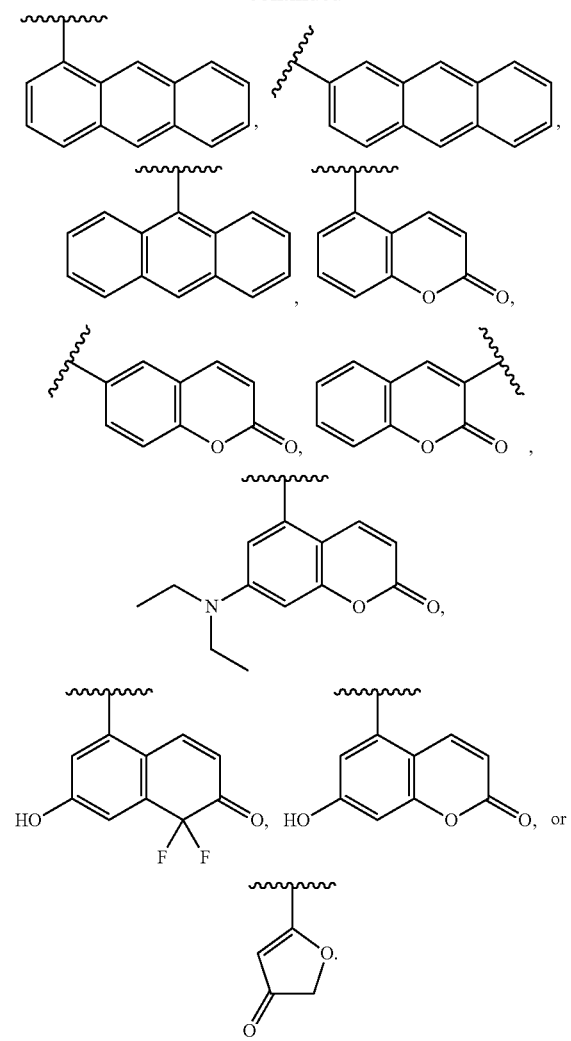
In embodiments, $R^6$ is
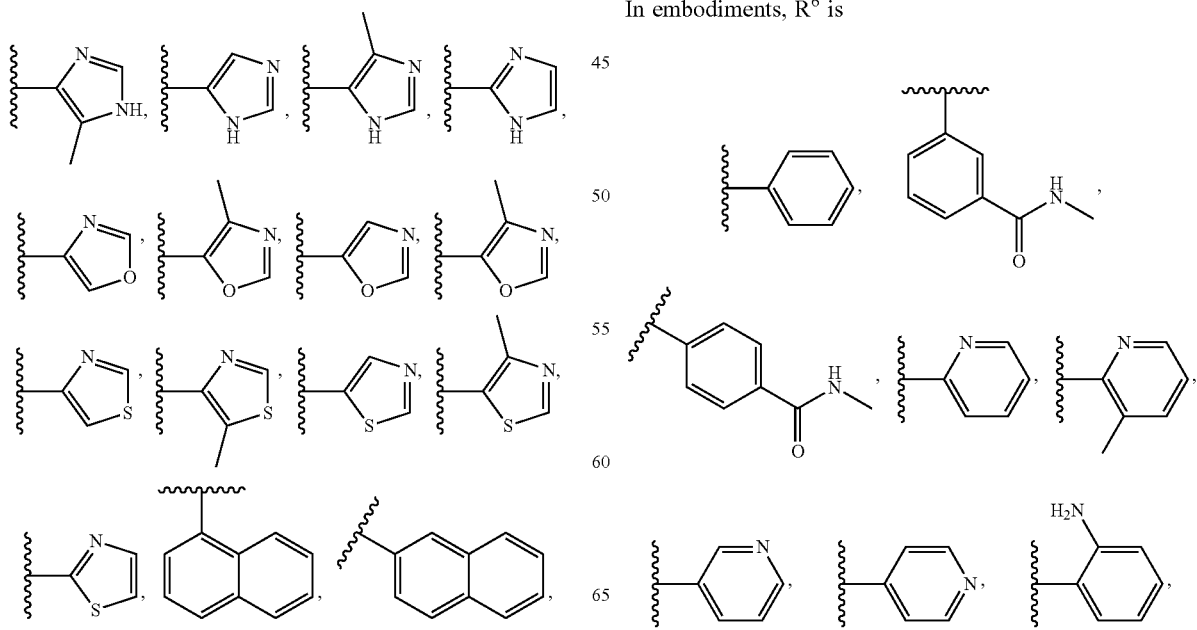

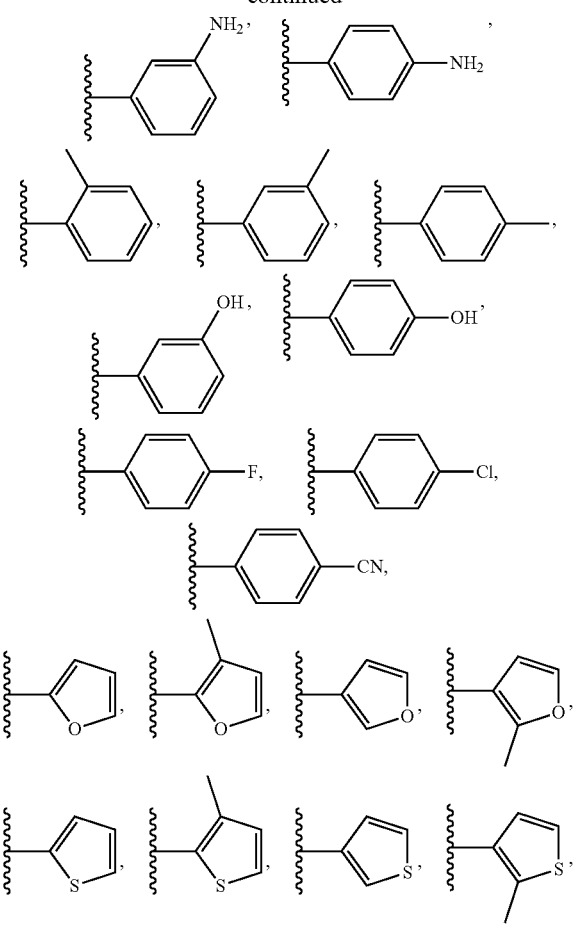
In embodiments, $R^6$ is

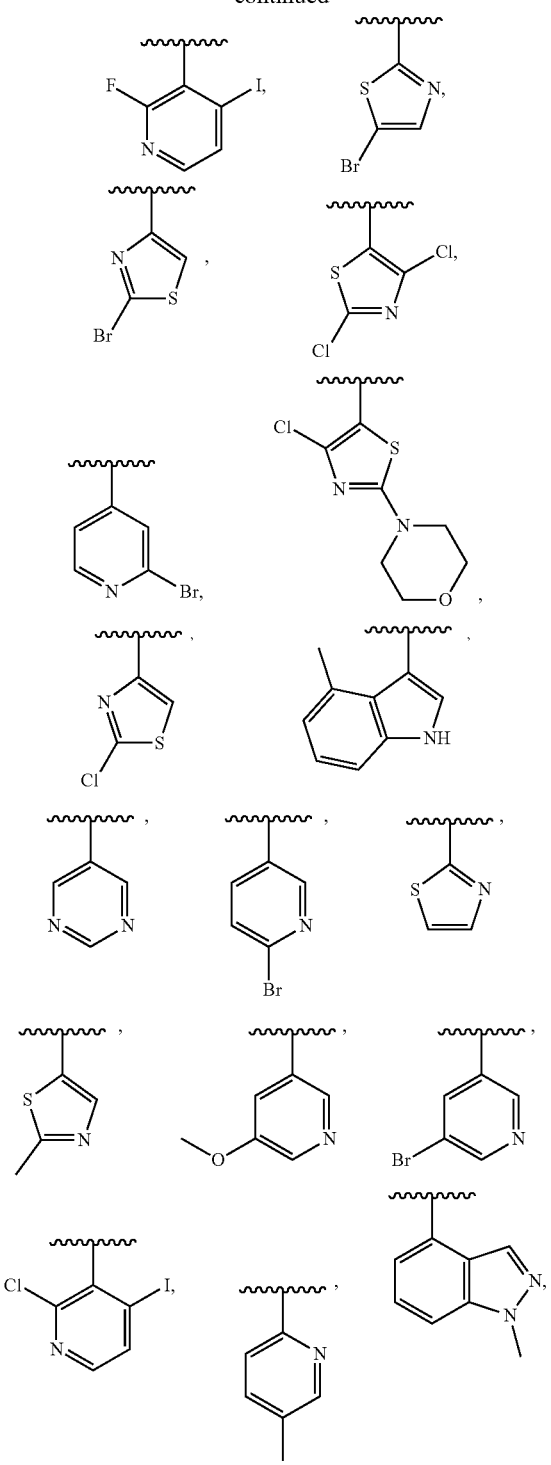
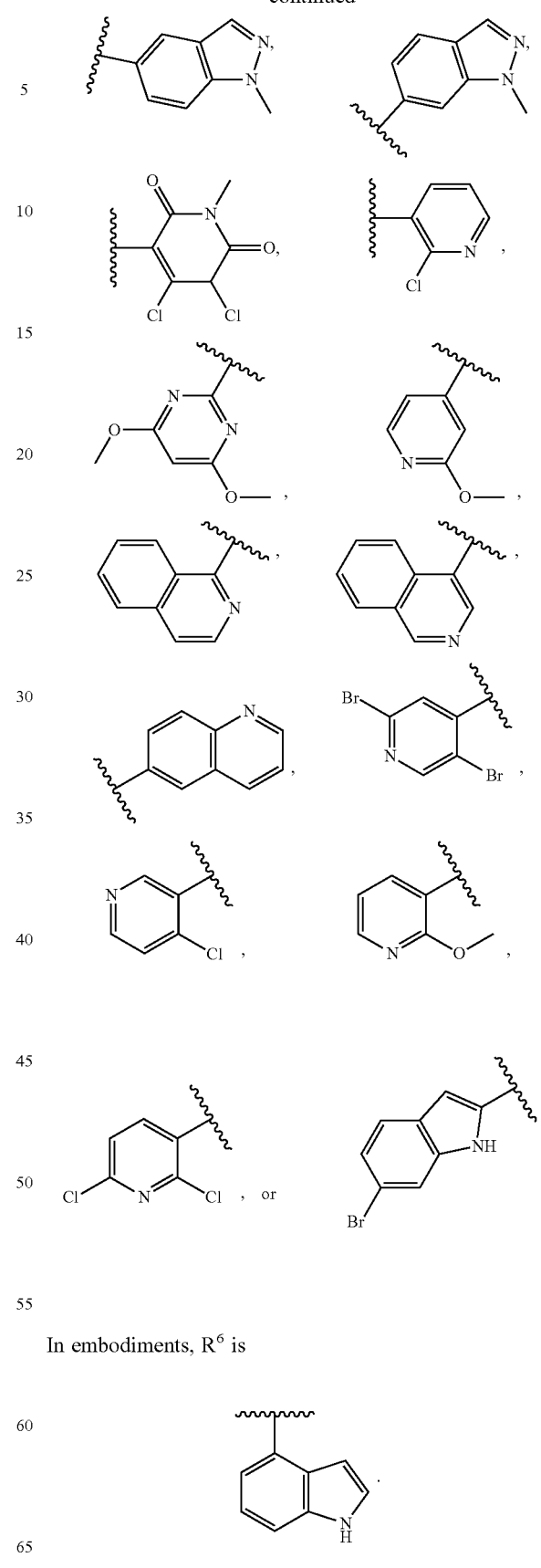
In embodiments, $R^6$ is

In embodiments, R⁶ is
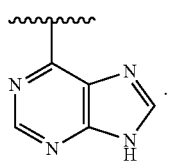
In embodiments, R⁶ is
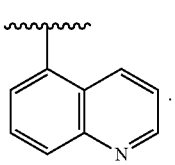 [SMILES: *c1cccc2ncccc12]
In embodiments R⁶ is
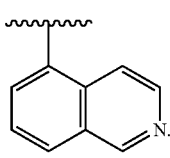 [SMILES: *c1cccc2cnccc12]
In embodiments, R⁶ is
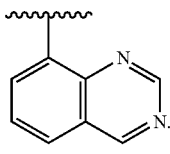 [SMILES: *c1cccc2cncnc12]
In embodiments, R⁶ is
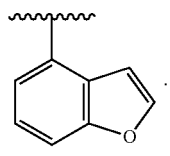 [SMILES: *c1cccc2occc12]
In embodiments, R⁶ is
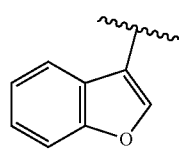
In embodiments, R⁶ is
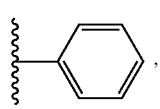 , 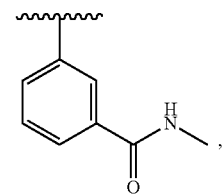
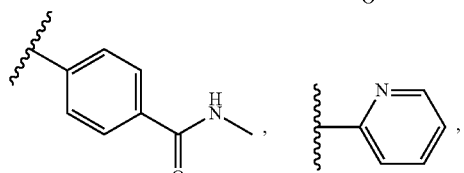
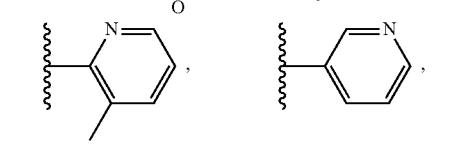
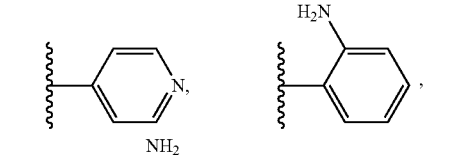
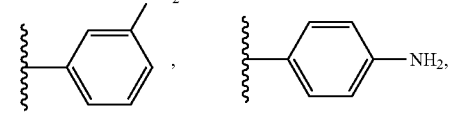
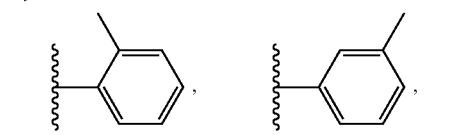
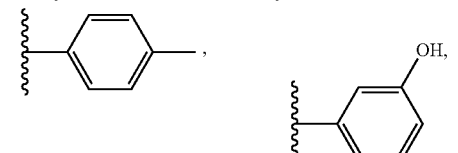
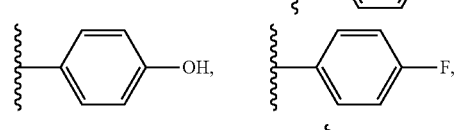
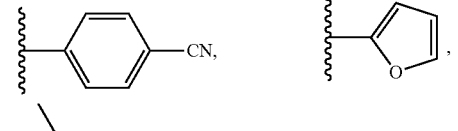
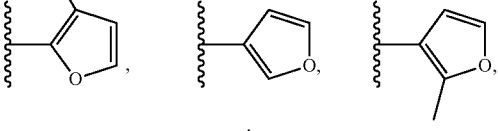
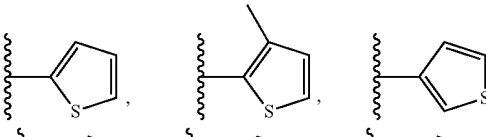
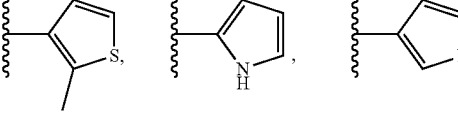

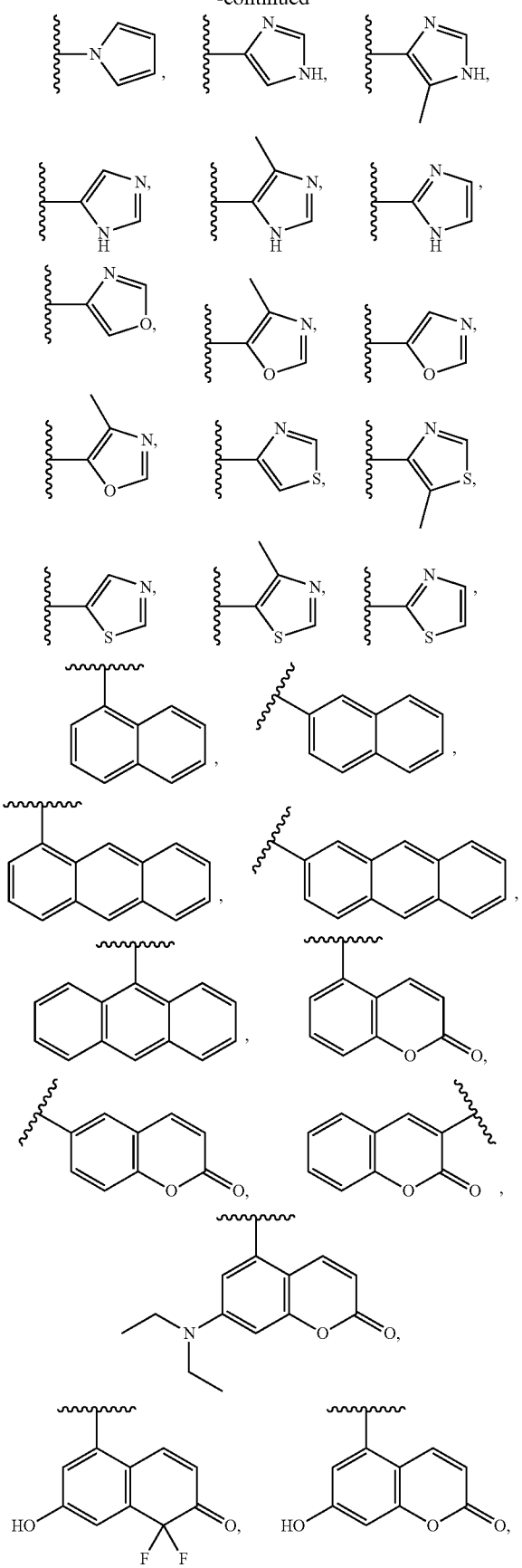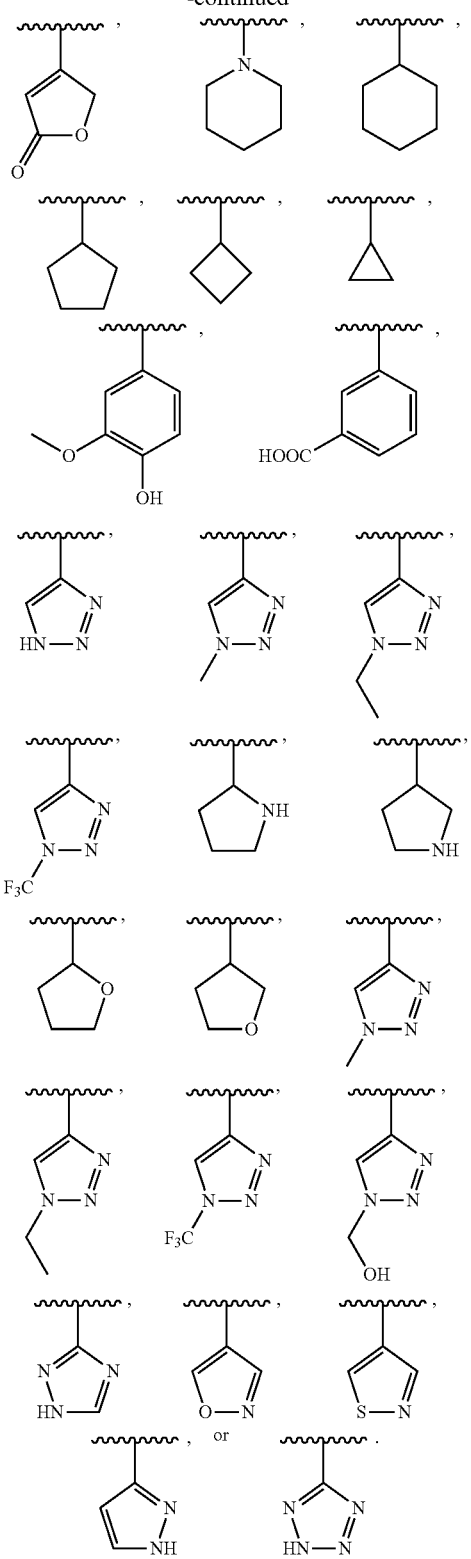

In embodiments, $R^5$ or $R^6$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ or $R^6$ are independently substituted or unsubstituted $C_1$-$C_6$ alkyl, substituted or unsubstituted 2 to 8 membered heteroalkyl, substituted or unsubstituted $C_3$-$C_6$ cycloalkyl, substituted or unsubstituted 2 to 8 membered heterocycloalkyl, substituted or unsubstituted $C_6$ to $C_{12}$ aryl, or substituted or unsubstituted 2 to 8 membered heteroaryl. In embodiments, $R^5$ or $R^6$ are independently substituted or unsubstituted alkyl, substituted or unsubstituted cycloalkyl, or substituted or unsubstituted aryl. In embodiments, $R^5$ or $R^6$ are independently substituted or unsubstituted cycloalkyl, substituted or unsubstituted heterocycloalkyl, substituted or unsubstituted aryl, or substituted or unsubstituted heteroaryl.

In embodiments, $R^{11}$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, or —$SF_5$. In embodiments, $R^{11}$ is —CN, —OH, —$NH_2$, —COOH, —$CONH_2$, —$NO_2$, —$SO_3H$, —$SO_4H$, —$SO_2NH_2$, —$NHNH_2$, or —$ONH_2$. In embodiments, $R^{11}$ is substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered). In embodiments, $R^{11}$ is $R^{11A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{11A}$-substituted or unsubstituted heteroalkyl (e.g., 2 to 20, 8 to 20, 2 to 10, 2 to 8, 2 to 6, or 2 to 4 membered), $R^{11A}$-substituted or unsubstituted cycloalkyl (e.g., $C_3$-$C_8$, $C_3$-$C_6$, or $C_5$-$C_6$), $R^{11A}$-substituted or unsubstituted heterocycloalkyl (e.g., 3 to 8, 3 to 6, or 5 to 6 membered), $R^{11A}$-substituted or unsubstituted aryl (e.g., $C_6$-$C_{10}$, $C_{10}$, or phenyl), or $R^{11A}$-substituted or unsubstituted heteroaryl (e.g., 5 to 10, 5 to 9, or 5 to 6 membered).

$R^{11A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{11B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{11B}$-substituted or unsubstituted heteroalkyl (e.g., 2 to 20, 8 to 20, 2 to 10, 2 to 8, 2 to 6, or 2 to 4 membered), $R^{11B}$-substituted or unsubstituted cycloalkyl (e.g., $C_3$-$C_8$, $C_3$-$C_6$, or $C_5$-$C_6$), $R^{11B}$-substituted or unsubstituted heterocycloalkyl (e.g., 3 to 8, 3 to 6, or 5 to 6 membered), $R^{11B}$-substituted or unsubstituted aryl (e.g., $C_6$-$C_{10}$, $C_{10}$, or phenyl), or $R^{11B}$-substituted or unsubstituted heteroaryl (e.g., 5 to 10, 5 to 9, or 5 to 6 membered).

$R^{11B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NH_4NH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_5Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{11C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{11C}$-substituted or unsubstituted heteroalkyl (e.g., 2 to 20, 8 to 20, 2 to 10, 2 to 8, 2 to 6, or 2 to 4 membered), $R^{11C}$-substituted or unsubstituted cycloalkyl (e.g., $C_3$-$C_8$, $C_3$-$C_6$, or $C_5$-$C_6$), $R^{11C}$-substituted or unsubstituted heterocycloalkyl (e.g., 3 to 8, 3 to 6, or 5 to 6 membered), $R^{11C}$-substituted or unsubstituted aryl (e.g., $C_6$-$C_{10}$, $C_{10}$, or phenyl), or $R^{11C}$-substituted or unsubstituted heteroaryl (e.g., 5 to 10, 5 to 9, or 5 to 6 membered).

$R^{11C}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_5Cl$, —$CH_5Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_5Cl$, —$OCH_5Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^{11}$ is substituted or unsubstituted $C_1$-$C_6$ alkyl. In embodiments, $R^{11}$ is substituted or unsubstituted $C_1$-$C_6$ alkyl. In embodiments, $R^{11}$ is substituted or unsubstituted $C_1$ alkyl. In embodiments, $R^{11}$ is substituted or unsubstituted $C_2$ alkyl. In embodiments, $R^{11}$ is substituted or unsubstituted $C_3$ alkyl. In embodiments, $R^{11}$ is substituted or unsubstituted $C_4$ alkyl. In embodiments, $R^{11}$ is substituted or unsubstituted $C_5$ alkyl. In embodiments, $R^{11}$ is substituted or unsubstituted $C_6$ alkyl. In embodiments, $R^{11}$ is substituted $C_1$ alkyl. In embodiments, $R^{11}$ is substituted $C_2$ alkyl. In embodiments, $R^{11}$ is substituted $C_3$ alkyl. In embodiments, $R^{11}$ is substituted $C_4$ alkyl. In embodiments, $R^{11}$ is substituted $C_5$ alkyl. In embodiments, $R^{11}$ is substituted $C_6$ alkyl. In embodiments, $R^{11}$ is unsubstituted $C_1$ alkyl. In embodiments, $R^{11}$ is unsubstituted $C_2$ alkyl. In embodiments, $R^{11}$ is unsubstituted $C_3$ alkyl. In embodiments, $R^{11}$ is unsubstituted $C_4$ alkyl. In embodiments, $R^{11}$ is unsubstituted $C_5$ alkyl. In embodiments, $R^{11}$ is unsubstituted $C_6$ alkyl. In embodiments, $R^{11}$ is hydrogen.

In embodiments, $R^{11}$ is substituted or unsubstituted 2 to 8 membered heteroalkyl. In embodiments, $R^{11}$ is substituted or unsubstituted 2 to 6 membered heteroalkyl. In embodiments, $R^{11}$ is substituted or unsubstituted 2 to 4 membered heteroalkyl. In embodiments, $R^{11}$ is substituted 2 to 8 membered heteroalkyl. In embodiments, $R^{11}$ is substituted 2 to 6 membered heteroalkyl. In embodiments, $R^{11}$ is substituted 2 to 4 membered heteroalkyl. In embodiments, $R^{11}$ is unsubstituted 2 to 8 membered heteroalkyl. In embodiments, $R^{11}$ is unsubstituted 2 to 6 membered heteroalkyl. In embodiments, $R^{11}$ is unsubstituted 2 to 4 membered heteroalkyl.

In embodiments, $R^{11}$ is substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{11}$ is substituted or unsubstituted cycloalkyl (e.g., $C_3$-$C_8$, $C_3$-$C_6$, $C_4$-$C_6$, or $C_5$-$C_6$). In embodiments, $R^{11}$ is substituted cycloalkyl (e.g., $C_3$-$C_8$, $C_3$-$C_6$, $C_4$-$C_6$, or $C_5$-$C_6$). In embodiments, $R^{11}$ is an unsubstituted cycloalkyl (e.g., $C_3$-$C_8$, $C_3$-$C_6$, $C_4$-$C_6$, or $C_5$-$C_6$). In embodiments, $R^{11}$ is substituted or unsubstituted heterocycloalkyl (e.g., 3 to 8 membered, 3 to 6 membered, 4 to 6 membered, 4 to 5 membered, or 5 to 6 membered). In embodiments, $R^{11}$ is substituted heterocycloalkyl (e.g., 3 to 8 membered, 3 to 6 membered, 4 to 6 membered, 4 to 5 membered, or 5 to 6 membered). In embodiments, $R^{11}$ is an unsubstituted heterocycloalkyl (e.g., 3 to 8 membered, 3 to 6 membered, 4 to 6 membered, 4 to 5 membered, or 5 to 6 membered).

In embodiments, $R^{11}$ is substituted or unsubstituted aryl (e.g., $C_6$-$C_{10}$, $C_{10}$, or phenyl). In embodiments, $R^{11}$ is substituted aryl (e.g., $C_6$-$C_{10}$, $C_{10}$, or phenyl). In embodiments, $R^{11}$ is unsubstituted aryl (e.g., $C_6$-$C_{10}$, $C_{10}$, or phenyl). In embodiments, $R^{11}$ is unsubstituted phenyl. In embodiments, $R^{11}$ is substituted or unsubstituted heteroaryl (e.g., 5 to 10, 5 to 9, or 5 to 6 membered). In embodiments, $R^{11}$ is substituted heteroaryl (e.g., 5 to 10, 5 to 9, or 5 to 6 membered). In embodiments, $R^{11}$ is unsubstituted heteroaryl (e.g., 5 to 10, 5 to 9, or 5 to 6 membered). In embodiments, $R^{11}$ is a substituted or unsubstituted 5 membered heteroaryl. In embodiments, $R^{11}$ is a substituted or unsubstituted 6 membered heteroaryl. In embodiments, $R^{11}$ is a substituted or unsubstituted 5 membered heteroaryl. In embodiments, $R^{11}$ is an unsubstituted 5 membered heteroaryl. In embodiments, $R^{11}$ is an unsubstituted 6 membered heteroaryl. In embodiments, $R^{11}$ is an unsubstituted 7 membered heteroaryl.

In embodiments $R^{11}$ is

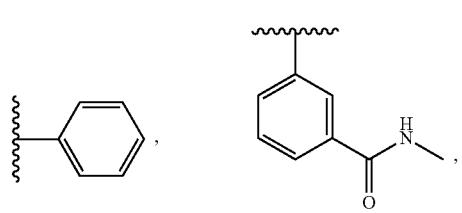

-continued

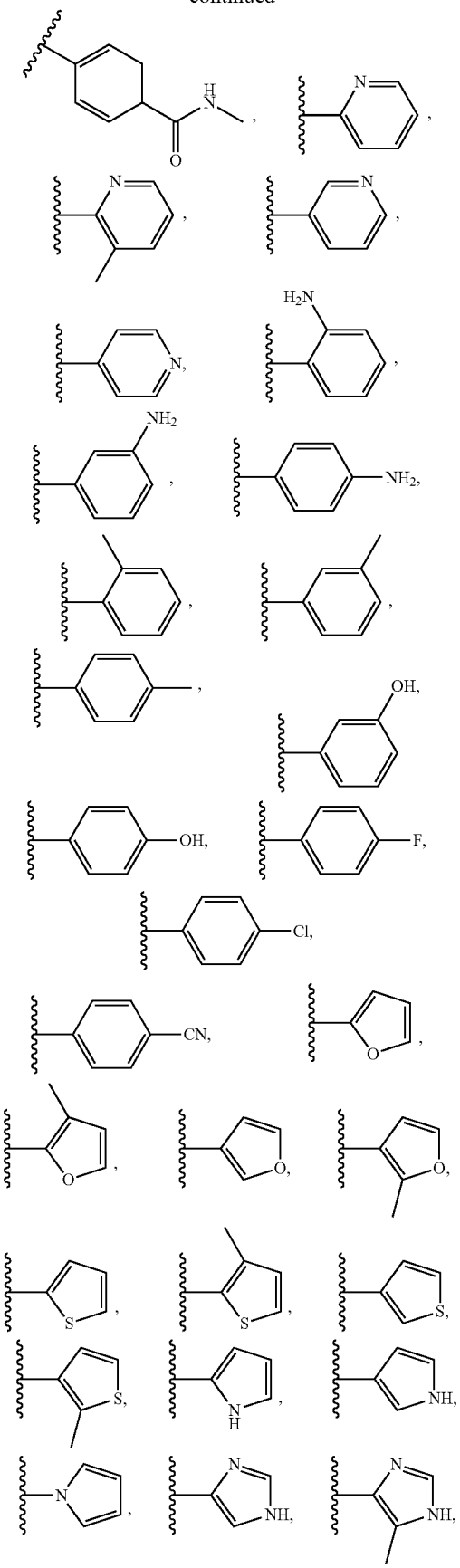

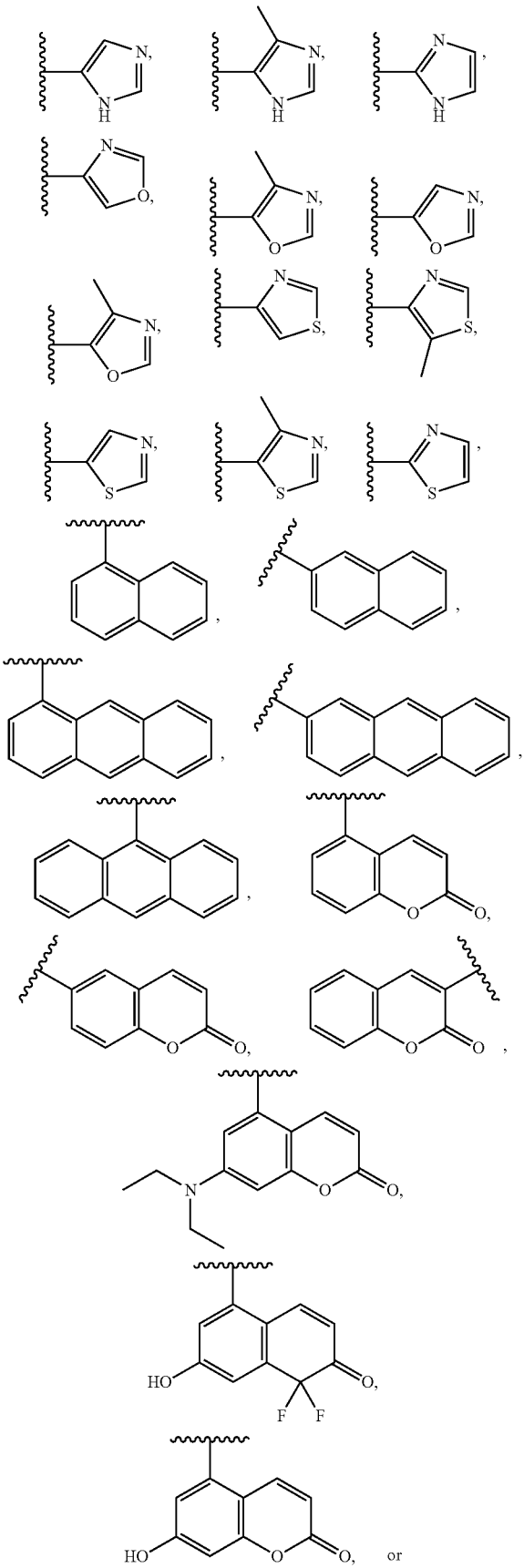
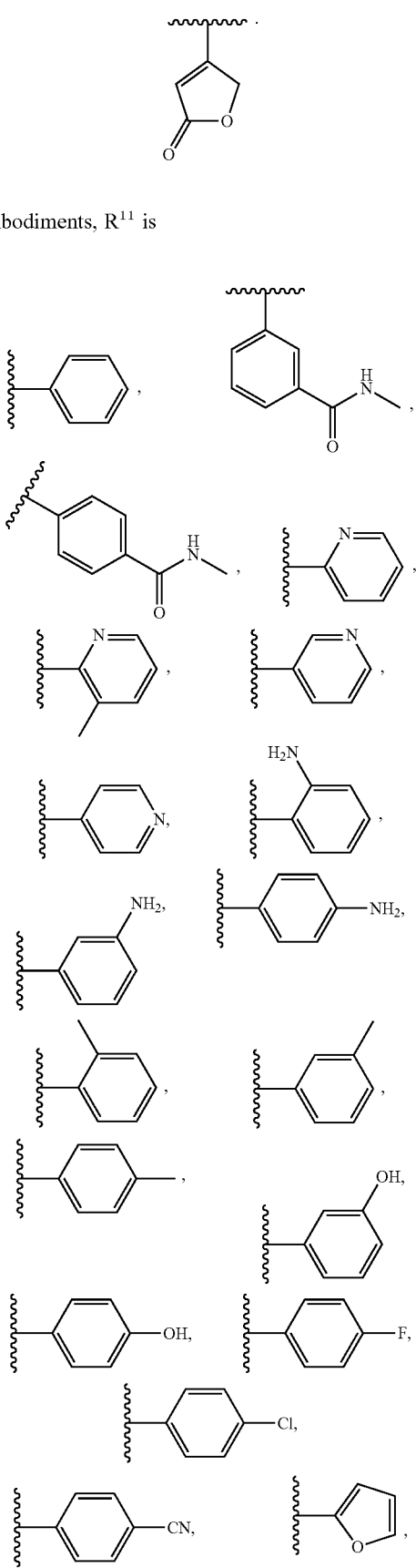
In embodiments, $R^{11}$ is

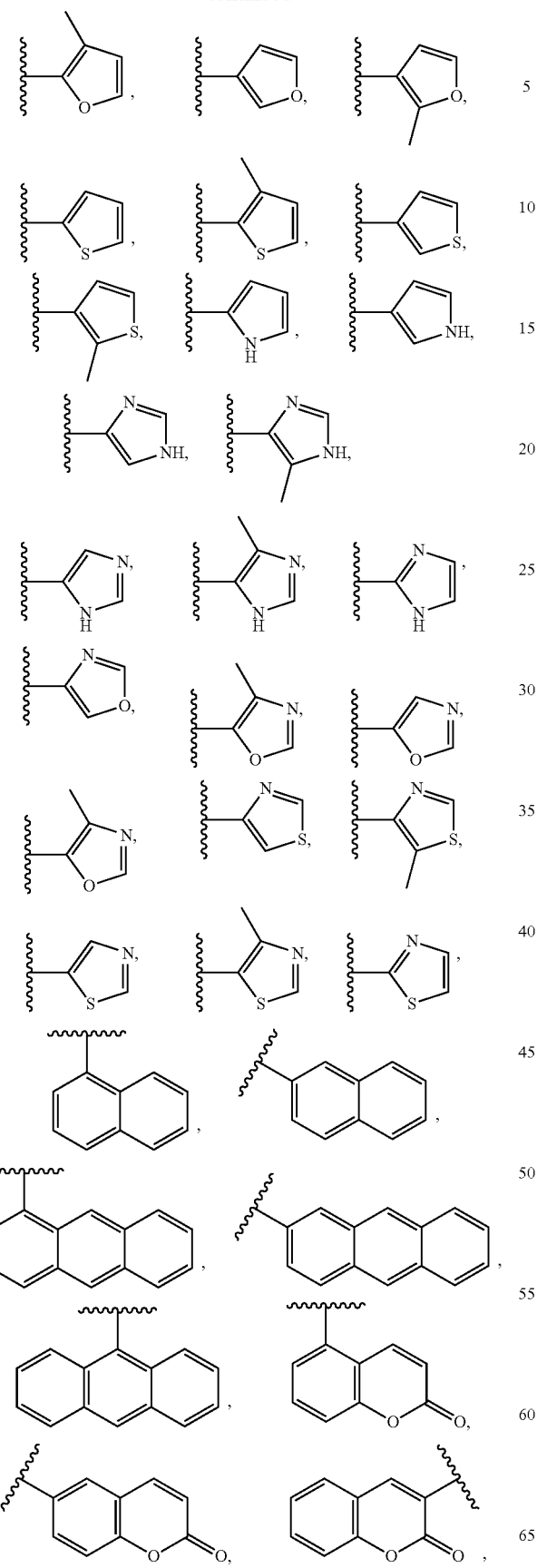
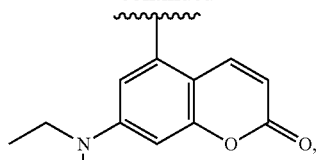
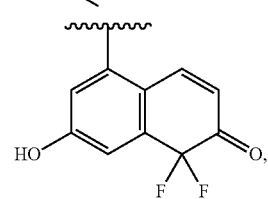
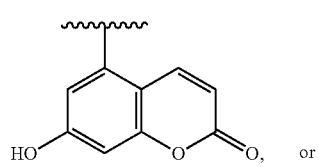
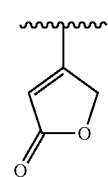
In embodiments, $R^{11}$ is
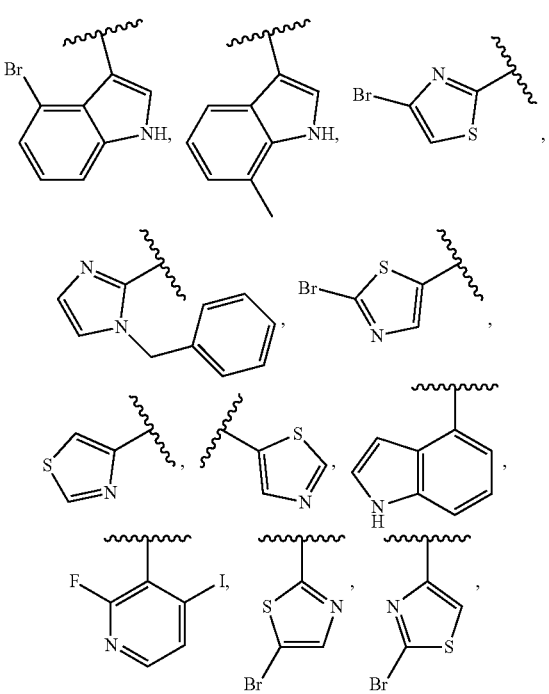

99
-continued
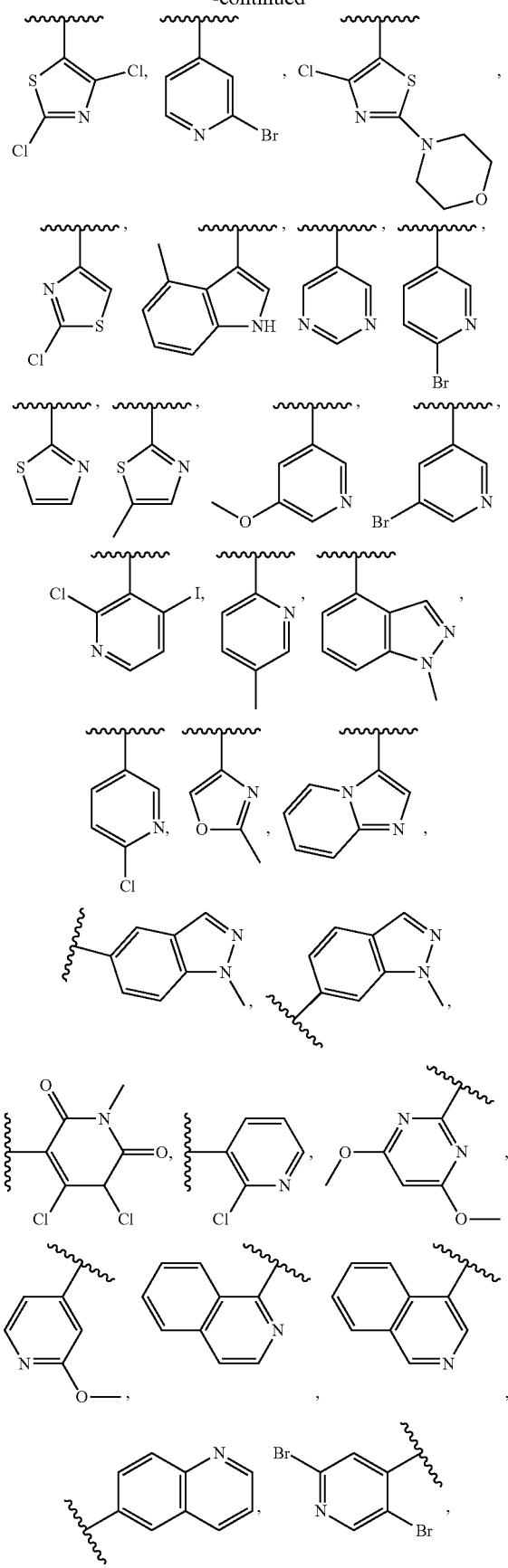
100
-continued
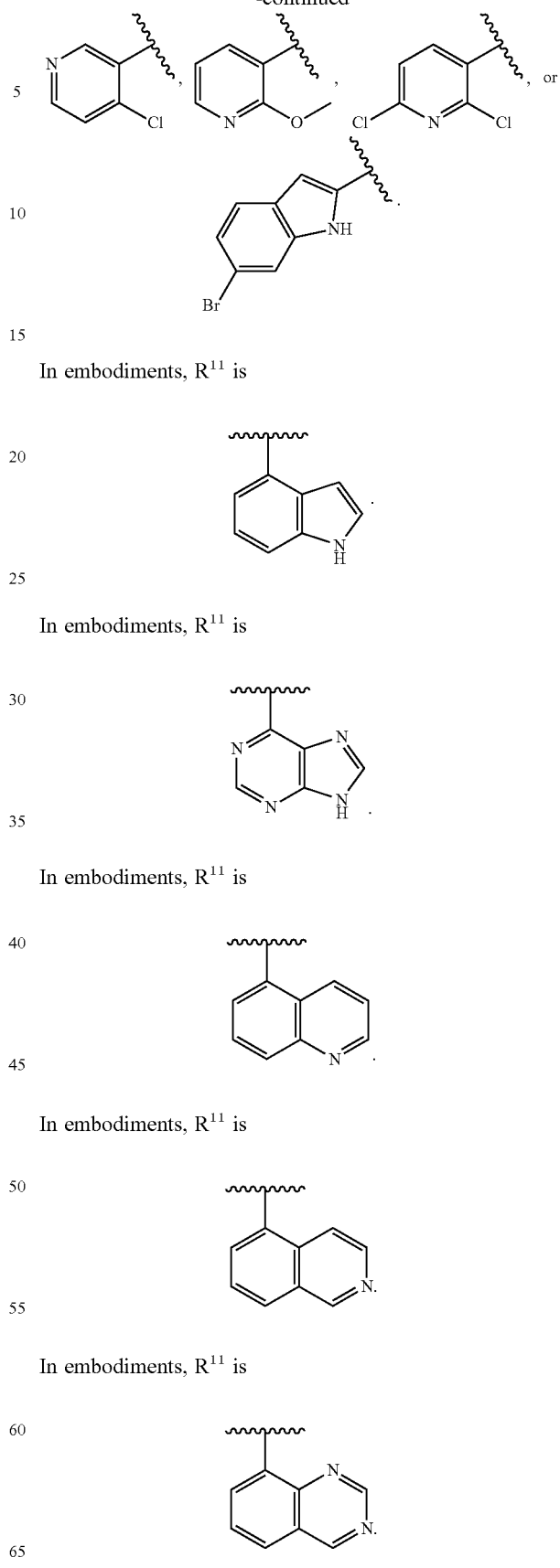
In embodiments, $R^{11}$ is
In embodiments, $R^{11}$ is
In embodiments, $R^{11}$ is
In embodiments, $R^{11}$ is
In embodiments, $R^{11}$ is In embodiments, $R^{11}$ is
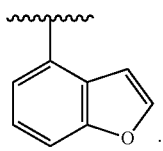
In embodiments, $R^{11}$ is
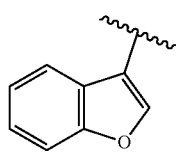
In embodiments, $R^{11}$ is
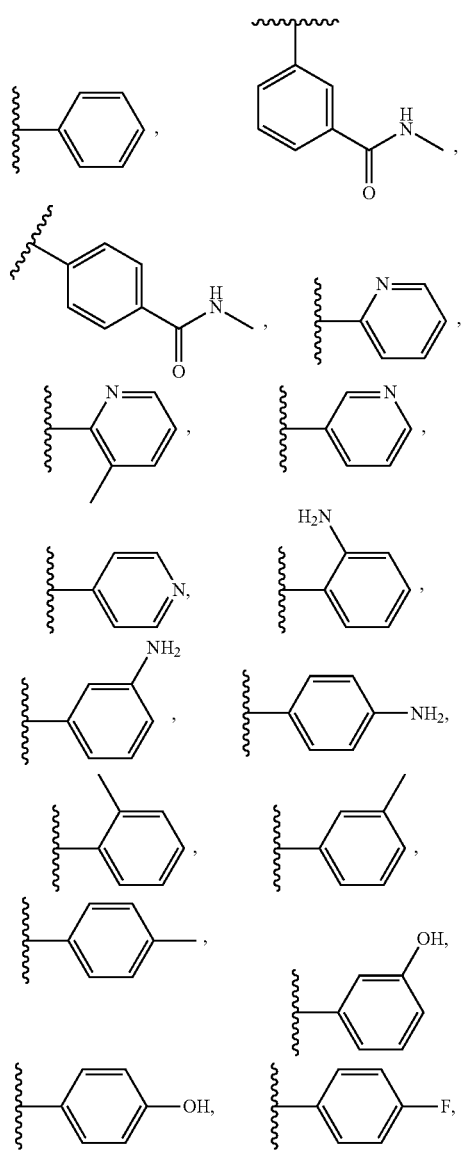
-continued
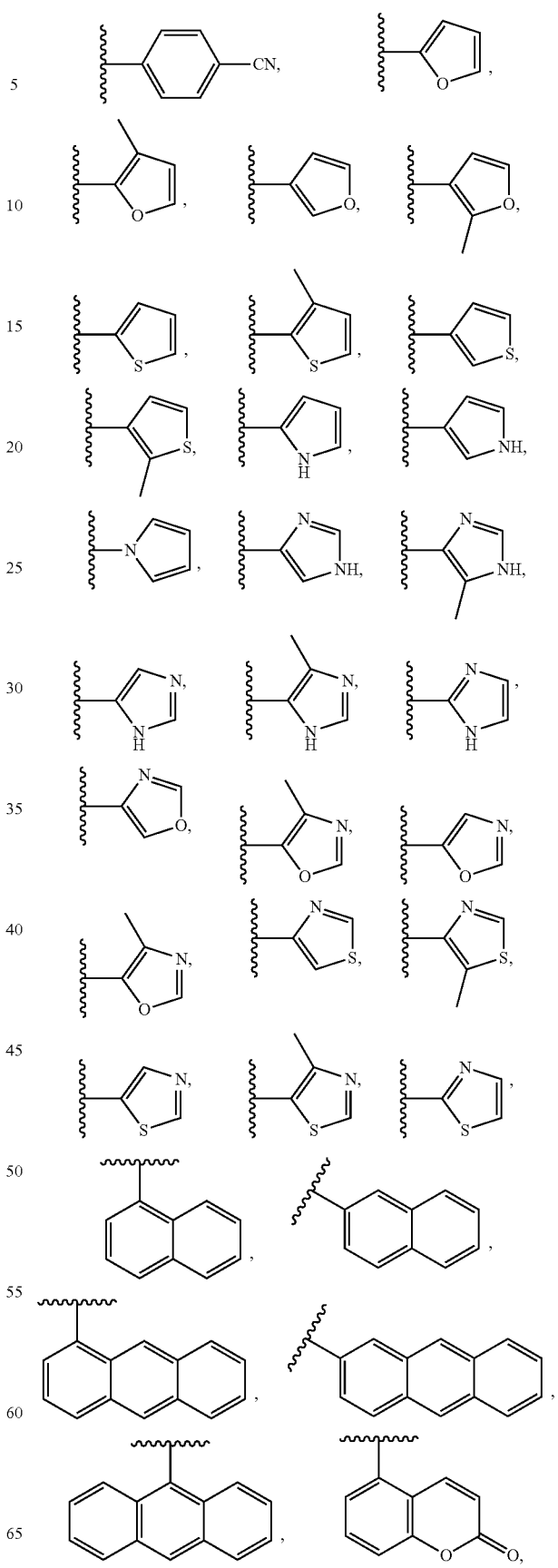

-continued

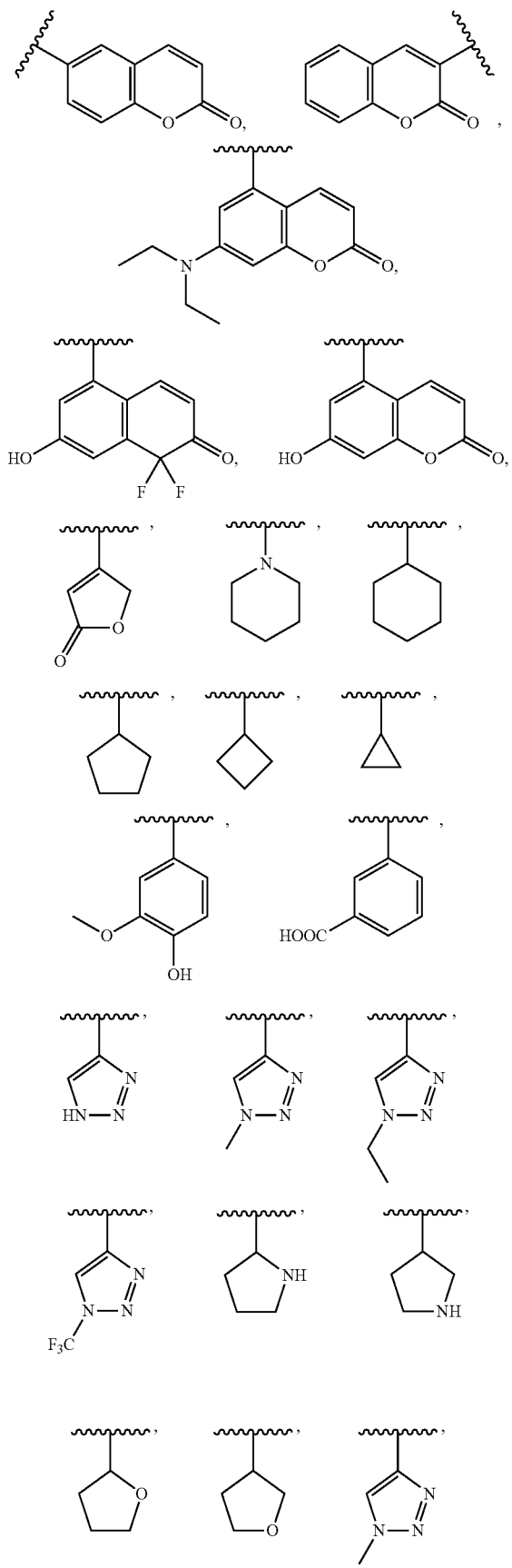

-continued

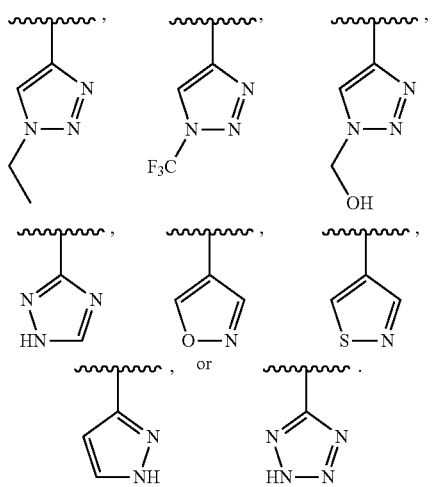

In embodiments, $R^{12}$ is hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, or $-SF_5$. In embodiments, $R^{12}$ is $-CN$, $-OH$, $-NH_2$, $-COOH$, $-CONH_2$, $-NO_2$, $-SO_3H$, $-SO_4H$, $-SO_2NH_2$, $-NHNH_2$, or $-ONH_2$. In embodiments, $R^{12}$ is substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered). In embodiments, $R^{12}$ is $R^{12A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{12}$-substituted or unsubstituted heteroalkyl (e.g., 2 to 20, 8 to 20, 2 to 10, 2 to 8, 2 to 6, or 2 to 4 membered), $R^{12A}$-substituted or unsubstituted cycloalkyl (e.g., $C_3$-$C_8$, $C_3$-$C_6$, or $C_5$-$C_6$), $R^{12}$-substituted or unsubstituted heterocycloalkyl (e.g., 3 to 8, 3 to 6, or 5 to 6 membered), $R^{12A}$-substituted or unsubstituted aryl (e.g., $C_6$-$C_{10}$, $C_{10}$, or phenyl), or $R^{12A}$-substituted or unsubstituted heteroaryl (e.g., 5 to 10, 5 to 9, or 5 to 6 membered).

$R^{12A}$ is independently oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NH-NH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, $-NH_3^+$, $-SO_3^-$, $-OPO_3H^-$, $-SCN$, $-ONO_2$, $R^{12B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{12B}$-substituted or unsubstituted heteroalkyl (e.g., 2 to 20, 8 to 20, 2 to 10, 2 to 8, 2 to 6, or 2 to 4 membered), $R^{12B}$-substituted or unsubstituted cycloalkyl (e.g., $C_3$-$C_8$, $C_3$-$C_6$, or $C_5$-$C_6$), $R^{12B}$-substituted or unsubstituted heterocycloalkyl (e.g., 3 to 8, 3 to 6, or 5 to 6 membered), $R^{12B}$-substituted or unsubstituted aryl (e.g., $C_6$-$C_{10}$, $C_{10}$, or phenyl), or $R^{12B}$-substituted or unsubstituted heteroaryl (e.g., 5 to 10, 5 to 9, or 5 to 6 membered). In embodiments, $R^{12A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{12B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{12B}$-substituted or unsubstituted heteroalkyl (e.g., 2 to 20, 8 to 20, 2 to 10, 2 to 8, 2 to 6, or 2 to 4 membered), $R^{12B}$-substituted or unsubstituted cycloalkyl (e.g., $C_3$-$C_8$, $C_3$-$C_6$, or $C_5$-$C_6$), $R^{12B}$-substituted or unsubstituted heterocycloalkyl (e.g., 3 to 8, 3 to 6, or 5 to 6 membered), $R^{12B}$-substituted or unsubstituted aryl (e.g., $C_6$-$C_{10}$, $C_{10}$, or phenyl), or $R^{12B}$-substituted or unsubstituted heteroaryl (e.g., 5 to 10, 5 to 9, or 5 to 6 membered).

$R^{12B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{12C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{12C}$-substituted or unsubstituted heteroalkyl (e.g., 2 to 20, 8 to 20, 2 to 10, 2 to 8, 2 to 6, or 2 to 4 membered), $R^{12C}$-substituted or unsubstituted cycloalkyl (e.g., $C_3$-$C_8$, $C_3$-$C_6$, or $C_5$-$C_6$), $R^{12C}$-substituted or unsubstituted heterocycloalkyl (e.g., 3 to 8, 3 to 6, or 5 to 6 membered), $R^{12C}$-substituted or unsubstituted aryl (e.g., $C_6$-$C_{10}$, $C_{10}$, or phenyl), or $R^{12C}$-substituted or unsubstituted heteroaryl (e.g., 5 to 10, 5 to 9, or 5 to 6 membered).

$R^{12C}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^{12}$ is substituted or unsubstituted $C_1$-$C_6$ alkyl. In embodiments, $R^{12}$ is substituted or unsubstituted $C_1$-$C_6$ alkyl. In embodiments, $R^{12}$ is substituted or unsubstituted $C_1$ alkyl. In embodiments, $R^{12}$ is substituted or unsubstituted $C_2$ alkyl. In embodiments, $R^{12}$ is substituted or unsubstituted $C_3$ alkyl. In embodiments, $R^{12}$ is substituted or unsubstituted $C_4$ alkyl. In embodiments, $R^{12}$ is substituted or unsubstituted $C_5$ alkyl. In embodiments, $R^{12}$ is substituted or unsubstituted $C_6$ alkyl. In embodiments, $R^{12}$ is substituted $C_1$ alkyl. In embodiments, $R^{12}$ is substituted $C_2$ alkyl. In embodiments, $R^{12}$ is substituted $C_3$ alkyl. In embodiments, $R^{12}$ is substituted $C_4$ alkyl. In embodiments, $R^{12}$ is substituted $C_5$ alkyl. In embodiments, $R^{12}$ is substituted $C_6$ alkyl. In embodiments, $R^{12}$ is unsubstituted $C_1$ alkyl. In embodiments, $R^{12}$ is unsubstituted $C_2$ alkyl. In embodiments, $R^{12}$ is unsubstituted $C_3$ alkyl. In embodiments, $R^{12}$ is unsubstituted $C_4$ alkyl. In embodiments, $R^{12}$ is unsubstituted $C_5$ alkyl. In embodiments, $R^{12}$ is unsubstituted $C_6$ alkyl. In embodiments, $R^{12}$ is hydrogen.

In embodiments, $R^{12}$ is substituted or unsubstituted 2 to 8 membered heteroalkyl. In embodiments, $R^{12}$ is substituted or unsubstituted 2 to 6 membered heteroalkyl. In embodiments, $R^{12}$ is substituted or unsubstituted 2 to 4 membered heteroalkyl. In embodiments, $R^{12}$ is substituted 2 to 8 membered heteroalkyl. In embodiments, $R^{12}$ is substituted 2 to 6 membered heteroalkyl. In embodiments, $R^{12}$ is substituted 2 to 4 membered heteroalkyl. In embodiments, $R^{12}$ is unsubstituted 2 to 8 membered heteroalkyl. In embodiments, $R^{12}$ is unsubstituted 2 to 6 membered heteroalkyl. In embodiments, $R^{12}$ is unsubstituted 2 to 4 membered heteroalkyl.

In embodiments, $R^{12}$ is substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{12}$ is substituted or unsubstituted cycloalkyl (e.g., $C_3$-$C_8$, $C_3$-$C_6$, $C_4$-$C_6$, or $C_5$-$C_6$). In embodiments, $R^{12}$ is substituted cycloalkyl (e.g., $C_3$-$C_8$, $C_3$-$C_6$, $C_4$-$C_6$, or $C_5$-$C_6$). In embodiments, $R^{12}$ is an unsubstituted cycloalkyl (e.g., $C_3$-$C_8$, $C_3$-$C_6$, $C_4$-$C_6$, or $C_5$-$C_6$). In embodiments, $R^{12}$ is substituted or unsubstituted heterocycloalkyl (e.g., 3 to 8 membered, 3 to 6 membered, 4 to 6 membered, 4 to 5 membered, or 5 to 6 membered). In embodiments, $R^{12}$ is substituted heterocycloalkyl (e.g., 3 to 8 membered, 3 to 6 membered, 4 to 6 membered, 4 to 5 membered, or 5 to 6 membered). In embodiments, $R^{12}$ is an unsubstituted heterocycloalkyl (e.g., 3 to 8 membered, 3 to 6 membered, 4 to 6 membered, 4 to 5 membered, or 5 to 6 membered).

In embodiments, $R^{12}$ is substituted or unsubstituted aryl (e.g., $C_6$-$C_{10}$, $C_{10}$, or phenyl). In embodiments, $R^{12}$ is substituted aryl (e.g., $C_6$-$C_{10}$, $C_{10}$, or phenyl). In embodiments, $R^{12}$ is unsubstituted aryl (e.g., $C_6$-$C_{10}$, $C_{10}$, or phenyl). In embodiments, $R^{12}$ is unsubstituted phenyl. In embodiments, $R^{12}$ is substituted or unsubstituted heteroaryl (e.g., 5 to 10, 5 to 9, or 5 to 6 membered). In embodiments, $R^{12}$ is substituted heteroaryl (e.g., 5 to 10, 5 to 9, or 5 to 6 membered). In embodiments, $R^{12}$ is unsubstituted heteroaryl (e.g., 5 to 10, 5 to 9, or 5 to 6 membered). In embodiments, $R^{12}$ is a substituted or unsubstituted 5 membered heteroaryl. In embodiments, $R^{12}$ is a substituted or unsubstituted 6 membered heteroaryl. In embodiments, $R^{12}$ is a substituted or unsubstituted 5 membered heteroaryl. In embodiments, $R^{12}$ is an unsubstituted 5 membered heteroaryl. In embodiments, $R^{12}$ is an unsubstituted 6 membered heteroaryl. In embodiments, $R^{12}$ is an unsubstituted 7 membered heteroaryl.
In embodiments, $R^{12}$ is
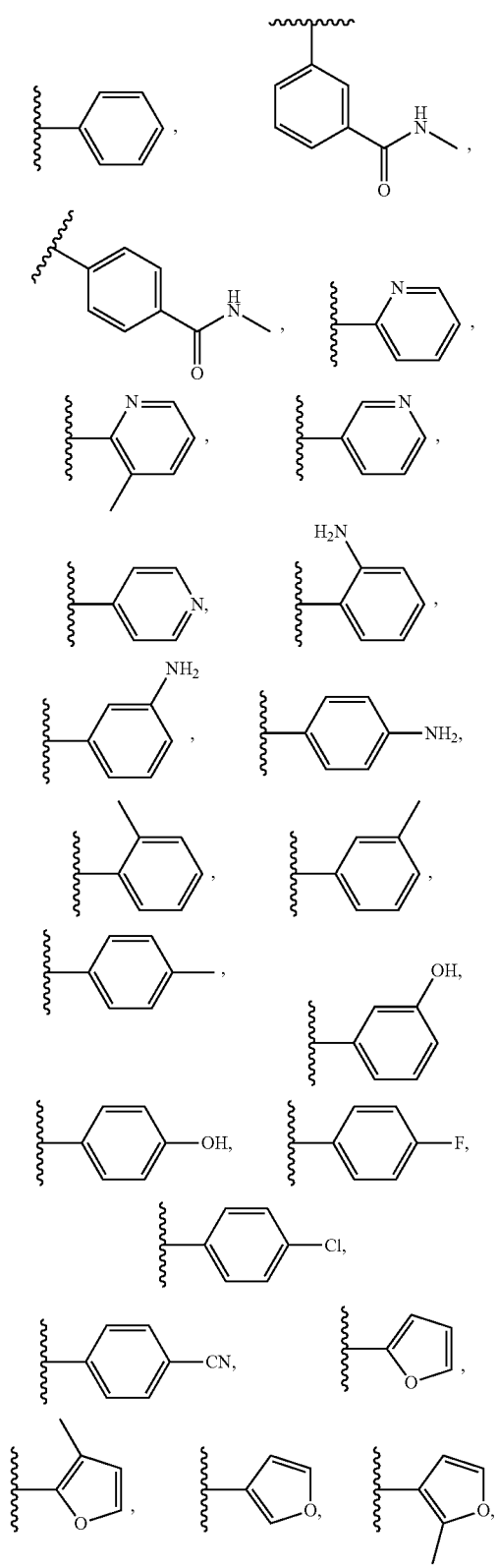
-continued
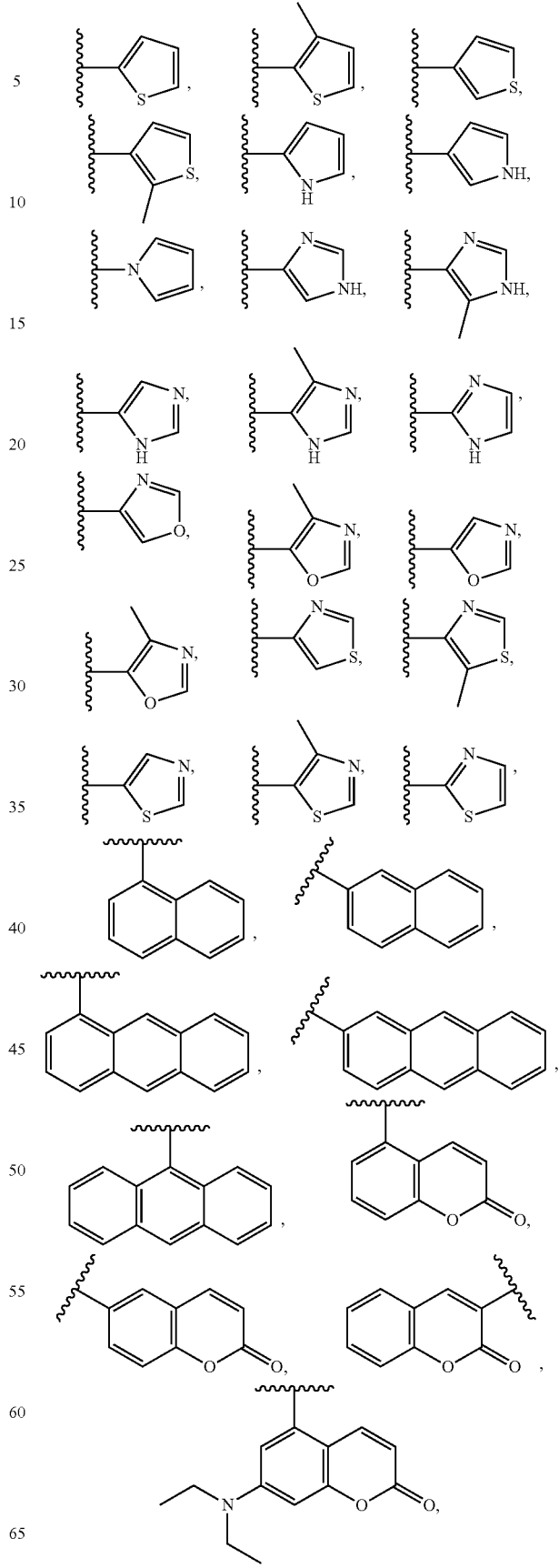

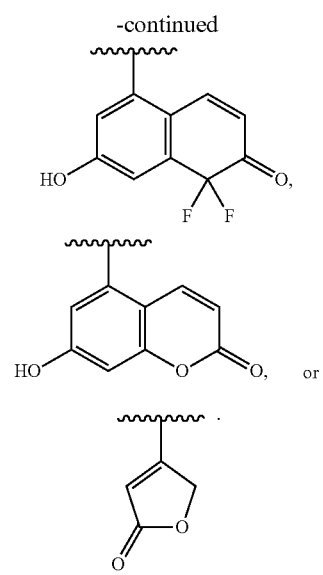
In embodiments, $R^{12}$ is
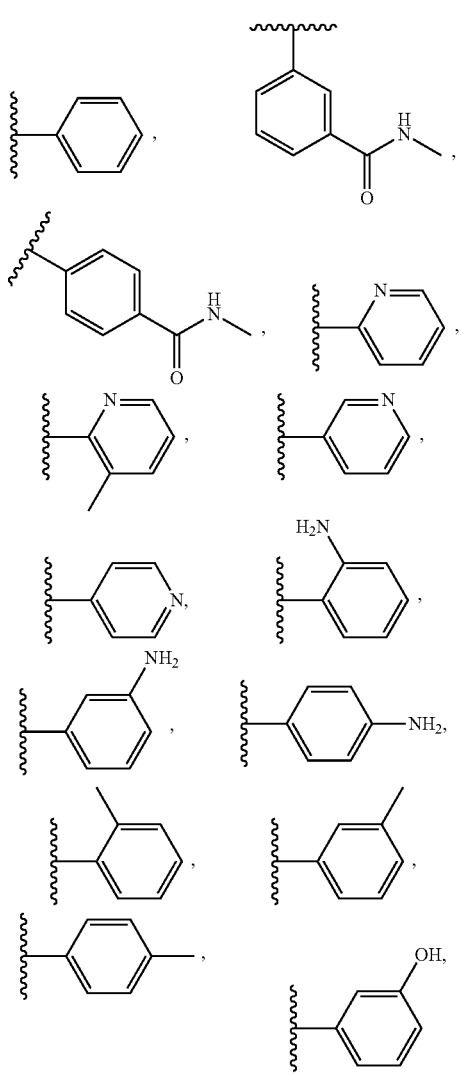
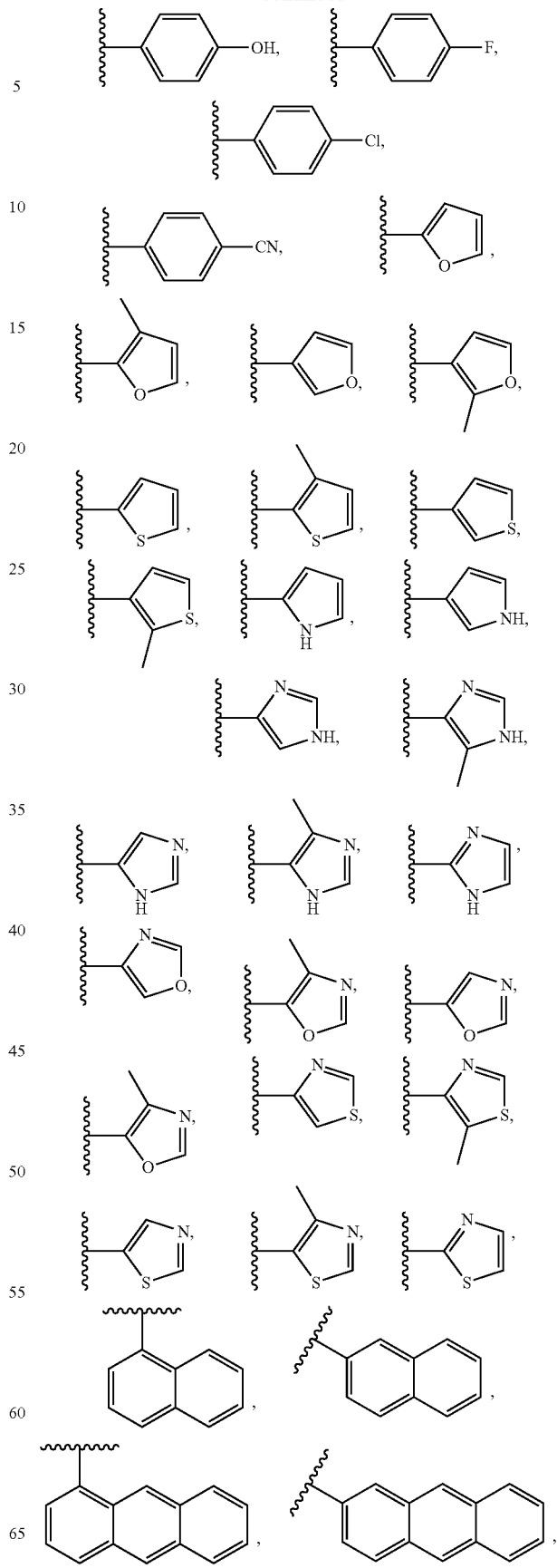

111
-continued
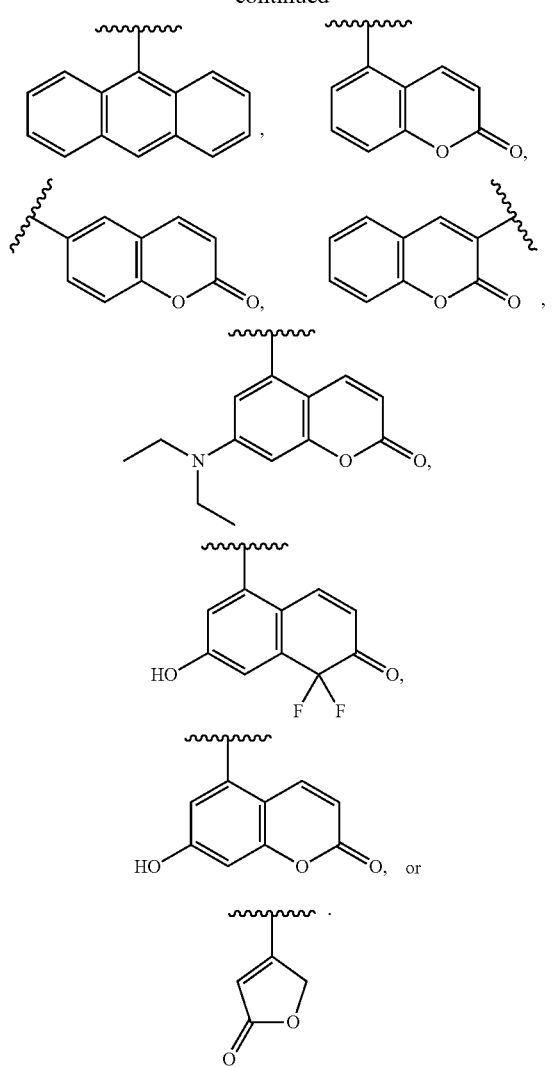
In embodiments, R$^{12}$ is
112
-continued
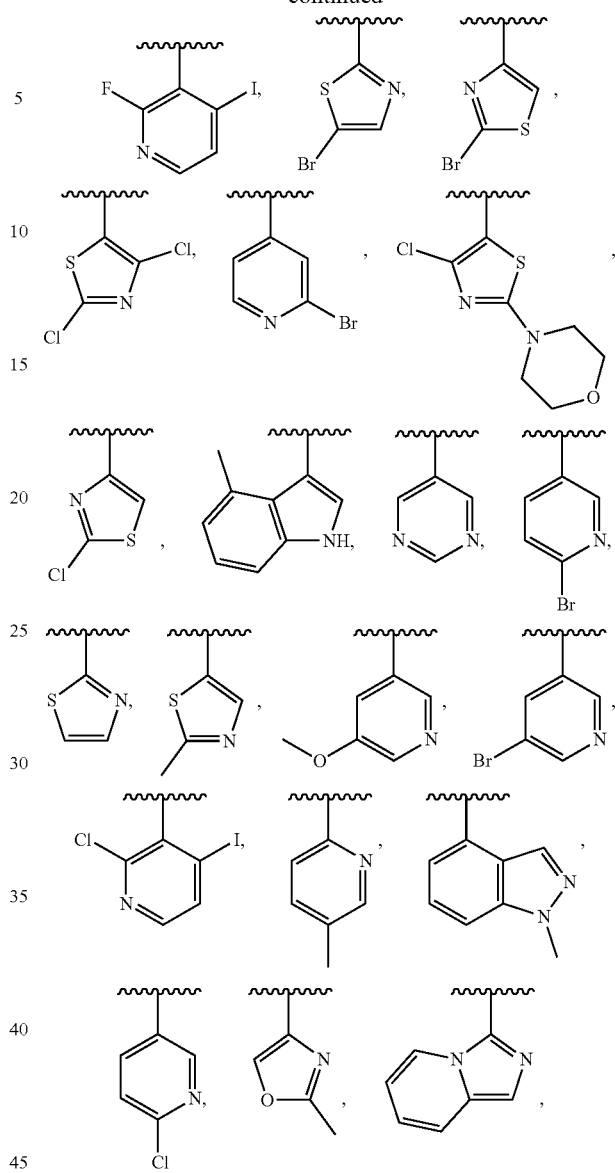
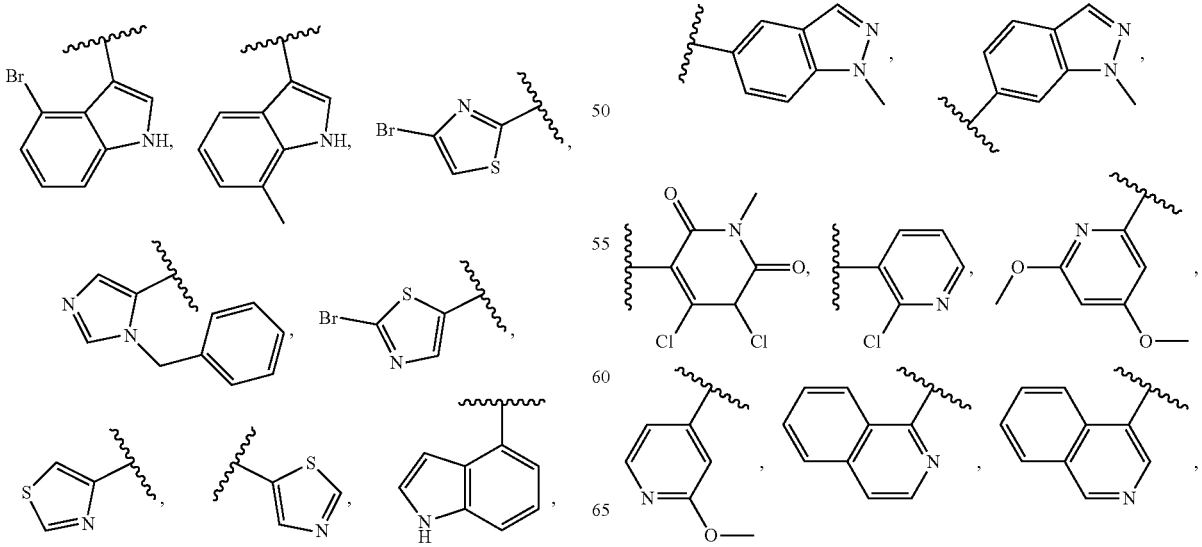

113
-continued
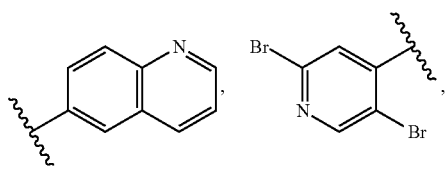
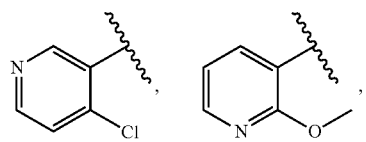
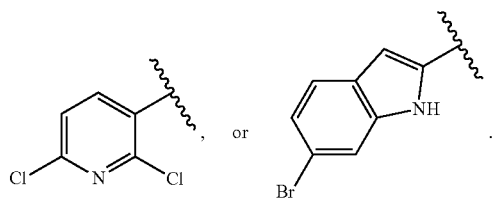
In embodiments, $R^{12}$ is
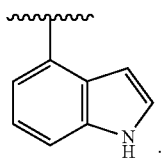 [SMILES: *c1cccc2[nH]ccc12]
In embodiments, $R^{12}$ is
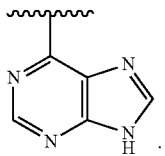 [SMILES: *c1ncnc2[nH]cnc12]
In embodiments, $R^{12}$ is
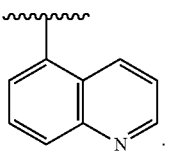
In embodiments, $R^{12}$ is
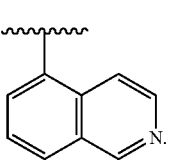
114
In embodiments, $R^{12}$ is
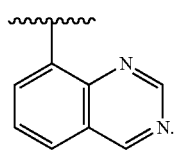 [SMILES: *c1cccc2cncnc12]
In embodiments, $R^{12}$ is
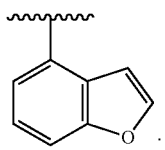 [SMILES: *c1cccc2occc12]
In embodiments, $R^{12}$ is
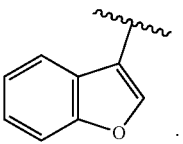 [SMILES: *c1coc2ccccc12]
In embodiments $R^{12}$ is
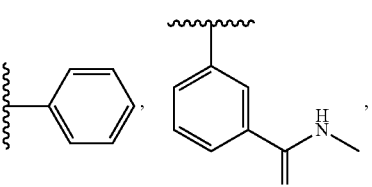
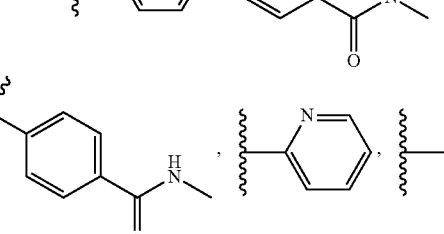
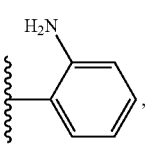
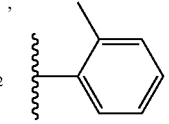
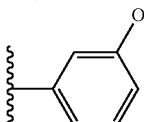
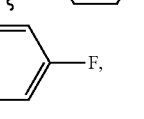

115
-continued

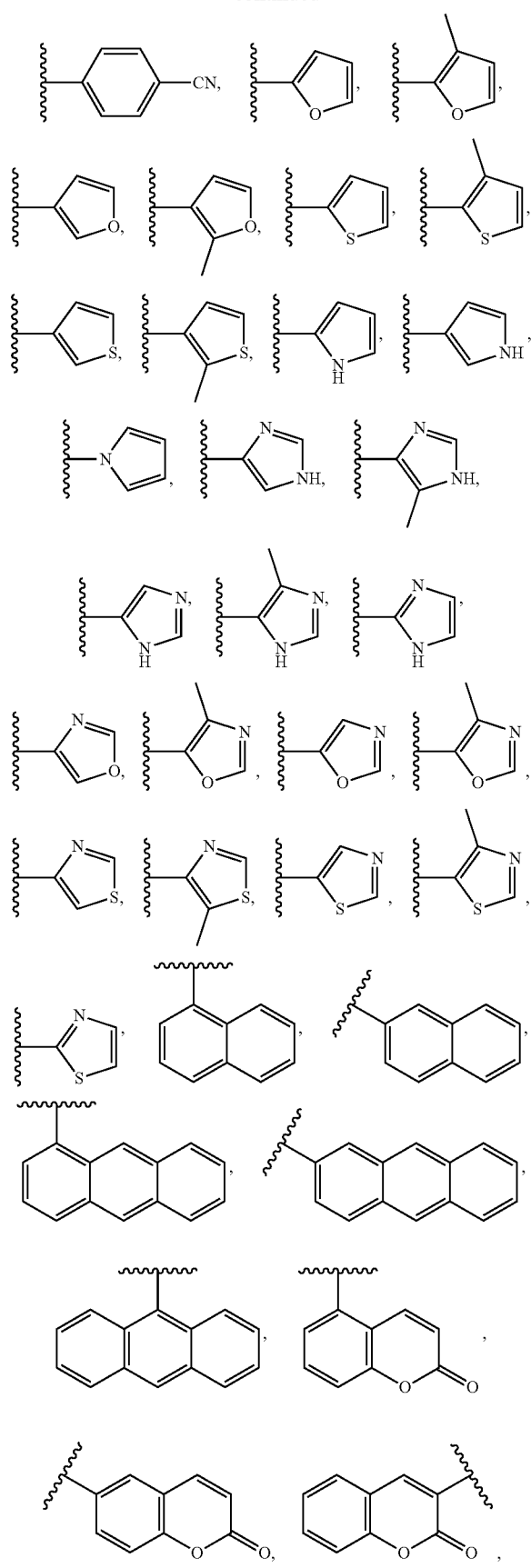

116
-continued

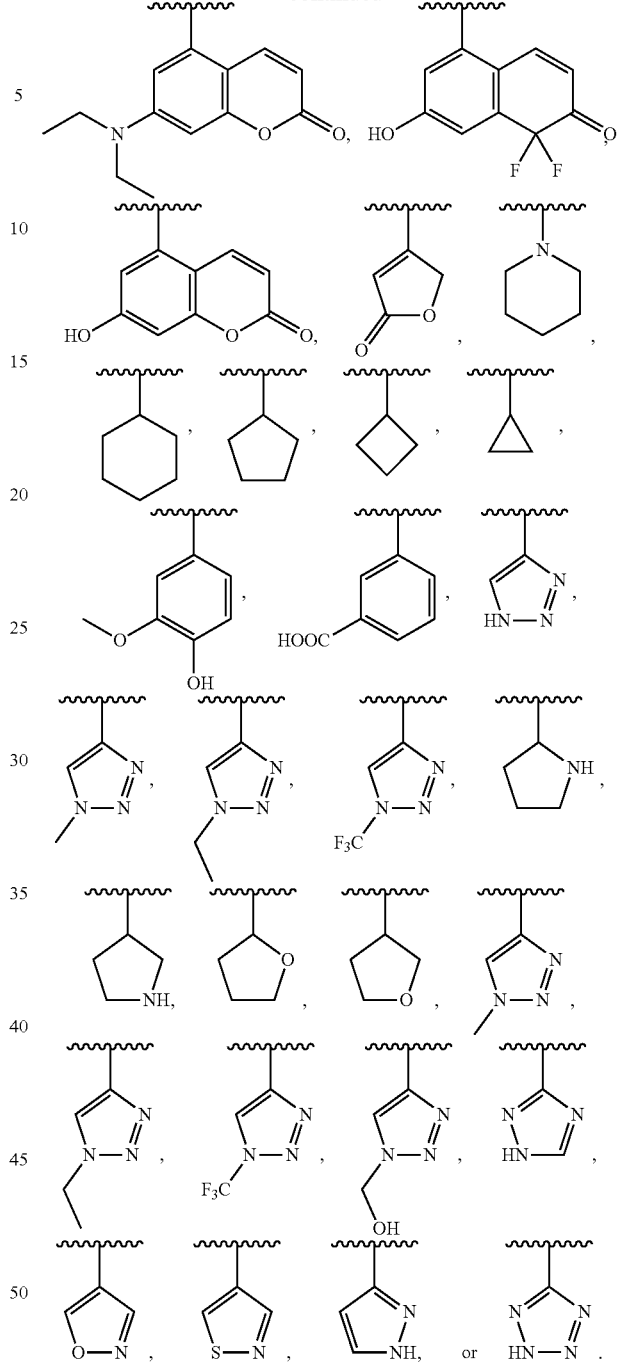

In embodiments, $R^{13}$ is hydrogen, halogen, —CCl$_3$, —CBr$_3$, —CF$_3$, —C$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NH—C(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, or —SF$_5$. In embodiments, $R^{13}$ is —CN, —OH, —NH$_2$, —COOH, —CONH$_2$, —NO$_2$, —SO$_3$H, —SO$_4$H, —SO$_2$NH$_2$, —NHNH$_2$, or —ONH$_2$. In embodiments, $R^{13}$ is substituted or unsubstituted alkyl (e.g., C$_1$-C$_{20}$, C$_{10}$-C$_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered). In embodiments, $R^{13}$ is $R^{13A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{13A}$-substituted or unsubstituted heteroalkyl (e.g., 2 to 20, 8 to 20, 2 to 10, 2 to 8, 2 to 6, or 2 to 4 membered), $R^{13A}$-substituted or unsubstituted cycloalkyl (e.g., $C_3$-$C_8$, $C_3$-$C_6$, or $C_5$-$C_6$), $R^{13A}$-substituted or unsubstituted heterocycloalkyl (e.g., 3 to 8, 3 to 6, or 5 to 6 membered), $R^{13A}$-substituted or unsubstituted aryl (e.g., $C_6$-$C_{10}$, $C_{10}$, or phenyl), or $R^{13A}$-substituted or unsubstituted heteroaryl (e.g., 5 to 10, 5 to 9, or 5 to 6 membered).

$R^{13A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NH_4NH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{13B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{13B}$-substituted or unsubstituted heteroalkyl (e.g., 2 to 20, 8 to 20, 2 to 10, 2 to 8, 2 to 6, or 2 to 4 membered), $R^{13B}$-substituted or unsubstituted cycloalkyl (e.g., $C_3$-$C_8$, $C_3$-$C_6$, or $C_5$-$C_6$), $R^{13B}$-substituted or unsubstituted heterocycloalkyl (e.g., 3 to 8, 3 to 6, or 5 to 6 membered), $R^{13B}$-substituted or unsubstituted aryl (e.g., $C_6$-$C_{10}$, $C_{10}$, or phenyl), or $R^{13B}$-substituted or unsubstituted heteroaryl (e.g., 5 to 10, 5 to 9, or 5 to 6 membered). In embodiments, $R^{13A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_5Cl$, —$OCH_5Br$, —$OCH_2I$, —$OCH_2F$, —$N_3$, —$SF_5$, —$NH_3^+$, —$SO_3^-$, —$OPO_3H^-$, —SCN, —$ONO_2$, $R^{13B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{13B}$-substituted or unsubstituted heteroalkyl (e.g., 2 to 20, 8 to 20, 2 to 10, 2 to 8, 2 to 6, or 2 to 4 membered), $R^{13B}$-substituted or unsubstituted cycloalkyl (e.g., $C_3$-$C_8$, $C_3$-$C_6$, or $C_5$-$C_6$), $R^{13B}$-substituted or unsubstituted heterocycloalkyl (e.g., 3 to 8, 3 to 6, or 5 to 6 membered), $R^{13B}$-substituted or unsubstituted aryl (e.g., $C_6$-$C_{10}$, $C_{10}$, or phenyl), or $R^{13B}$-substituted or unsubstituted heteroaryl (e.g., 5 to 10, 5 to 9, or 5 to 6 membered).

$R^{13B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NH—$NH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_5Cl$, —$OCH_5Br$, —$OCH_2I$, —$OCH_2F$, —$N_3$, —$SF_5$, —$NH_3^+$, —$SO_3^-$, —$OPO_3H^-$, —SCN, —$ONO_2$, $R^{13C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{13C}$-substituted or unsubstituted heteroalkyl (e.g., 2 to 20, 8 to 20, 2 to 10, 2 to 8, 2 to 6, or 2 to 4 membered), $R^{13C}$-substituted or unsubstituted cycloalkyl (e.g., $C_3$-$C_8$, $C_3$-$C_6$, or $C_5$-$C_6$), $R^{13C}$-substituted or unsubstituted heterocycloalkyl (e.g., 3 to 8, 3 to 6, or 5 to 6 membered), $R^{13C}$-substituted or unsubstituted aryl (e.g., $C_6$-$C_{10}$, $C_{10}$, or phenyl), or $R^{13C}$-substituted or unsubstituted heteroaryl (e.g., 5 to 10, 5 to 9, or 5 to 6 membered).

$R^{13C}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_5Cl$, —$CH_5Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NH—$NH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_5Cl$, —$OCH_5Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^{13}$ is substituted or unsubstituted $C_1$-$C_6$ alkyl. In embodiments, $R^{13}$ is substituted or unsubstituted $C_1$-$C_6$ alkyl. In embodiments, $R^{13}$ is substituted or unsubstituted $C_1$ alkyl. In embodiments, $R^{13}$ is substituted or unsubstituted $C_2$ alkyl. In embodiments, $R^{13}$ is substituted or unsubstituted $C_3$ alkyl. In embodiments, $R^{13}$ is substituted or unsubstituted $C_4$ alkyl. In embodiments, $R^{13}$ is substituted or unsubstituted $C_5$ alkyl. In embodiments, $R^{13}$ is substituted or unsubstituted $C_6$ alkyl. In embodiments, $R^{13}$ is substituted $C_1$ alkyl. In embodiments, $R^{13}$ is substituted $C_2$ alkyl. In embodiments, $R^{13}$ is substituted $C_3$ alkyl. In embodiments, $R^{13}$ is substituted $C_4$ alkyl. In embodiments, $R^{13}$ is substituted $C_5$ alkyl. In embodiments, $R^{13}$ is substituted $C_6$ alkyl. In embodiments, $R^{13}$ is unsubstituted $C_1$ alkyl. In embodiments, $R^{13}$ is unsubstituted $C_2$ alkyl. In embodiments, $R^{13}$ is unsubstituted $C_3$ alkyl. In embodiments, $R^{13}$ is unsubstituted $C_4$ alkyl. In embodiments, $R^{13}$ is unsubstituted $C_5$ alkyl. In embodiments, $R^{13}$ is unsubstituted $C_6$ alkyl. In embodiments, $R^{13}$ is hydrogen.

In embodiments, $R^{13}$ is substituted or unsubstituted 2 to 8 membered heteroalkyl. In embodiments, $R^{13}$ is substituted or unsubstituted 2 to 6 membered heteroalkyl. In embodiments, $R^{13}$ is substituted or unsubstituted 2 to 4 membered heteroalkyl. In embodiments, $R^{13}$ is substituted 2 to 8 membered heteroalkyl. In embodiments, $R^{13}$ is substituted 2 to 6 membered heteroalkyl. In embodiments, $R^{13}$ is substituted 2 to 4 membered heteroalkyl. In embodiments, $R^{13}$ is unsubstituted 2 to 8 membered heteroalkyl. In embodiments, $R^{13}$ is unsubstituted 2 to 6 membered heteroalkyl. In embodiments, $R^{13}$ is unsubstituted 2 to 4 membered heteroalkyl.

In embodiments, $R^{13}$ is substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{13}$ is substituted or unsubstituted cycloalkyl (e.g., $C_3$-$C_8$, $C_3$-$C_6$, $C_4$-$C_6$, or $C_5$-$C_6$). In embodiments, $R^{13}$ is substituted cycloalkyl (e.g., $C_3$-$C_8$, $C_3$-$C_6$, $C_4$-$C_6$, or $C_5$-$C_6$). In embodiments, $R^{13}$ is an unsubstituted cycloalkyl (e.g., $C_3$-$C_8$, $C_3$-$C_6$, $C_4$-$C_6$, or $C_5$-$C_6$). In embodiments, $R^{13}$ is substituted or unsubstituted heterocycloalkyl (e.g., 3 to 8 membered, 3 to 6 membered, 4 to 6 membered, 4 to 5 membered, or 5 to 6 membered). In embodiments, $R^{13}$ is substituted heterocycloalkyl (e.g., 3 to 8 membered, 3 to 6 membered, 4 to 6 membered, 4 to 5 membered, or 5 to 6 membered). In embodiments, $R^{13}$ is an unsubstituted heterocycloalkyl (e.g., 3 to 8 membered, 3 to 6 membered, 4 to 6 membered, 4 to 5 membered, or 5 to 6 membered).

In embodiments, $R^{13}$ is substituted or unsubstituted aryl (e.g., $C_6$-$C_{10}$, $C_{10}$, or phenyl). In embodiments, $R^{13}$ is substituted aryl (e.g., $C_6$-$C_{10}$, $C_{10}$, or phenyl). In embodiments, $R^{13}$ is unsubstituted aryl (e.g., $C_6$-$C_{10}$, $C_{10}$, or phenyl). In embodiments, $R^{13}$ is unsubstituted phenyl. In embodiments, $R^{13}$ is substituted or unsubstituted heteroaryl (e.g., 5 to 10, 5 to 9, or 5 to 6 membered). In embodiments, $R^{13}$ is substituted heteroaryl (e.g., 5 to 10, 5 to 9, or 5 to 6 membered). In embodiments, $R^{13}$ is unsubstituted heteroaryl (e.g., 5 to 10, 5 to 9, or 5 to 6 membered). In embodiments, $R^{13}$ is a substituted or unsubstituted 5 membered heteroaryl. In embodiments, $R^{13}$ is a substituted or unsubstituted 6 membered heteroaryl. In embodiments, $R^{13}$ is a substituted or unsubstituted 5 membered heteroaryl. In embodiments, $R^{13}$ is an unsubstituted 5 membered heteroaryl. In embodiments, $R^{13}$ is an unsubstituted 6 membered heteroaryl. In embodiments, $R^{13}$ is an unsubstituted 7 membered heteroaryl.

In embodiments $R^{13}$ is

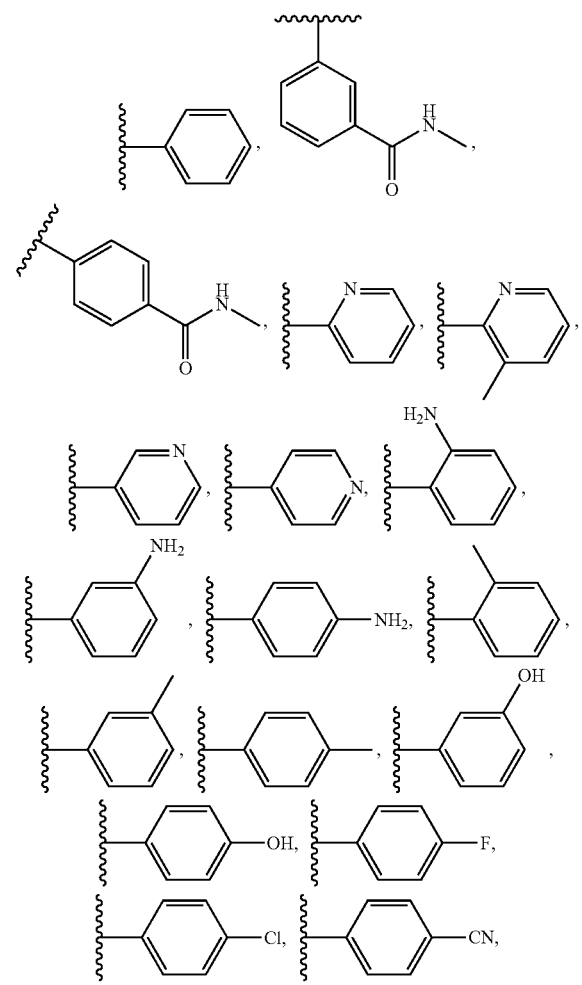

-continued

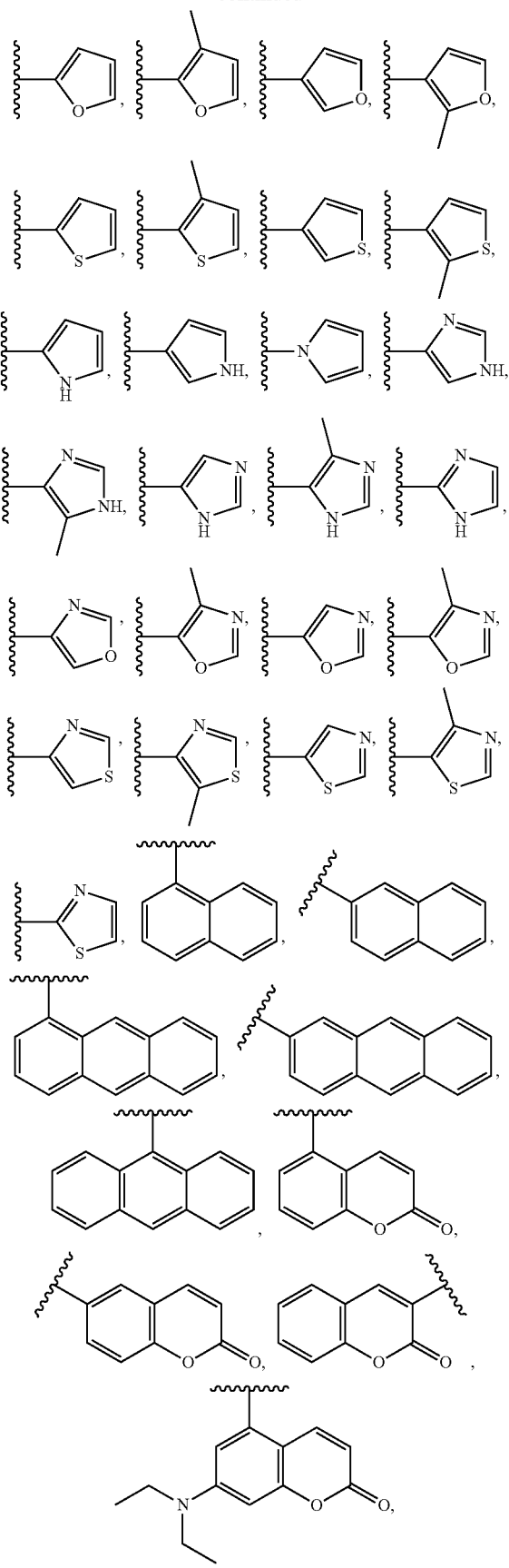

-continued
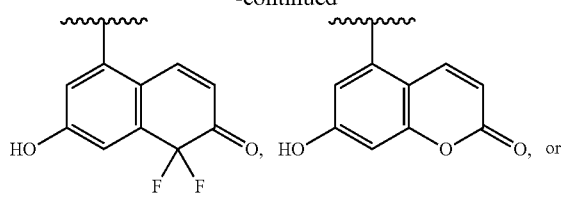
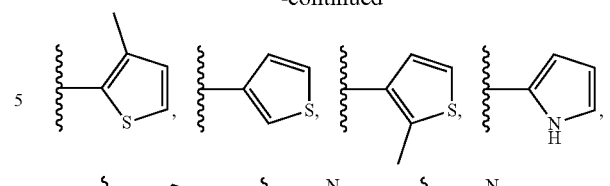
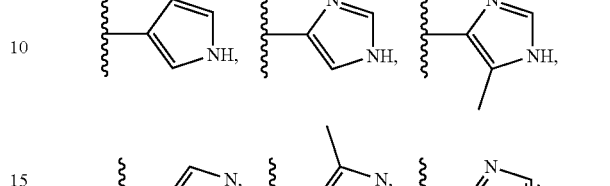
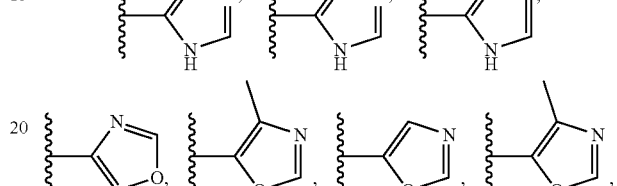
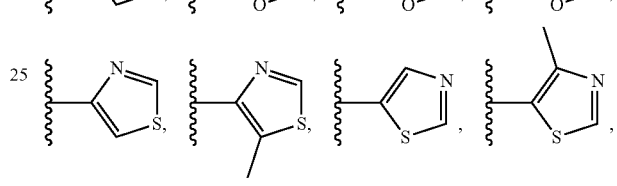
In embodiments, R¹³ is
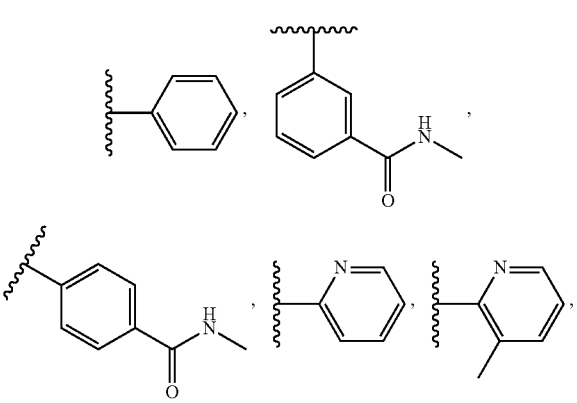
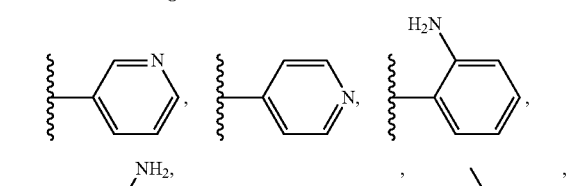
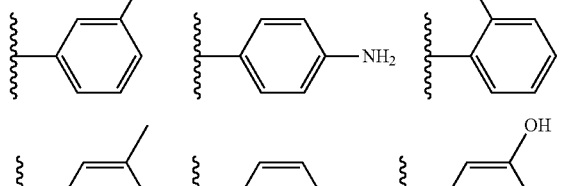
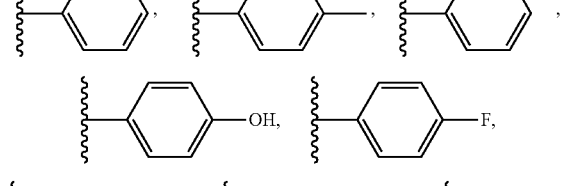
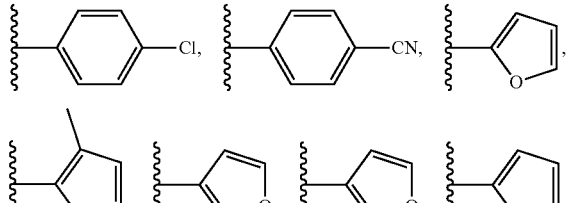
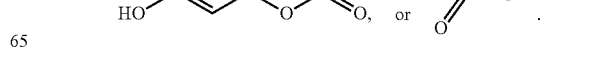

In embodiments, $R^{13}$ is
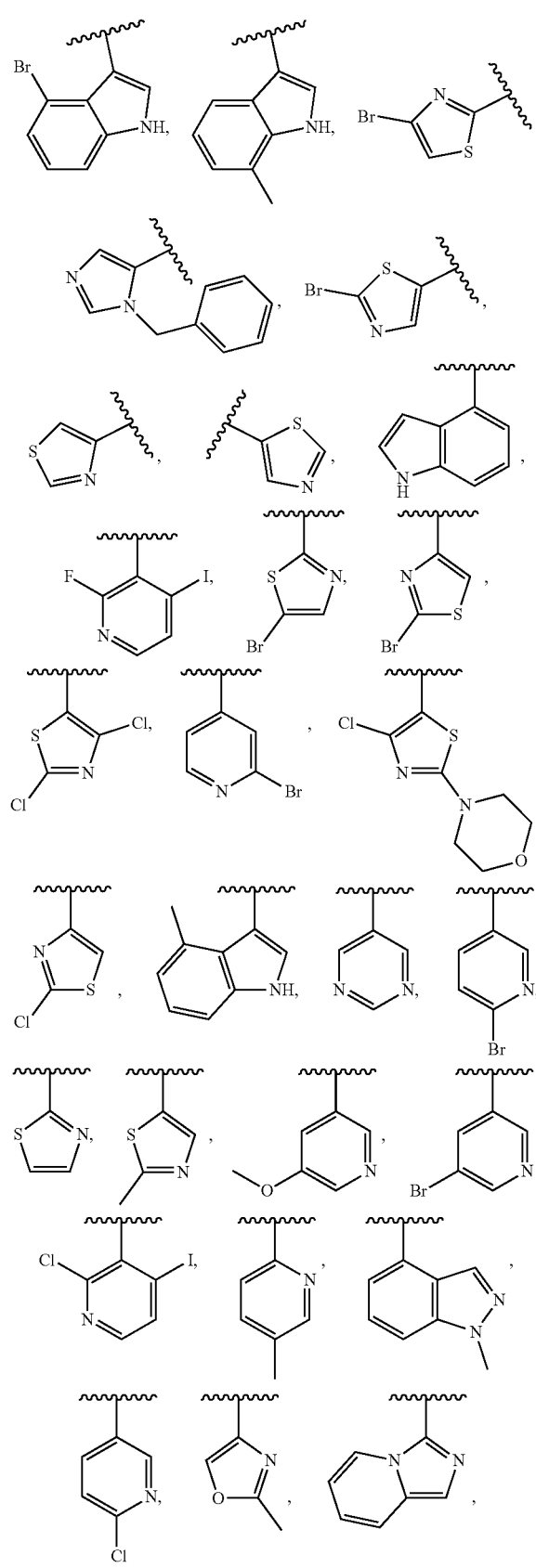
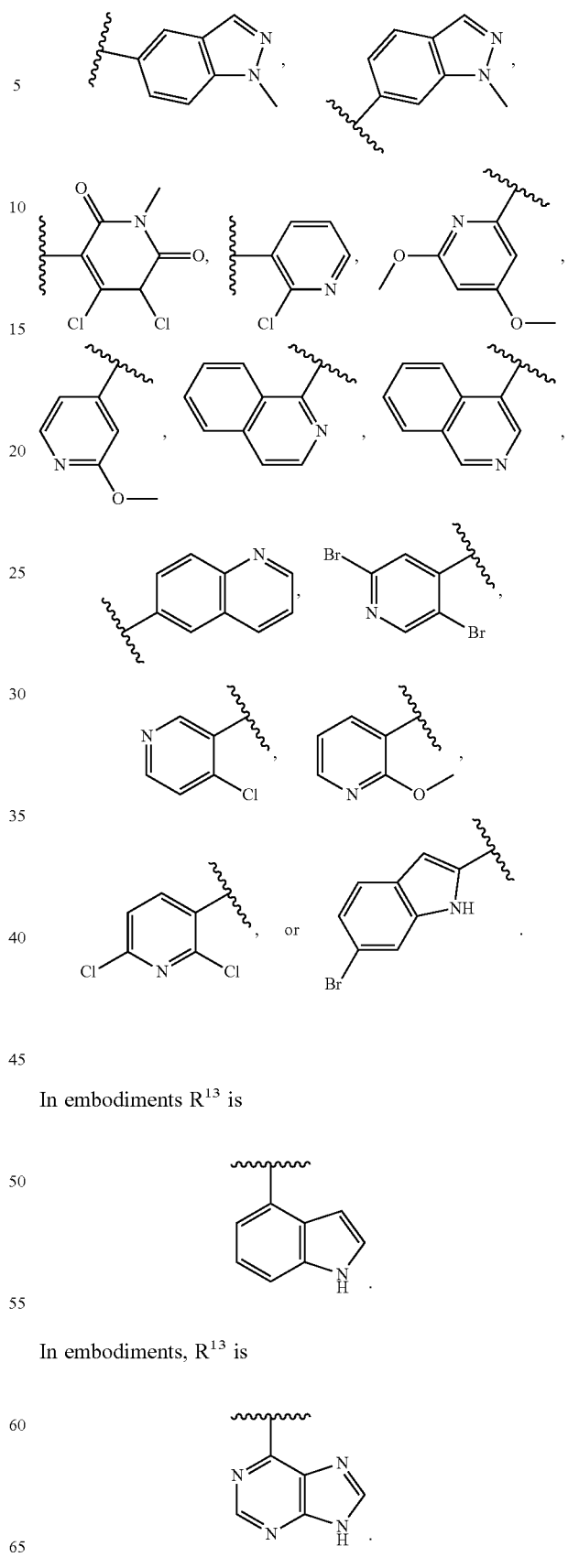
In embodiments $R^{13}$ is
In embodiments, $R^{13}$ is In embodiments, $R^{13}$ is
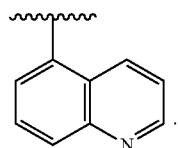
In embodiments, $R^{13}$ is
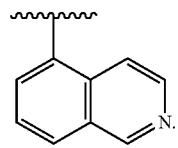 [SMILES: *c1cccc2cnccc12]
In embodiments, $R^{13}$ is
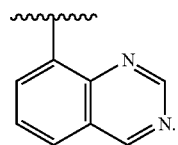
In embodiments, $R^{13}$ is
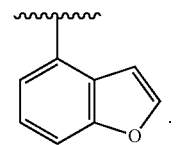 [SMILES: *c1cccc2occc12]
In embodiments, $R^{13}$ is
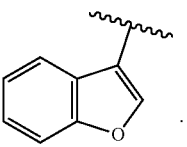 [SMILES: *c1coc2ccccc12]
In embodiments, $R^{13}$ is
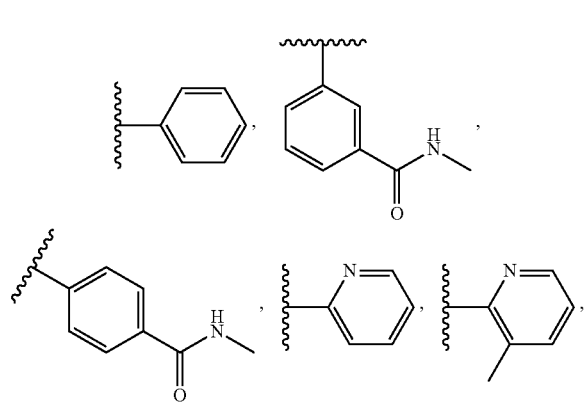
-continued
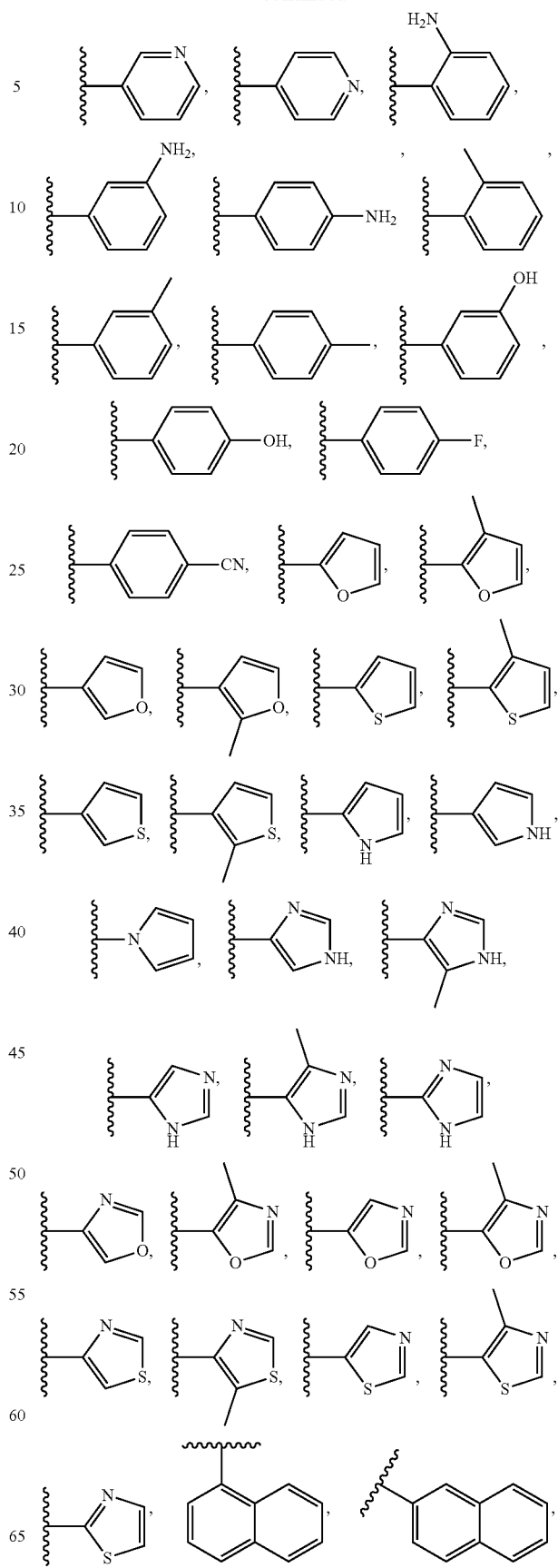

127
-continued

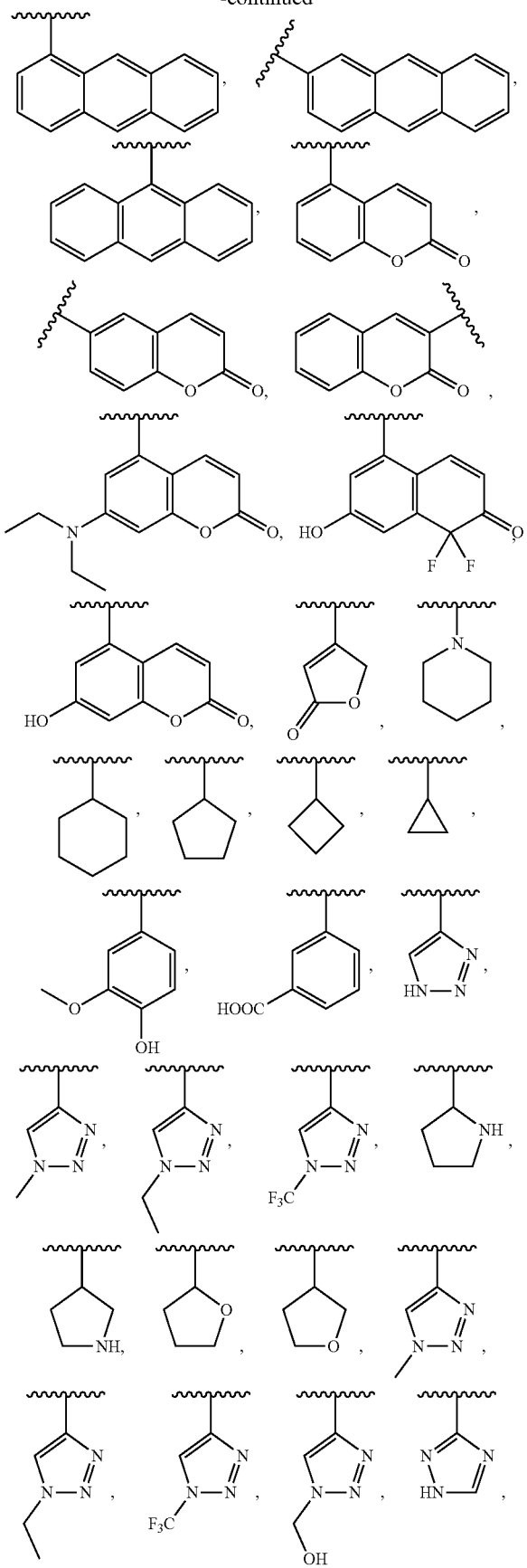

128
-continued

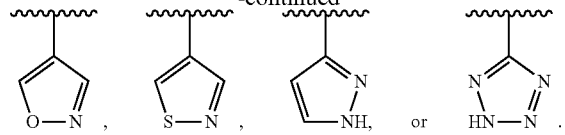

In embodiments, $R^{14}$ is hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, or —SF$_5$. In embodiments, $R^{14}$ is —CN, —OH, —NH$_2$, —COOH, —CONH$_2$, —NO$_2$, —SO$_3$H, —SO$_4$H, —SO$_2$NH$_2$, —NHNH$_2$, or —ONH$_2$. In embodiments, $R^{14}$ is substituted or unsubstituted alkyl (e.g., C$_1$-C$_{20}$, C$_{10}$-C$_{20}$, C$_1$-C$_8$, C$_1$-C$_6$, or C$_1$-C$_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., C$_3$-C$_8$, C$_3$-C$_6$, or C$_5$-C$_6$), substituted or unsubstituted heterocycloalkyl (e.g., 3 to 8, 3 to 6, or 5 to 6 membered), substituted or unsubstituted aryl (e.g., C$_6$-C$_{10}$, C$_{10}$, or phenyl), or substituted or unsubstituted heteroaryl (e.g., 5 to 10, 5 to 9, or 5 to 6 membered). In embodiments, $R^{14}$ is $R^{14A}$-substituted or unsubstituted alkyl (e.g., C$_1$-C$_{20}$, C$_{10}$-C$_{20}$, C$_1$-C$_8$, C$_1$-C$_6$, or C$_1$-C$_4$), $R^{14A}$-substituted or unsubstituted heteroalkyl (e.g., 2 to 20, 8 to 20, 2 to 10, 2 to 8, 2 to 6, or 2 to 4 membered), $R^{14A}$-substituted or unsubstituted cycloalkyl (e.g., C$_3$-C$_8$, C$_3$-C$_6$, or C$_5$-C$_6$), $R^{14A}$-substituted or unsubstituted heterocycloalkyl (e.g., 3 to 8, 3 to 6, or 5 to 6 membered), $R^{14A}$-substituted or unsubstituted aryl (e.g., C$_6$-C$_{10}$, C$_{10}$, or phenyl), or $R^{14A}$-substituted or unsubstituted heteroaryl (e.g., 5 to 10, 5 to 9, or 5 to 6 membered).

$R^{14A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NH$_4$NH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —NH$_3^+$, —SO$_3^-$, —OPO$_3$H$^-$, —SCN, —ONO$_2$, $R^{14B}$-substituted or unsubstituted alkyl (e.g., C$_1$-C$_{20}$, C$_{10}$-C$_{20}$, C$_1$-C$_8$, C$_1$-C$_6$, or C$_1$-C$_4$), $R^{14B}$-substituted or unsubstituted heteroalkyl (e.g., 2 to 20, 8 to 20, 2 to 10, 2 to 8, 2 to 6, or 2 to 4 membered), $R^{14B}$-substituted or unsubstituted cycloalkyl (e.g., C$_3$-C$_8$, C$_3$-C$_6$, or C$_5$-C$_6$), $R^{14B}$-substituted or unsubstituted heterocycloalkyl (e.g., 3 to 8, 3 to 6, or 5 to 6 membered), $R^{14B}$-substituted or unsubstituted aryl (e.g., C$_6$-C$_{10}$, C$_{10}$, or phenyl), or $R^{14B}$-substituted or unsubstituted heteroaryl (e.g., 5 to 10, 5 to 9, or 5 to 6 membered). In embodiments, $R^{14A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —NH$_3^+$, —SO$_3^-$, —OPO$_3$H$^-$, —SCN, —ONO$_2$, R$^{14B}$-substituted or unsubstituted alkyl (e.g., C$_1$-C$_{20}$, C$_{10}$-C$_{20}$, C$_1$-C$_8$, C$_1$-C$_6$, or C$_1$-C$_4$), R$^{14B}$-substituted or unsubstituted heteroalkyl (e.g., 2 to 20, 8 to 20, 2 to 10, 2 to 8, 2 to 6, or 2 to 4 membered), R$^{14B}$-substituted or unsubstituted cycloalkyl (e.g., C$_3$-C$_8$, C$_3$-C$_6$, or C$_5$-C$_6$), R$^{14B}$-substituted or unsubstituted heterocycloalkyl (e.g., 3 to 8, 3 to 6, or 5 to 6 membered), R$^{14B}$-substituted or unsubstituted aryl (e.g., C$_6$-C$_{10}$, C$_{10}$, or phenyl), or R$^{14B}$-substituted or unsubstituted heteroaryl (e.g., 5 to 10, 5 to 9, or 5 to 6 membered).

R$^{14B}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_5$Cl, —OCH$_2$Br, —OCH$_2$I, —OCH$_2$F, —N$_3$, —SF$_5$, —NH$_3^+$, —SO$_3^-$, —OPO$_3$H$^-$, —SCN, —ONO$_2$, R$^{14C}$-substituted or unsubstituted alkyl (e.g., C$_1$-C$_{20}$, C$_{10}$-C$_{20}$, C$_1$-C$_8$, C$_1$-C$_6$, or C$_1$-C$_4$), R$^{14C}$-substituted or unsubstituted heteroalkyl (e.g., 2 to 20, 8 to 20, 2 to 10, 2 to 8, 2 to 6, or 2 to 4 membered), R$^{14C}$-substituted or unsubstituted cycloalkyl (e.g., C$_3$-C$_8$, C$_3$-C$_6$, or C$_5$-C$_6$), R$^{14C}$-substituted or unsubstituted heterocycloalkyl (e.g., 3 to 8, 3 to 6, or 5 to 6 membered), R$^{14C}$-substituted or unsubstituted aryl (e.g., C$_6$-C$_{10}$, C$_{10}$, or phenyl), or R$^{14C}$-substituted or unsubstituted heteroaryl (e.g., 5 to 10, 5 to 9, or 5 to 6 membered).

R$^{14C}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_5$Cl, —CH$_5$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NH$_4$NH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_5$Cl, —OCH$_5$Br, —OCH$_2$I, —OCH$_2$F, —N$_3$, —SF$_5$, —NH$_3^+$, —SO$_3^-$, —OPO$_3$H$^-$, —SCN, —ONO$_2$, unsubstituted alkyl (e.g., C$_1$-C$_{20}$, C$_{10}$-C$_{20}$, C$_1$-C$_8$, C$_1$-C$_6$, or C$_1$-C$_4$), unsubstituted heteroalkyl (e.g., 2 to 20, 8 to 20, 2 to 10, 2 to 8, 2 to 6, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8, 3 to 6, or 5 to 6 membered), unsubstituted aryl (e.g., C$_6$-C$_{10}$, C$_{10}$, or phenyl), or unsubstituted heteroaryl (e.g., 5 to 10, 5 to 9, or 5 to 6 membered).

In embodiments, R$^{14}$ is substituted or unsubstituted C$_1$-C$_6$ alkyl. In embodiments, R$^{14}$ is substituted or unsubstituted C$_1$-C$_6$ alkyl. In embodiments, R$^{14}$ is substituted or unsubstituted C$_1$ alkyl. In embodiments, R$^{14}$ is substituted or unsubstituted C$_2$ alkyl. In embodiments, R$^{14}$ is substituted or unsubstituted C$_3$ alkyl. In embodiments, R$^{14}$ is substituted or unsubstituted C$_4$ alkyl. In embodiments, R$^{14}$ is substituted or unsubstituted C$_5$ alkyl. In embodiments, R$^{14}$ is substituted or unsubstituted C$_6$ alkyl. In embodiments, R$^{14}$ is substituted C$_1$ alkyl. In embodiments, R$^{14}$ is substituted C$_2$ alkyl. In embodiments, R$^{14}$ is substituted C$_3$ alkyl. In embodiments, R$^{14}$ is substituted C$_4$ alkyl. In embodiments, R$^{14}$ is substituted C$_5$ alkyl. In embodiments, R$^{14}$ is substituted C$_6$ alkyl. In embodiments, R$^{14}$ is unsubstituted C$_1$ alkyl. In embodiments, R$^{14}$ is unsubstituted C$_2$ alkyl. In embodiments, R$^{14}$ is unsubstituted C$_3$ alkyl. In embodiments, R$^{14}$ is unsubstituted C$_4$ alkyl. In embodiments, R$^{14}$ is unsubstituted C$_5$ alkyl. In embodiments, R$^{14}$ is unsubstituted C$_6$ alkyl.

In embodiments, R$^{14}$ is substituted or unsubstituted 2 to 8 membered heteroalkyl. In embodiments, R$^{14}$ is substituted or unsubstituted 2 to 6 membered heteroalkyl. In embodiments, R$^{14}$ is substituted or unsubstituted 2 to 4 membered heteroalkyl. In embodiments, R$^{14}$ is substituted 2 to 8 membered heteroalkyl. In embodiments, R$^{14}$ is substituted 2 to 6 membered heteroalkyl. In embodiments, R$^{14}$ is substituted 2 to 4 membered heteroalkyl. In embodiments, R$^{14}$ is unsubstituted 2 to 8 membered heteroalkyl. In embodiments, R$^{14}$ is unsubstituted 2 to 6 membered heteroalkyl. In embodiments, R$^{14}$ is unsubstituted 2 to 4 membered heteroalkyl.

In embodiments, R$^{14}$ is substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, R$^{14}$ is substituted or unsubstituted cycloalkyl (e.g., C$_3$-C$_8$, C$_3$-C$_6$, C$_4$-C$_6$, or C$_5$-C$_6$). In embodiments, R$^{14}$ is substituted cycloalkyl (e.g., C$_3$-C$_8$, C$_3$-C$_6$, C$_4$-C$_6$, or C$_5$-C$_6$). In embodiments, R$^{14}$ is an unsubstituted cycloalkyl (e.g., C$_3$-C$_8$, C$_3$-C$_6$, C$_4$-C$_6$, or C$_5$-C$_6$). In embodiments, R$^{14}$ is substituted or unsubstituted heterocycloalkyl (e.g., 3 to 8 membered, 3 to 6 membered, 4 to 6 membered, 4 to 5 membered, or 5 to 6 membered). In embodiments, R$^{14}$ is substituted heterocycloalkyl (e.g., 3 to 8 membered, 3 to 6 membered, 4 to 6 membered, 4 to 5 membered, or 5 to 6 membered). In embodiments, R$^{14}$ is an unsubstituted heterocycloalkyl (e.g., 3 to 8 membered, 3 to 6 membered, 4 to 6 membered, 4 to 5 membered, or 5 to 6 membered).

In embodiments, R$^{14}$ is substituted or unsubstituted aryl (e.g., C$_6$-C$_{10}$, C$_{10}$, or phenyl). In embodiments, R$^{14}$ is substituted aryl (e.g., C$_6$-C$_{10}$, C$_{10}$, or phenyl). In embodiments, R$^{14}$ is unsubstituted aryl (e.g., C$_6$-C$_{10}$, C$_{10}$, or phenyl). In embodiments, R$^{14}$ is unsubstituted phenyl. In embodiments, R$^{14}$ is substituted or unsubstituted heteroaryl (e.g., 5 to 10, 5 to 9, or 5 to 6 membered). In embodiments, R$^{14}$ is substituted heteroaryl (e.g., 5 to 10, 5 to 9, or 5 to 6 membered). In embodiments, R$^{14}$ is unsubstituted heteroaryl (e.g., 5 to 10, 5 to 9, or 5 to 6 membered). In embodiments, R$^{14}$ is a substituted or unsubstituted 5 membered heteroaryl. In embodiments, R$^{14}$ is a substituted or unsubstituted 6 membered heteroaryl. In embodiments, R$^{14}$ is a substituted or unsubstituted 5 membered heteroaryl. In embodiments, R$^{14}$ is an unsubstituted 5 membered heteroaryl. In embodiments, R$^{14}$ is an unsubstituted 6 membered heteroaryl. In embodiments, R$^{14}$ is an unsubstituted 7 membered heteroaryl.

In embodiments, R$^{14}$ is

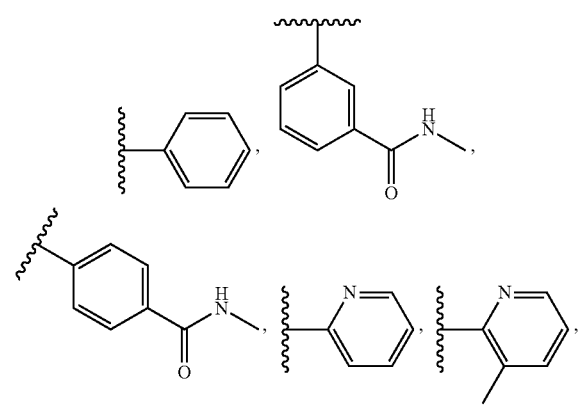

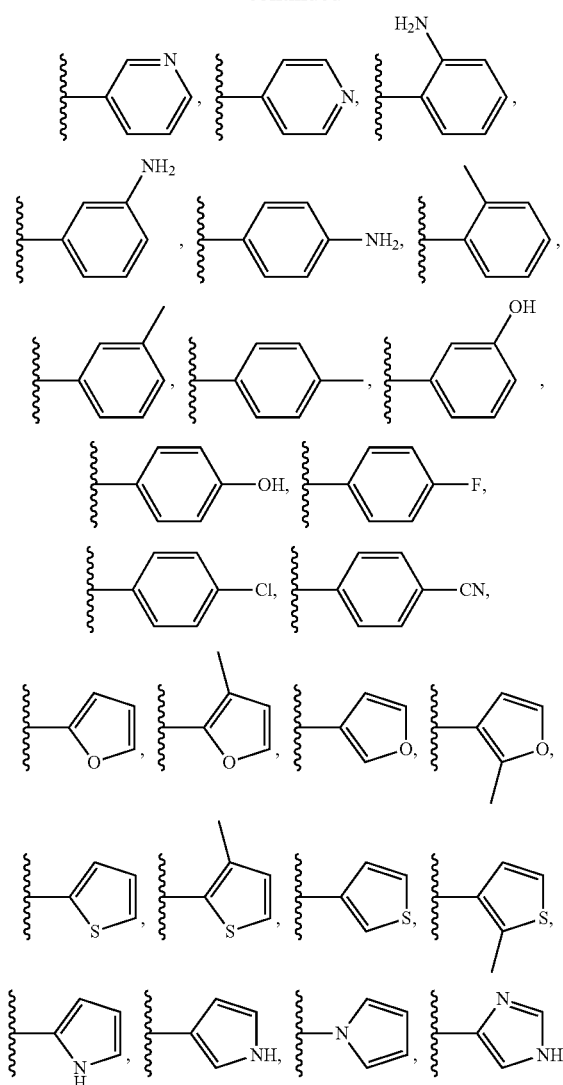
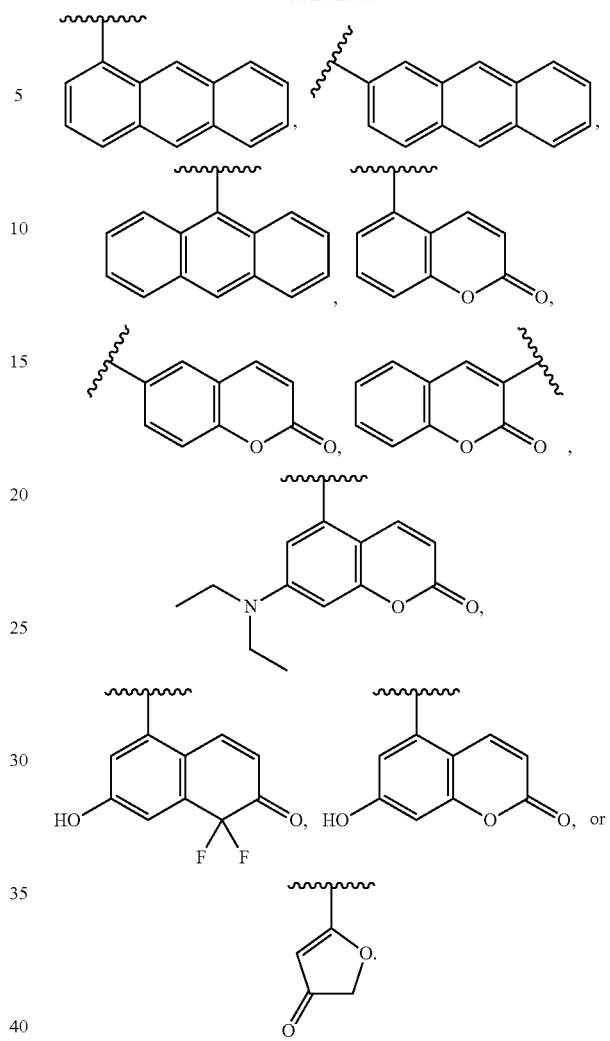
In embodiments, $R^{14}$ is
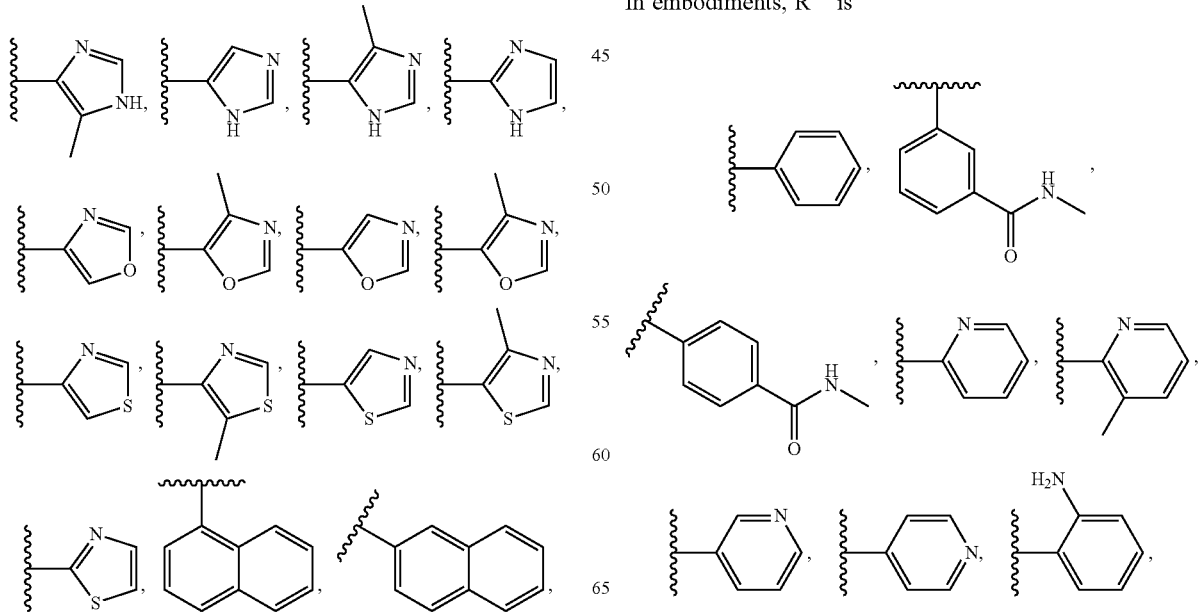

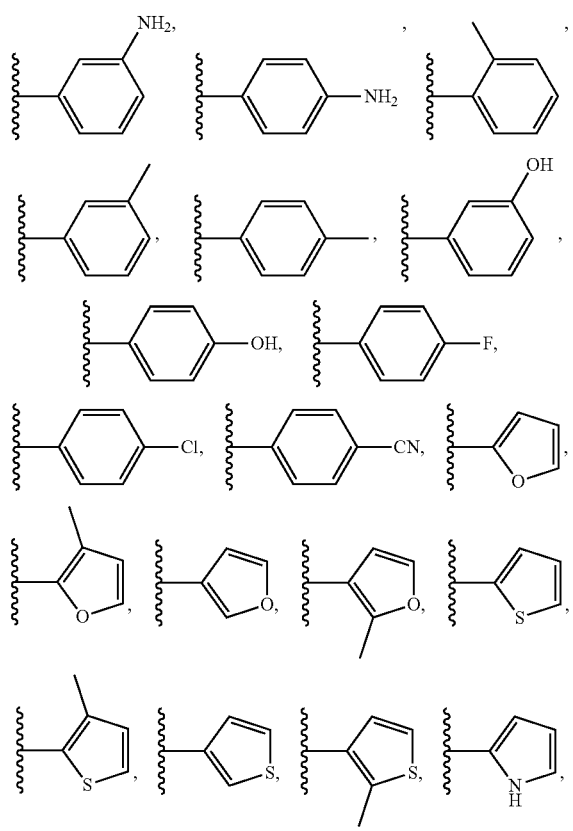
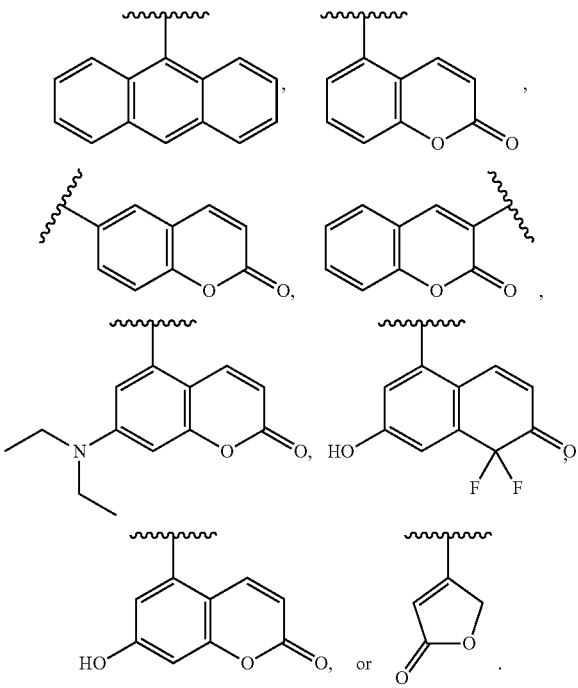
In embodiments, $R^{14}$ is
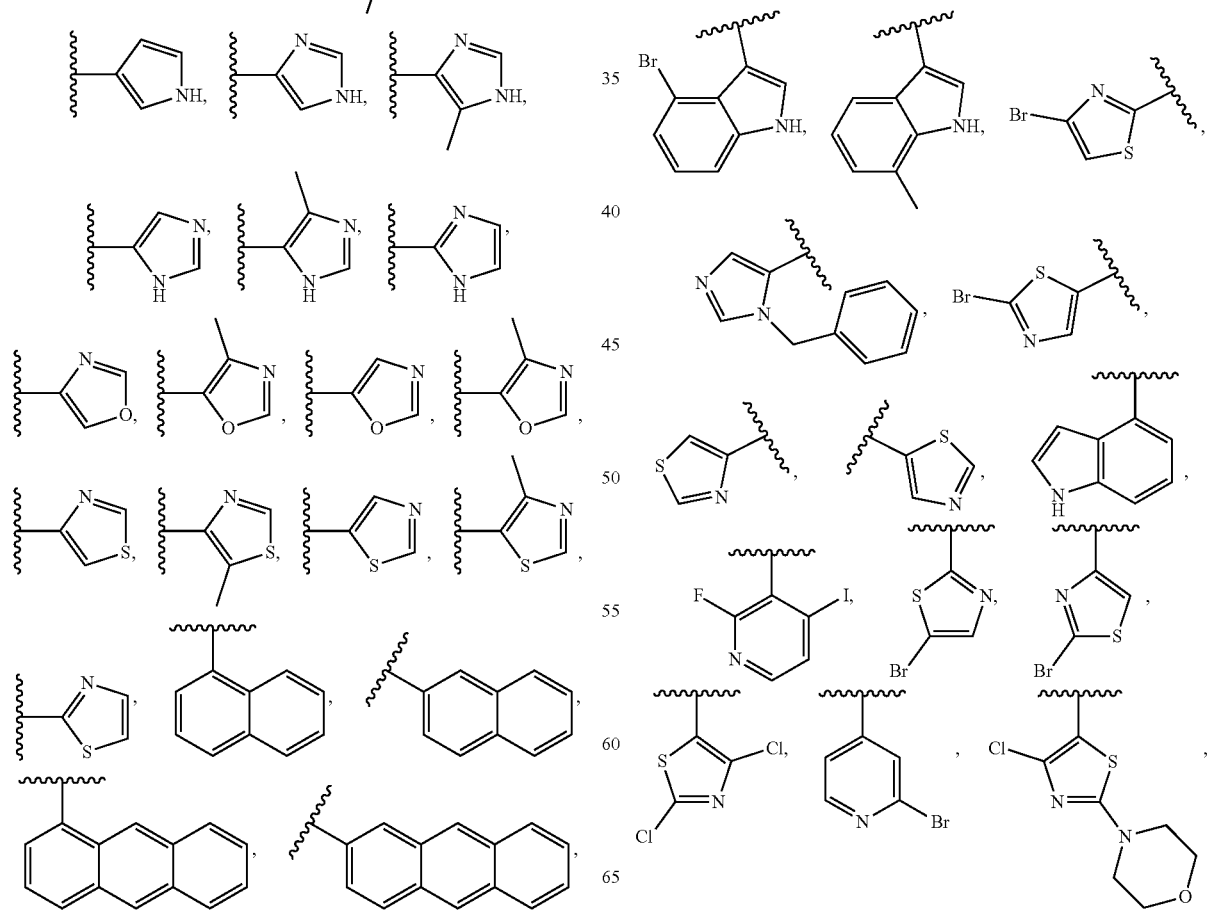

-continued
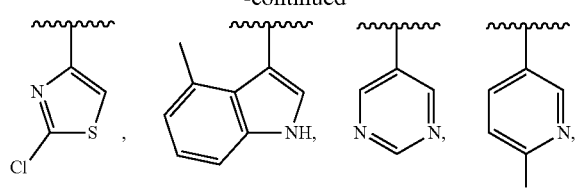
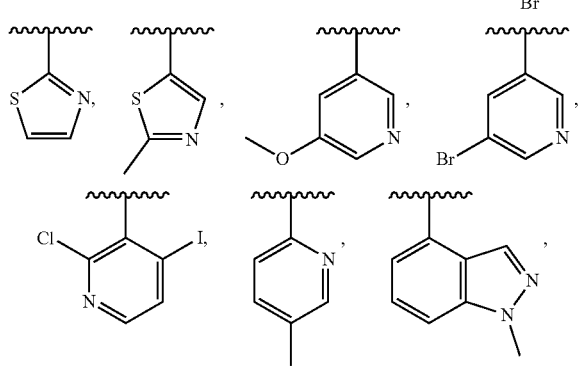
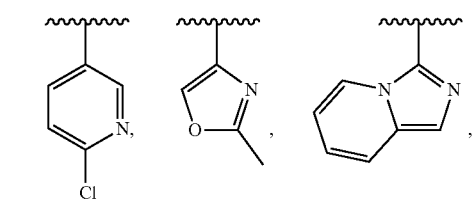
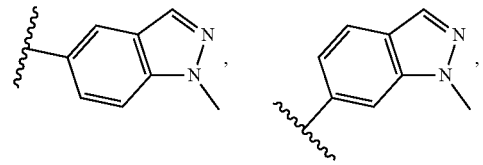
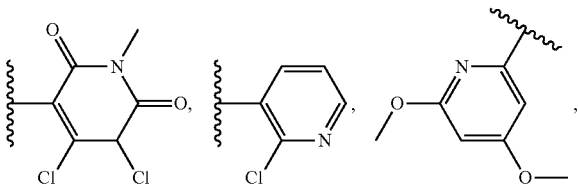
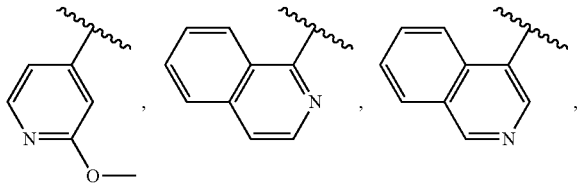
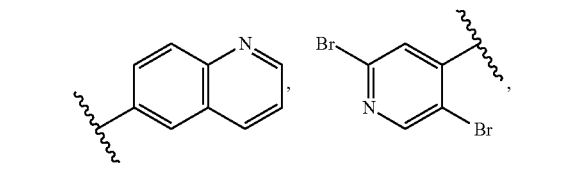
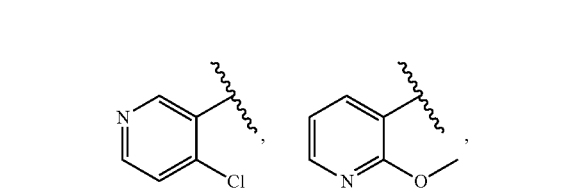
-continued
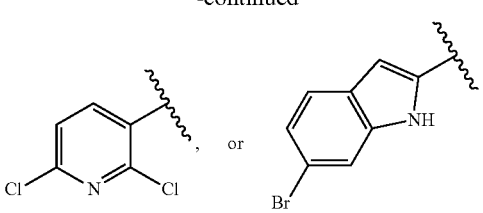
In embodiments, $R^{14}$ is
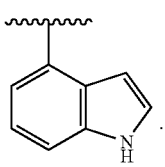 [SMILES: *c1cccc2[nH]ccc12]
In embodiments, $R^{14}$ is
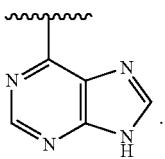 [SMILES: *c1ncnc2[nH]cnc12]
In embodiments, $R^{14}$ is
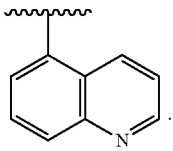 [SMILES: *c1cccc2ncccc12]
In embodiments, $R^{14}$ is
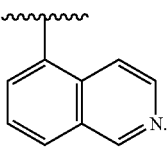 [SMILES: *c1cccc2cnccc12]
In embodiments, $R^{14}$ is
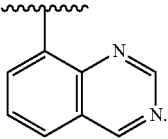

In embodiments, $R^{14}$ is
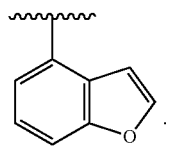 [SMILES: *c1cccc2occc12]
In embodiments, $R^{14}$ is
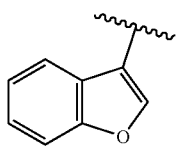
In embodiments, $R^{14}$ is
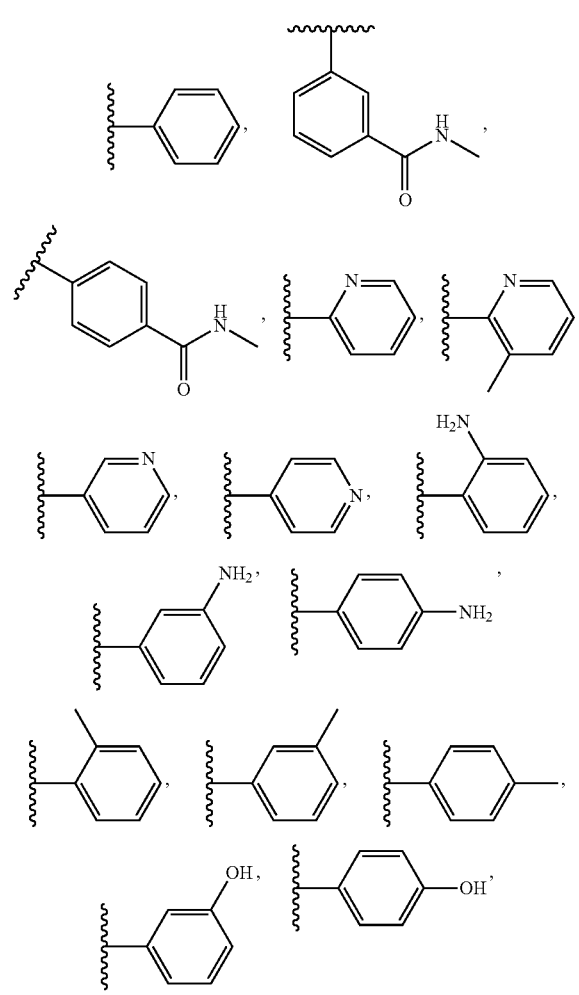
-continued
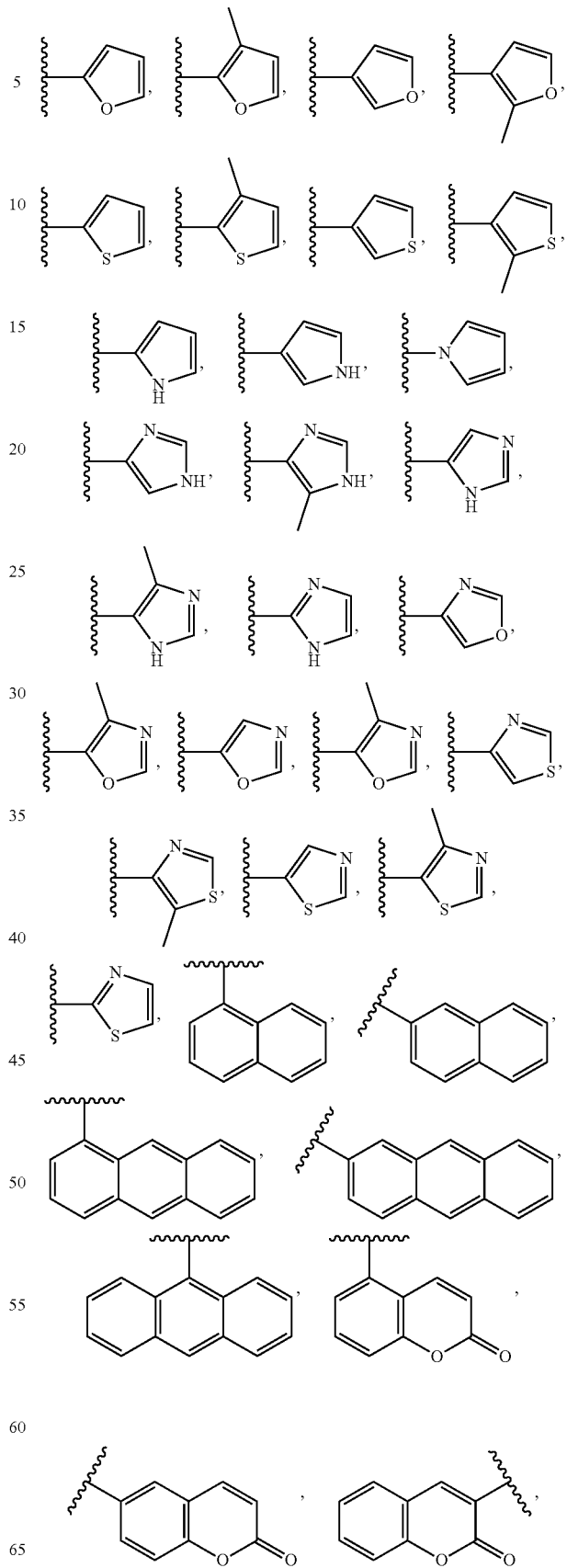

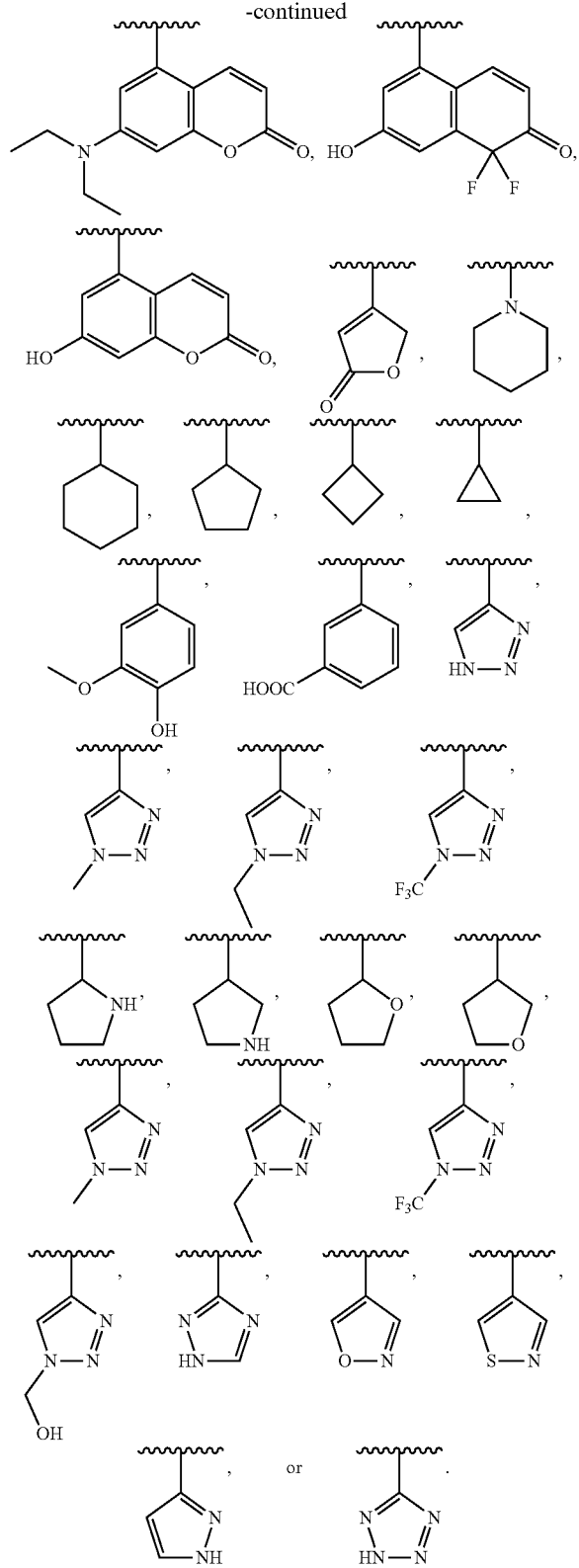

In embodiments, $R^1$, $R^{12}$, $R^{13}$, and $R^{14}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —SH, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{11}$, $R^{12}$, $R^{13}$, and $R^{14}$ are not all hydrogen. In embodiments, R", $R^{12}$, $R^{13}$, and $R^{14}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{11}$, $R^{12}$, $R^{13}$, and $R^{14}$ are not all hydrogen.

In embodiments, $R^{11}$ is hydrogen, and $R^{12}$, $R^{13}$, and $R^{14}$ are independently selected from hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —SH, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^1$, $R^{12}$, $R^{13}$, and $R^{14}$ are not all hydrogen.

In embodiments, $R^{13}$ is hydrogen, and R", $R^{12}$, and $R^{14}$ are independently selected from hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —SH, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{11}$, $R^{12}$, $R^{13}$, and $R^{14}$ are not all hydrogen.

In embodiments, $R^{11}$ and $R^{13}$ are hydrogen, and $R^{12}$ and $R^{14}$ are independently selected from hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —SH, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^1$, $R^{12}$, $R^{13}$, and $R^{14}$ are not all hydrogen.

In embodiments, $R^{11}$ and $R^{13}$ are hydrogen, and $R^{12}$ and $R^{14}$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{11}$ and $R^{13}$ are hydrogen, and $R^{12}$ and $R^{14}$ are independently substituted or unsubstituted $C_1$-$C_6$ alkyl, substituted or unsubstituted 2 to 8 membered heteroalkyl, substituted or unsubstituted $C_3$-$C_6$ cycloalkyl, substituted or unsubstituted 2 to 8 membered heterocycloalkyl, substituted or unsubstituted $C_6$ to $C_{12}$ aryl, or substituted or unsubstituted 2 to 8 membered heteroaryl. In embodiments, $R^{11}$ and $R^{13}$ are hydrogen, and $R^{12}$ and $R^{14}$ are independently substituted or unsubstituted alkyl, substituted or unsubstituted cycloalkyl, or substituted or unsubstituted aryl. In embodiments, $R^{11}$ and $R^{13}$ are hydrogen, and $R^{12}$ and $R^{14}$ are independently substituted or unsubstituted cycloalkyl, substituted or unsubstituted heterocycloalkyl, substituted or unsubstituted aryl, or substituted or unsubstituted heteroaryl.

In embodiments, $R^{11}$ and $R^{12}$ are joined to form a substituted or unsubstituted cycloalkyl, substituted or unsubstituted heterocycloalkyl, substituted or unsubstituted aryl, or substituted or unsubstituted heteroaryl. In embodiments, $R^{11}$ and $R^{12}$ are joined to form a substituted or unsubstituted $C_3$-$C_6$ cycloalkyl, substituted or unsubstituted 2 to 8 membered heterocycloalkyl, substituted or unsubstituted $C_6$ to $C_{12}$ aryl, or substituted or unsubstituted 2 to 8 membered heteroaryl.

In embodiments, $R^{13}$ and $R^{14}$ are joined to form a substituted or unsubstituted cycloalkyl, substituted or unsubstituted heterocycloalkyl, substituted or unsubstituted aryl, or substituted or unsubstituted heteroaryl. In embodiments, $R^{13}$ and $R^{14}$ are joined to form a substituted or unsubstituted $C_3$-$C_6$ cycloalkyl, substituted or unsubstituted 2 to 8 membered heterocycloalkyl, substituted or unsubstituted $C_6$ to $C_{12}$ aryl, or substituted or unsubstituted 2 to 8 membered heteroaryl.

In embodiments, $L^{100}$ includes

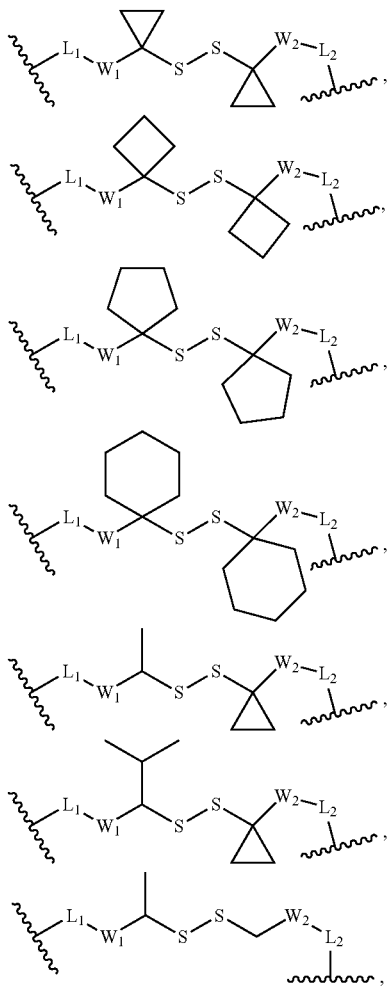

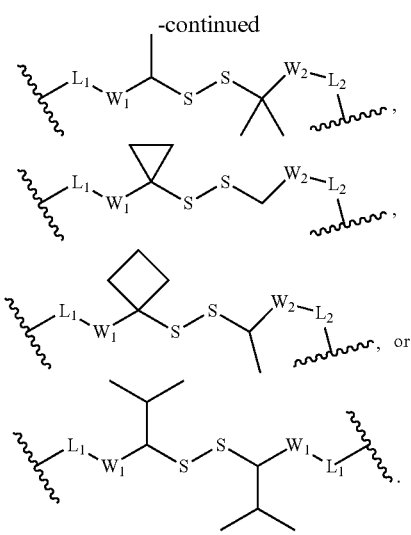

In embodiments, $R^{11}$ and $R^{13}$ are hydrogen and $R^{12}$ and $R^{14}$ are not hydrogen.

In embodiments, $L^{100}$ includes

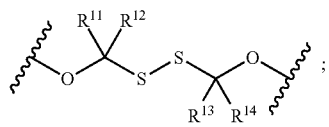

wherein $R^{11}$ and $R^{13}$ are hydrogen, and $R^{12}$ and $R^{14}$ are unsubstituted alkyl. In embodiments, $L^{100}$ is

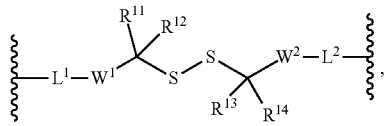

wherein $L^1$ has the formula -$L^{101}$-$L^{102}$-$L^{103}$-; $L^{101}$, $L^{102}$, and $L^{103}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^2$ has the formula -$L^{201}$-$L^{202}$-$L^{203}$-; and $L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{100}$ includes

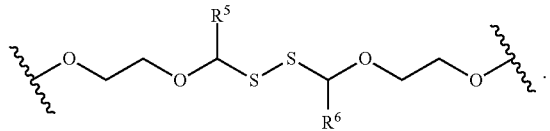

In embodiments, $L^{100}$ is a divalent linker including

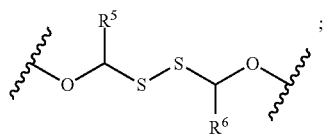

wherein $R^5$ or $R^6$ are unsubstituted alkyl. In embodiments, $L^{100}$ includes

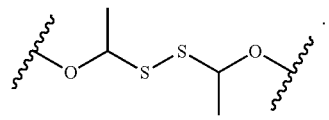 [SMILES: *OC(C)SSC(C)O*]

In embodiments, $L^{100}$ includes

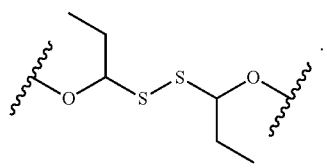 [SMILES: *OC(CC)SSC(CC)O*]

In embodiments, $L^{100}$ includes

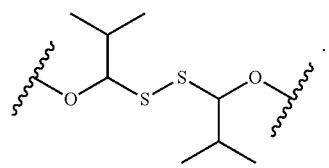 [SMILES: *OC(SSC(O*)C(C)C)C(C)C]

In embodiments, $L^{100}$ includes

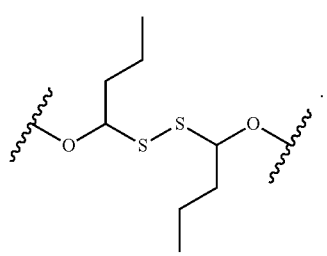 [SMILES: *OC(CCC)SSC(CCC)O*]

In embodiments, $L^{100}$ includes

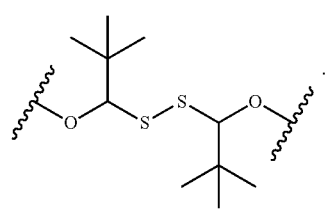 [SMILES: *OC(SSC(O*)C(C)(C)C)C(C)(C)C]

In embodiments, $L^{100}$ includes

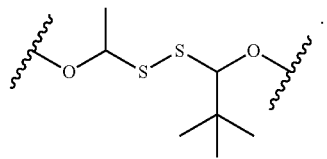 [SMILES: *OC(C)SSC(O*)C(C)(C)C]

In embodiments, $L^{100}$ includes

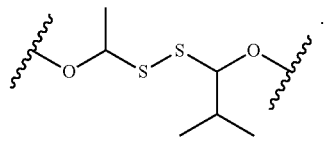 [SMILES: *OC(C)SSC(O*)C(C)C]

In embodiments, $L^{100}$ includes

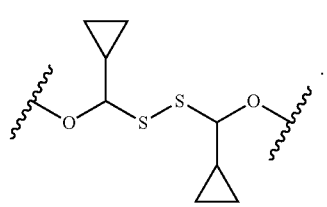 [SMILES: *OC(SSC(O*)C1CC1)C1CC1]

In embodiments, $L^{100}$ includes

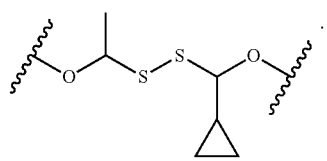 [SMILES: *OC(C)SSC(O*)C1CC1]

In embodiments, $L^{100}$ has the formula:

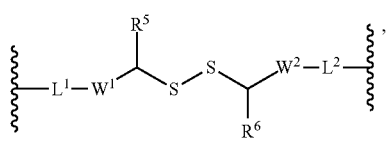

wherein $L^1$ and $L^2$ are independent divalent linkers. In embodiments, $L^{100}$ has the formula:

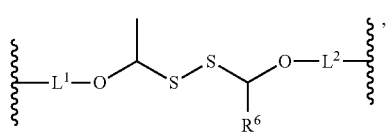

wherein $R^6$ is as described herein. In embodiments, $L^1$ has the formula -$L^{101}$-$L^{102}$-$L^{103}$-. $L^{101}$, $L^{102}$, and $L^{103}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^2$ has the formula $-L^{201}-L^{202}-L^{203}-$. $L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{101}$, $L^{102}$, $L^{103}$, $L^{201}$, $L^{202}$, and $L^{203}$ independently includes PEG.

In embodiments, $L^{101}$, $L^{102}$, $L^{103}$, $L^{201}$, $L^{202}$, and $L^{203}$ independently includes

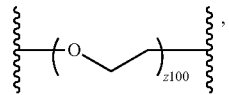

wherein z100 is an integer from 1 to 8. In embodiments, z100 is 1. In embodiments, z100 is 2. In embodiments, z100 is 3. In embodiments, z100 is 4. In embodiments, z100 is 5. In embodiments, z100 is 6. In embodiments, z100 is 7. In embodiments, z100 is 8. In embodiments, z100 is 2 to 8. In embodiments, z100 is 4 to 6.

In embodiments, $L^{101}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{101}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, $R^{101}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{101}$-substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), $R^{101}$-substituted or unsubstituted cycloalkylene (e.g., $C_3$-$C_8$, $C_3$-$C_6$, or $C_5$-$C_6$), $R^{101}$-substituted or unsubstituted heterocycloalkylene (e.g., 3 to 8, 3 to 6, or 5 to 6 membered), $R^{101}$-substituted or unsubstituted arylene (e.g., $C_6$-$C_{10}$, $C_{10}$, or phenylene), or $R^{101}$-substituted or unsubstituted heteroarylene (e.g., 5 to 10, 5 to 9, or 5 to 6 membered).

$R^{101}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{101A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{101A}$-substituted or unsubstituted heteroalkyl (e.g., 2 to 20, 8 to 20, 2 to 10, 2 to 8, 2 to 6, or 2 to 4 membered), $R^{101A}$-substituted or unsubstituted cycloalkyl (e.g., $C_3$-$C_8$, $C_3$-$C_6$, or $C_5$-$C_6$), $R^{101A}$-substituted or unsubstituted heterocycloalkyl (e.g., 3 to 8, 3 to 6, or 5 to 6 membered), $R^{101A}$-substituted or unsubstituted aryl (e.g., $C_6$-$C_{10}$, $C_{10}$, or phenyl), or $R^{101A}$-substituted or unsubstituted heteroaryl (e.g., 5 to 10, 5 to 9, or 5 to 6 membered).

$R^{101A}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{102}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{102}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, $R^{102}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{102}$-substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), $R^{102}$-substituted or unsubstituted cycloalkylene (e.g., $C_3$-$C_8$, $C_3$-$C_6$, or $C_5$-$C_6$), $R^{102}$-substituted or unsubstituted heterocycloalkylene (e.g., 3 to 8, 3 to 6, or 5 to 6 membered), $R^{102}$-substituted or unsubstituted arylene (e.g., $C_6$-$C_{10}$, $C_{10}$, or phenylene), or $R^{102}$-substituted or unsubstituted heteroarylene (e.g., 5 to 10, 5 to 9, or 5 to 6 membered).

$R^{102}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{102A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{102A}$-substituted or unsubstituted heteroalkyl (e.g., 2 to 20, 8 to 20, 2 to 10, 2 to 8, 2 to 6, or 2 to 4 membered), $R^{102A}$-substituted or unsubstituted cycloalkyl (e.g., $C_3$-$C_8$, $C_3$-$C_6$, or $C_5$-$C_6$), $R^{102A}$-substituted or unsubstituted heterocycloalkyl (e.g., 3 to 8, 3 to 6, or 5 to 6 membered), $R^{102A}$-substituted or unsubstituted aryl (e.g., $C_6$-$C_{10}$, $C_{10}$, or phenyl), or $R^{102A}$-substituted or unsubstituted heteroaryl (e.g., 5 to 10, 5 to 9, or 5 to 6 membered).

$R^{102A}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_{20}$, C$_{10}$-C$_{20}$, C$_1$-C$_8$, C$_1$-C$_6$, or C$_1$-C$_4$), unsubstituted heteroalkyl (e.g., 2 to 20, 8 to 20, 2 to 10, 2 to 8, 2 to 6, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8, 3 to 6, or 5 to 6 membered), unsubstituted aryl (e.g., C$_6$-C$_{10}$, C$_{10}$, or phenyl), or unsubstituted heteroaryl (e.g., 5 to 10, 5 to 9, or 5 to 6 membered).

In embodiments, L$^{103}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., C$_1$-C$_{20}$, C$_{10}$-C$_{20}$, C$_1$-C$_8$, C$_1$-C$_6$, or C$_1$-C$_4$), substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), substituted or unsubstituted cycloalkylene (e.g., C$_3$-C$_8$, C$_3$-C$_6$, or C$_5$-C$_6$), substituted or unsubstituted heterocycloalkylene (e.g., 3 to 8, 3 to 6, or 5 to 6 membered), substituted or unsubstituted arylene (e.g., C$_6$-C$_{10}$, C$_{10}$, or phenylene), or substituted or unsubstituted heteroarylene (e.g., 5 to 10, 5 to 9, or 5 to 6 membered).

In embodiments, L$^{103}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, R$^{103}$-substituted or unsubstituted alkylene (e.g., C$_1$-C$_{20}$, C$_{10}$-C$_{20}$, C$_1$-C$_8$, C$_1$-C$_6$, or C$_1$-C$_4$), R$^{103}$-substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), R$^{103}$-substituted or unsubstituted cycloalkylene (e.g., C$_3$-C$_8$, C$_3$-C$_6$, or C$_5$-C$_6$), R$^{103}$-substituted or unsubstituted heterocycloalkylene (e.g., 3 to 8, 3 to 6, or 5 to 6 membered), R$^{103}$-substituted or unsubstituted arylene (e.g., C$_6$-C$_{10}$, C$_{10}$, or phenylene), or R$^{103}$-substituted or unsubstituted heteroarylene (e.g., 5 to 10, 5 to 9, or 5 to 6 membered).

R$^{103}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, R$^{103A}$-substituted or unsubstituted alkyl (e.g., C$_1$-C$_{20}$, C$_{10}$-C$_{20}$, C$_1$-C$_8$, C$_1$-C$_6$, or C$_1$-C$_4$), R$^{103A}$-substituted or unsubstituted heteroalkyl (e.g., 2 to 20, 8 to 20, 2 to 10, 2 to 8, 2 to 6, or 2 to 4 membered), R$^{103A}$-substituted or unsubstituted cycloalkyl (e.g., C$_3$-C$_8$, C$_3$-C$_6$, or C$_5$-C$_6$), R$^{103A}$-substituted or unsubstituted heterocycloalkyl (e.g., 3 to 8, 3 to 6, or 5 to 6 membered), R$^{103A}$-substituted or unsubstituted aryl (e.g., C$_6$-C$_{10}$, C$_{10}$, or phenyl), or R$^{103A}$-substituted or unsubstituted heteroaryl (e.g., 5 to 10, 5 to 9, or 5 to 6 membered).

R$^{103A}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_{20}$, C$_{10}$-C$_{20}$, C$_1$-C$_8$, C$_1$-C$_6$, or C$_1$-C$_4$), unsubstituted heteroalkyl (e.g., 2 to 20, 8 to 20, 2 to 10, 2 to 8, 2 to 6, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8, 3 to 6, or 5 to 6 membered), unsubstituted aryl (e.g., C$_6$-C$_{10}$, C$_{10}$, or phenyl), or unsubstituted heteroaryl (e.g., 5 to 10, 5 to 9, or 5 to 6 membered).

In embodiments, L$^{201}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., C$_1$-C$_{20}$, C$_{10}$-C$_{20}$, C$_1$-C$_8$, C$_1$-C$_6$, or C$_1$-C$_4$), substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), substituted or unsubstituted cycloalkylene (e.g., C$_3$-C$_8$, C$_3$-C$_6$, or C$_5$-C$_6$), substituted or unsubstituted heterocycloalkylene (e.g., 3 to 8, 3 to 6, or 5 to 6 membered), substituted or unsubstituted arylene (e.g., C$_6$-C$_{10}$, C$_{10}$, or phenylene), or substituted or unsubstituted heteroarylene (e.g., 5 to 10, 5 to 9, or 5 to 6 membered).

In embodiments, L$^{201}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, R$^{201}$-substituted or unsubstituted alkylene (e.g., C$_1$-C$_{20}$, C$_{10}$-C$_{20}$, C$_1$-C$_8$, C$_1$-C$_6$, or C$_1$-C$_4$), R$^{201}$-substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), R$^{201}$-substituted or unsubstituted cycloalkylene (e.g., C$_3$-C$_8$, C$_3$-C$_6$, or C$_5$-C$_6$), R$^{201}$-substituted or unsubstituted heterocycloalkylene (e.g., 3 to 8, 3 to 6, or 5 to 6 membered), R$^{201}$-substituted or unsubstituted arylene (e.g., C$_6$-C$_{10}$, C$_{10}$, or phenylene), or R$^{201}$-substituted or unsubstituted heteroarylene (e.g., 5 to 10, 5 to 9, or 5 to 6 membered).

R$^{201}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, R$^{201A}$-substituted or unsubstituted alkyl (e.g., C$_1$-C$_{20}$, C$_{10}$-C$_{20}$, C$_1$-C$_8$, C$_1$-C$_6$, or C$_1$-C$_4$), R$^{201A}$-substituted or unsubstituted heteroalkyl (e.g., 2 to 20, 8 to 20, 2 to 10, 2 to 8, 2 to 6, or 2 to 4 membered), R$^{201A}$-substituted or unsubstituted cycloalkyl (e.g., C$_3$-C$_8$, C$_3$-C$_6$, or C$_5$-C$_6$), R$^{201A}$-substituted or unsubstituted heterocycloalkyl (e.g., 3 to 8, 3 to 6, or 5 to 6 membered), R$^{201A}$-substituted or unsubstituted aryl (e.g., C$_6$-C$_{10}$, C$_{10}$, or phenyl), or R$^{201A}$-substituted or unsubstituted heteroaryl (e.g., 5 to 10, 5 to 9, or 5 to 6 membered).

R$^{201A}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_{20}$, C$_{10}$-C$_{20}$, C$_1$-C$_8$, C$_1$-C$_6$, or C$_1$-C$_4$), unsubstituted heteroalkyl (e.g., 2 to 20, 8 to 20, 2 to 10, 2 to 8, 2 to 6, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8, 3 to 6, or 5 to 6 membered), unsubstituted aryl (e.g., C$_6$-C$_{10}$, C$_{10}$, or phenyl), or unsubstituted heteroaryl (e.g., 5 to 10, 5 to 9, or 5 to 6 membered).

In embodiments, L$^{202}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., C$_1$-C$_{20}$, C$_{10}$-C$_{20}$, C$_1$-C$_8$, C$_1$-C$_6$, or C$_1$-C$_4$), substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), substituted or unsubstituted cycloalkylene (e.g., C$_3$-C$_8$, C$_3$-C$_6$, or C$_5$-C$_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{202}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, $R^{202}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{202}$-substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), $R^{202}$-substituted or unsubstituted cycloalkylene (e.g., $C_3$-$C_8$, $C_3$-$C_6$, or $C_5$-$C_6$), $R^{202}$-substituted or unsubstituted heterocycloalkylene (e.g., 3 to 8, 3 to 6, or 5 to 6 membered), $R^{202}$-substituted or unsubstituted arylene (e.g., $C_6$-$C_{10}$, $C_{10}$, or phenylene), or $R^{202}$-substituted or unsubstituted heteroarylene (e.g., 5 to 10, 5 to 9, or 5 to 6 membered).

$R^{202}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{202A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{202A}$-substituted or unsubstituted heteroalkyl (e.g., 2 to 20, 8 to 20, 2 to 10, 2 to 8, 2 to 6, or 2 to 4 membered), $R^{202A}$-substituted or unsubstituted cycloalkyl (e.g., $C_3$-$C_8$, $C_3$-$C_6$, or $C_5$-$C_6$), $R^{202A}$-substituted or unsubstituted heterocycloalkyl (e.g., 3 to 8, 3 to 6, or 5 to 6 membered), $R^{202A}$-substituted or unsubstituted aryl (e.g., $C_6$-$C_{10}$, $C_{10}$, or phenyl), or $R^{202A}$-substituted or unsubstituted heteroaryl (e.g., 5 to 10, 5 to 9, or 5 to 6 membered).

$R^{202A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{203}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_{20}$, $C_{10}$-$C_{20}$, $C_1$-$C_5$, $C_1$-$C_6$, or $C_1$-$C_4$), substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{203}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, $R^{203}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{203}$-substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), $R^{203}$-substituted or unsubstituted cycloalkylene (e.g., $C_3$-$C_8$, $C_3$-$C_6$, or $C_5$-$C_6$), $R^{203}$-substituted or unsubstituted heterocycloalkylene (e.g., 3 to 8, 3 to 6, or 5 to 6 membered), $R^{203}$-substituted or unsubstituted arylene (e.g., $C_6$-$C_{10}$, $C_{10}$, or phenylene), or $R^{203}$-substituted or unsubstituted heteroarylene (e.g., 5 to 10, 5 to 9, or 5 to 6 membered).

$R^{203}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{203A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{203A}$-substituted or unsubstituted heteroalkyl (e.g., 2 to 20, 8 to 20, 2 to 10, 2 to 8, 2 to 6, or 2 to 4 membered), $R^{203A}$-substituted or unsubstituted cycloalkyl (e.g., $C_3$-$C_8$, $C_3$-$C_6$, or $C_5$-$C_6$), $R^{203A}$-substituted or unsubstituted heterocycloalkyl (e.g., 3 to 8, 3 to 6, or 5 to 6 membered), $R^{203A}$-substituted or unsubstituted aryl (e.g., $C_6$-$C_{10}$, $C_{10}$, or phenyl), or $R^{203A}$-substituted or unsubstituted heteroaryl (e.g., 5 to 10, 5 to 9, or 5 to 6 membered).

$R^{203A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{101}$, $L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{101}$, $L^{201}$, $L^{202}$, and $L^{203}$ are independently —C(O)NH— or NHC(O)—.

In embodiments, $L^{101}$ is a substituted or unsubstituted $C_1$-$C_4$ alkylene or substituted or unsubstituted 8 to 20 membered heteroalkylene. In embodiments, $L^{101}$ is a substituted or unsubstituted $C_2$-$C_4$ alkynylene. In embodiments, $L^{101}$ is

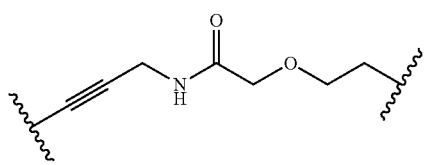

In embodiments, L¹⁰¹ is
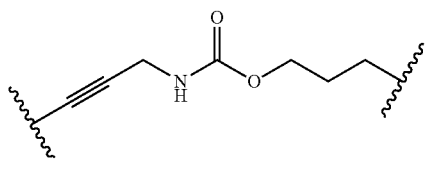
In embodiments, L¹⁰¹ is
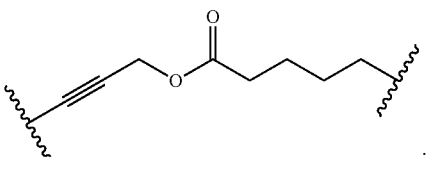
In embodiments, L¹⁰¹ is
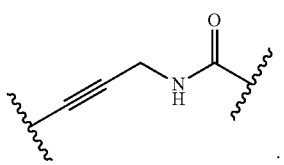 [SMILES: *C#CCNC(*)=O]
In embodiments, L¹⁰¹ is
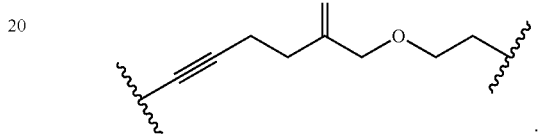
In embodiments, L¹⁰¹ is
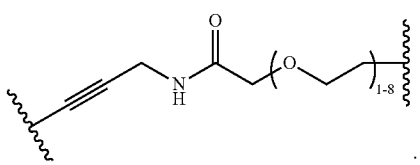
In embodiments, L¹⁰¹ is
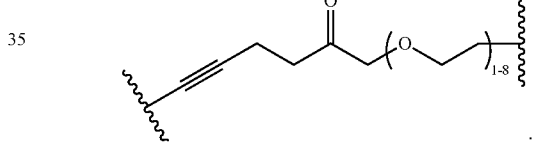
In embodiments, L¹⁰¹ is
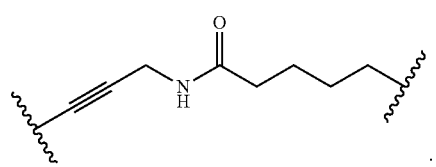
In embodiments, L¹⁰¹ is
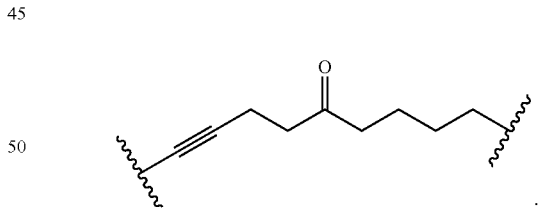
In embodiments, L¹⁰¹ is
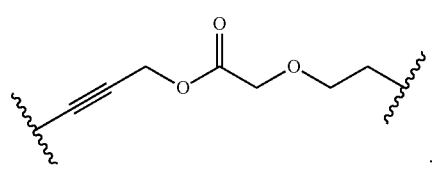
In embodiments, L¹⁰¹ is
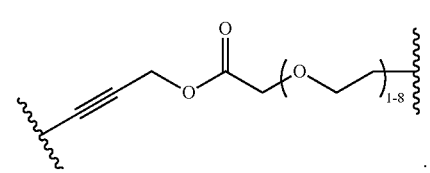
In embodiments, L¹⁰⁰ is
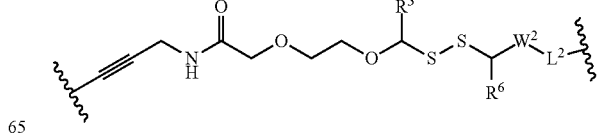

In embodiments, $L^{100}$ is:
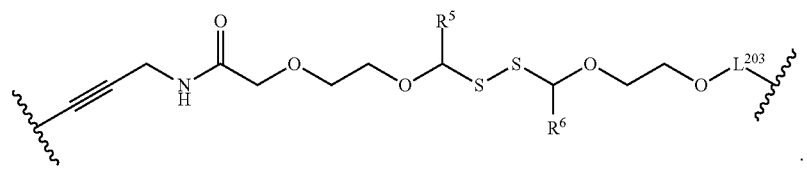
In embodiments, $L^{100}$ is:
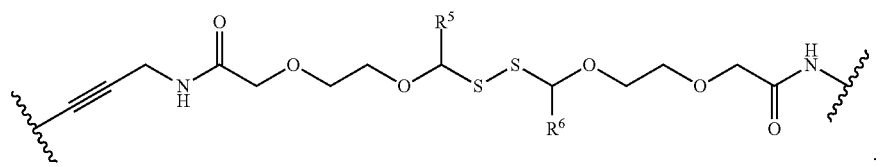
In embodiments, $L^{100}$ is
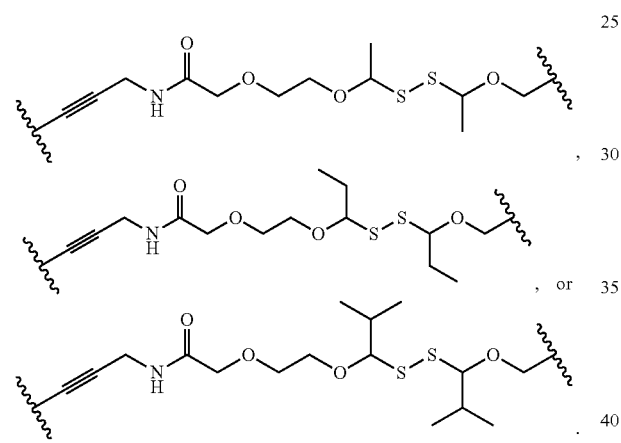
In embodiments, $L^{100}$ is:
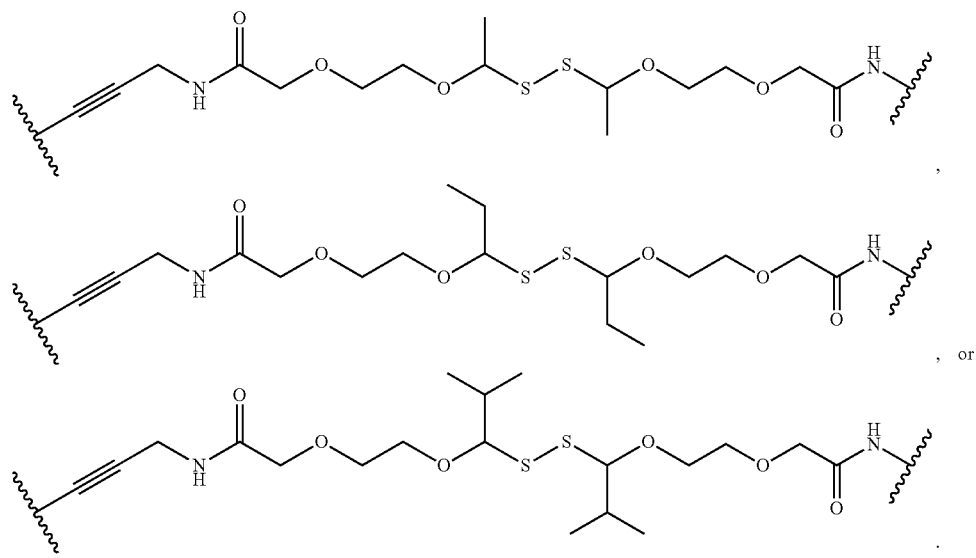

In embodiments $L^{100}$ is
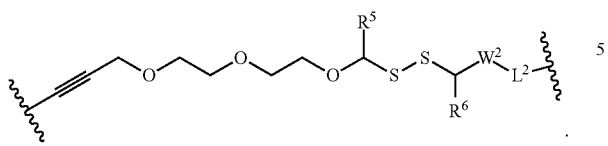
In embodiments, $L^{100}$ is:
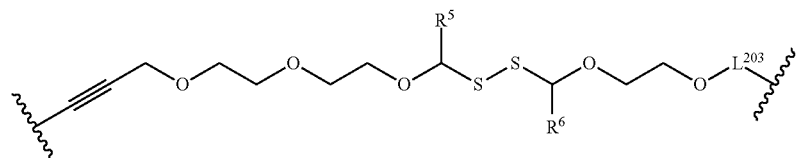
In embodiments, $L^{100}$ is:
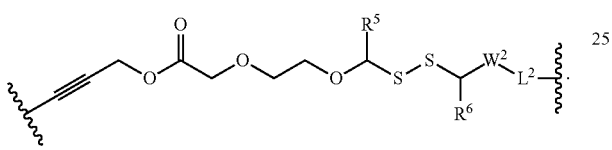
In embodiments, $L^{100}$ is:
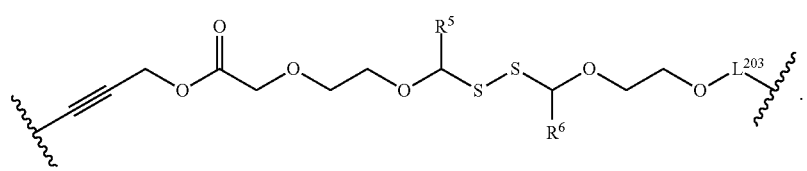
In embodiments, $L^{100}$ is:
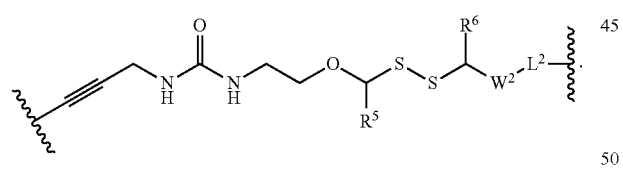
In embodiments $L^{100}$ is:
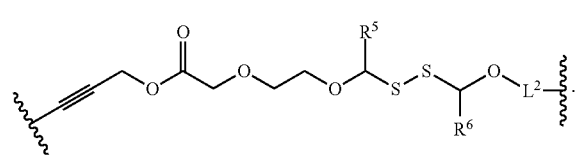
In embodiments, $L^{100}$ is:
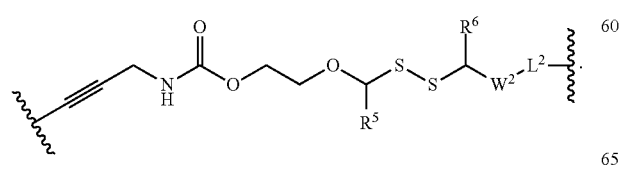
In embodiments, $L^{100}$ is:

In embodiments, L$^{100}$ is:
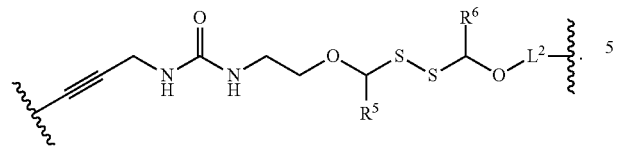
In embodiments, L$^{100}$ is:
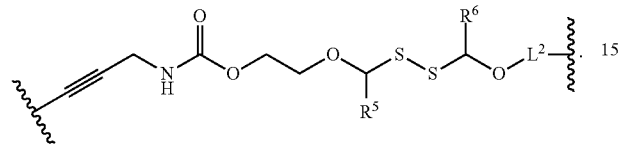
In embodiments, L$^{100}$ is:
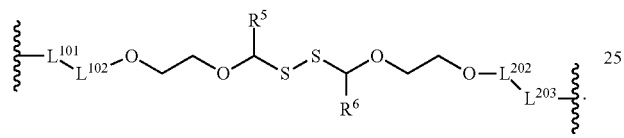
In embodiments, L$^{100}$ is:
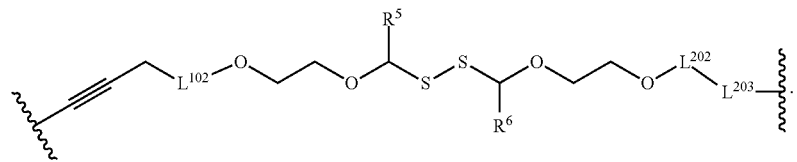
In embodiments, the compound is
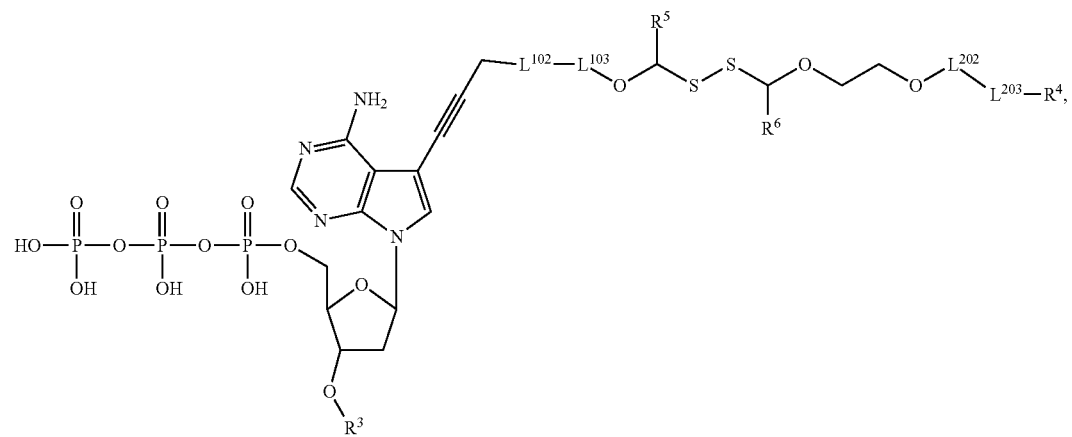

-continued
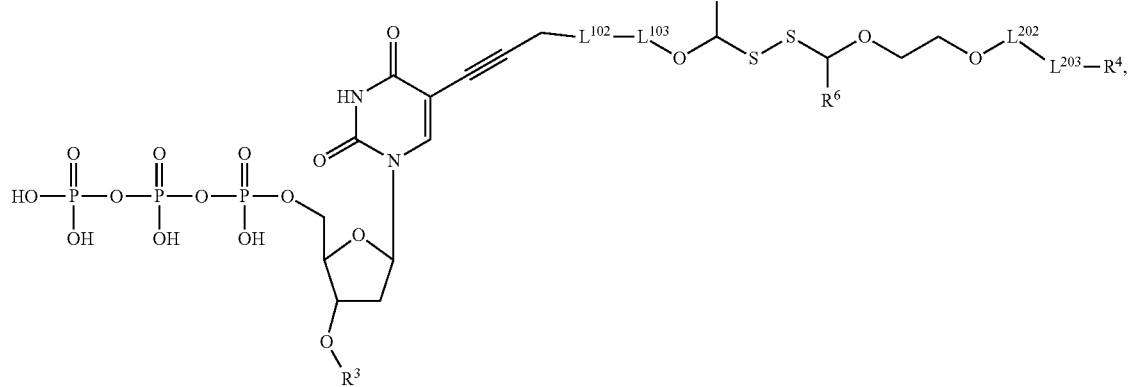
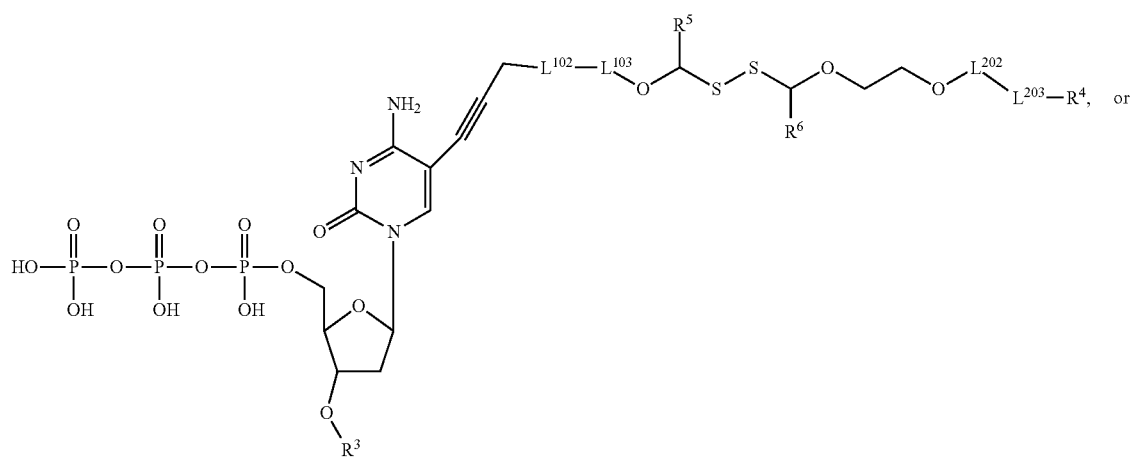 or
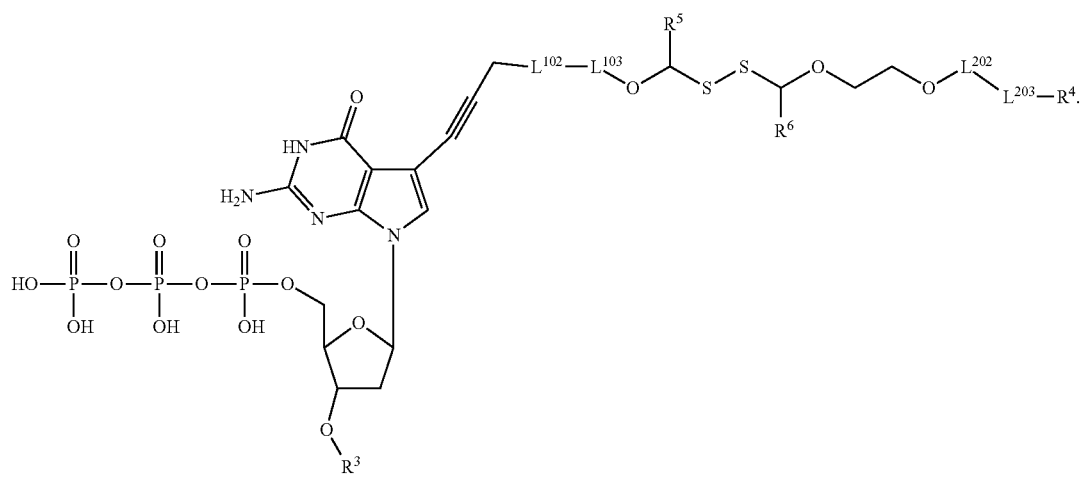

In embodiments, the compound is
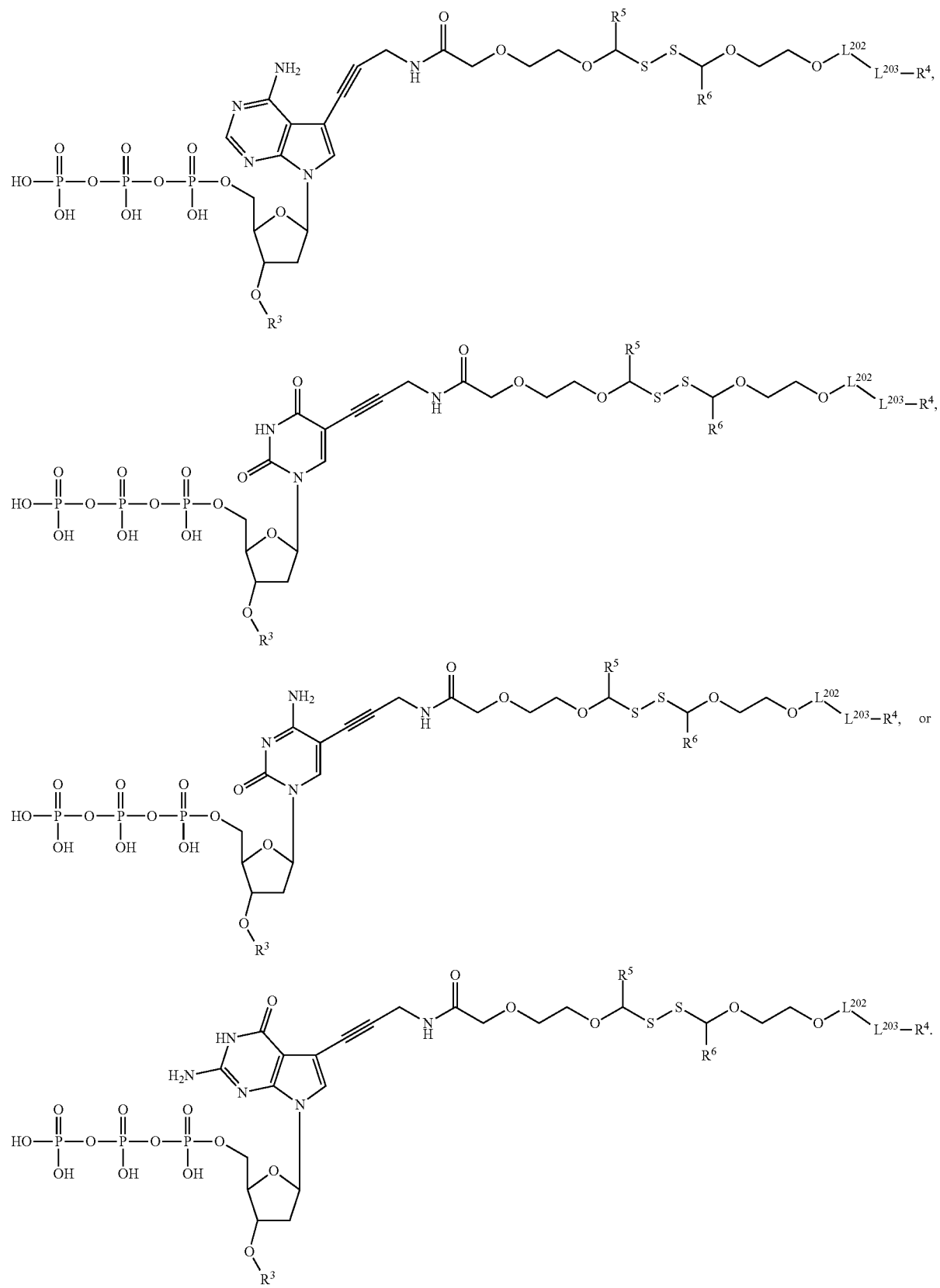

In embodiments, $R^5$ and $R^6$ are unsubstituted alkyl. In embodiments, $R^5$ and $R^6$ are unsubstituted cyclopropyl. In embodiments, $R^3$ is
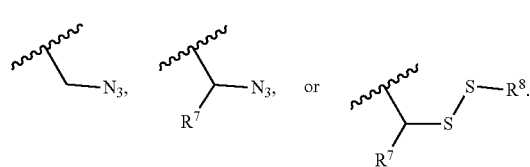
In embodiments, the compound is
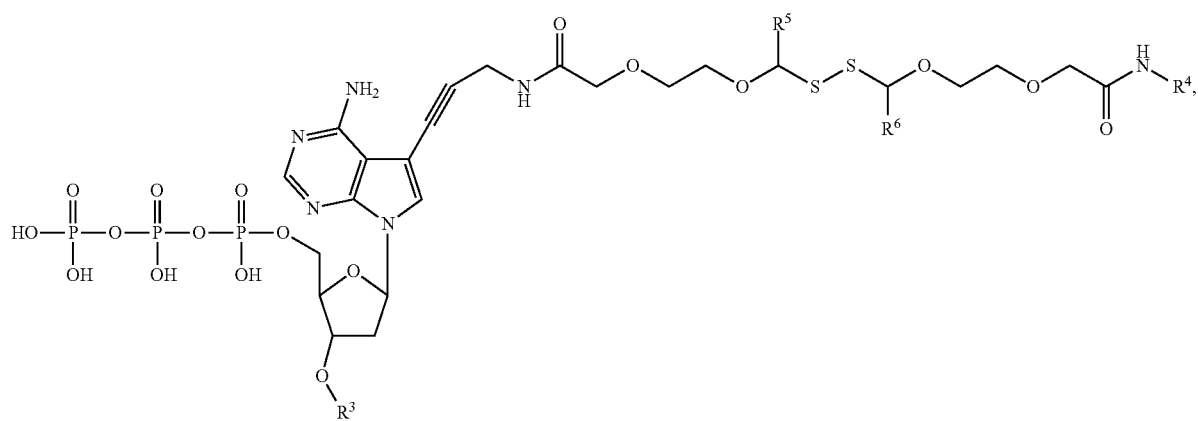
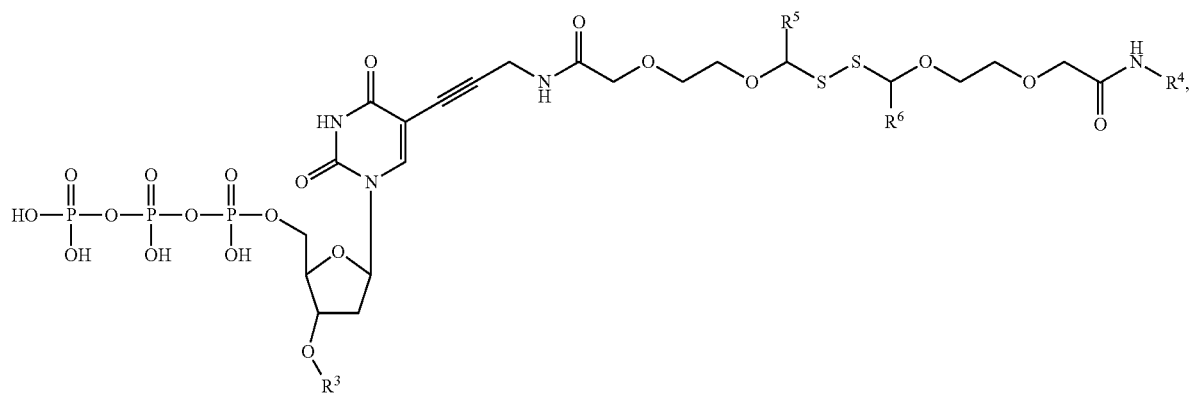
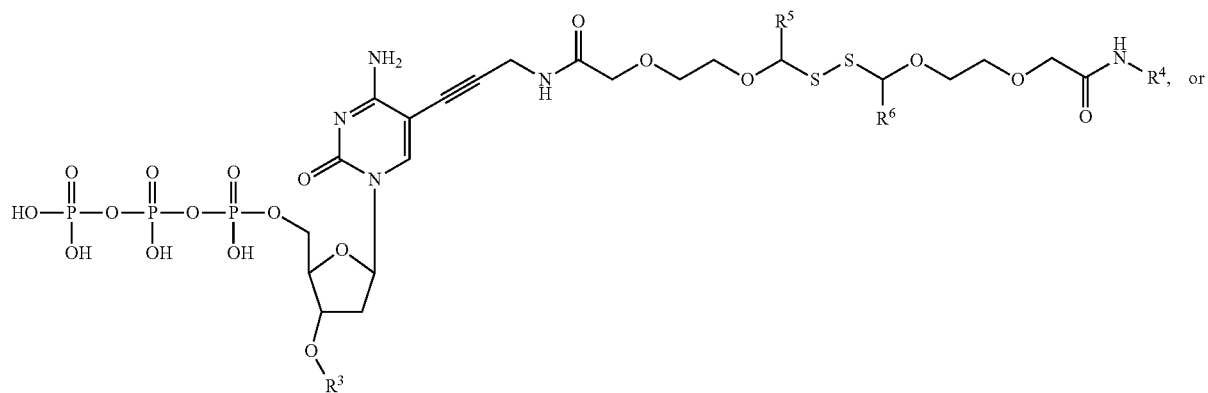

-continued

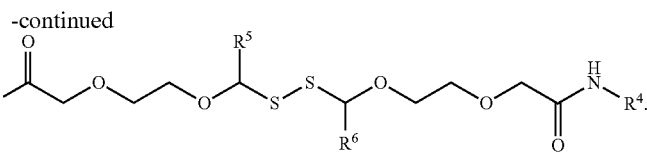
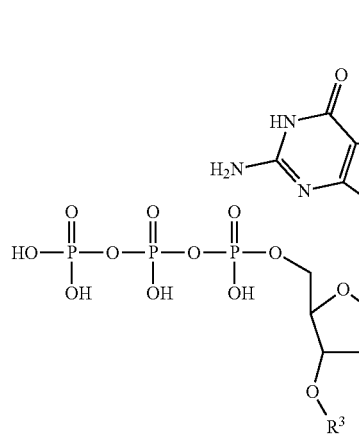

In embodiments, $R^5$ and $R^6$ are unsubstituted alkyl. In embodiments, $R^5$ and $R^6$ are methyl. In embodiments, $R^5$ and $R^6$ are ethyl. In embodiments, $R^5$ and $R^6$ are isopropyl or n-propyl. In embodiments, $R^5$ and $R^6$ are unsubstituted cyclopropyl. In embodiments, $R^3$ is

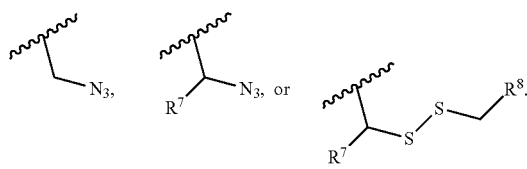

In embodiments, the polymerase-compatible cleavable moiety is

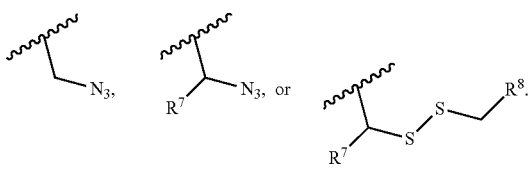

In embodiments, $R^3$ is

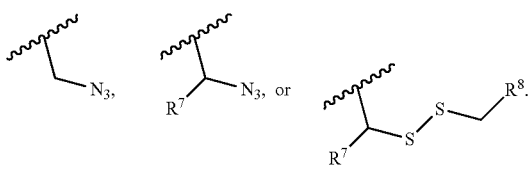

$R^7$ is hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^8$ is substituted or unsubstituted alkyl.

In embodiments, $R^7$ is hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 3 to 8 membered, 3 to 6 membered, 4 to 6 membered, 4 to 5 membered, or 5 to 6 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$, $C_{10}$, or phenyl), substituted or unsubstituted heteroaryl (e.g., 5 to 10, 5 to 9, or 5 to 6 membered).

In embodiments, $R^7$ is unsubstituted $C_1$-$C_6$ or unsubstituted $C_1$-$C_4$ alkyl. In embodiments, $R^7$ is unsubstituted $C_1$-$C_4$ alkyl. In embodiments, $R^7$ is unsubstituted $C_1$-$C_6$ alkyl. In embodiments, $R^7$ is unsubstituted methyl. In embodiments, $R^7$ is unsubstituted $C_2$ alkyl. In embodiments, $R^7$ is unsubstituted $C_3$ alkyl. In embodiments, $R^7$ is unsubstituted $C_4$ alkyl. In embodiments, $R^7$ is unsubstituted $C_5$ alkyl. In embodiments, $R^7$ is unsubstituted $C_6$ alkyl.

In embodiments, $R^7$ is substituted or unsubstituted heteroalkyl (e.g., 3 to 8 membered, 3 to 6 membered, 4 to 6 membered, 4 to 5 membered, or 5 to 6 membered). In embodiments, $R^7$ is substituted heteroalkyl (e.g., 3 to 8 membered, 3 to 6 membered, 4 to 6 membered, 4 to 5 membered, or 5 to 6 membered). In embodiments, $R^7$ is an unsubstituted heteroalkyl (e.g., 3 to 8 membered, 3 to 6 membered, 4 to 6 membered, 4 to 5 membered, or 5 to 6 membered).

In embodiments, $R^7$ is substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^7$ is substituted or unsubstituted cycloalkyl (e.g., $C_3$-$C_8$, $C_3$-$C_6$, $C_4$-$C_6$, or $C_5$-$C_6$). In embodiments, $R^7$ is substituted cycloalkyl (e.g., $C_3$-$C_8$, $C_3$-$C_6$, $C_4$-$C_6$, or $C_5$-$C_6$). In embodiments, $R^7$ is an unsubstituted cycloalkyl (e.g., $C_3$-$C_8$, $C_3$-$C_6$, $C_4$-$C_6$, or $C_5$-$C_6$). In embodiments, $R^7$ is substituted or unsubstituted heterocycloalkyl (e.g., 3 to 8 membered, 3 to 6 membered, 4 to 6 membered, 4 to 5 membered, or 5 to 6 membered). In embodiments, $R^7$ is substituted heterocycloalkyl (e.g., 3 to 8 membered, 3 to 6 membered, 4 to 6 membered, 4 to 5 membered, or 5 to 6 membered). In embodiments, $R^7$ is an unsubstituted heterocycloalkyl (e.g., 3 to 8 membered, 3 to 6 membered, 4 to 6 membered, 4 to 5 membered, or 5 to 6 membered).

In embodiments, $R^7$ is unsubstituted cycloalkyl (e.g., $C_3$-$C_8$, $C_3$-$C_6$, $C_4$-$C_6$, or $C_5$-$C_6$). In embodiments, $R^7$ is unsubstituted $C_3$-$C_8$ cycloalkyl. In embodiments, $R^7$ is unsubstituted $C_3$-$C_6$ cycloalkyl. In embodiments, $R^7$ is unsubstituted $C_4$-$C_6$ cycloalkyl. In embodiments, $R^7$ is unsubstituted $C_5$-$C_6$ cycloalkyl. In embodiments, $R^7$ is unsubstituted cyclopropyl. In embodiments, $R^7$ is unsubstituted cyclobutyl. In embodiments, $R^7$ is unsubstituted cyclopentyl. In embodiments, $R^7$ is unsubstituted cyclohexyl. In embodiments, $R^7$ is unsubstituted cycloheptyl. In embodiments, $R^7$ is unsubstituted cyclooctyl.

In embodiments, $R^7$ is substituted cycloalkyl (e.g., $C_3$-$C_8$, $C_3$-$C_6$, $C_4$-$C_6$, or $C_5$-$C_6$). In embodiments, $R^7$ is substituted $C_3$-$C_8$ cycloalkyl. In embodiments, $R^7$ is substituted $C_3$-$C_6$ cycloalkyl. In embodiments, $R^7$ is substituted $C_4$-$C_6$ cycloalkyl. In embodiments, $R^7$ is substituted $C_5$-$C_6$ cycloalkyl. In embodiments, $R^7$ is substituted cyclopropyl. In embodiments, $R^7$ is substituted cyclobutyl. In embodiments, $R^7$ is substituted cyclopentyl. In embodiments, $R^7$ is substituted cyclohexyl. In embodiments, $R^7$ is substituted cycloheptyl. In embodiments, $R^7$ is substituted cyclooctyl.

In embodiments, $R^7$ is substituted or unsubstituted heterocycloalkyl (e.g., 3 to 8 membered, 3 to 6 membered, 4 to 6 membered, 4 to 5 membered, or 5 to 6 membered). In embodiments, $R^7$ is substituted heterocycloalkyl (e.g., 3 to 8 membered, 3 to 6 membered, 4 to 6 membered, 4 to 5 membered, or 5 to 6 membered). In embodiments, $R^7$ is an unsubstituted heterocycloalkyl (e.g., 3 to 8 membered, 3 to 6 membered, 4 to 6 membered, 4 to 5 membered, or 5 to 6 membered).

In embodiments, $R^7$ is unsubstituted 3 to 8 membered heterocycloalkyl. In embodiments, $R^7$ is unsubstituted 3 to 6 membered heterocycloalkyl. In embodiments, $R^7$ is unsubstituted 4 to 6 membered heterocycloalkyl. In embodiments, $R^7$ is unsubstituted 4 to 5 membered heterocycloalkyl. In embodiments, $R^7$ is unsubstituted 5 to 6 membered heterocycloalkyl. In embodiments, $R^7$ is a substituted 3 to 8 membered heterocycloalkyl. In embodiments, $R^7$ is a substituted 3 to 6 membered heterocycloalkyl. In embodiments, $R^7$ is a substituted 4 to 6 membered heterocycloalkyl. In embodiments, $R^7$ is a substituted 4 to 5 membered heterocycloalkyl. In embodiments, $R^7$ is a substituted 5 to 6 membered heterocycloalkyl.

In embodiments, $R^7$ is substituted or unsubstituted aryl (e.g., $C_6$-$C_{10}$, $C_{10}$, or phenyl). In embodiments, $R^7$ is substituted aryl (e.g., $C_6$-$C_{10}$, $C_{10}$, or phenyl). In embodiments, $R^7$ is unsubstituted aryl (e.g., $C_6$-$C_{10}$, $C_{10}$, or phenyl). In embodiments, $R^7$ is unsubstituted phenyl. In embodiments, $R^7$ is substituted or unsubstituted heteroaryl (e.g., 5 to 10, 5 to 9, or 5 to 6 membered). In embodiments, $R^7$ is substituted heteroaryl (e.g., 5 to 10, 5 to 9, or 5 to 6 membered). In embodiments, $R^7$ is unsubstituted heteroaryl (e.g., 5 to 10, 5 to 9, or 5 to 6 membered). In embodiments, $R^7$ is a substituted 5 membered heteroaryl. In embodiments, $R^7$ is a substituted or unsubstituted 6 membered heteroaryl. In embodiments, $R^7$ is a substituted or unsubstituted 7 membered heteroaryl. In embodiments, $R^7$ is an unsubstituted 5 membered heteroaryl. In embodiments, $R^7$ is an unsubstituted 6 membered heteroaryl. In embodiments, $R^7$ is an unsubstituted 7 membered heteroaryl.

In embodiments, $R^7$ is $R^{7A}$-substituted or unsubstituted alkyl, $R^{7A}$-substituted or unsubstituted heteroalkyl, $R^{7A}$-substituted or unsubstituted cycloalkyl, $R^{7A}$-substituted or unsubstituted heterocycloalkyl, $R^{7A}$-substituted or unsubstituted aryl, $R^{7A}$-substituted or unsubstituted heteroaryl.

In embodiments, $R^7$ is $R^{7A}$-substituted or unsubstituted aryl (e.g., $C_6$-$C_{10}$, $C_{10}$, or phenyl), or $R^{7A}$-substituted or unsubstituted heteroaryl (e.g., 5 to 10, 5 to 9, or 5 to 6 membered). $R^{7A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NH_4NH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$OPO_3H$, $R^{7B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{7B}$-substituted or unsubstituted heteroalkyl (e.g., 2 to 20, 8 to 20, 2 to 10, 2 to 8, 2 to 6, or 2 to 4 membered), $R^{7B}$-substituted or unsubstituted cycloalkyl (e.g., $C_3$-$C_8$, $C_3$-$C_6$, or $C_5$-$C_6$), $R^{7B}$-substituted or unsubstituted heterocycloalkyl (e.g., 3 to 8, 3 to 6, or 5 to 6 membered), $R^{7B}$-substituted or unsubstituted aryl (e.g., $C_6$-$C_{10}$, $C_{10}$, or phenyl), or $R^{7B}$-substituted or unsubstituted heteroaryl (e.g., 5 to 10, 5 to 9, or 5 to 6 membered). In embodiments, $R^{7A}$ is independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, or —$OPO_3H$. $R^{7B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{7C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{7C}$-substituted or unsubstituted heteroalkyl (e.g., 2 to 20, 8 to 20, 2 to 10, 2 to 8, 2 to 6, or 2 to 4 membered), $R^{7C}$-substituted or unsubstituted cycloalkyl (e.g., $C_3$-$C_8$, $C_3$-$C_6$, or $C_5$-$C_6$), $R^{7C}$-substituted or unsubstituted heterocycloalkyl (e.g., 3 to 8, 3 to 6, or 5 to 6 membered), $R^{7C}$-substituted or unsubstituted aryl (e.g., $C_6$-$C_{10}$, $C_{10}$, or phenyl), or $R^{7C}$-substituted or unsubstituted heteroaryl (e.g., 5 to 10, 5 to 9, or 5 to 6 membered). $R^{7C}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NH—$NH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., C$_1$-C$_{20}$, C$_{10}$-C$_{20}$, C$_1$-C$_8$, C$_1$-C$_6$, or C$_1$-C$_4$), unsubstituted heteroalkyl (e.g., 2 to 20, 8 to 20, 2 to 10, 2 to 8, 2 to 6, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8, 3 to 6, or 5 to 6 membered), unsubstituted aryl (e.g., C$_6$-C$_{10}$, C$_{10}$, or phenyl), or unsubstituted heteroaryl (e.g., 5 to 10, 5 to 9, or 5 to 6 membered).

In embodiments, R$^7$ is R$^{7A}$-substituted cycloalkyl (e.g., C$_3$-C$_8$, C$_3$-C$_6$, C$_4$-C$_6$, or C$_5$-C$_6$). In embodiments, R$^7$ is R$^{7A}$-substituted heterocycloalkyl (e.g., 3 to 8 membered, 3 to 6 membered, 4 to 6 membered, 4 to 5 membered, or 5 to 6 membered). In embodiments, R$^{7A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —OPO$_3$H, R$^{7B}$-substituted or unsubstituted alkyl (e.g., C$_1$-C$_{20}$, C$_{10}$-C$_{20}$, C$_1$-C$_8$, C$_1$-C$_6$, or C$_1$-C$_4$), R$^{7B}$-substituted or unsubstituted heteroalkyl (e.g., 2 to 20, 8 to 20, 2 to 10, 2 to 8, 2 to 6, or 2 to 4 membered), R$^{7B}$-substituted or unsubstituted cycloalkyl (e.g., C$_3$-C$_8$, C$_3$-C$_6$, or C$_5$-C$_6$), R$^{7B}$-substituted or unsubstituted heterocycloalkyl (e.g., 3 to 8, 3 to 6, or 5 to 6 membered), R$^{7B}$-substituted or unsubstituted aryl (e.g., C$_6$-C$_{10}$, C$_{10}$, or phenyl), or R$^{7B}$-substituted or unsubstituted heteroaryl (e.g., 5 to 10, 5 to 9, or 5 to 6 membered).

In embodiments, R$^7$ is R$^{7A}$-substituted cycloalkyl (e.g., C$_3$-C$_8$, C$_3$-C$_6$, C$_4$-C$_6$, or C$_5$-C$_6$). In embodiments, R$^7$ is R$^{7A}$-substituted C$_3$-C$_8$ cycloalkyl. In embodiments, R$^7$ is R$^{7A}$-substituted C$_3$-C$_6$ cycloalkyl. In embodiments, R$^7$ is R$^{7A}$-substituted C$_4$-C$_6$ cycloalkyl. In embodiments, R$^7$ is R$^{7A}$-substituted C$_5$-C$_6$ cycloalkyl. In embodiments, R$^7$ is R$^{7A}$-substituted cyclopropyl. In embodiments, R$^7$ is R$^{7A}$-substituted cyclobutyl. In embodiments, R$^7$ is R$^{7A}$-substituted cyclopentyl. In embodiments, R$^7$ is R$^{7A}$-substituted cyclohexyl. In embodiments, R$^7$ is R$^{7A}$-substituted cycloheptyl. In embodiments, R$^7$ is R$^{7A}$-substituted cyclooctyl.

In embodiments, R$^8$ is substituted or unsubstituted alkyl (e.g., C$_1$-C$_{20}$, C$_{10}$-C$_{20}$, C$_1$-C$_8$, C$_1$-C$_6$, or C$_1$-C$_4$). In embodiments, R$^8$ is R$^{8A}$-substituted alkyl. In embodiments, R$^8$ is RBA-substituted C$_1$-C$_6$ or R$^{8A}$-substituted C$_1$-C$_4$ alkyl. In embodiments, R$^8$ is RBA-substituted C$_1$-C$_4$ alkyl. In embodiments, R$^8$ is RBA-substituted C$_1$-C$_6$ alkyl. In embodiments, R$^8$ is RBA-substituted methyl. In embodiments, R$^8$ is RBA-substituted C$_2$ alkyl. In embodiments, R$^8$ is RBA-substituted C$_3$ alkyl. In embodiments, R$^8$ is R$^{8A}$-substituted C$_4$ alkyl. In embodiments, R$^8$ is RBA-substituted C$_5$ alkyl. In embodiments, R$^8$ is R$^{8A}$-substituted C$_6$ alkyl. R$^{8A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., C$_1$-C$_{20}$, C$_{10}$-C$_{20}$, C$_1$-C$_8$, C$_1$-C$_6$, or C$_1$-C$_4$), unsubstituted heteroalkyl (e.g., 2 to 20, 8 to 20, 2 to 10, 2 to 8, 2 to 6, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8, 3 to 6, or 5 to 6 membered), unsubstituted aryl (e.g., C$_6$-C$_{10}$, C$_{10}$, or phenyl), or unsubstituted heteroaryl (e.g., 5 to 10, 5 to 9, or 5 to 6 membered).

In embodiments, R$^8$ is unsubstituted C$_1$-C$_6$ or unsubstituted C$_1$-C$_4$ alkyl. In embodiments, R$^8$ is unsubstituted C$_1$-C$_4$ alkyl. In embodiments, R$^8$ is unsubstituted C$_1$-C$_6$ alkyl. In embodiments, R$^8$ is unsubstituted methyl. In embodiments, R$^8$ is unsubstituted C$_2$ alkyl. In embodiments, R$^8$ is unsubstituted C$_3$ alkyl. In embodiments, R$^8$ is unsubstituted C$_4$ alkyl. In embodiments, R$^8$ is unsubstituted C$_5$ alkyl. In embodiments, R$^8$ is unsubstituted C$_6$ alkyl.

In embodiments, R$^8$ is unsubstituted C$_1$-C$_6$ or unsubstituted C$_1$-C$_4$ saturated alkyl. In embodiments, R$^8$ is unsubstituted C$_1$-C$_4$ saturated alkyl. In embodiments, R$^8$ is unsubstituted C$_1$-C$_6$ saturated alkyl. In embodiments, R$^8$ is unsubstituted methyl. In embodiments, R$^8$ is unsubstituted C$_2$ saturated alkyl. In embodiments, R$^8$ is unsubstituted C$_3$ saturated alkyl. In embodiments, R$^8$ is unsubstituted C$_4$ saturated alkyl. In embodiments, R$^8$ is unsubstituted C$_5$ saturated alkyl. In embodiments, R$^8$ is unsubstituted C$_6$ saturated alkyl.

In embodiments, the polymerase-compatible cleavable moiety is independently:

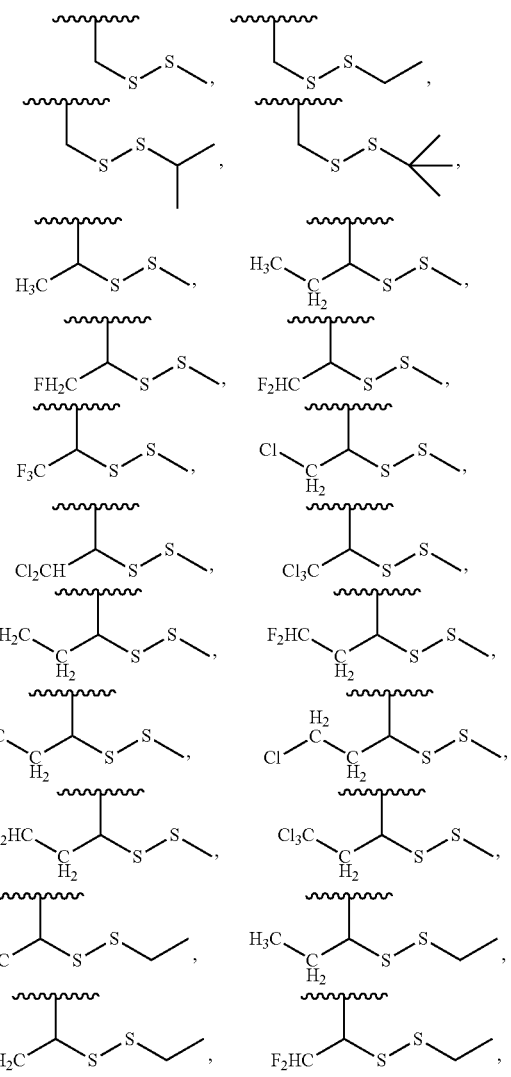

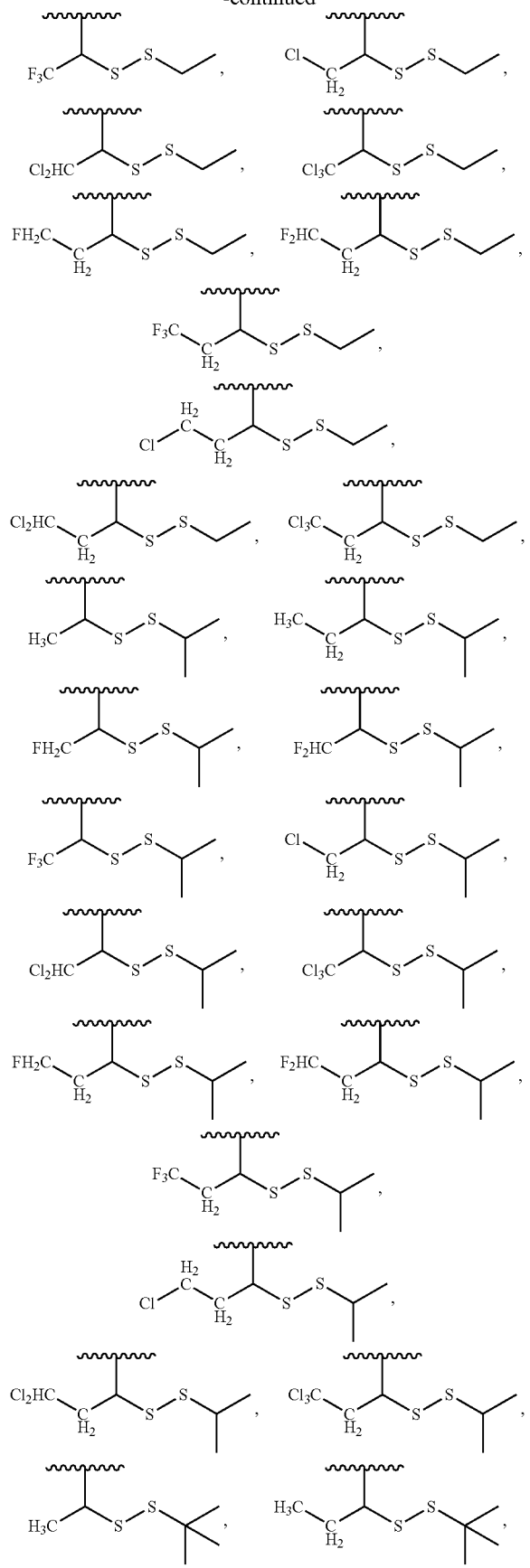
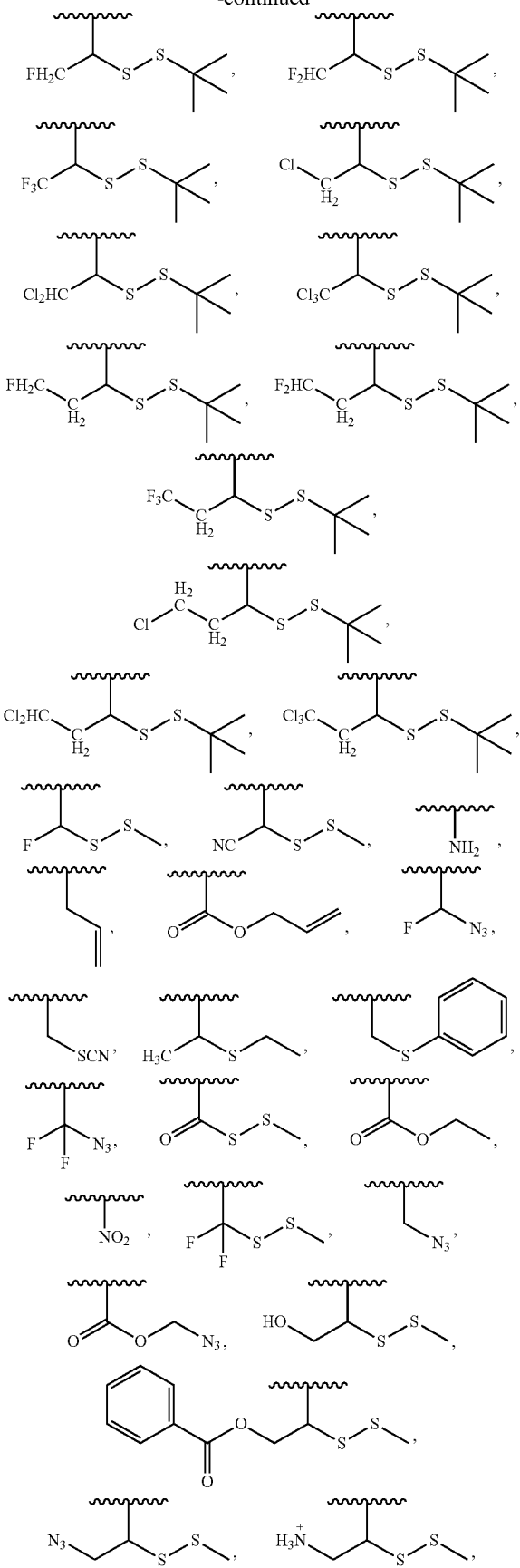

-continued
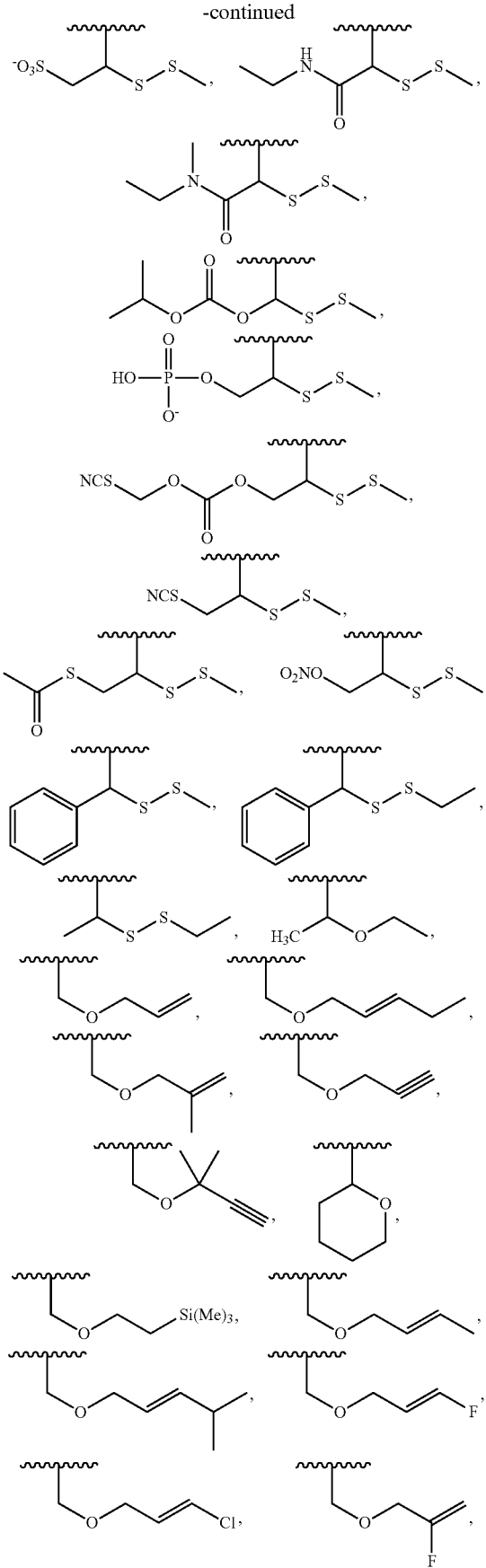
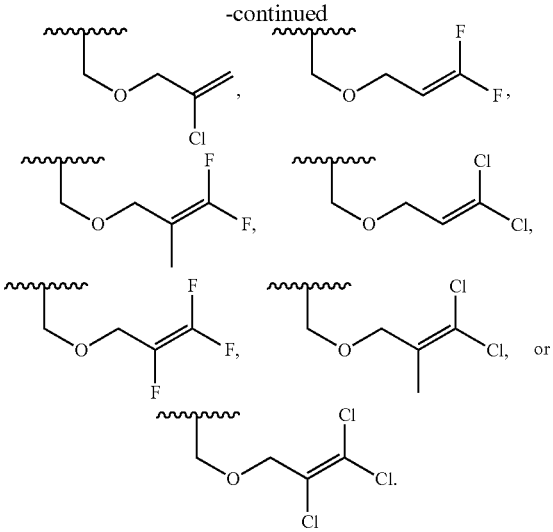
In embodiments, the polymerase-compatible cleavable moiety is
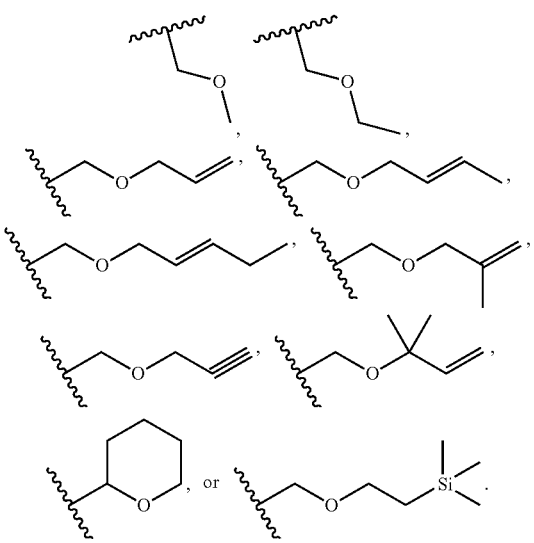
In embodiments, the polymerase-compatible cleavable moiety is
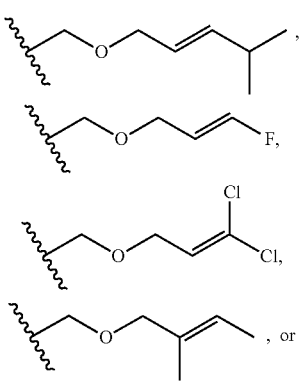

-continued

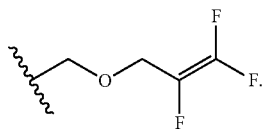

In embodiments, R⁴ is a detectable moiety. In embodiments, R⁴ is a fluorescent dye moiety. In embodiments, R⁴ is a detectable moiety described herein (e.g., a dye identified within Table 1). In embodiments, R⁴ is a detectable moiety described in Table 1. In embodiments, R4 is a monovalent Bodipy© 493/503, monovalent aminomethylcoumarin (AMCA), monovalent ANT, monovalent MANT, monovalent AmNS, monovalent 7-diethylaminocoumarin-3-carboxylic acid (DEAC), monovalent ATTO 390, monovalent Alexa Fluor© 350, monovalent Marina Blue, monovalent Cascade Blue, or monovalent Pacific Blue. In embodiments, the R⁴ is a fluorescent molecule (e.g., acridine dye, cyanine, dye, fluorine dye, oxazine dye, phenanthridine dye, or rhodamine dye).

In embodiments, R⁴ is a fluorescent dye moiety wherein the maximum emission of the fluorescent dye moiety is greater than about 530, 540, or 550 nm. In embodiments, R⁴ is a fluorescent dye moiety wherein the maximum emission of the fluorescent dye moiety is greater than 530 nm. In embodiments, R⁴ is a fluorescent dye moiety wherein the maximum emission of the fluorescent dye moiety is less than about 700, 690, or 680 nm. In embodiments, R⁴ is a fluorescent dye moiety wherein the maximum emission of the fluorescent dye moiety is less than 680 nm. In embodiments, R⁴ is a fluorescent dye moiety wherein the maximum emission of the fluorescent dye moiety is greater than about 530 and less than about 680 nm. In embodiments, R⁴ is a fluorescent dye moiety wherein the maximum emission of the fluorescent dye moiety is greater than 530 and less than 680 nm. For example, R⁴ may be any fluorescent moiety described in US Publication 2020/0216682, which is incorporated herein by reference.

TABLE 1

Detectable moieties to be used in selected embodiments.

| Nucleoside/nucleotide abbreviation | Dye name | λmax (nm) |
| --- | --- | --- |
| dC | Atto 532 | 532 |
| dC | Atto Rho 6G | 535 |
| dC | R6G | 534 |
| dC | Tet | 521 |
| dT | Atto Rho 11 | 572 |
| dT | Atto 565 | 564 |
| dT | Alexa Fluor 568 | 578 |
| dT | dTamra | 578 |
| dA | Alexa Fluor 647 | 650 |
| dA | Atto 647N | 644 |
| dA | Janelia Fluor 646 | 646 |
| dG | Alexa Fluor 680 | 682 |
| dG | Alexa Fluor 700 | 696 |
| dG | CF680R | 680 |

In embodiments, R⁴ is

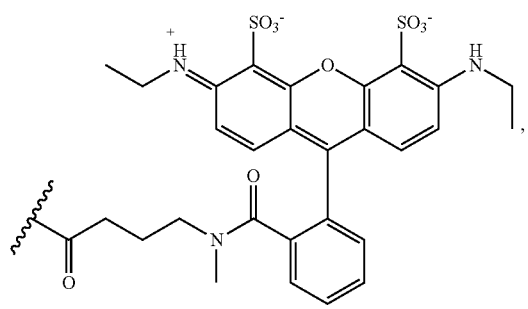

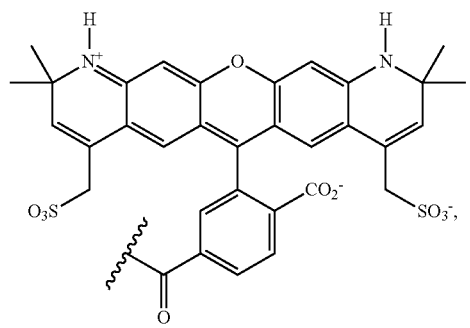

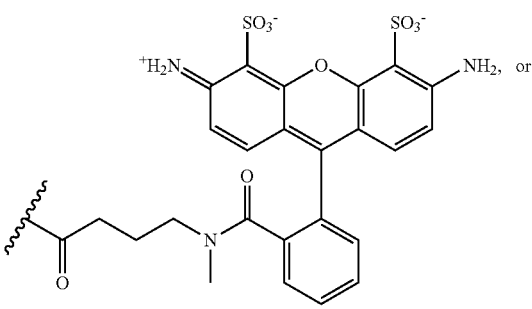

In embodiments, $R^4$ is a quenching moiety. In embodiments, $R^4$ is a quencher. The quencher may provide an additional benefit by quenching (i.e., absorbing) any remaining fluorescence before the next sequencing cycle. For example, quenching moieties reduce signal cross-talk thereby simplifying nucleotide detection. Non-limiting examples of quenching moieties include monovalent species of Dabsyl (dimethylaminoazobenzenesulfonic acid), Black Hole Quenchers (BHQ) (e.g., (BHQ), BHQ-2, and BHQ-3), BMN Quenchers (e.g., BMN-Q460, BMN-Q535, BMN-Q590, BMN-Q620, BMN-Q650) Qxl, Tide Quenchers (e.g., TQ2, TQ3), Iowa black FQ, Iowa black RQ, Deep Dark Quencher (e.g., DDQ I, DDQ II), or IRDye QC-1. In embodiments, $R^4$ is BMN-Q460, Dabcyl, DDQ-I, BMN-Q535, HHQ-1, TQ2, BMN-Q620, BMN-Q590, BHQ-2, TQ3, BMN-Q650, or BBQ-650. In embodiments, $R^4$ is a quenching moiety capable of quenching fluorescence in Range of 400-530 nm, 480-580 nm, 550-650 nm, 480-720 nm, or 550-720 nm.

In embodiments, $R^9$ is a bioconjugate reactive moiety, a nucleic acid, or a detectable moiety. In embodiments, $R^9$ is a bioconjugate reactive moiety. In embodiments, $R^9$ is a nucleic acid moiety. In embodiments, $R^9$ is a detectable moiety. In embodiments, $R^9$ is a protein. In embodiments, $R^9$ is isothiocyanate, isocyanate, sulfonyl chloride, aldehyde, acyl azide, anhydride, fluorobenzene, carbonate, N-Hydroxysuccinimide-ester (NHS-ester), imidoester, epoxide, maleimide, —COOH, —NH$_2$, or fluorophenylester. In embodiments, $R^9$ is

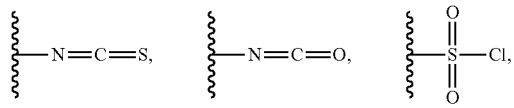

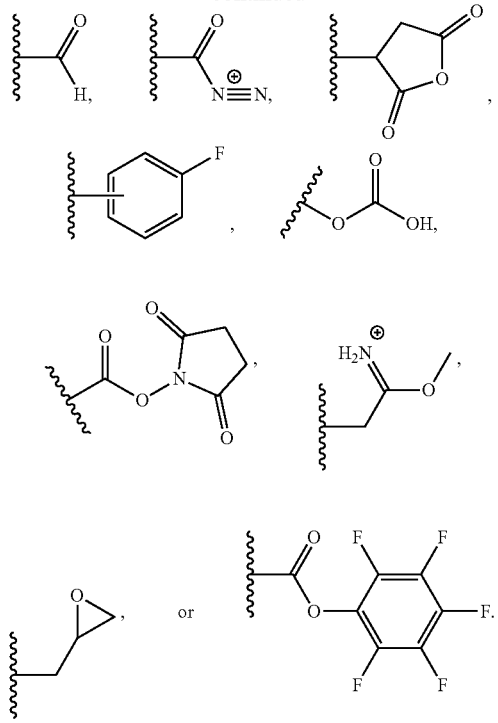

In embodiments, $R^9$ is an azide or thiol. In embodiments, $R^9$ is a nucleotide or a detectable moiety. In embodiments, $R^9$ is a therapeutic moiety.

In embodiments, $R^9$ is

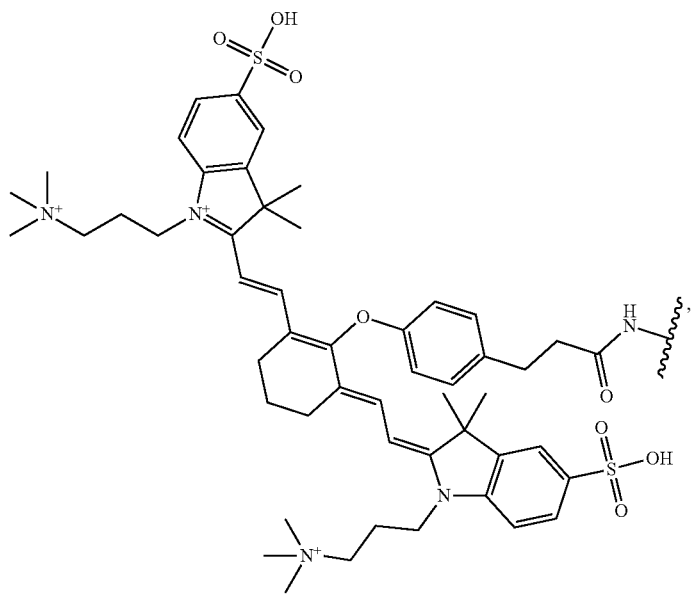

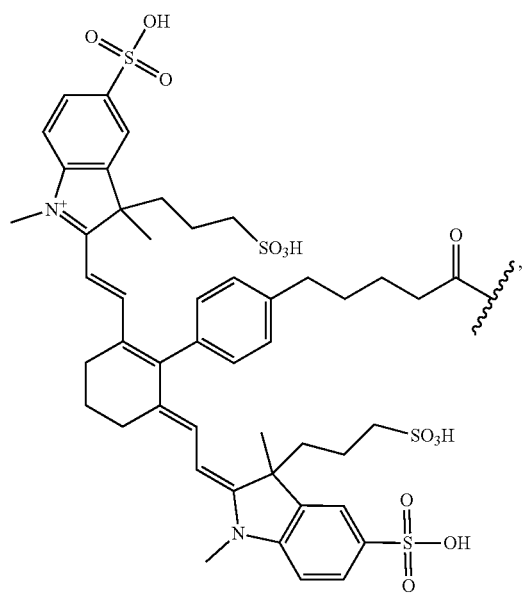
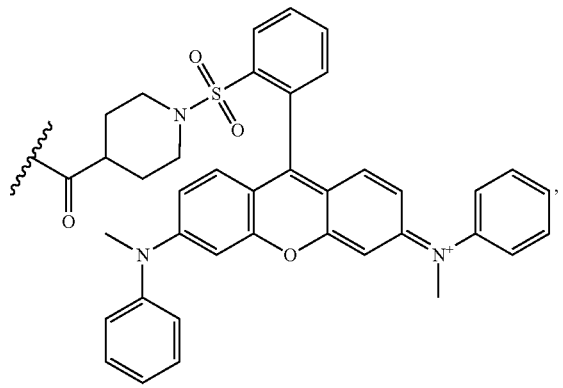
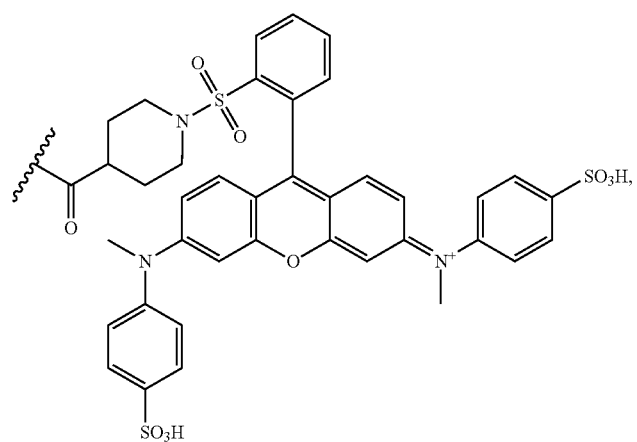
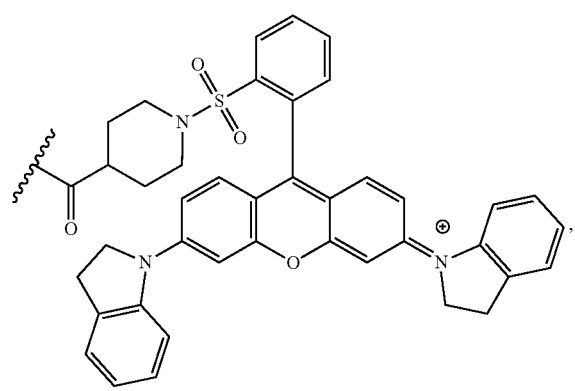
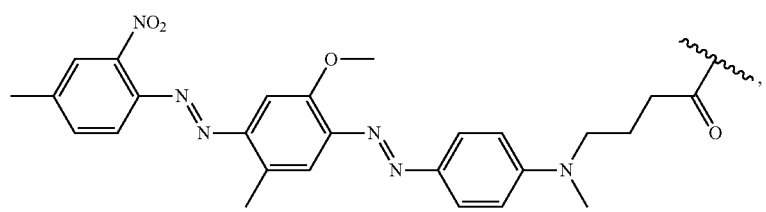

-continued
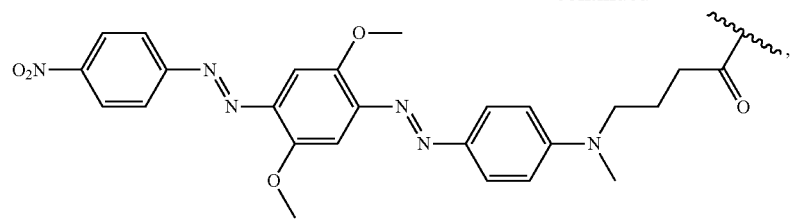
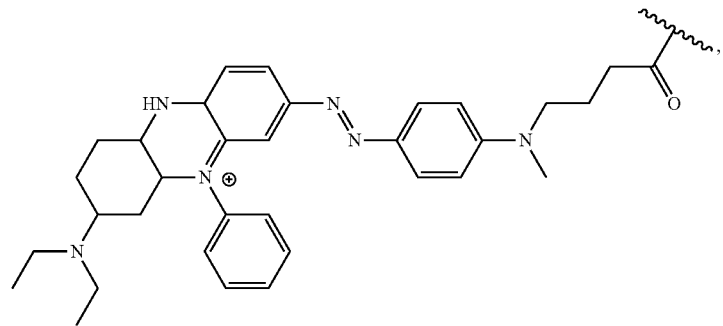
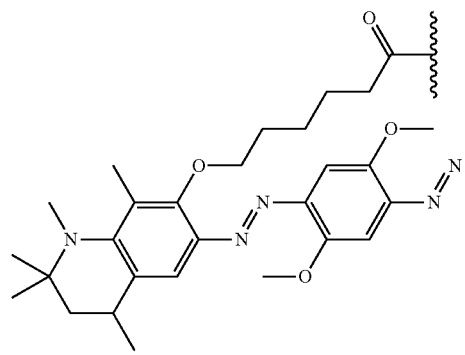
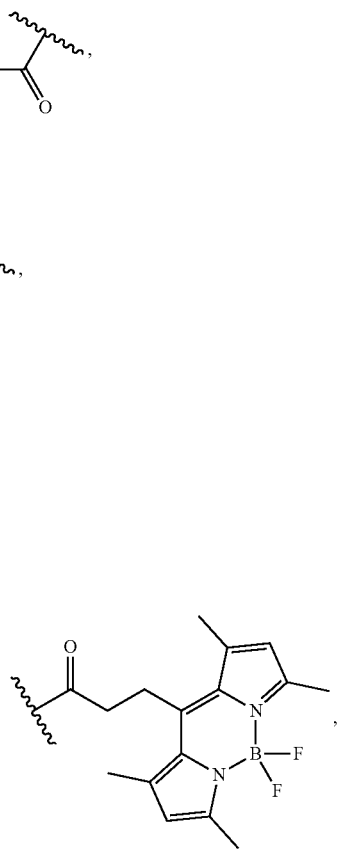
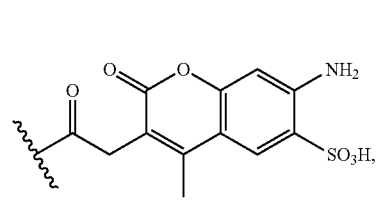
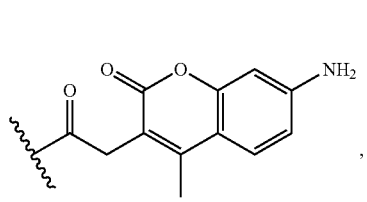
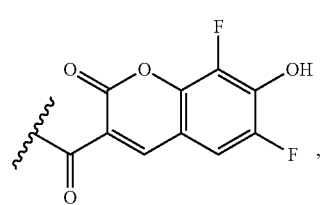
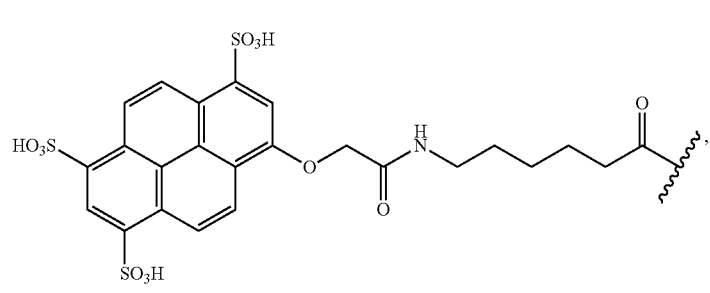
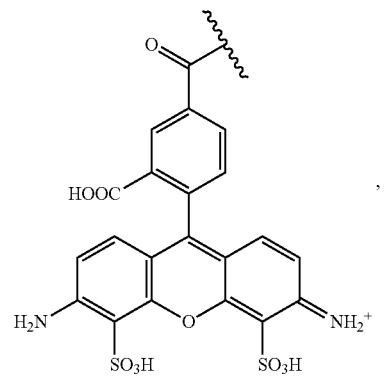

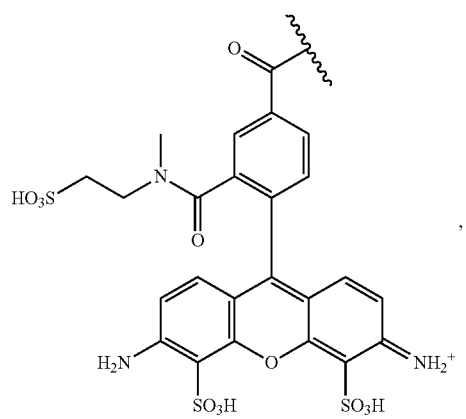

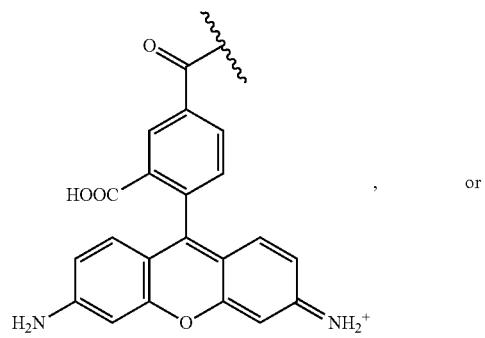

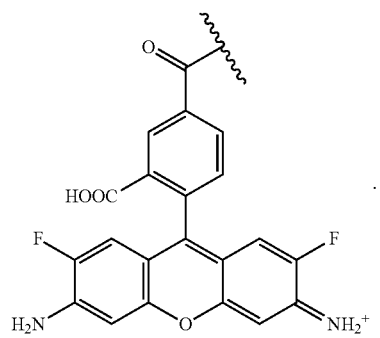

In embodiments, $R^9$ is a detectable moiety. In embodiments, the detectable moiety is a quenching moiety. In embodiments, the detectable moiety is a quencher. The quencher may provide an additional benefit by quenching (i.e., absorbing) any remaining fluorescence before the next sequencing cycle. For example, quenching moieties reduce signal cross-talk thereby simplifying nucleotide detection. Non-limiting examples of quenching moieties include monovalent species of Dabsyl (dimethylaminoazobenzenesulfonic acid), Black Hole Quenchers (BHQ) (e.g., (BHQ), BHQ-2, and BHQ-3), BMN Quenchers (e.g., BMN-Q460, BMN-Q535, BMN-Q590, BMN-Q620, BMN-Q650) Qxl, Tide Quenchers (e.g., TQ2, TQ3), Iowa black FQ, Iowa black RQ, Deep Dark Quencher (e.g., DDQ I, DDQ II), or IRDye QC-1. In embodiments, the detectable moiety is BMN-Q460, Dabcyl, DDQ-I, BMN-Q535, HHQ-1, TQ2, BMN-Q620, BMN-Q590, BHQ-2, TQ3, BMN-Q650, or BBQ-650. In embodiments, the detectable moiety is a quenching moiety capable of quenching fluorescence in the range of 400-530 nm, 480-580 nm, 550-650 nm, 480-720 nm, or 550-720 nm.

In embodiments, $R^{10}$ is a bioconjugate reactive moiety, a nucleic acid, or a detectable moiety. In embodiments, $R^{10}$ is a bioconjugate reactive moiety. In embodiments, $R^{10}$ is a nucleic acid moiety. In embodiments, $R^{10}$ is a detectable moiety. In embodiments, $R^{10}$ is a protein. In embodiments, $R^{10}$ is isothiocyanate, isocyanate, sulfonyl chloride, aldehyde, acyl azide, anhydride, fluorobenzene, carbonate, N-Hydroxysuccinimide-ester (NHS-ester), imidoester, epoxide, maleimide, —COOH, —NH$_2$, or fluorophenylester. In embodiments, $R^{10}$ is

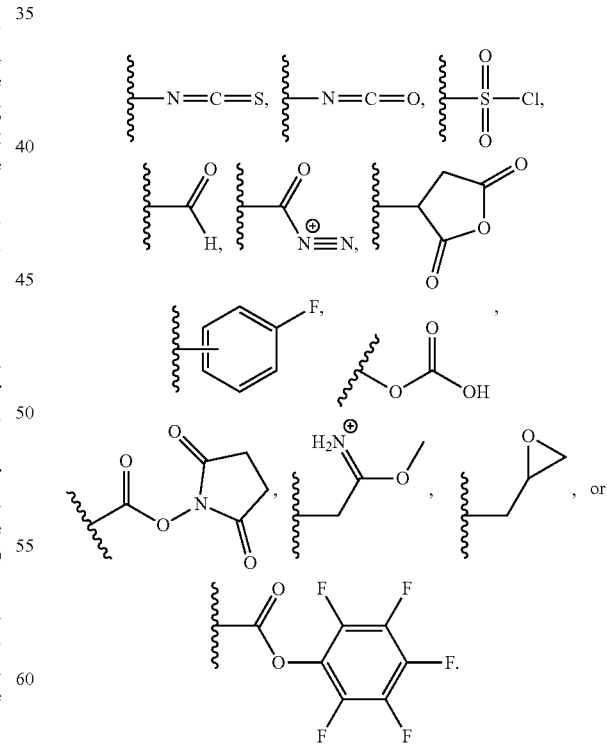

In embodiments, $R^{10}$ is an azide or thiol. In embodiments, $R^{10}$ is a nucleotide or a detectable moiety. In embodiments, $R^9$ is a therapeutic moiety.

In embodiments, $R^{10}$ is
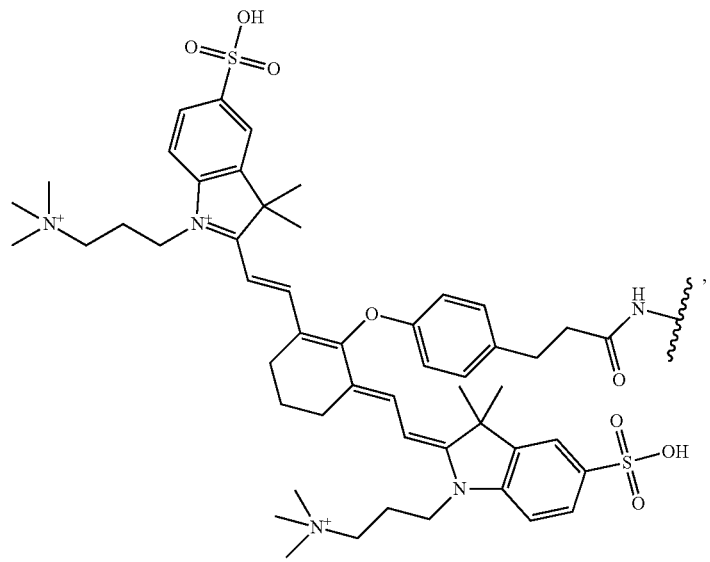
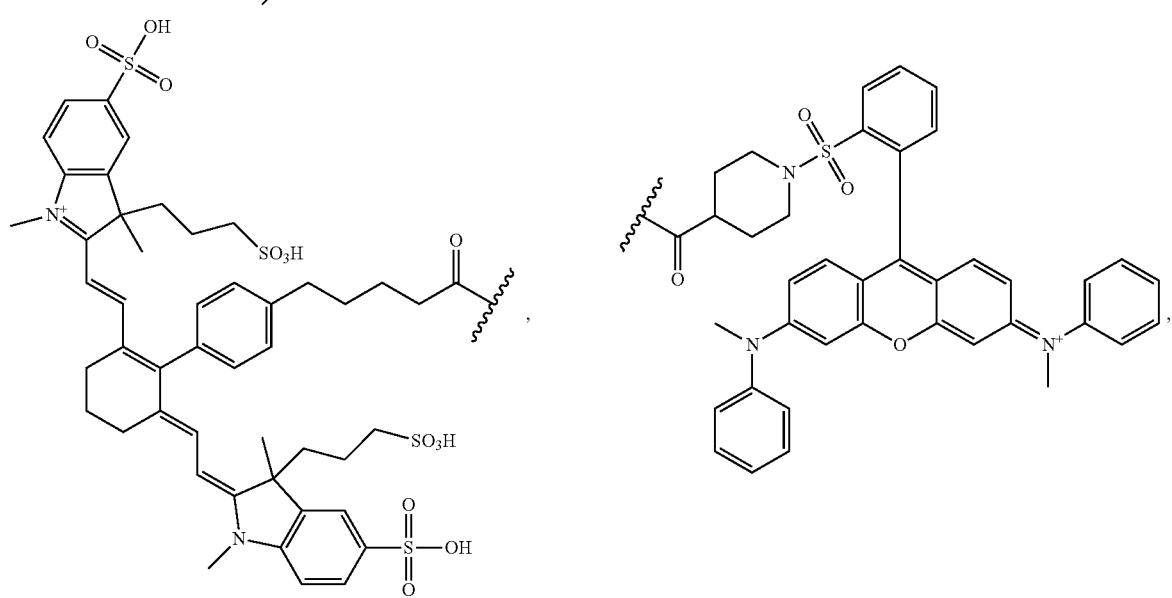
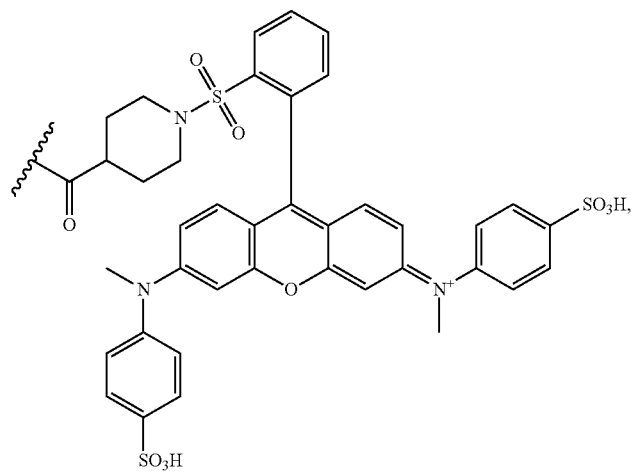

-continued
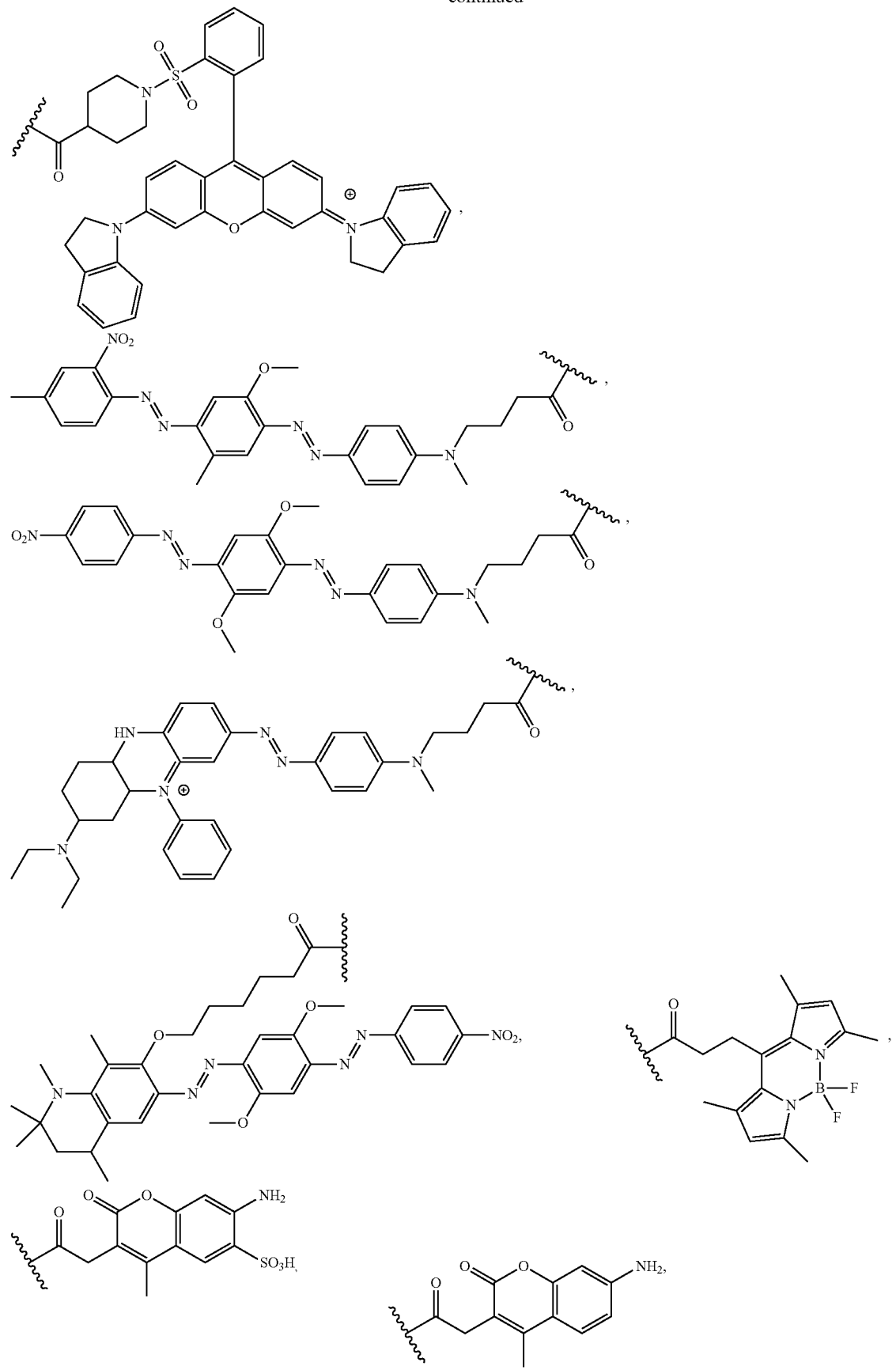

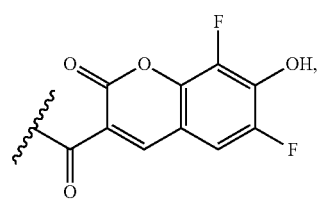

-continued

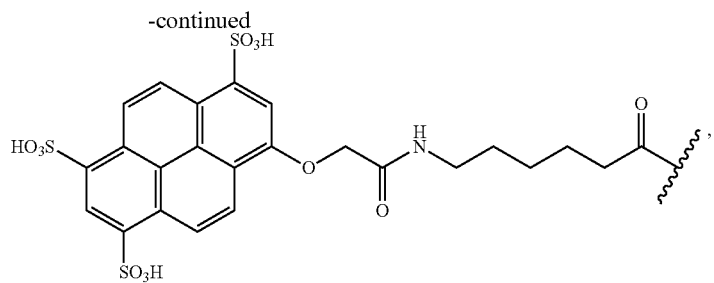

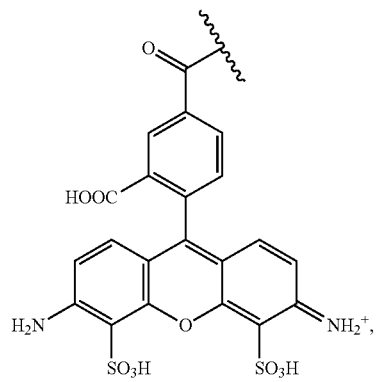

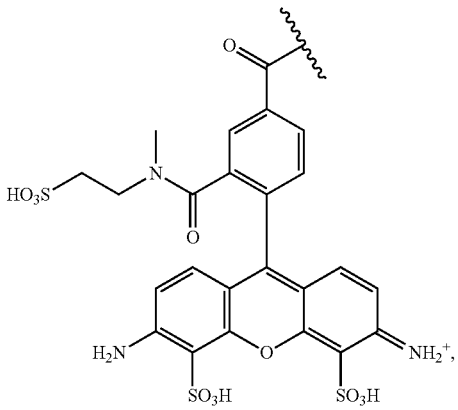

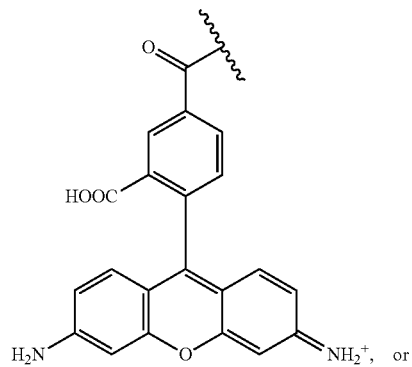, or

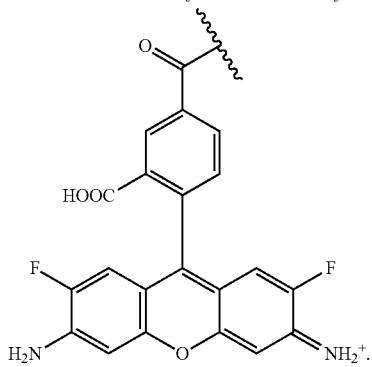.

In embodiments, $R^{10}$ is a detectable moiety. In embodiments, the detectable moiety is a quenching moiety. In embodiments, the detectable moiety is a quencher. The quencher may provide an additional benefit by quenching (i.e., absorbing) any remaining fluorescence before the next sequencing cycle. For example, quenching moieties reduce signal cross-talk thereby simplifying nucleotide detection. Non-limiting examples of quenching moieties include monovalent species of Dabsyl (dimethylaminoazobenzenesulfonic acid), Black Hole Quenchers (BHQ) (e.g., (BHQ), BHQ-2, and BHQ-3), BMN Quenchers (e.g., BMN-Q460, BMN-Q535, BMN-Q5100, BMN-Q620, BMN-Q650) Qxl, Tide Quenchers (e.g., TQ2, TQ3), Iowa black FQ, Iowa black RQ, Deep Dark Quencher (e.g., DDQ I, DDQ II), or IRDye QC-1. In embodiments, the detectable moiety is BMN-Q460, Dabcyl, DDQ-I, BMN-Q535, HHQ-1, TQ2, BMN-Q620, BMN-Q5100, BHQ-2, TQ3, BMN-Q650, or BBQ-650. In embodiments, the detectable moiety is a quenching moiety capable of quenching fluorescence in the range of 400-530 nm, 480-580 nm, 550-650 nm, 480-720 nm, or 550-720 nm.

In an aspect is provided a nucleic acid polymerase complex including a nucleic acid polymerase, wherein the nucleic acid polymerase is bound to a compound as described herein (e.g., a compound of Formula I) and in related embodiments. In embodiments, the complex is further bound to a primer, wherein the primer is hybridized to a template polynucleotide.

In embodiments, the nucleic acid polymerase is a Taq polymerase, Therminator γ, 9° N polymerase (exo-), Therminator II, Therminator III, or Therminator IX. In embodiments, the nucleic acid polymerase is Therminator γ. In embodiments, the nucleic acid polymerase is 9° N polymerase (exo-). In embodiments, the nucleic acid polymerase is Therminator II. In embodiments, the nucleic acid polymerase is Therminator III. In embodiments, the nucleic acid polymerase is Therminator IX. In embodiments, the nucleic acid polymerase is a Taq polymerase. In embodiments, the nucleic acid polymerase is a nucleic acid polymerase. In embodiments, the nucleic acid polymerase is 9° N and mutants thereof. In embodiments, the nucleic acid polymerase is Phi29 and mutants thereof. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044).

In an aspect is provided a kit. Some embodiments disclosed herein relate to kits including a labeled nucleoside or nucleotide (e.g., a compound as described herein) including a linker between the fluorophore and the nucleoside or nucleotide, wherein the linker is a linker as described herein. In embodiments, the kit includes a compound described herein. In embodiments, the kit includes a plurality of compounds described herein. In embodiments, the kit includes labeled nucleotides including differently labeled nucleotides (e.g., compounds described herein). In embodiments, the kit further includes instructions for use thereof. In embodiments, kits described herein include a polymerase. In embodiments, the polymerase is a DNA polymerase. In embodiments, the DNA polymerase is a thermophilic nucleic acid polymerase. In embodiments, the DNA polymerase is a modified archaeal DNA polymerase. In embodiments, the kit includes a sequencing solution. In embodiments, the sequencing solution include labeled nucleotides including differently labeled nucleotides, wherein the label (or lack thereof) identifies the type of nucleotide. For example, each adenine nucleotide, or analog thereof; a thymine nucleotide; a cytosine nucleotide, or analog thereof; and a guanine nucleotide, or analog thereof may be labeled with a different fluorescent label.

In embodiments, the sequencing solution includes a buffer solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, Tricine, HEPES, TES, MOPS, MOPSO and PIPES. In embodiments, the buffer includes ethanolamine (EA), tris(hydroxymethyl)aminomethane (Tris), glycine, a carbonate salt, a phosphate salt, a borate salt, 2-dimethyalaminomethanol (DMEA), 2-diethylaminomethanol (DEEA), N,N,N',N'-tetramethylethylenediamine (TEMED), and N,N,N',N'-tetraethylethylenediamine (TEEDA), or a combination thereof. Additionally, other buffer agents that can be used in enzyme reactions, hybridization reactions, and detection reactions are well known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid. In some embodiments, a concentration can be more than about 1 µM, more than about 2 µM, more than about 5 µM, more than about 10 µM, more than about 25 µM, more than about 50 µM, more than about 75 µM, more than about 100 µM, more than about 200 µM, more than about 300 µM, more than about 400 µM, more than about 500 µM, more than about 750 µM, more than about 1 mM, more than about 2 mM, more than about 5 mM, more than about 10 mM, more than about 20 mM, more than about 30 mM, more than about 40 mM, more than about 50 mM, more than about 60 mM, more than about 70 mM, more than about 80 mM, more than about 90 mM, more than about 100 mM, more than about 150 mM, more than about 200 mM, more than about 250 mM, more than about 300 mM, more than about 350 mM, more than about 400 mM, more than about 450 mM, more than about 500 mM, more than about 550 mM, more than about 600 mM, more than about 650 mM, more than about 700 mM, more than about 750 mM, more than about 800 mM, more than about 850 mM, more than about 900 mM, more than about 950 mM or more than about 1 M.

In embodiments, the kit includes nucleotides in a buffer. In embodiments, the kit includes a buffer. For example, the sequencing solution and/or the chase solution may include a buffer such as ethanolamine (EA), tris(hydroxymethyl)aminomethane (Tris), glycine, a carbonate salt, a phosphate salt, a borate salt, 2-dimethyalaminomethanol (DMEA), 2-diethylaminomethanol (DEEA), N,N,N',N'-tetramethylethylenediamine (TEMED), and N,N,N',N'-tetraethylethylenediamine (TEEDA), and combinations thereof. For example, the buffer may Tris-HCl (pH 9.2 at 25° C.), ammonium sulfate, $MgCl_2$, 0.1% Tween® 20, and dNTPs.

In embodiments, the kit includes a solid support (e.g., a flow cell or microplate). Flow cells provide a convenient format for housing an array of clusters produced by the methods described herein, in particular when subjected to an SBS or other detection technique that involves repeated delivery of reagents in cycles. For example, to initiate a first SBS cycle, one or more labeled nucleotides and a DNA polymerase in a buffer can be flowed into/through a flow cell that houses an array of clusters. The clusters of an array where primer extension causes a labeled nucleotide to be incorporated can then be detected. Optionally, the nucleotides can further include a reversible termination moiety that temporarily halts further primer extension once a nucleotide has been added to a primer. For example, a nucleotide analog having a reversible terminator moiety can be added to a primer such that subsequent extension cannot occur until a deblocking agent (e.g., a reducing agent) is delivered to remove the moiety. Thus, for embodiments that use reversible termination, a deblocking reagent (e.g., a reducing agent) can be delivered to the flow cell (before, during, or after detection occurs). Washes can be carried out between the various delivery steps as needed. The cycle can then be repeated N times to extend the primer by nucleotides, thereby detecting a sequence of length N. Example SBS procedures, fluidic systems and detection platforms that can be readily adapted for use with an array produced by the methods of the present disclosure are described, for example, in Bentley et al., Nature 456:53-59 (2008).

In embodiments, the kit includes a plurality of primers for amplifying and/or for sequencing nucleic acids isolated from the sample. The kit may provide at least 1, 2, 3, 4, 5, 6, 7, 8, 9, 10, 20, 50, 100, 200, 500, 1000, or more primers. The kit may provide between about 1-3, 1-10, 5-20, 1-1000, 10-500, 20-200, or 50-100 primers. In embodiments, the primers include 5, 10, 15, 20, 25, 30, 40, 50, 100, 150, 200 or more nucleotides.

In embodiments, the kit includes a buffer. In embodiments, the kit includes a buffered solution. For example, the sequencing solution and/or the chase solution may include a buffer such as ethanolamine (EA), tris(hydroxymethyl)aminomethane (Tris), glycine, a carbonate salt, a phosphate salt, a borate salt, 2-dimethyalaminomethanol (DMEA), 2-diethylaminomethanol (DEEA), N,N,N',N'-tetramethylethylenediamine (TEMED), and N,N,N',N'-tetraethylethylenediamine (TEEDA), and combinations thereof. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, Bicine, Tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid. In embodiments, the buffer includes PEG (polyethylene glycol), PVP (polyvinylpyrrolidone), trehalose, ficoll, or dextran. In embodiments, the buffer includes additives such as Tween-20 or NP-40.

In an aspect is provided a cell, wherein the cell includes a compound or complex as described herein. In embodiments, the cell is in a tissue section. Tissue sections, e.g., tumor tissue samples, may be obtained surgically or using a laparoscope. A tissue section may be a tissue sample obtained from any part of the body to examine it for disease or injury, e.g., presence of cancer tissue or cells, or the extent or characteristics thereof. In particular embodiments, the tissue section includes abdominal tissue, bone, bone marrow, breast tissue, endometrial tissue, kidney tissue, liver tissue, lung or chest tissue, lymph node, nerve tissue, skin, testicular tissue, head or neck tissue, or thyroid tissue. In certain embodiments, the tissue is obtained from brain, breast, skin, bone, joint, skeletal muscle, smooth muscle, red bone marrow, thymus, lymphatic vessel, thoracic duct, spleen, lymph node, nasal cavity, pharynx, larynx, trachea, bronchus, lung, oral cavity, esophagus, liver, stomach, small intestine, large intestine, rectum, anus, spinal cord, nerve, pineal gland, pituitary gland, thyroid gland, thymus, adrenal gland, pancreas, ovary, testis, heart, blood vessel, kidney, uterus, urinary bladder, urethra, prostate gland, penis, prostate, testis, scrotum, ductus deferens, mammary glands, ovary, uterus, vagina, or uterine tube.

In embodiments, the tissue section includes one or more prokaryotic cells. In embodiments, the tissue section includes one or more eukaryotic cells. In embodiments, the tissue section includes a bacterial cell (e.g., a bacterial cell or bacterial spore), a fungal cell (e.g., a fungal spore), a plant cell, or a mammalian cell. In embodiments, the tissue section includes a stem cell. In embodiments, the stem cell is an embryonic stem cell, a tissue-specific stem cell, a mesenchymal stem cell, or an induced pluripotent stem cell. In embodiments, the tissue section includes an endothelial cell, muscle cell, myocardial, smooth muscle cell, skeletal muscle cell, mesenchymal cell, epithelial cell; hematopoietic cell, such as lymphocytes, including T cell, e.g., (Th1 T cell, Th2 T cell, ThO T cell, cytotoxic T cell); B cell, pre-B cell; monocytes; dendritic cell; neutrophils; or a macrophage.

In embodiments, the tissue section is obtained from a subject (e.g., human or animal tissue). Once obtained, the tissue section is placed in an artificial environment in plastic or glass containers supported with specialized medium containing essential nutrients and growth factors to support proliferation. In embodiments, the tissue section is permeabilized and immobilized to a solid support surface. In embodiments, the tissue section is permeabilized and immobilized to an array (i.e., to discrete locations arranged in an array). In embodiments, the tissue section is immobilized to a solid support surface. In embodiments, the surface includes a patterned surface (e.g., suitable for immobilization of a plurality of cells in an ordered pattern. The discrete regions of the ordered pattern may have defined locations in a regular array, which may correspond to a rectilinear pattern, circular pattern, hexagonal pattern, or the like. These discrete regions are separated by interstitial regions. As used herein, the term "interstitial region" refers to an area in a substrate or on a surface that separates other areas of the substrate or surface. In embodiments, a plurality of cells are immobilized on a patterned surface that have a mean or median separation from one another of about 10-20 μm. In embodiments, a plurality of cells are immobilized on a patterned surface that have a mean or median separation from one another of about 10-20; 10-50; or 100 μm. In embodiments, a plurality of cells are arrayed on a substrate. In embodiments, a plurality of cells are immobilized in a 96-well microplate having a mean or median well-to-well spacing of about 8 mm to about 12 mm (e.g., about 9 mm). In embodiments, a plurality of cells are immobilized in a 384-well microplate having a mean or median well-to-well spacing of about 3 mm to about 6 mm (e.g., about 4.5 mm).

In embodiments, the kit can further include one or more biological stain(s) (e.g., any of the biological stains as described herein). For example, the kit can further include eosin and hematoxylin. In other examples, the kit can include a biological stain such as acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, or any combination thereof.

III. Methods

In an aspect is a method for sequencing a nucleic acid, including: (i) incorporating in series with a nucleic acid polymerase, within a reaction vessel, one of four different compounds into a primer to create an extension strand, wherein the primer is hybridized to the nucleic acid and wherein each of the four different compounds includes a unique detectable label; (ii) detecting the unique detectable label of each incorporated compound, so as to thereby identify each incorporated compound in the extension strand, thereby sequencing the nucleic acid; wherein each of the four different compounds is independently a compound as described herein and in related embodiments. In embodiments, the method includes cleaving the linker (e.g., cleaving $L^{100}$). In embodiments, cleaving the linker includes contacting the compound with a reducing agent (e.g., tris (3-hydroxypropyl)phosphine). In embodiments, the method includes removing (e.g., cleaving) the reversible terminator moiety. In embodiments, the method includes removing (e.g., cleaving) $R^3$ to generate a 3'-OH. In embodiments, the method includes chemically cleaving the linker and/or the polymerase-compatible cleavable moiety as described herein (e.g., $L^{100}$ and/or $R^3$ of Formula I).

A variety of sequencing methodologies can be used such as sequencing-by synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568; and. 6,274,320, each of which is incorporated herein by reference in its entirety). In pyrosequencing, released PPi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, that are present at features of an array are subjected to repeated cycles of oligonucleotide delivery and detection. SBL methods, include those described in Shendure et al. Science 309:1728-1732 (2005); U.S. Pat. Nos. 5,599,675; and 5,750,341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting of steps. In embodiments, the methods include sequencing one or more bases of a target nucleic acid by extending a sequencing primer hybridized to a target nucleic acid (e.g., an amplification product produced by the amplification methods described herein). In embodiments, the sequencing step may be accomplished by a sequencing-by-synthesis (SBS) process. In embodiments, sequencing includes a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, alternatively referred to as reversible terminators or polymerase-compatible cleavable moieties as described herein, for example as described in U.S. Pat. Nos. 10,738,072, 10,822,653, and 11,174,281. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template (e.g., by obtaining a sequencing read).

In embodiments, chemical cleavage of a compound (e.g., cleavage of the 3' moiety of a compound described herein, cleavage of a linker (e.g., a linker including $L^{100}$) as described herein, or cleavage of an SS bond in a 3' moiety of a compound described herein) described herein (e.g., in an aspect or embodiment) includes contacting the compound with a reducing agent (e.g., tris(hydroxypropyl)phosphine (THPP), tris-(2-carboxyethyl)phosphine (TCEP), tris(hydroxymethyl)phosphine (THMP), or tris(hydroxyethyl) phosphine (THEP), DTT, dithiobutylamine (DTBA)). In embodiments, chemical cleavage of a compound (e.g., cleavage of the 3' moiety of a compound described herein, cleavage of a linker (e.g., a linker including $L^{100}$) as described herein, or cleavage of an SS bond in a 3' moiety of a compound described herein) described herein (e.g., in an aspect or embodiment) includes contacting the compound with THPP (e.g., about 10 mM THPP, or at least 1 mM THPP). In embodiments, chemical cleavage of a compound (e.g., cleavage of the 3' moiety of a compound described herein, cleavage of a linker (e.g., a linker including $L^{100}$) as described herein, or cleavage of an SS bond in a 3' moiety of a compound described herein) described herein (e.g., in an aspect or embodiment) is performed at less than about 65° C. In embodiments, chemical cleavage of a compound (e.g., cleavage of the 3' moiety of a compound described herein, cleavage of a linker (e.g., a linker including $L^{100}$) as described herein, or cleavage of an SS bond in a 3' moiety of a compound described herein) described herein (e.g., in an aspect or embodiment) is performed at less than 65° C. In embodiments, chemical cleavage of a compound (e.g., cleavage of the 3' moiety of a compound described herein, cleavage of a linker (e.g., a linker including $L^{100}$) as described herein, or cleavage of an SS bond in a 3' moiety of a compound described herein) described herein (e.g., in an aspect or embodiment) is performed at about 45-65° C. In embodiments, chemical cleavage of a compound (e.g., cleavage of the 3' moiety of a compound described herein, cleavage of a linker (e.g., a linker including $L^{100}$) as described herein, or cleavage of an SS bond in a 3' moiety of a compound described herein) described herein (e.g., in an aspect or embodiment) is performed at 45-65° C. In embodiments, chemical cleavage of a compound (e.g., cleavage of the 3' moiety of a compound described herein, cleavage of a linker (e.g., a linker including $L^{100}$) as described herein, or cleavage of an SS bond in a 3' moiety of a compound described herein) described herein (e.g., in an aspect or embodiment) is performed at 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., or 65° C. In embodiments, chemical cleavage of a compound (e.g., cleavage of the 3' moiety of a compound described herein, cleavage of a linker (e.g., a linker including $L^{100}$) as described herein, or cleavage of an SS bond in a 3' moiety of a compound described herein) described herein (e.g., in an aspect or embodiment) is performed at about 55° C. In embodiments, chemical cleavage of a compound (e.g., cleavage of the 3' moiety of a compound described herein, cleavage of a linker (e.g., a linker including $L^{100}$) as described herein, or cleavage of an SS bond in a 3' moiety of a compound described herein) described herein (e.g., in an aspect or embodiment) is performed at a temperature of at least 55° C. In embodiments, chemical cleavage of a compound (e.g., cleavage of the 3' moiety of a compound described herein, cleavage of a linker (e.g., a linker including $L^{100}$) as described herein, or cleavage of an SS bond in a 3' moiety of a compound described herein) described herein (e.g., in an aspect or embodiment) is performed at about pH 9.5. In embodiments, chemical cleavage of a compound (e.g., cleavage of the 3' moiety of a compound described herein, cleavage of a linker (e.g., a linker including $L^{100}$) as described herein, or cleavage of an SS bond in a 3' moiety of a compound described herein) described herein (e.g., in an aspect or embodiment) is performed at about pH 9.5. In embodiments, chemical cleavage of a compound (e.g., cleavage of the 3' moiety of a compound described herein, cleavage of a linker (e.g., a linker including $L^{100}$) as described herein, or cleavage of an SS bond in a 3' moiety of a compound described herein) described herein (e.g., in an aspect or embodiment) is performed at pH 9.5. In embodiments, chemical cleavage of a compound (e.g., cleavage of the 3' moiety of a compound described herein, cleavage of a linker (e.g., a linker including $L^{100}$) as described herein, or cleavage of an SS bond in a 3' moiety of a compound described herein) described herein (e.g., in an aspect or embodiment) is performed using 0.1, 0.2, 0.3, 0.4, 0.5, 0.6, 0.7, 0.8, 0.9, or 1.0 mM of THPP. In embodiments, the chemical cleavage is performed using less than 1.0 mM THPP. In embodiments, the chemical cleavage is performed using about 1.0 mM THPP. In embodiments, the chemical cleavage is performed using about 0.05 to about 1.0 mM THPP. In embodiments, the chemical cleavage is performed using about 1.0 to about 5.0 mM THPP. In embodiments, the chemical cleavage is performed using about 10 mM THPP. In embodiments, the chemical cleavage is performed using 1.0 mM THPP. In embodiments, the chemical cleavage is performed using about 0.05 to 1.0 mM THPP. In embodiments, the chemical cleavage is performed using 1.0 to about 5.0 mM THPP. In embodiments, the chemical cleavage is performed using 10 mM THPP.

A number of new techniques have been described for reading out RNA transcription levels in tissue sections directly (i.e., in-situ), without requiring spatial barcoding, based on single molecule fluorescence in situ hybridization. These include MERFISH (Multiplexed Error-Robust Fluorescence In Situ Hybridization), STARmap (Spatially-resolved Transcript Amplicon Readout mapping), DART-FISH, seq-FISH (Sequential Fluorescence In Situ Hybridization), FISSEQ (fluorescent in situ sequencing), and others (see for example Chen, K. H., et al. (2015). Science, 348(6233), aaa6090; Wang, G., Moffitt, J. R. & Zhuang, X. Sci Rep. 2018; 8, 4847; Wang X. et al; Science, 2018; 27, Vol 361, Issue 6400, eaat5691; Cai, M. *Dissertation*, (2019) UC San Diego. ProQuest ID: Cai_ucsd_0033D_18822; Lee J H et al. Nat. Protoc. 2015; 10(3):442-58); and Sansone, A. Nat Methods 16, 458; 2019). In all of these techniques, individual RNA transcripts are individually resolved, typically with pre-amplification or requiring multiple instances of labeled probes. Some of these techniques have been combined with super-resolution microscopy, expansion microscopy, or both, to increase the resolution and allow more transcripts to be resolved and thus counted. In embodiments, the method includes extending a primer hybridized to a nucleic acid template in situ. The term "in situ" is used in accordance with its ordinary meaning in the art and refers to a sample surrounded by at least a portion of its native environment, such as may preserve the relative position of two or more elements. For example, an extracted human cell obtained is considered in situ when the cell is retained in its local microenvironment so as to avoid extracting the target (e.g., nucleic acid molecules or proteins) away from their native environment. An in situ sample (e.g., a cell) can be obtained from a suitable subject. An in situ cell sample may refer to a cell and its surrounding milieu, or a tissue. A sample can be isolated or obtained directly from a subject or part thereof. In embodiments, the methods described herein (e.g., sequencing a plurality of target nucleic acids of a cell in situ) are applied to an isolated cell (i.e., a cell not surrounded by least a portion of its native environment). For the avoidance of any doubt, when the method is performed within a cell (e.g., an isolated cell) the method may be considered in situ. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid). A sample may include a cell and RNA transcripts. A sample can comprise nucleic acids obtained from one or more subjects. In some embodiments a sample comprises nucleic acid obtained from a single subject. A subject can be any living or non-living organism, including but not limited to a human, non-human animal, plant, bacterium, fungus, virus, or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a plant. In some embodiments, a subject is a human subject. A subject can be a patient (e.g., a human patient).

In an aspect is a method of sequencing nucleic acid including: i) extending a primer hybridized to a nucleic acid template with a compound as described herein and in related embodiments and ii) identifying the compound, so as to sequence the nucleic acid. In an aspect is a method of sequencing nucleic acid including: i) providing a nucleic acid template hybridized to a primer; ii) extending the primer hybridized to the nucleic acid template with a compound as described herein and in related embodiments and iii) identifying the compound, so as to sequence the nucleic acid. In embodiments, identifying includes detecting the detectable moiety. In embodiments, the method includes generating one or more sequencing reads. In embodiments, the nucleic acid is one of many nucleic acids is confined to an area of a discrete region (referred to as a cluster). The discrete regions may have defined locations in a regular array, which may correspond to a rectilinear pattern, circular pattern, hexagonal pattern, or the like. A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. Interstitial regions will typically have a surface material that differs from the surface material of the features on the surface. In embodiments of the methods provided herein, the clusters have a mean or median separation from one another of about 0.5-5 µm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 µm or a number or a range between any two of these values.

In an aspect is a method of incorporating a compound into a primer, the method including combining a polymerase, a primer hybridized to nucleic acid template and the compound within a reaction vessel and allowing the polymerase to incorporate the compound into the primer thereby forming an extended primer, wherein the compound is a compound as described herein and in related embodiments. In embodiments, the method includes detecting the compound (e.g., detecting the detectable moiety). In embodiments, the method includes removing the detectable moiety. Sequencing includes, for example, detecting a sequence of signals. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging. A variety of sequencing chemistries are available, non-limiting examples of which are described herein.

In embodiments, the methods of the invention (e.g., methods of incorporating a compound into a primer and/or methods of sequencing) herein are performed in situ on isolated cells or in tissue sections that have been prepared according to methodologies known in the art. Methods for permeabilization and fixation of cells and tissue samples are known in the art, as exemplified by Cremer et al., The Nucleus: Volume 1: Nuclei and Subnuclear Components, R. Hancock (ed.) 2008; and Larsson et al., Nat. Methods (2010) 7:395-397, the content of each of which is incorporated herein by reference in its entirety. In embodiments, the cell is cleared (e.g., digested) of proteins, lipids, or proteins and lipids.

In embodiments, the cell in situ is obtained from a subject (e.g., human or animal tissue). Once obtained, the cell is placed in an artificial environment in plastic or glass containers supported with specialized medium containing essential nutrients and growth factors to support proliferation. In embodiments, the cell is permeabilized and immobilized to a solid support surface. In embodiments, the cell is permeabilized and immobilized to an array (i.e., to discrete locations arranged in an array). In embodiments, the cell is immobilized to a solid support surface. In embodiments, the surface includes a patterned surface (e.g., suitable for immobilization of a plurality of cells in an ordered pattern. In embodiments, a plurality of cells are immobilized on a patterned surface that have a mean or median separation from one another of about 10-20 µm. In embodiments, a plurality of cells are immobilized on a patterned surface that have a mean or median separation from one another of about 1-10 µm. In embodiments, a plurality of cells are immobilized on a patterned surface that have a mean or median separation from one another of about 10-20; 10-50; or 100 µm. In embodiments, a plurality of cells are arrayed on a substrate. In embodiments, a plurality of cells are immobilized in a 96-well microplate having a mean or median well-to-well spacing of about 8 mm to about 12 mm (e.g., about 9 mm). In embodiments, a plurality of cells are immobilized in a 384-well microplate having a mean or median well-to-well spacing of about 3 mm to about 6 mm (e.g., about 4.5 mm).

EXAMPLES

Example 1. Novel Modified Nucleotides

DNA sequencing is a fundamental tool in biological and medical research with sequencing by synthesis (SBS) being the dominant method. The widely used high-throughput SBS technology utilizes nucleotide reversible terminator (NRT) sequencing chemistry in which the 4 nucleotides are modified by attaching a unique cleavable detectable moiety to specific location of the base. After incorporation and signal detection of the nucleotide, the detectable moiety is cleaved and removed, and SBS cycles continues. Synthesis of NRTs with faster cleavage rates, higher enzymatic incorporation speed, high fidelity and short cleavage residue on the base remains an ongoing goal. Increasing the rate of nucleotide incorporation during SBS and elimination of any unwanted side reactions to improve efficiency of the sequencing method is especially desirable.

An important feature of a NRT is that the detectable moiety may be efficiently and rapidly cleaved to release the detectable moiety. The detectable moiety is attached to the modified nucleotide through a cleavable linker. The use of a cleavable linker ensures that if required, the label can be removed after detection. Suitable linkers can be adapted from standard chemical blocking groups, as disclosed in Greene & Wuts, Protective Groups in Organic Synthesis, John Wiley & Sons and in Guillier et al (Chem Rev, 100: 2092-2157, 2000).

A typical linker used in SBS methodologies is a disulfide linker (also referred to herein as an SS linker) having the formula

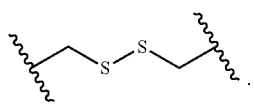 [SMILES: *CSSC*]

This SS linker has a disulfide (—SS—) bond that is cleaved upon exposure to a reducing agent to form a free thiol groups (—SH); see FIG. 1A. Generating reactive species, for example one or more free thiol groups, contaminates the detection process. For example, a free thiol group on the linker connected to the detectable moiety, such as a dye, may react with the surrounding environment (e.g., a biomolecule or protein, or a surface in the reaction vessel), causing an increase in background signal or interact with the polymerase, decreasing the efficiency of the overall sequencing. Additionally, within the context of DNA sequencing, free thiols can reduce other disulfide moieties and prematurely remove the linker and/or a disulfide containing reversible terminator moiety of another labeled modified nucleotide.

Figure 3:
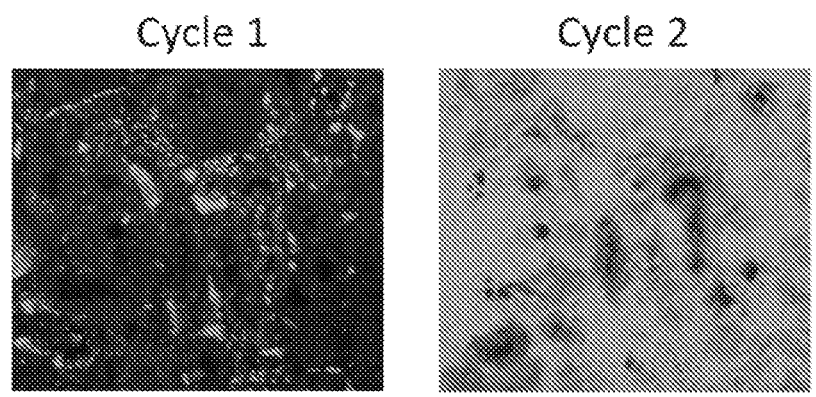
FIG. 3 presents a set of fluorescence microscopy images of cells probed in a multiplex fashion (i.e., simultaneous detection) for different genes across two in situ sequencing cycles on tissue sections. The transcript for each gene was targeted by a barcoded oligonucleotide and, in the presence of a polymerase, a labeled modified nucleotide was incorporated (cycle 1) to detect the barcode. The labeled modified nucleotides included a disulfide (—SS—) linker that was cleaved upon exposure to a reducing agent and released the fluorophores that included a thiol moiety (—SH). The fluorophores reacted with the surrounding environment (e.g., antibodies, receptors, organelles, hormones and enzymes) and remained attached to the cellular structures. A second sequencing cycle (Cycle 2) was initiated, however as depicted in FIG. 3, the background level saturated the image, thus complicating an accurate detection of the incorporated nucleotide.

Reducing the formation of thiol groups becomes more important as in situ sequencing approaches (i.e., sequencing one or more nucleic molecule within a cell) are considered. Within a cell, many different types of proteins (e.g., antibodies, receptors, organelles, hormones and enzymes) often contain the amino acid cysteine (Cys). The thiol group in Cys is inherently reactive and may cause unwanted intramolecular disulfide scrambling or covalent oligomerization via intermolecular disulfide formation (see Curr Protein Pept Sci, 2009, 10(6), p. 614-625). Therefore, the presence of the thiol groups generated following cleavage of the disulfide bond during in situ sequencing of nucleic acids in cells can prove to be especially problematic due to the relative abundance of Cys residues present in the cellular environment. For example, see two in situ sequencing cycles depicted in FIG. 3. To circumvent potential side reactions of the highly reactive thiol groups, a new class of compounds that upon cleavage of the disulfide bond form less reactive, or even non-reactive, terminal groups have been developed.

Figure 1B:
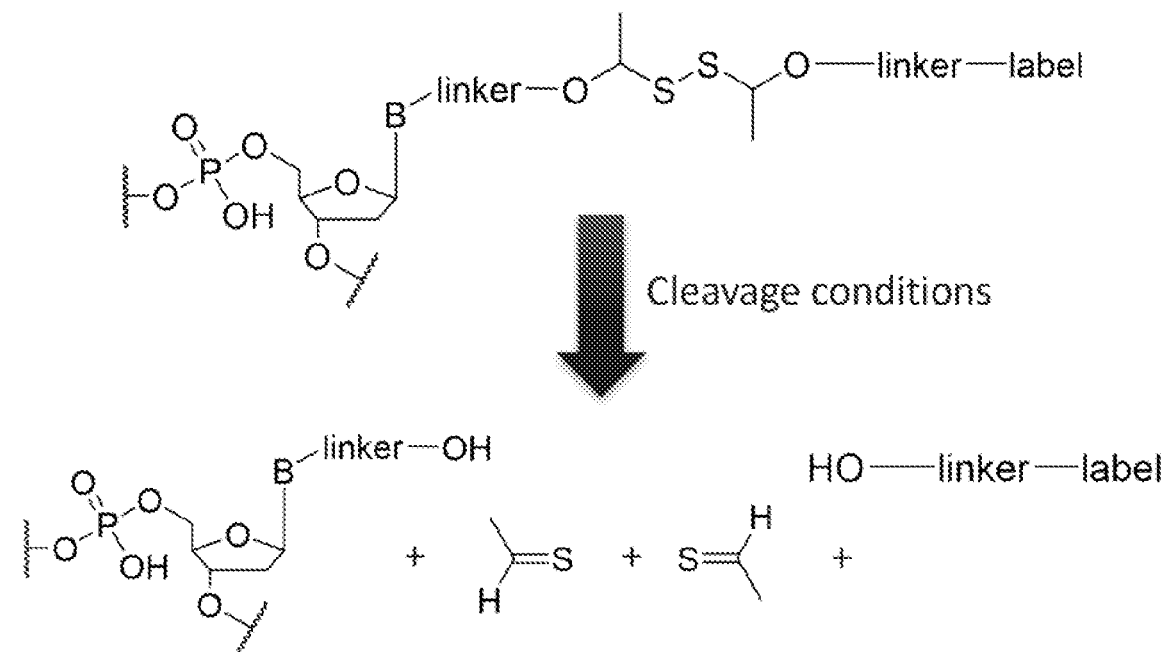

The compounds described herein include a cleavable site, that upon contact with a suitable reducing agent, reacts to form moieties such as a hydroxyl group rather than a thiol group; see FIG. 1B for an illustrative, non-limiting overview. Thiol moieties are more nucleophilic and acidic than alcohol moieties, and under suitable conditions (e.g., within a sequencing reaction) a thiol is more reactive than alcohols. An important feature of the compounds having the disulfide linker is that following cleavage, the resulting product does not have a thiol group as shown in FIG. 1B. As shown in FIG. 1B, the products linked to the nucleotide and label have a free hydroxyl group which is far less susceptible to side reactions with other nucleotides or proteins in situ than products with a free thiol group since a free hydroxyl group is less nucleophilic and acidic than a free thiol group (see Principles of Organic Chemistry, Ouellette and Rawn, 2015, Elsevier, p. 194-195).

Example 2. Cleavage Kinetics and Thioaldehyde Stability

The speed of sequencing cycle (e.g., the time to incorporate, detect, and cleave a modified nucleotide) is limited by the reaction kinetics. Improvements in sequencing cycle times may be realized if the kinetics of cleaving the linker and/or the reversible terminator of a labeled modified nucleotide is increased. Reaction rates can generally be predicted by the Hammond Postulate, which suggests that the activation energy of the rate determining step is inversely proportional to the stability of the transition state. Therefore, the more geometrically similar the transition state generated is to the product, the more quickly the reaction should progress (see for example March's Advanced Organic Chemistry, 6th Ed., Wiley, 2007, Michael B. Smith and Jerry March, Chapter 6 Methods of determining mechanisms, page 308). Transition states have only a transitory existence and are difficult, if not impossible, to observe, isolate, and quantify. In the compounds described herein, following the cleavage of the disulfide bond, the resultant thiol as only a transitory existence before becoming a thioaldehyde. Shown in Scheme 1 is a proposed mechanism for formation of the thioaldehyde products generated following cleavage of the disulfide bond.

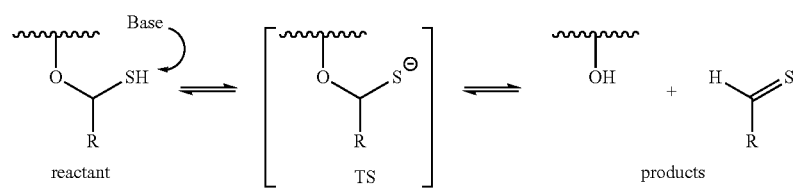

Scheme 1. The proposed fragmentation mechanism following disulfide cleavage, wherein a base removes a hydrogen from the thiol (note, the disulfide bond has already been reduced via a reducing agent). The resulting transition state (TS) is then converted to a hydroxyl and a thioaldehyde. R is as described herein (e.g., $R^5$ or $R^6$).

By invoking the Hammond Postulate, one would also expect that the thermodynamic stability of the resultant thioaldehyde to influence the cleavage rate. Simple thermodynamics provides the enthalpy changes of the reaction, ΔH, as a measure of the thermodynamic stability. The enthalpy change is calculated as the difference in the enthalpy of the products and reactants, $\Delta H = \Delta H_{products} - \Delta H_{reactants}$, as provided in Scheme 2.

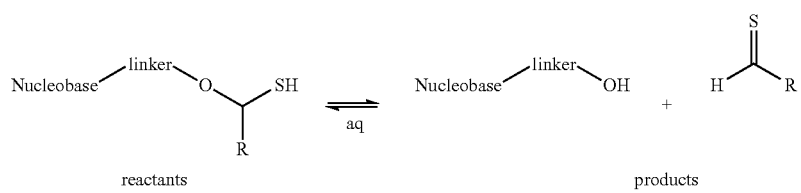

reactants  products

Scheme 2. A nucleotide with a linker having an alkylthiol converting to a nucleotide with an OH group and a thioaldehyde.

Using ΔH as a corollary for the reaction rate, it is possible to predict which reversible terminators will cleave rapidly under suitable conditions. Gas phase calculations were performed on a model system using hybrid Density Functional Theory (B3LYP) with a large basis set (Valence triple-zeta with two sets of polarization functions); to determine the optimized structure and energy of the reactants and the products were performed to derive a ΔH for a variety of compounds, see U.S. Pat. No. 11,174,281, which is incorporated herein by reference. Experimental evidence supports using ΔH as a proxy for the reaction rate, as reported in see U.S. Pat. No. 11,174,281, showing the experimentally derived cleavage halftime for RT #1, RT #2, and RT #3 as a function of the calculated ΔH. Reducing the energetic burden on the system, i.e., reducing the enthalpy, corresponds to faster cleavage rates.

Given the proposed reaction mechanism and suggested transition state (TS), a thioaldehyde with a substituent (R, in scheme 2) that better stabilizes the sp2 carbon should result in a more stable TS and permit for faster cleavage since the kinetics of a reaction depend on the activation energy, i.e., the difference between the energy of the reactants and the transition state. The thioaldehyde has a corresponding ylide as shown in Scheme 3.

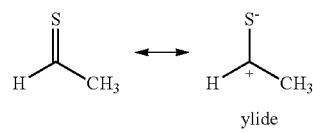

ylide

Scheme 3. A thioaldehyde and its corresponding ylide structure.

In theory, a substituent that better stabilizes the sp² carbon of the ylide would result in a transitional state that is more thermodynamically favored and geometrically similar to the resultant thioaldehyde, which would result in a faster reaction. An example of such a substituent would be a cyclic moiety (e.g., an aromatic or heteroaromatic moiety) at the R position as shown in Scheme 4:

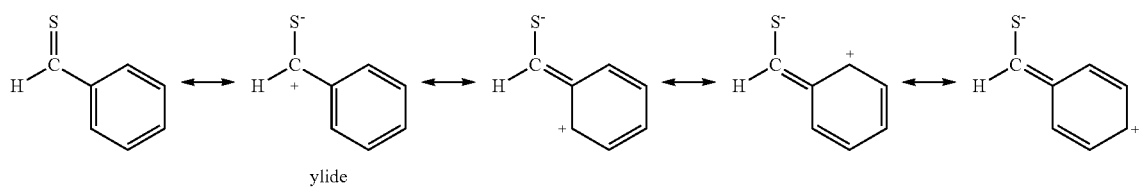

ylide

Scheme 4. A thioaldehyde which has R=phenyl and its multiple resonance structures.

The multiple possible resonance structures allows for greater electron delocalization, thereby increasing the stability of the transition state. Therefore, going from reactants to products should involve smaller reorganization of the molecular structures, lowering the activation energy of the reaction, which results in a faster generation of the resultant thioaldehyde.

Given that the stability of the resultant thioaldehyde plays a role in the reaction rate, a model compound with the chemical group

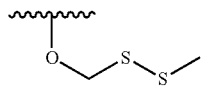

(referred to as a methylene disulfide, or RT #1) would be expected to cleave at a slower rate than a model compound with the chemical group

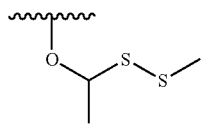

(RT #2) due to the stabilizing effect of the methyl substituent on the methylene carbon on the suggested transition state. It was found that an RT that includes a methyl substituent on the methylene carbon having the structure

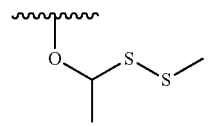 [SMILES: *OC(C)SSC]

(RT #2) cleaves approximately 10-fold faster than

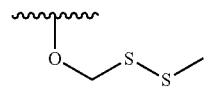 [SMILES: *OCSSC]

(RT #1), see U.S. Pat. Nos. 11,174,281 and 10,738,072, which are each incorporated herein by reference for all purposes.

Example 3. Chemical Synthesis of Cleavable Linkers

Described herein is a generalized process for synthesizing compounds described herein.

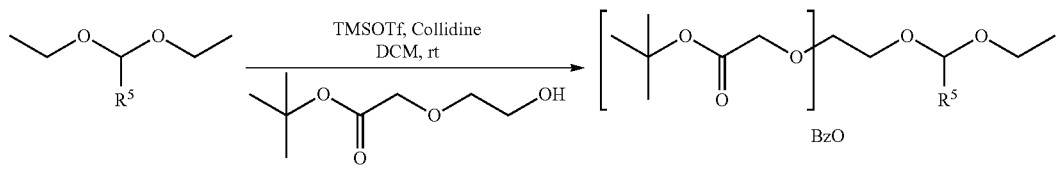

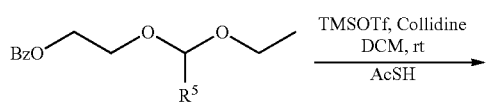

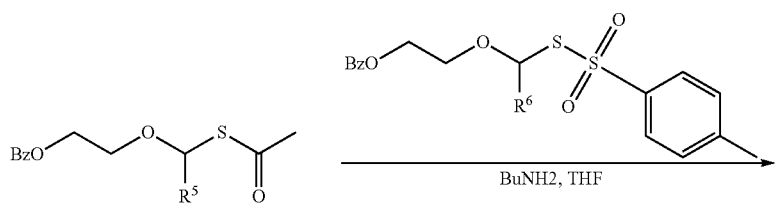

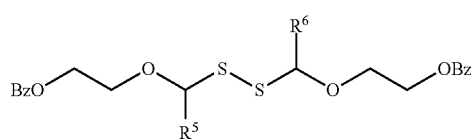

Scheme 5. A generalized synthetic protocol for producing a compound as described herein, wherein $R^5$ and $R^6$ are as described herein.

The initial acetal depicted in Scheme 5 may be synthesized according to Scheme 6.

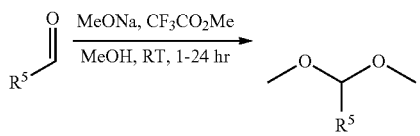

Scheme 6. Synthetic protocol for the synthesis of acetals under basic conditions from aldehydes, wherein $R^5$ is as described herein. This reaction is modified to generate alternative acetals by modifying the reactants (e.g., sodium ethoxide is substituted for sodium methoxide).

The compounds synthesized in Scheme 5 were further modified as shown in Scheme-7.

Scheme 7 may be further generalized, as depicted in Scheme 8. Depicted in Scheme 8 is a suitable means for adding $L^{101}$ and $L^{102}$ to a compound produced using Scheme 5. Following deprotection of OBz to generate the corresponding hydroxy group, the desired linker, $L^{101}$ and $L^{102}$, covalently bonded to a leaving group is added to a reaction vessel with this compound. The term "leaving group" is used in accordance with its ordinary meaning in chemistry and refers to a moiety (e.g., atom, functional group, or molecule) that separates from the molecule following a chemical reaction (e.g., bond formation, reductive elimination, condensation, or cross-coupling reaction) involving an atom or chemical moiety to which the leaving group is attached, also referred to herein as the "leaving group reactive moiety", and a complementary reactive moiety (i.e., a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive

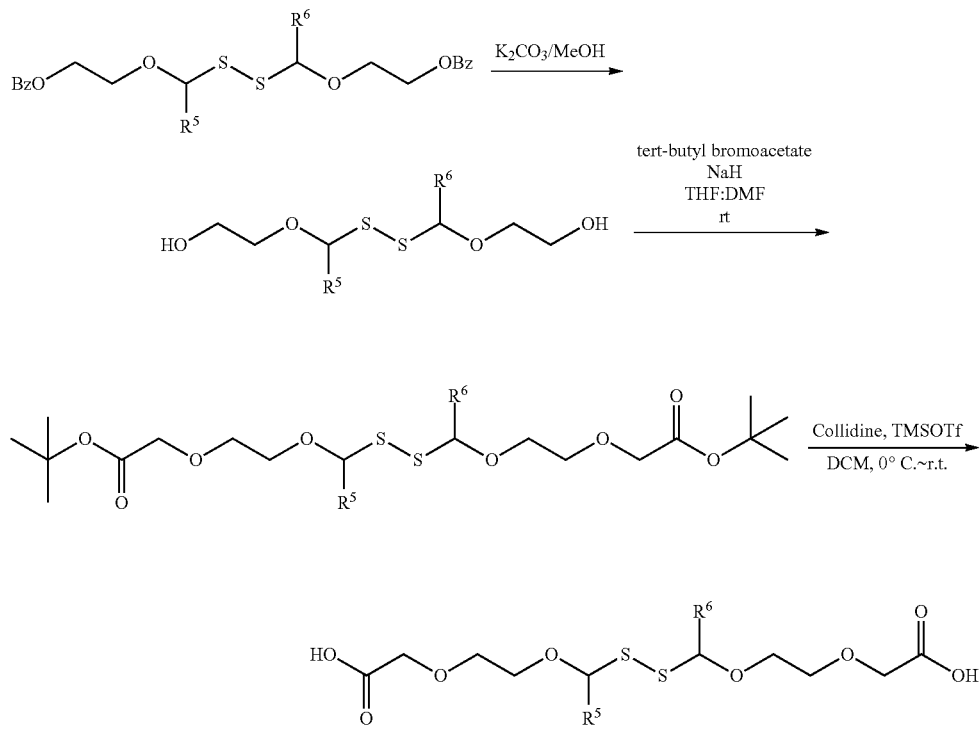

Scheme 7. A generalized synthetic protocol for producing linkers of formula

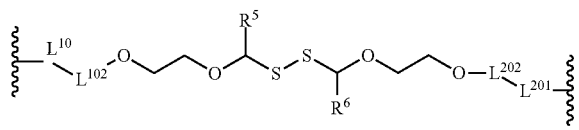

wherein $R^5$, $R^6$ are as described herein and a) one of $L^{101}$ or $L^{102}$ is a bond and the other is C(O)O and one of $L^{202}$ or $L^{201}$ is a bond and the other is C(O)O or b) $L^{102}$ and $L^{202}$ are C(O) and $L^{101}$ and $L^{201}$ are O.

group pair. Non limiting examples of leaving groups include hydrogen, hydroxide, halogen (e.g., Br), perfluoroalkylsulfonates (e.g., triflate), tosylates, mesylates, water, alcohols, nitrate, phosphate, thioether, amines, ammonia, fluoride, carboxylate, phenoxides, boronic acid, boronate esters, substituted or unsubstituted piperazinyl, and alkoxides. In embodiments, two molecules are allowed to contact, wherein at least one of the molecules has a leaving group, and upon a reaction and/or bond formation (e.g., acyloin condensation, aldol condensation, Claisen condensation, or Stille reaction) the leaving group(s) separate from the respective molecule. In embodiments, a leaving group is a bioconjugate reactive moiety. In embodiments, the leaving groups is designed to facilitate the reaction. In embodiments, the leaving group is a substituent group.

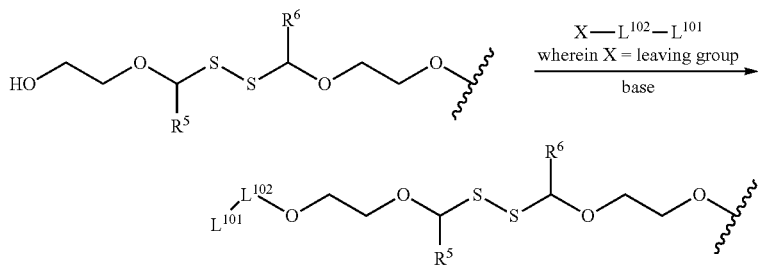

Scheme 8. Generalized synthetic protocol for the synthesis of linkers with various functional groups under basic conditions from the corresponding hydroxy compound, wherein $R^5$, $R^6$, $L^{101}$, and $L^{102}$ are as described herein. This reaction may be modified to generate alternative carboxylate groups by modifying the reactants (e.g., iso-propyl bromoacetate is substituted for tert-butyl bromoacetate). This reaction can be modified further by reacting an amine with the carboxylate to form an amide ($L^{102}$ or $L^{202}$=C(O)NH).

Experimental procedures used for the synthesis of a linker are described herein. Dry DCM is added to a round bottom flask containing ethylene glycol and triethylamine. Benzoyl chloride is added dropwise over 30 min with stirring at room temperature under argon. The reaction mixture was stirred at room temperature for 4 hours. The organic phase was extracted with DCM, dried over sodium sulfate, concentrated and purified by normal phase chromatography to obtain 2-hydroxyethyl benzoate as colorless oily liquid. $^1$H NMR (500 MHz, CDCl$_3$) δ 8.06 (m, 2H), 7.56 (tt, J=7.4, 1.6 Hz, 1H), 7.44 (m, 2H), 4.46 (m, 2H), 3.95 (m, 2H), 2.21 (s (br), 1H).

To a solution of 1,1-diethoxy-2-methylpropane in DCM was added 2,4,6-trimethylpyridine. The reaction mixture was cooled to 0° C. and trimethylsilyl trifluoromethanesulfonate was added. The reaction mixture was stirred at this temperature for 30 minutes after which 2-hydroxyethyl benzoate was added. The subsequent reaction mixture was allowed to warm up to room temperature, quenched with saturated sodium bicarbonate solution and the organic phase was extracted. The crude mixture was purified by normal phase chromatography to obtain 2-(1-ethoxy-2-methylpropoxy)ethyl benzoate as colorless oil. $^1$H NMR (500 MHz, CDCl$_3$) δ 8.06 (t, J=7.2 Hz, 2H), 7.62-7.50 (m, 1H), 7.49-7.37 (m, 2H), 4.50-4.44 (m, 2H), 4.18 (d, J=7.2 Hz, 1H), 3.92-3.86 (m, 1H), 3.86-3.77 (m, 1H), 3.75-3.61 (m, 1H), 3.57-3.43 (m, 1H), 1.99-1.83 (m, 1H), 1.20 (dd, J=9.2, 5.0 Hz, 3H), 0.93 (dt, J=7.0, 3.6 Hz, 6H). MS for (M+Na)=289.

To a solution of 2-(1-ethoxy-2-methylpropoxy)ethyl benzoate in DCM was added 2,4,6-trimethylpyridine. The reaction mixture was cooled to 0° C. and trimethylsilyl trifluoromethanesulfonate was added dropwise. The resulting reaction mixture was stirred and upon complete consumption of starting material as monitored by TLC, thioacetic acid was added. The subsequent reaction mixture was warmed to room temperature. The crude reaction mixture was concentrated in vacuo and purified by normal phase chromatography to obtain of 2-(1-(acetylthio)-2-methylpropoxy)ethyl benzoate as colorless oil. $^1$H NMR (499 MHz, CDCl$_3$) δ 8.14-7.97 (m, 2H), 7.56 (ddd, J=7.0, 2.6, 1.3 Hz, 1H), 7.52-7.36 (m, 2H), 5.29 (d, J=4.9 Hz, 1H), 4.49-4.39 (m, 2H), 3.97-3.85 (m, 1H), 3.77-3.67 (m, 1H), 2.38 (s, 3H), 2.09 (m, 1H), 0.96 (ddd, J=8.3, 6.7, 2.0 Hz, 6H). MS for (M+Na)=319.

To a solution of 2-(1-ethoxy-2-methylpropoxy)ethyl benzoate in DCM was added 2,4,6-trimethylpyridine. The reaction mixture was cooled to 0° C. and trimethylsilyl trifluoromethanesulfonate was added dropwise. The subsequent reaction mixture was stirred and upon complete consumption of starting material as monitored by TLC, potassium p-toluene thiosulfonate was added. The crude mixture was filtered using filter paper, concentrated in vacuo and dissolved in THF. 2-(1-(acetylthio)-2-methylpropoxy)ethyl benzoate was then added followed by the addition of 2M butylamine in THF. The resulting mixture was stirred for 2 hours, concentrated in vacuo and purified by reverse phase chromatography using acetonitrile and water to obtain ((disulfanediylbis(2-methylpropane-1,1-diyl))bis(oxy))bis(ethane-2,1-diyl) dibenzoate as a colorless oil. $^1$H NMR (500 MHz, CDCl$_3$) δ 7.59-7.50 (m, 4H), 7.47-7.35 (m, 2H), 4.60-4.40 (m, 4H), 4.30 (dd, J=6.0, 2.2 Hz, 2H), 4.18 (dddd, J=11.2, 5.5, 3.4, 2.2 Hz, 2H), 3.83-3.67 (m, 2H), 2.18 (dq, J=13.5, 6.7 Hz, 2H), 1.04 (dd, J=6.7, 3.1 Hz, 6H), 1.00 (dd, J=6.8, 4.2 Hz, 6H). MS for (M+Na)=529.

To a solution of ((disulfanediylbis(2-methylpropane-1,1-diyl))bis(oxy))bis(ethane-2,1-diyl) dibenzoate in methanol was added potassium carbonate. The reaction mixture was stirred at room temperature. Upon consumption of starting material as monitored by TLC, the reaction mixture was concentrated in vacuo and was purified by normal phase chromatography to obtain of 2,2'-((disulfanediylbis(2-methylpropane-1,1-diyl))bis(oxy))bis(ethan-1-ol). $^1$H NMR (500 MHz, CDCl$_3$) δ 4.27 (d, J=7.1 Hz, 1H), 4.03-3.90 (m, 3H), 3.86-3.71 (m, 4H), 3.60 (dddd, J=17.2, 7.2, 5.2, 2.8 Hz, 2H), 3.08 (s, 1H), 2.62 (s, 1H), 2.29 (qd, J=13.5, 6.7 Hz, 1H), 2.19 (dq, J=13.6, 6.8 Hz, 1H), 1.09-0.97 (m, 12H). MS for (M+Na)=337.

To a solution of 2,2'-((disulfanediylbis(2-methylpropane-1,1-diyl))bis(oxy))bis(ethan-1-ol) and tert-butyl bromoacetate in THF:DMF, was added 90% sodium hydride. The reaction mixture was stirred at room temperature. Upon consumption of starting material as monitored by TLC, the reaction mixture was filtered and concentrated in vacuo. The crude was purified by reverse phase chromatography HPLC using acetonitrile and water as the eluent system to obtain of di-tert-butyl 7,10-diisopropyl-3,6,11,14-tetraoxa-8,9-dithiahexadecanedioate. $^1$H NMR (500 MHz, CDCl$_3$) δ 4.30 (dd, J=5.8, 2.6 Hz, 1H), 4.06-4.01 (m, 3H), 3.79-3.68 (m, 2H), 3.68-3.57 (m, 1H), 2.23-2.10 (m, 1H), 1.48 (s, 9H), 1.02 (ddd, J=11.8, 6.8, 4.1 Hz, 6H). MS for (M+Na)=549.

To a solution of di-tert-butyl 7,10-diisopropyl-3,6,11,14-tetraoxa-8,9-dithiahexadecanedioate in DCM was added 2,4,6-trimethylpyridine and trimethylsilyl trifluoromethanesulfonate. The reaction mixture was stirred at room temperature and purified by reverse phase chromatography HPLC using acetonitrile and water as the eluent system to obtain 7,10-diisopropyl-3,6,11,14-tetraoxa-8,9-dithiahexadecanedioic acid. ¹H NMR (500 MHz, DMSO) δ 4.43 (dd, J=5.9, 2.2 Hz, 2H), 3.95 (s, 4H), 3.93-3.87 (m, 2H), 3.62 (ddd, J=26.9, 14.8, 7.2 Hz, 6H), 2.11 (dd, J=13.0, 6.6 Hz, 2H), 1.06-0.91 (m, 12H). MS for (M+Na)=413.

To confirm the formation of a hydroxyl moiety results following cleavage, a model compound was synthesized. A first fluorescent label was conjugated to a compound described herein, followed by conjugation to a second fluorescent label; see FIG. 2A for an illustrative representation of the model compound [MS: calc'd: 1962.62; observed 1964.47]. Following contact with a reducing agent, the disulfide bond was cleaved, and a hydroxyl terminated dye was detected, see FIG. 2B for an illustrative representation of the hydroxyl terminated dye, [MS: calc'd: 894.28; observed: 895.07].

Figure 2A:
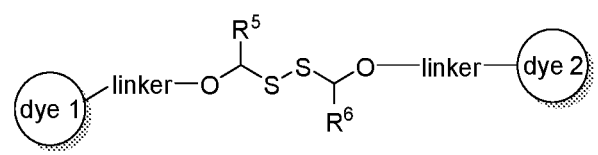
FIGS. 2A-2B. A dye-linker-dye construct is shown in FIG. 2A, wherein $R^5$ and $R^6$ are as described herein. Following contact with a reducing agent, the disulfide bond was cleaved, and a hydroxyl terminated dye was detected, see FIG. 2B for an illustrative representation of the hydroxyl terminated dye.
Figure 2B:
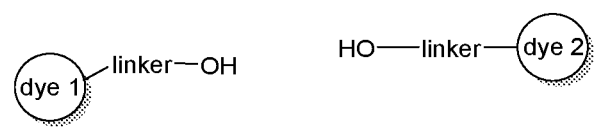

The model compound depicted in FIG. 2A is useful to quantify the byproduct formation, or lack thereof, following cleaving the linker. In embodiments, dye1 and/or dye2 may be replaced with any substance or molecule requiring detection. For example dye1 of FIG. 2A, referred to as $R^9$ herein, may be a protein and dye2 of FIG. 2A, referred to as $R^{10}$ herein, may be a fluorophore. Following cleavage (e.g., contacting the disulfide portion of the linker with a reducing agent) the fluorophore is separated from the protein and does not contain a reactive thiol.

P-Embodiments

The present disclosure provides the following illustrative embodiments.

Embodiment P1. A compound having the formula:

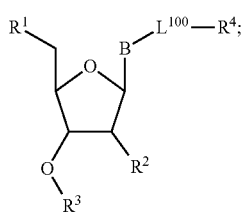

(I)

wherein

B is a divalent nucleobase;

$R^1$ is a 5'-nucleoside protecting group, monophosphate moiety, polyphosphate moiety, or nucleic acid moiety;

$R^2$ and $R^3$ are independently hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety;

$R^4$ is a detectable moiety;

$L^{100}$ is a divalent linker comprising

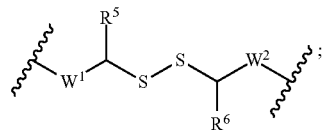

wherein $R^5$ and $R^6$ are independently —CN, —OH, —NH₂, —COOH, —CONH₂, —NO₂, —SO₃H, —SO₄H, —SO₂NH₂, —NHNH₂, —ONH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $W^1$ and $W^2$ are independently —O—, —NH—, —Si—, or —PH—.

Embodiment P2. The compound of Embodiment P1, wherein $R^2$ is hydrogen.

Embodiment P3. The compound of Embodiment P1 or Embodiment P2, wherein $R^1$ is a triphosphate moiety.

Embodiment P4. The compound of any one of Embodiments P1 to P3, wherein B is a cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

Embodiment P5. The compound of Embodiment P1, having the formula:

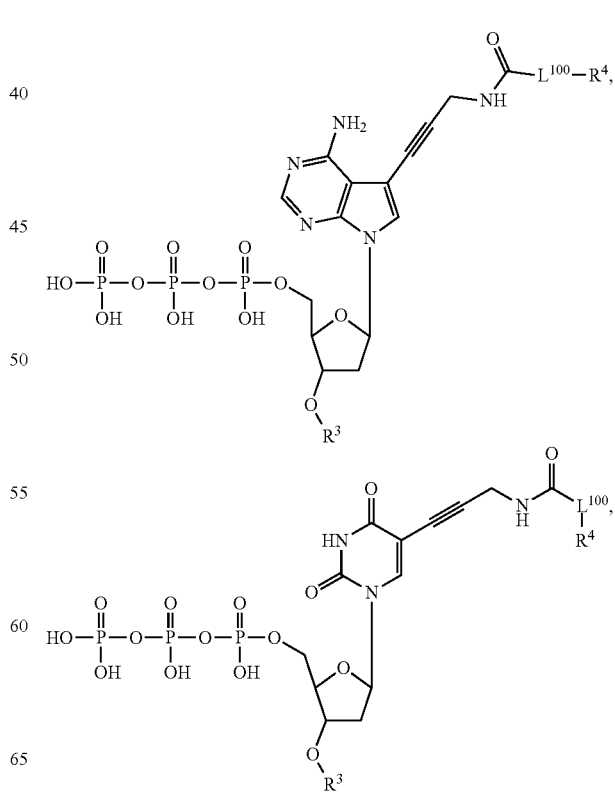

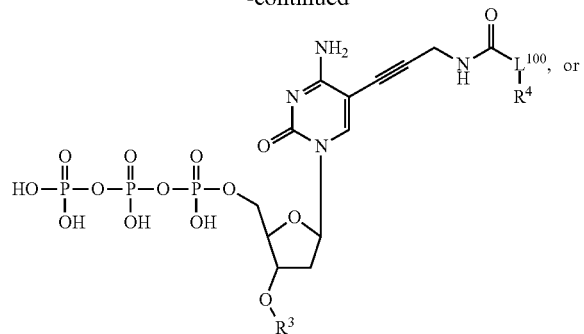

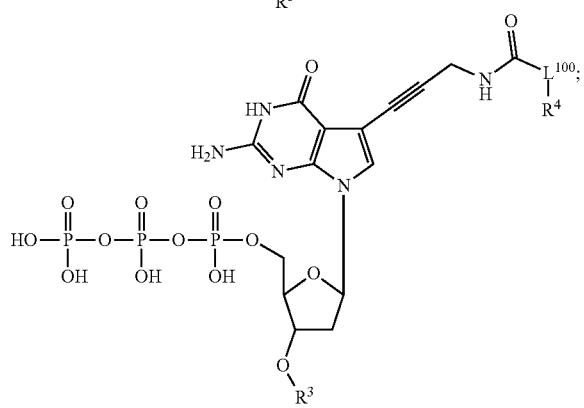

wherein $L^{100}$ is a cleavable linker comprising

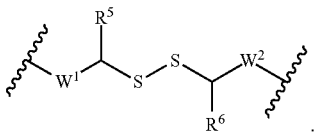

Embodiment P6. The compound of any one of Embodiments P1 to P5, wherein $W^1$ and $W^2$ are independently —O— or —NH.

Embodiment P7. The compound of any one of Embodiments P1 to P5, wherein $W^1$ and $W^2$ are —O—.

Embodiment P8. The compound of any one of Embodiments P1 to P7, wherein $R^5$ and $R^6$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P9. The compound of any one of Embodiments P1 to P7, wherein $R^5$ and $R^6$ are independently substituted or unsubstituted $C_1$-$C_6$ alkyl, substituted or unsubstituted 2 to 8 membered heteroalkyl, substituted or unsubstituted $C_3$-$C_6$ cycloalkyl, substituted or unsubstituted 2 to 8 membered heterocycloalkyl, substituted or unsubstituted $C_6$ to $C_{12}$ aryl, or substituted or unsubstituted 2 to 8 membered heteroaryl.

Embodiment P10. The compound of any one of Embodiments P1 to P7, wherein $R^5$ and $R^6$ are independently substituted or unsubstituted alkyl, substituted or unsubstituted cycloalkyl, or substituted or unsubstituted aryl.

Embodiment P11. The compound of any one of Embodiments P1 to P7, wherein $R^5$ and $R^6$ are independently substituted or unsubstituted cycloalkyl, substituted or unsubstituted heterocycloalkyl, substituted or unsubstituted aryl, or substituted or unsubstituted heteroaryl.

Embodiment P12. The compound of any one of Embodiments P1 to P11, wherein $L^{100}$ is a divalent linker comprising

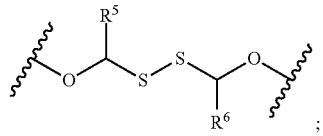

wherein $R^5$ and $R^6$ are unsubstituted alkyl.

Embodiment P13. The compound of any one of Embodiments P1 to P11, wherein $L^{100}$ has the formula:

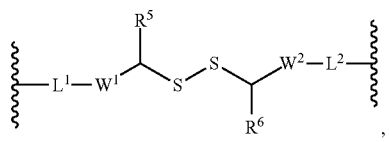

wherein $L^1$ has the formula $-L^{101}-L^{102}-L^{103}-$.

$L^{101}$, $L^{102}$, and $L^{103}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^2$ has the formula $-L^{201}-L^{202}-L^{203}-$; and $L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment P14. The compound of Embodiment P13, wherein $L^{100}$ has the formula:

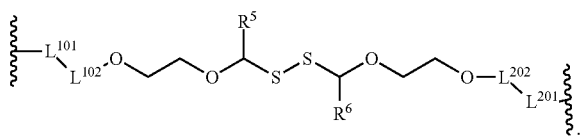

Embodiment P15. The compound of Embodiment P13, wherein $L^{100}$ has the formula:

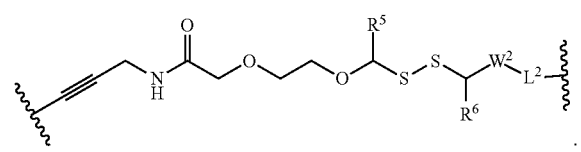

Embodiment P16. The compound of any one of Embodiments P1 to P15, wherein the polymerase-compatible cleavable moiety is

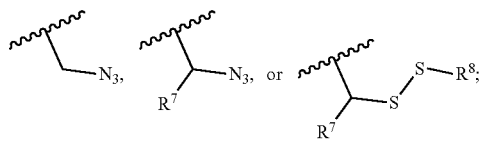

wherein

R⁷ is substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and R⁸ is substituted or unsubstituted alkyl.

Embodiment P17. The compound of any one of Embodiments P1 to P15, wherein the polymerase-compatible cleavable moiety is independently:

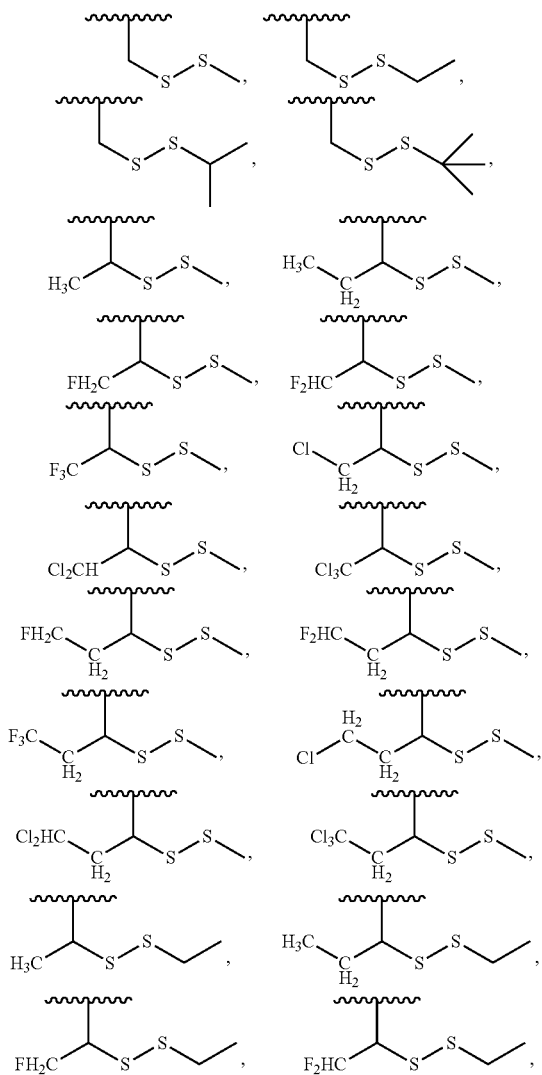

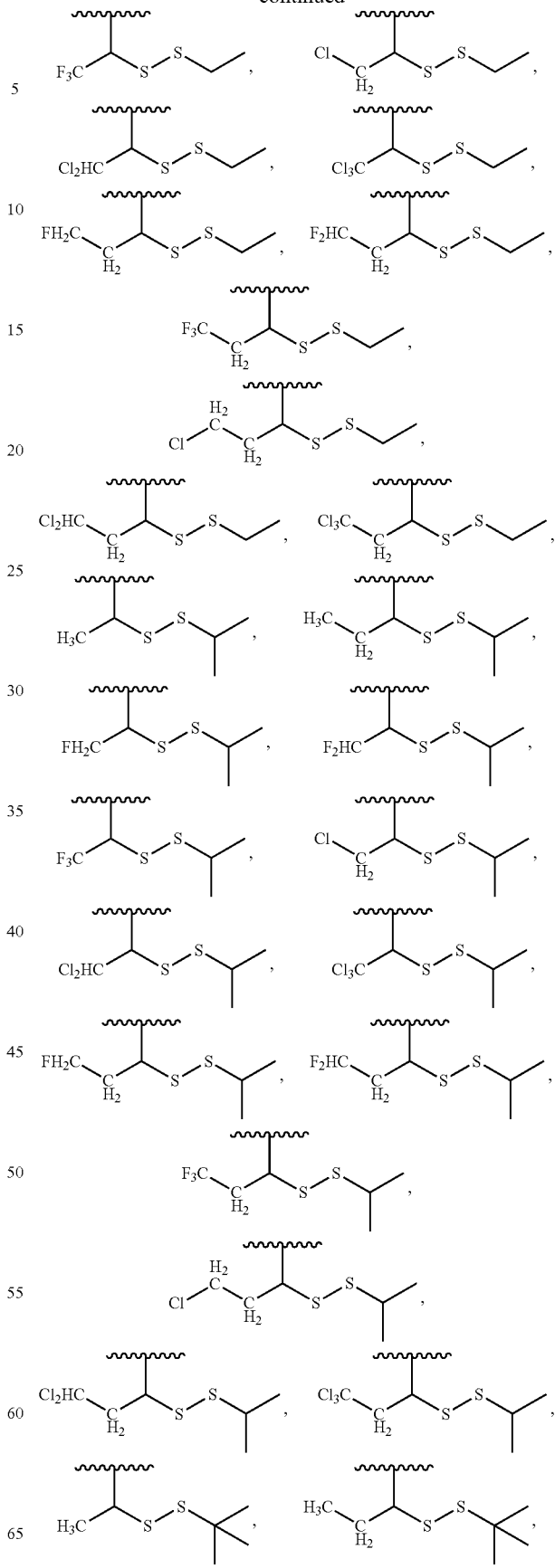

-continued
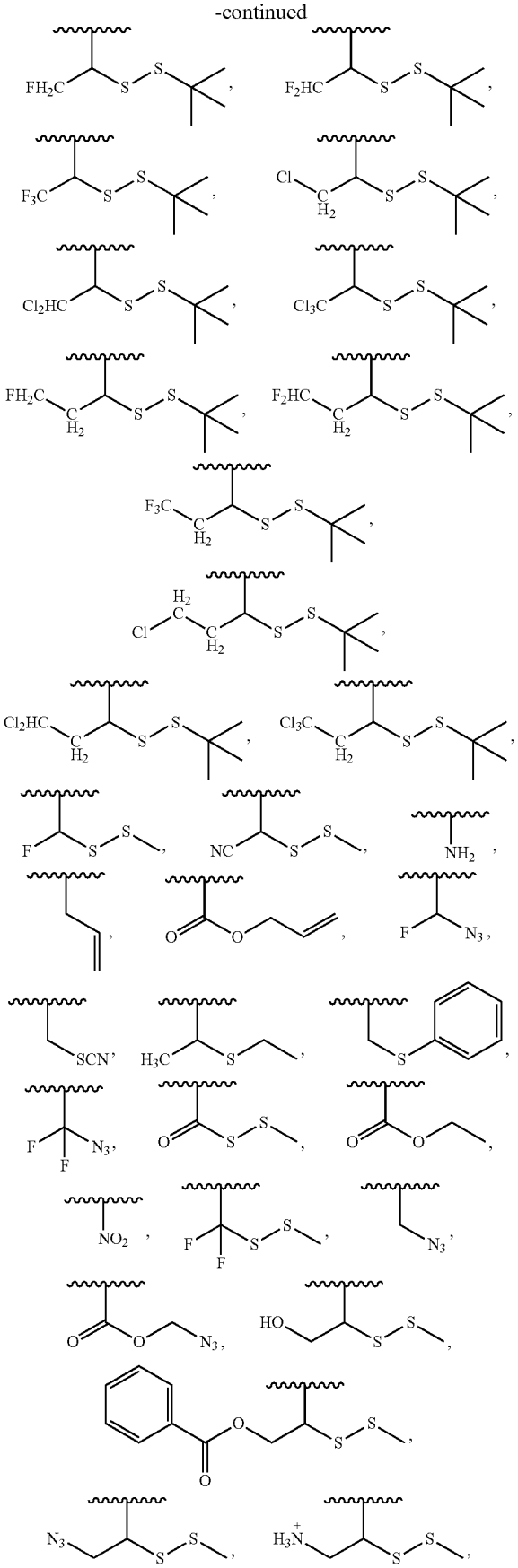
-continued
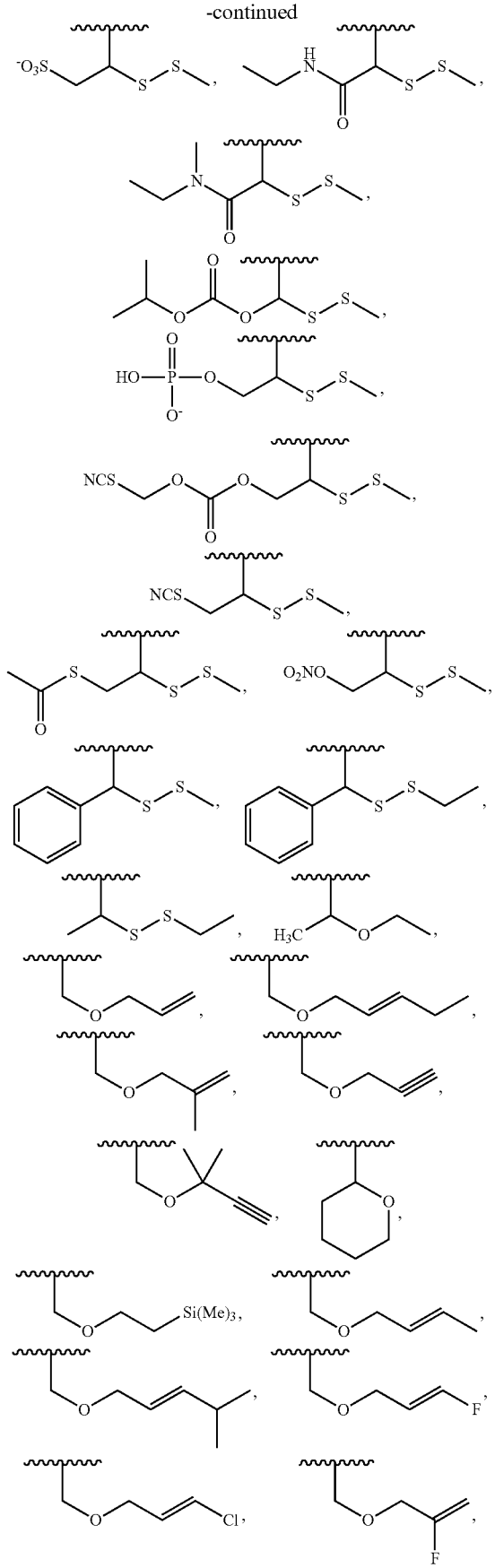

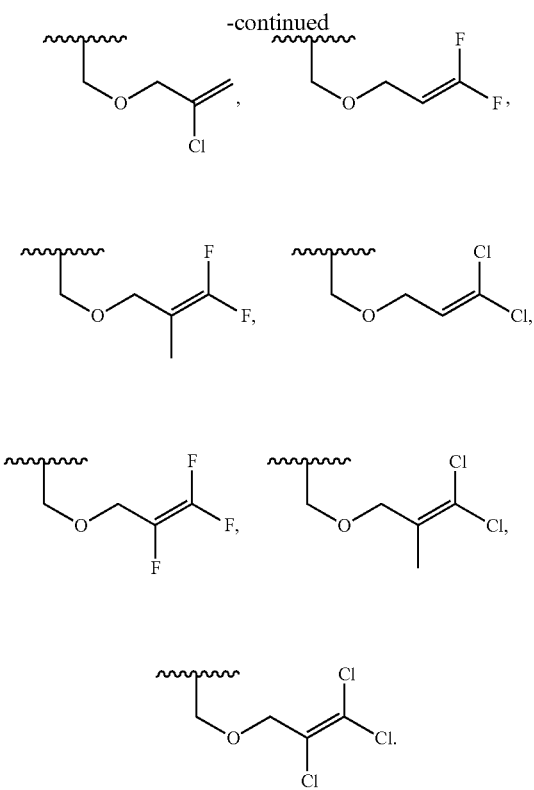

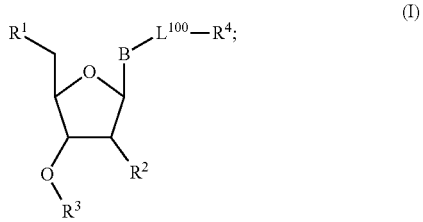

Additional Embodiments

Embodiment 1. A compound having the formula:

(I)

wherein B is a divalent nucleobase; $R^1$ is a polyphosphate moiety, 5'-nucleoside protecting group, monophosphate moiety, or nucleic acid moiety; $R^2$ is hydrogen or —OH; $R^3$ is a reversible terminator moiety, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is a detectable moiety; $L^{100}$ is a divalent linker comprising

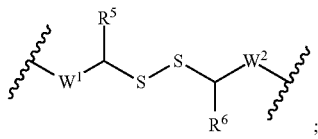

wherein $R^5$ and $R^6$ are independently unsubstituted alkyl, —CN, —OH, —NH$_2$, —COOH, —CONH$_2$, —NO$_2$, —SO$_3$H, —SO$_4$H, —SO$_2$NH$_2$, —NHNH$_2$, —ONH$_2$, substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $W^1$ and $W^2$ are independently —O—, —NH—, —Si—, or —PH—.

Embodiment 2. The compound of Embodiment 1, wherein $R^2$ is hydrogen.

Embodiment 3. The compound of Embodiment 1 or Embodiment 2, wherein $R^1$ is a triphosphate moiety.

Embodiment 4. The compound of any one of Embodiments 1 to 3, wherein B is a cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

Embodiment P18. A method for sequencing a nucleic acid, comprising:
(i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label;
(ii) detecting said unique detectable label of each incorporated compound, so as to thereby identify each incorporated compound in said extension strand, thereby sequencing the nucleic acid;
wherein each of said four different compounds is independently a compound of any one of Embodiments P1 to P17.

Embodiment P19. A method of sequencing nucleic acid comprising:
(i) providing a nucleic acid template hybridized to a primer;
(ii) extending the primer hybridized to said nucleic acid template with a compound of any one of Embodiments P1 to P17; and
(iii) identifying the compound, so as to sequence the nucleic acid.

Embodiment P20. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound any one of Embodiments P1 to P17.

Embodiment P21. A nucleic acid polymerase complex comprising a nucleic acid polymerase, wherein said nucleic acid polymerase is bound to a compound of any one of Embodiments P1 to P17.

Embodiment 5. The compound of Embodiment 1, having the formula:

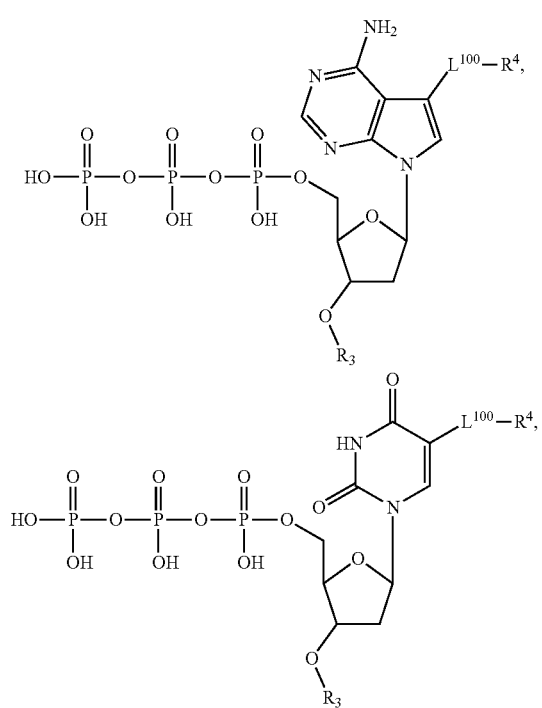

wherein $L^{100}$ has the formula:

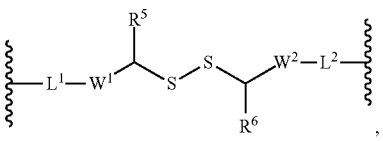

wherein $L^1$ has the formula -$L^{101}$-$L^{102}$-$L^{103}$-; $L^{101}$, $L^{102}$, and $L^{103}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^2$ has the formula -$L^{201}$-$L^{202}$-$L^{203}$-; and $L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 6. The compound of any one of Embodiments 1 to 5, wherein $W^1$ and $W^2$ are independently —O— or —NH.

Embodiment 7. The compound of any one of Embodiments 1 to 5, wherein $W^1$ and $W^2$ are —O—.

Embodiment 8. The compound of any one of Embodiments 1 to 7, wherein $R^5$ and $R^6$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or unsubstituted or unsubstituted heteroaryl.

Embodiment 9. The compound of any one of Embodiments 1 to 7, wherein $R^5$ and $R^6$ are independently substituted or unsubstituted $C_1$-$C_6$ alkyl, substituted or unsubstituted 2 to 8 membered heteroalkyl, substituted or unsubstituted $C_3$-$C_6$ cycloalkyl, substituted or unsubstituted 2 to 8 membered heterocycloalkyl, substituted or unsubstituted $C_6$ to $C_{12}$ aryl, or substituted or unsubstituted 2 to 8 membered heteroaryl.

Embodiment 10. The compound of any one of Embodiments 1 to 7, wherein $R^5$ and $R^6$ are independently substituted or unsubstituted alkyl, substituted or unsubstituted cycloalkyl, or substituted or unsubstituted aryl.

Embodiment 11. The compound of any one of Embodiments 1 to 7, wherein $R^5$ and $R^6$ are independently substituted or unsubstituted cycloalkyl, substituted or unsubstituted heterocycloalkyl, substituted or unsubstituted aryl, or substituted or unsubstituted heteroaryl.

Embodiment 12. The compound of any one of Embodiments 1 to 11, wherein $L^{100}$ is a divalent linker comprising

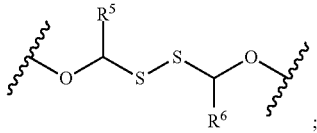

wherein $R^5$ and $R^6$ are unsubstituted alkyl.

Embodiment 13. The compound of any one of Embodiments 1 to 11, wherein $L^{100}$ has the formula:

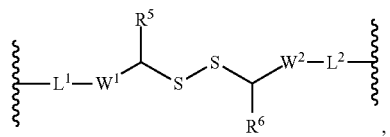

wherein $L^1$ has the formula $-L^{101}-L^{102}-L^{103}-$; $L^{101}$, $L^{102}$ and $L^{103}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^2$ has the formula $-L^{201}-L^{202}-L^{203}-$; and
$L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 14. The compound of Embodiment 13, wherein $L^{100}$ has the formula:

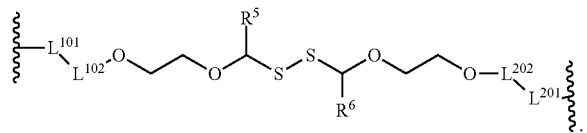

Embodiment 15. The compound of Embodiment 13, wherein $L^{100}$ has the formula:

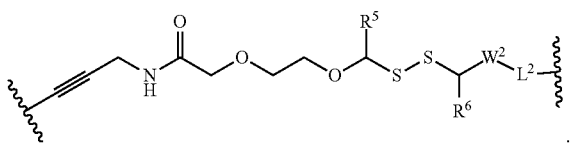

Embodiment 16. The compound of any one of Embodiments 1 to 15, wherein the reversible terminator moiety is

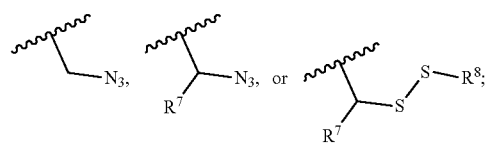

wherein $R^7$ is substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and $R^8$ is substituted or unsubstituted alkyl.

Embodiment 17. The compound of any one of Embodiments 1 to 15, wherein the reversible terminator moiety is:

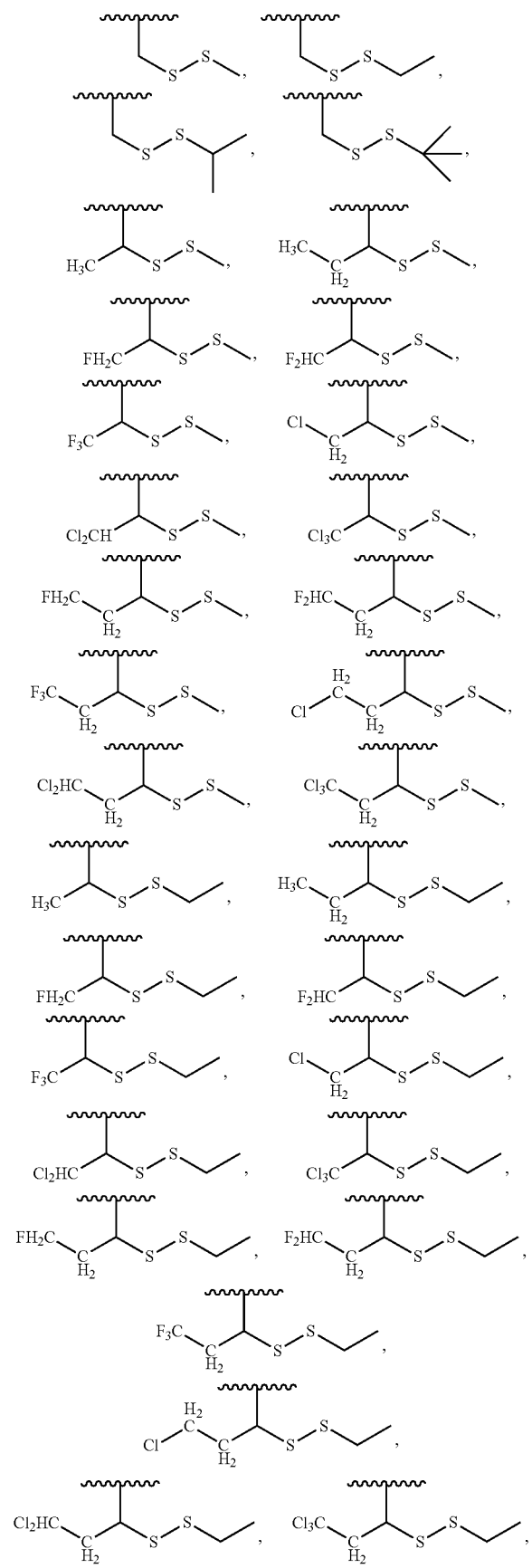

225
-continued
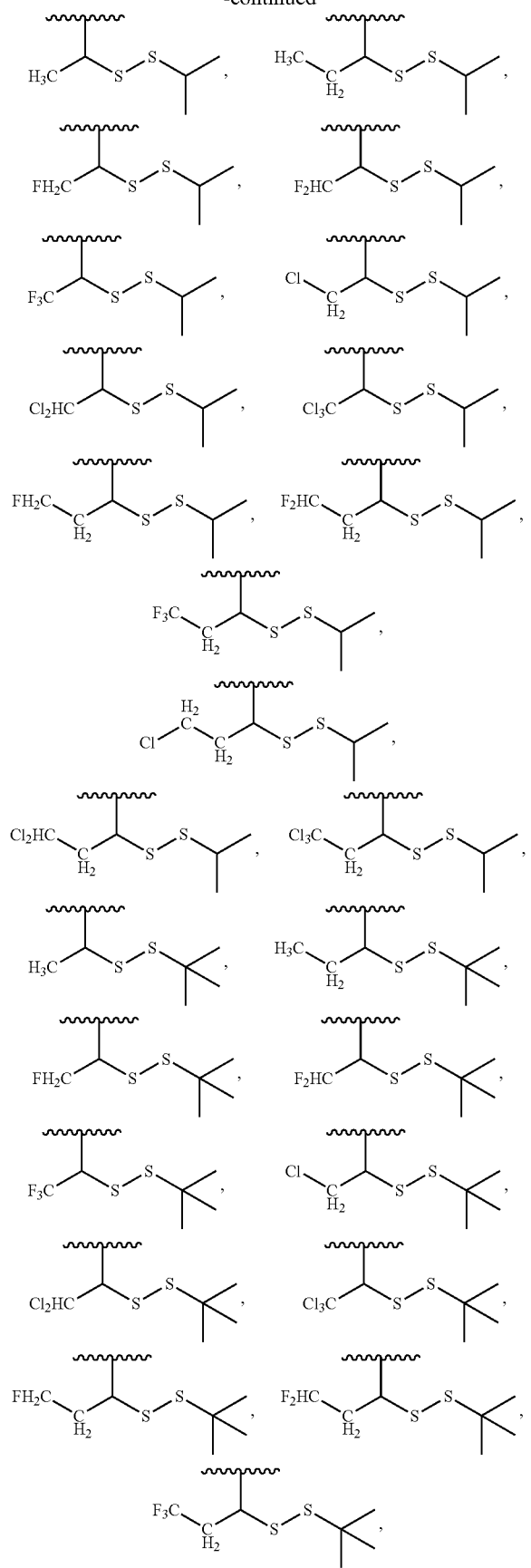
226
-continued
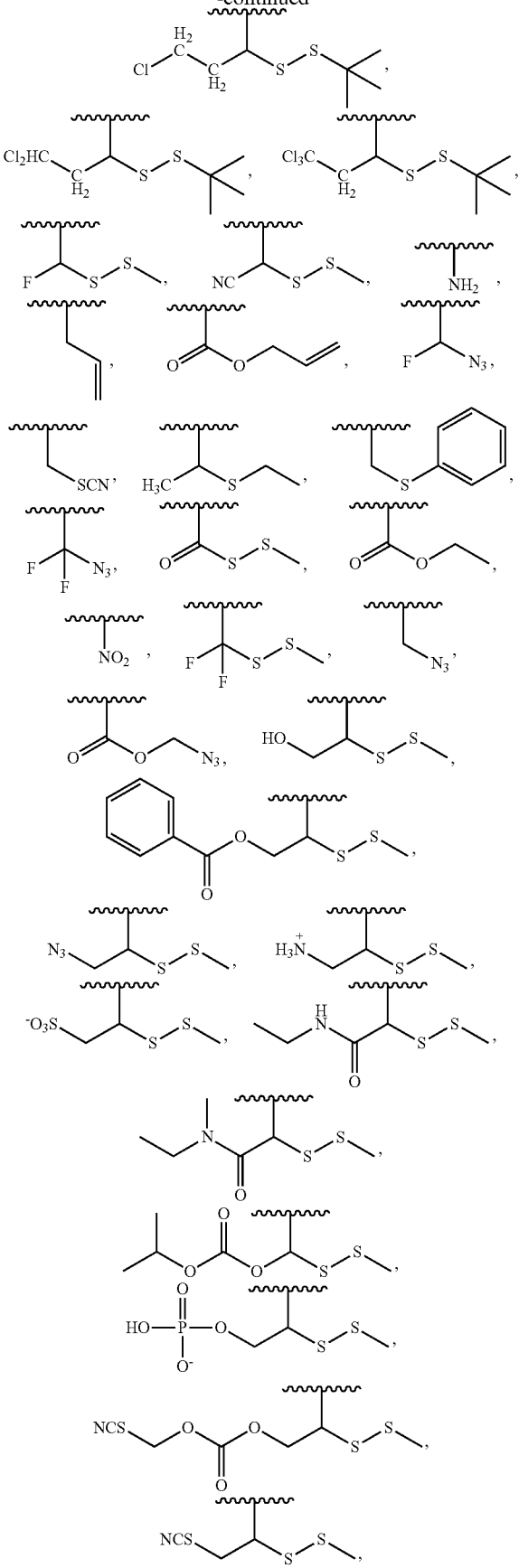

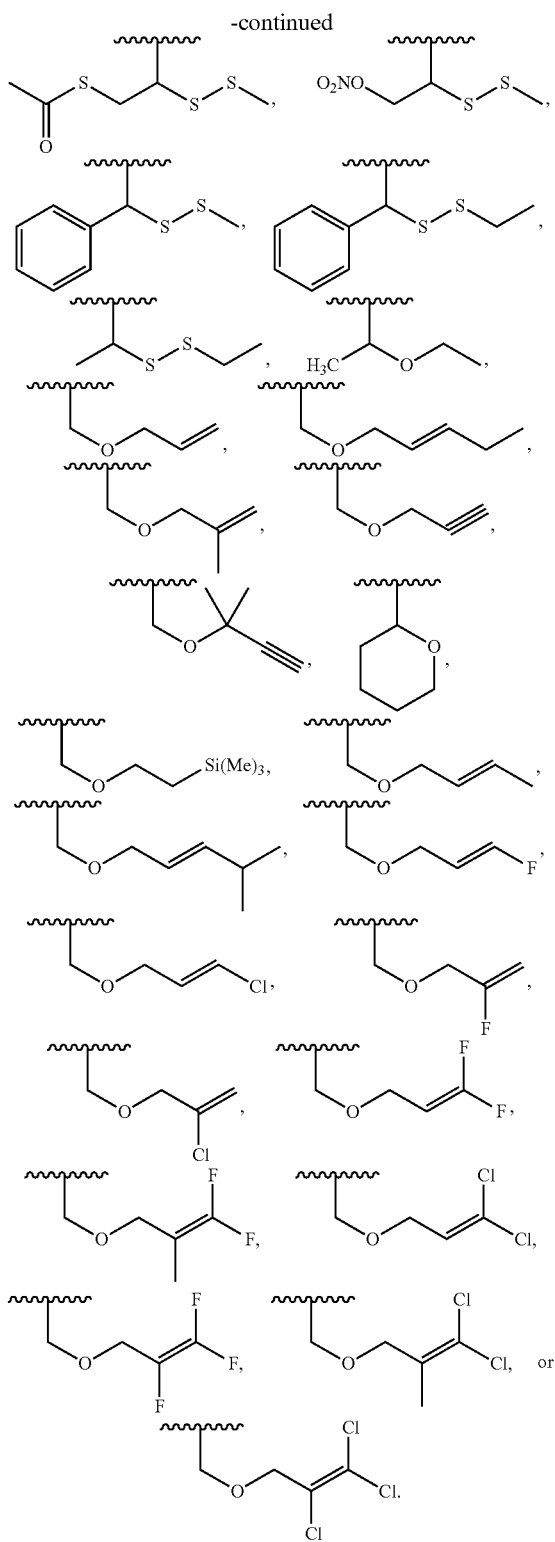

Embodiment 18. A method for sequencing a nucleic acid, comprising:
incorporating in series with a nucleic acid polymerase, within a reaction vessel, one of four different compounds into a primer to create an extension strand, wherein said primer is hybridized to said nucleic acid and wherein each of the four different compounds comprises a unique detectable label;
detecting said unique detectable label of each incorporated compound, so as to thereby identify each incorporated compound in said extension strand, thereby sequencing the nucleic acid;
wherein each of said four different compounds is independently a compound of any one of Embodiments 1 to 17.

Embodiment 19. A method of sequencing nucleic acid comprising: (i) providing a nucleic acid template hybridized to a primer; (ii) extending the primer hybridized to said nucleic acid template with a compound of any one of Embodiments 1 to 17; and (iii) identifying the compound, so as to sequence the nucleic acid.

Embodiment 20. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound any one of Embodiments 1 to 17.

Embodiment 21. A nucleic acid polymerase complex comprising a nucleic acid polymerase, wherein said nucleic acid polymerase is bound to a compound of any one of Embodiments 1 to 17.

Embodiment 22. A compound having the formula

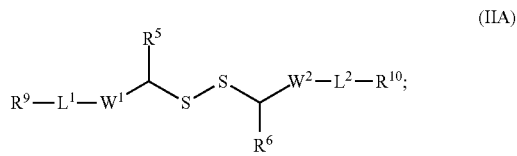

(IIA)

wherein $R^9$ and $R^{10}$ are independently a protein, bioconjugate reactive moiety, nucleotide, therapeutic moiety, nucleic acid, or a detectable moiety; $L^1$ and $L^2$ are independently a divalent linker; $R^5$ and $R^6$ are independently unsubstituted alkyl, —CN, —OH, —NH$_2$, —COOH, —CONH$_2$, —NO$_2$, —SO$_3$H, —SO$_4$H, —SO$_2$NH$_2$, —NHNH$_2$, —ONH$_2$, substituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and $W^1$ and $W^2$ are independently —O—, —NH—, —Si—, or —PH.

Embodiment 23. The compound of Embodiment 22, wherein $L^1$ has the formula -$L^{101}$-$L^{102}$-$L^{103}$-, wherein $L^{101}$, $L^{102}$, and $L^{103}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 24. The compound of Embodiment 22, wherein $L^2$ has the formula -$L^{201}$-$L^{202}$-$L^{203}$-, wherein $L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 25. The compound of Embodiment 22, wherein $R^9$ is a protein, bioconjugate reactive moiety, nucleotide, or nucleic acid.

Embodiment 26. The compound of Embodiment 25, wherein $R^{10}$ is a detectable moiety.

Embodiment 27. A compound having the formula:

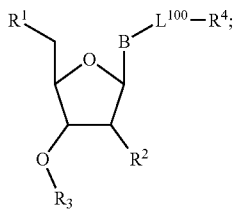

(I-K)

wherein B is a divalent nucleobase; $R^1$ is a polyphosphate moiety, 5'-nucleoside protecting group, monophosphate moiety, or nucleic acid moiety; $R^2$ is hydrogen or —OH; $R^3$ is a reversible terminator moiety, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is a detectable moiety;

$L^{100}$ is a divalent linker comprising

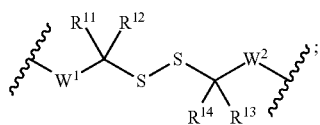

wherein $R^{11}$, $R^{12}$, $R^{13}$ and $R^{14}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein at least one $R^{11}$, $R^{12}$, $R^{13}$, and $R^{14}$ is not hydrogen; and $W^1$ and $W^2$ are independently —O—, —NH—, —Si—, or —PH—.

Embodiment 28. The compound of Embodiment 27, wherein $R^2$ is hydrogen.

Embodiment 29. The compound of Embodiment 27 or Embodiment 28, wherein $R^1$ is a triphosphate moiety.

Embodiment 30. The compound of any one of Embodiments 27 to 29, wherein B is a cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

Embodiment 31. The compound of Embodiment 27, having the formula:

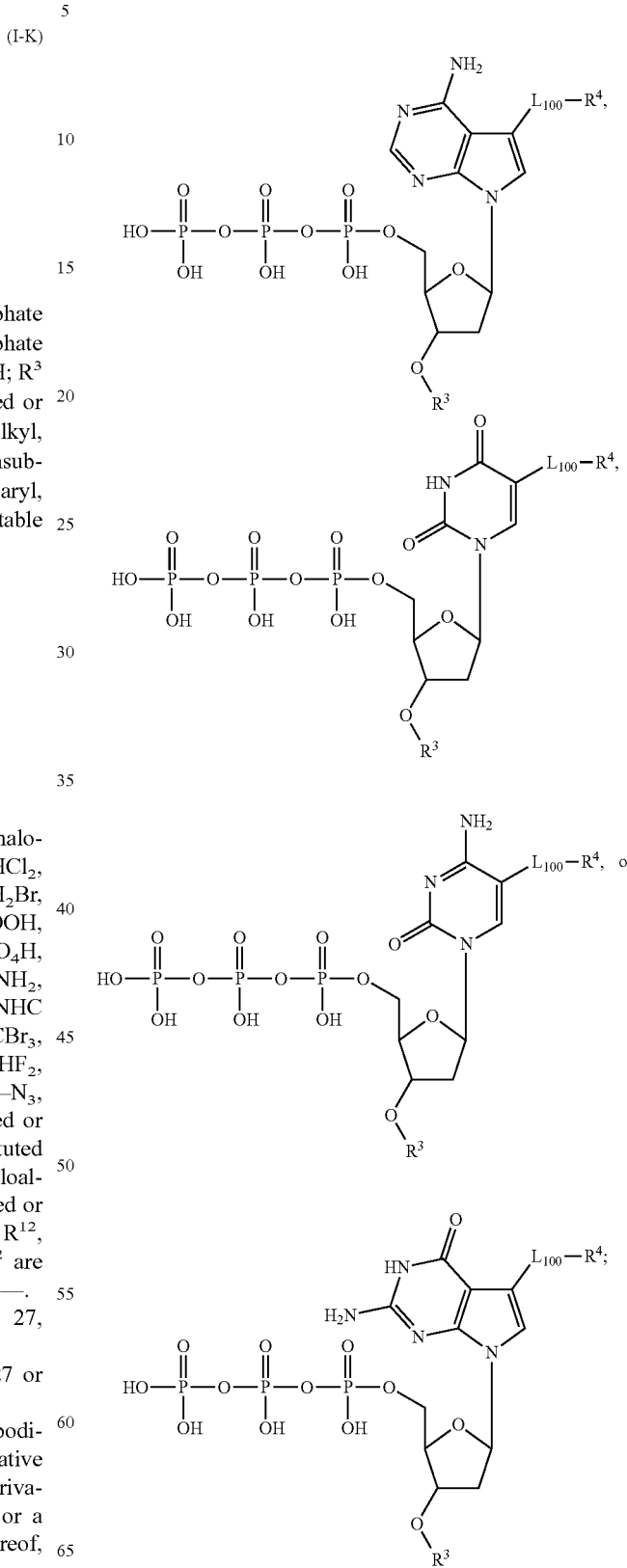

wherein $L^{100}$ has the formula:

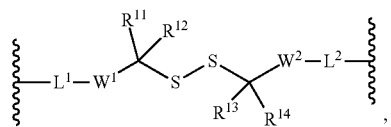

wherein $L^1$ has the formula $-L^{101}-L^{102}-L^{103}-$; $L^{101}$, $L^{102}$, and $L^{103}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^2$ has the formula $-L^{201}-L^{202}-L^{203}-$; and $L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 32. The compound of any one of Embodiments 27 to 31, wherein $W^1$ and $W^2$ are independently —O— or —NH.

Embodiment 33. The compound of any one of Embodiments 27 to 31, wherein $W^1$ and $W^2$ are —O—.

Embodiment 34. The compound of any one of Embodiments 27 to 33, wherein $R^{11}$ and $R^{13}$ are hydrogen, and $R^{12}$ and $R^{14}$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 35. The compound of any one of Embodiments 27 to 33, wherein $R^{11}$ and $R^{13}$ are hydrogen, and $R^{12}$ and $R^{14}$ are independently substituted or unsubstituted $C_1$-$C_6$ alkyl, substituted or unsubstituted 2 to 8 membered heteroalkyl, substituted or unsubstituted $C_3$-$C_6$ cycloalkyl, substituted or unsubstituted 2 to 8 membered heterocycloalkyl, substituted or unsubstituted $C_6$ to $C_{12}$ aryl, or substituted or unsubstituted 2 to 8 membered heteroaryl.

Embodiment 36. The compound of any one of Embodiments 27 to 33, wherein $R^{11}$ and $R^{13}$ are hydrogen, and $R^{12}$ and $R^{14}$ are independently substituted or unsubstituted alkyl, substituted or unsubstituted cycloalkyl, or substituted or unsubstituted aryl.

Embodiment 37. The compound of any one of Embodiments 27 to 33, wherein $R^{11}$ and $R^{13}$ are hydrogen, and $R^{12}$ and $R^{14}$ are independently substituted or unsubstituted cycloalkyl, substituted or unsubstituted heterocycloalkyl, substituted or unsubstituted aryl, or substituted or unsubstituted heteroaryl.

Embodiment 38. The compound of any one of Embodiments 27 to 37, wherein $L^{100}$ is a divalent linker comprising

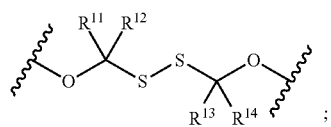

wherein $R^{11}$ and $R^{13}$ are hydrogen, and $R^{12}$ and $R^{14}$ are unsubstituted alkyl.

Embodiment 39. The compound of any one of Embodiments 27 to 37, wherein $L^{100}$ has the formula:

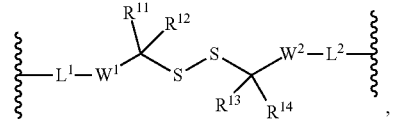

wherein $L^1$ has the formula $-L^{101}-L^{102}-L^{103}-$; $L^{101}$, $L^{102}$, and $L^{103}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^2$ has the formula $-L^{201}-L^{202}-L^{203}-$; and $L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 40. The compound of Embodiment 39, wherein $R^{11}$ and $R^{12}$ are joined to form a substituted or unsubstituted cycloalkyl.

Embodiment 41. The compound of Embodiment 39 or Embodiment 40, wherein $R^{13}$ and $R^{14}$ are joined to form a substituted or unsubstituted cycloalkyl.

Embodiment 42. The compound of any one of Embodiments 27 to 41, wherein the reversible terminator moiety is

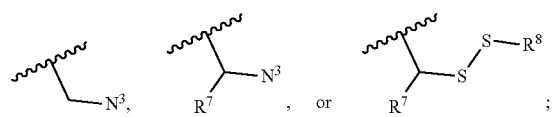

wherein $R^7$ is substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and $R^8$ is substituted or unsubstituted alkyl.

Embodiment 43. The compound of any one of Embodiments 27 to 41, wherein the reversible terminator moiety is:

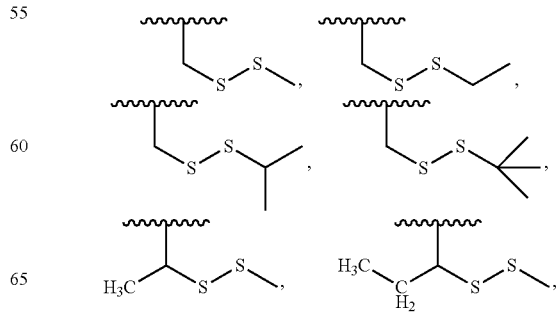

233 -continued
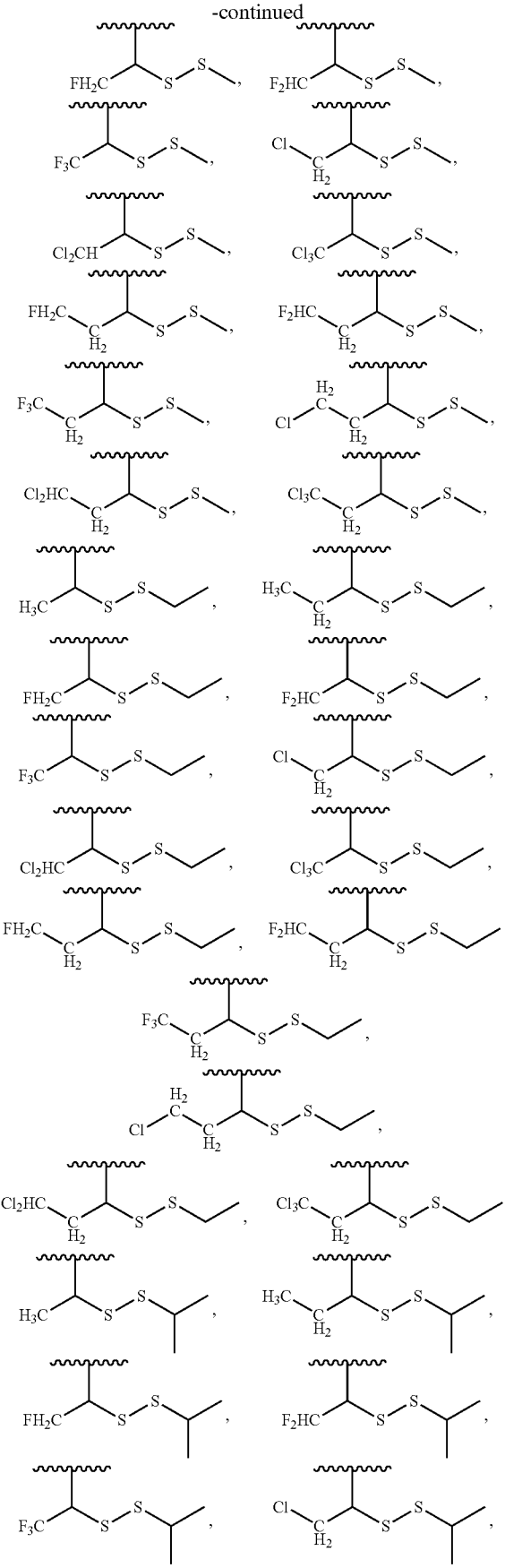
234 -continued
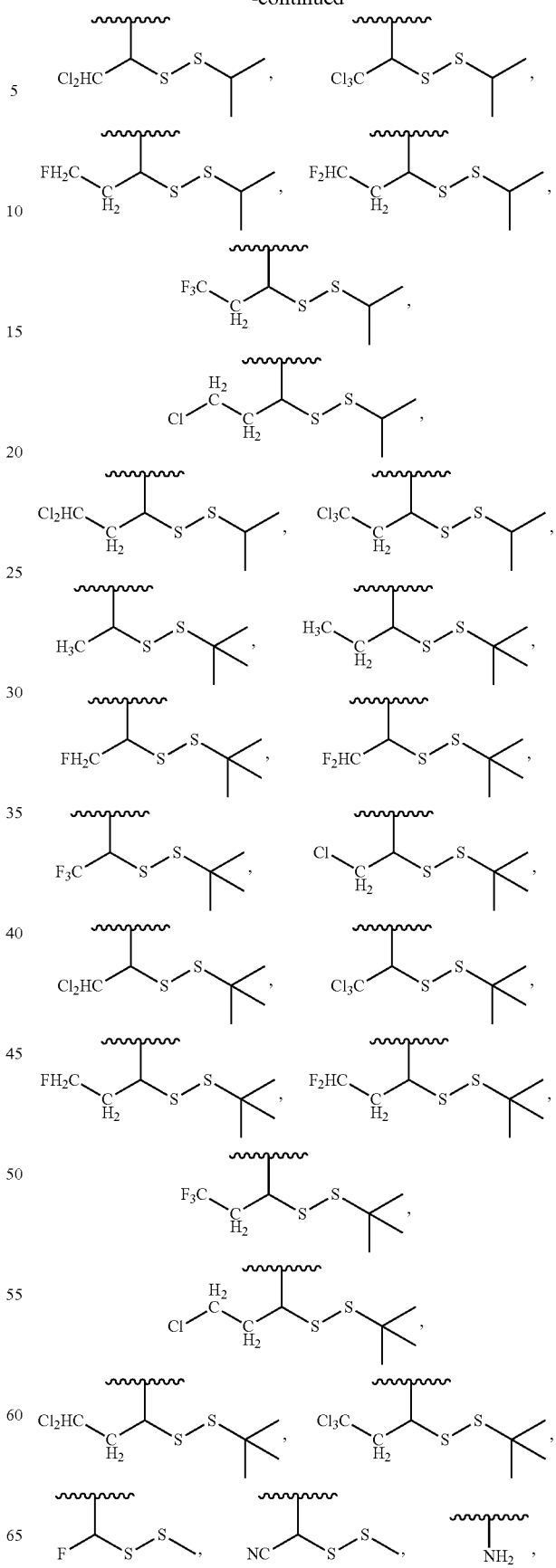

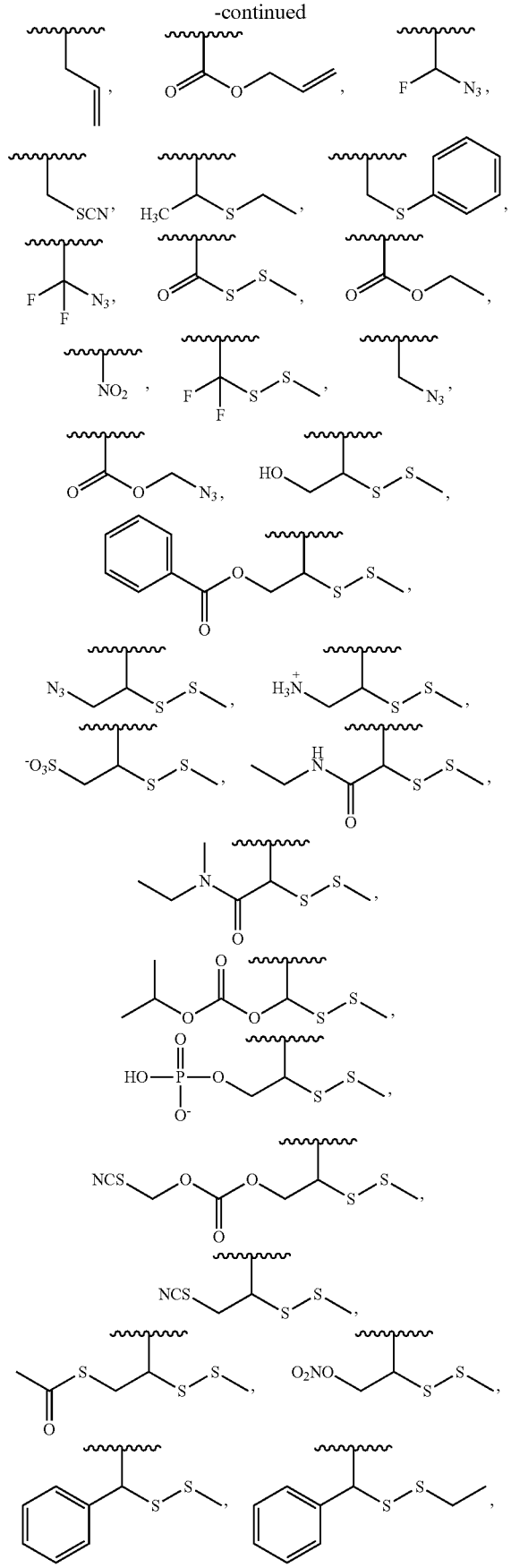
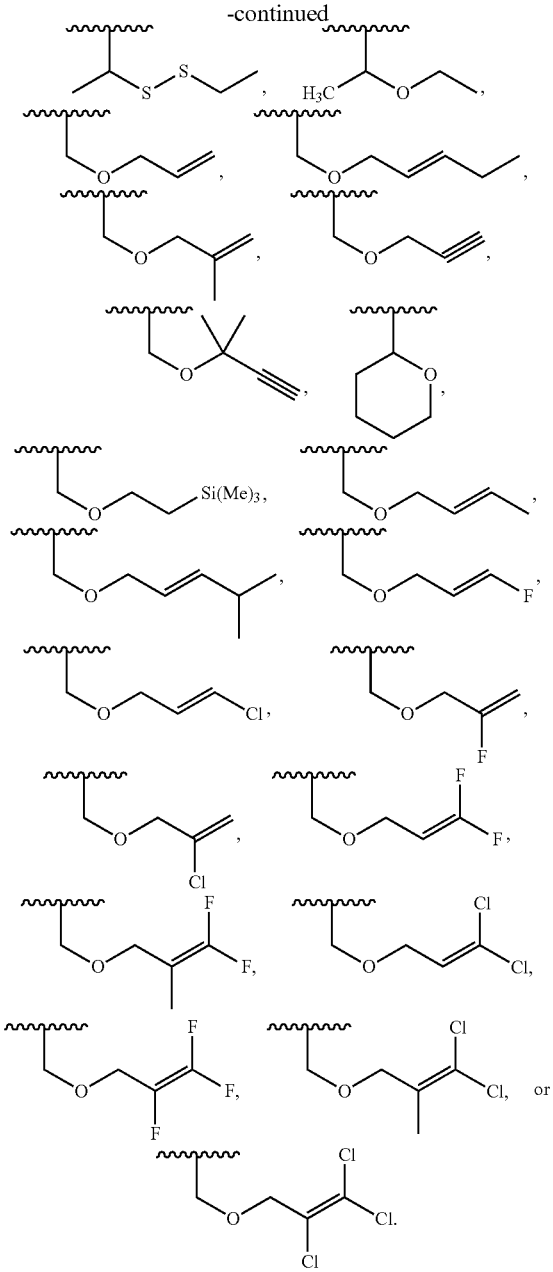
Embodiment 44. A kit comprising the compound of Embodiment 1, the compound of Embodiment 22, or the compound of Embodiment 27.
What is claimed is:
1. A compound having the formula:
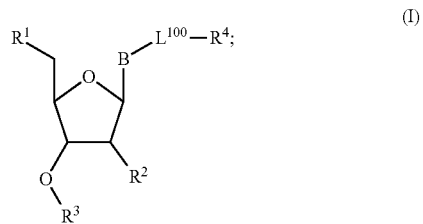

wherein

B is a divalent nucleobase;

$R^1$ is a polyphosphate moiety, 5'-nucleoside protecting group, monophosphate moiety, or nucleic acid moiety;

$R^2$ is hydrogen or —OH;

$R^3$ is a reversible terminator moiety, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is a detectable moiety;

$L^{100}$ is a divalent linker comprising

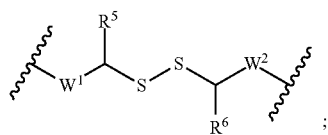

wherein $R^5$ and $R^6$ are independently unsubstituted alkyl, —CN, —OH, —NH$_2$, —COOH, —CONH$_2$, —NO$_2$, —SO$_3$H, —SO$_4$H, —SO$_2$NH$_2$, —NHNH$_2$, —ONH$_2$, substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $W^1$ and $W^2$ are —O—.

2. The compound of claim 1, wherein $R^2$ is hydrogen.

3. The compound of claim 1, wherein $R^1$ is a triphosphate moiety.

4. The compound of claim 1, wherein B is a cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

5. The compound of claim 1, having the formula:

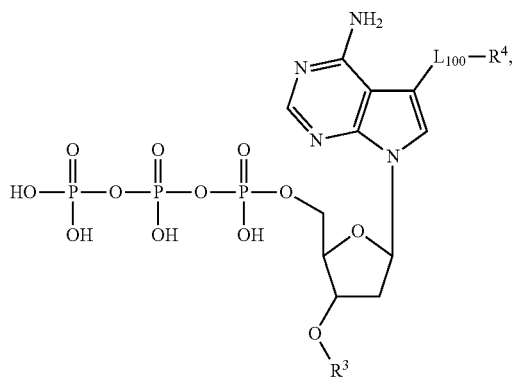

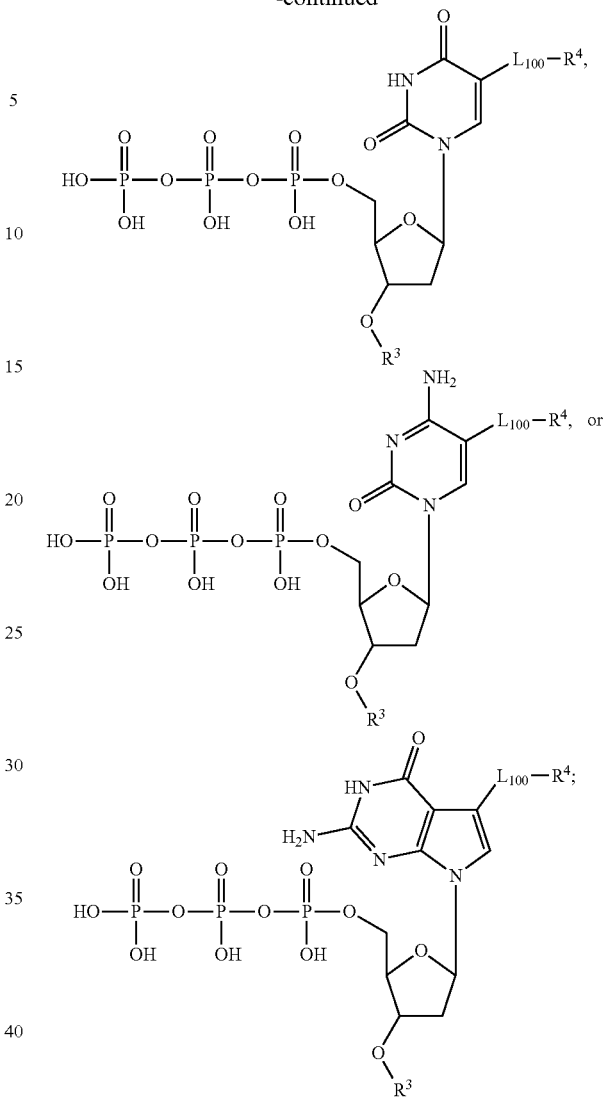

wherein $L^{100}$ has the formula:

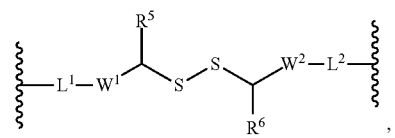

wherein $L^1$ has the formula -$L^{101}$-$L^{102}$-$L^{103}$-;

$L^{101}$, $L^{102}$ and $L^{103}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^2$ has the formula -$L^{201}$-$L^{202}$-$L^{203}$-; and $L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkyl ene, substituted or unsubstituted cycloalkylene, substituted or unsubstituted heterocycloalkylene, substituted or unsubstituted arylene, or substituted or unsubstituted heteroarylene.

6. The compound of claim 1, wherein $R^5$ and $R^6$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

7. The compound of claim 1, wherein $R^5$ and $R^6$ are independently substituted or unsubstituted $C_1$-$C_6$ alkyl, substituted or unsubstituted 2 to 8 membered heteroalkyl, substituted or unsubstituted $C_3$-$C_6$ cycloalkyl, substituted or unsubstituted 2 to 8 membered heterocycloalkyl, substituted or unsubstituted $C_6$ to $C_{12}$ aryl, or substituted or unsubstituted 2 to 8 membered heteroaryl.

8. The compound of claim 1, wherein $R^5$ and $R^6$ are independently substituted or unsubstituted alkyl, substituted or unsubstituted cycloalkyl, or substituted or unsubstituted aryl.

9. The compound of claim 1, wherein $R^5$ and $R^6$ are independently substituted or unsubstituted cycloalkyl, substituted or unsubstituted heterocycloalkyl, substituted or unsubstituted aryl, or substituted or unsubstituted heteroaryl.

10. The compound of claim 1, wherein $L^{100}$ is a divalent linker comprising

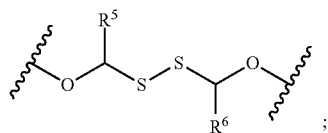

wherein $R^5$ and $R^6$ are unsubstituted alkyl.

11. The compound of claim 1, wherein $L^{100}$ has the formula:

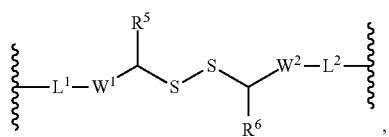

wherein
$L^1$ has the formula -$L^{101}$-$L^{102}$-$L^{103}$-;
$L^{101}$, $L^{102}$, and $L^{103}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$L^2$ has the formula -$L^{201}$-$L^{202}$-$L^{203}$-; and
$L^{201}$, $L^{202}$, and $L^{203}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

12. The compound of claim 11, wherein $L^{100}$ has the formula:

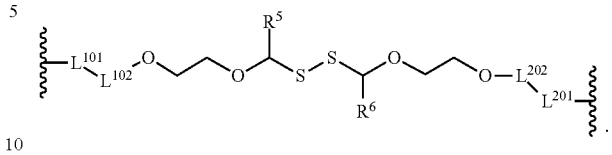

13. The compound of claim 11, wherein $L^{100}$ has the formula:

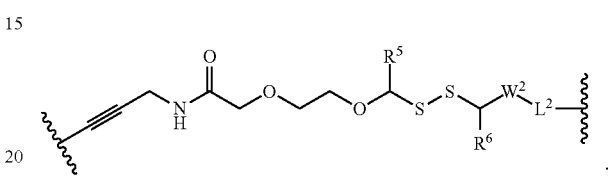

14. The compound of claim 1, wherein the reversible terminator moiety is

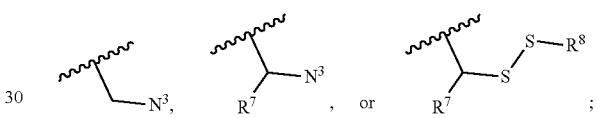

wherein $R^7$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^8$ is substituted or unsubstituted alkyl.

15. The compound of claim 1, wherein the reversible terminator moiety is:

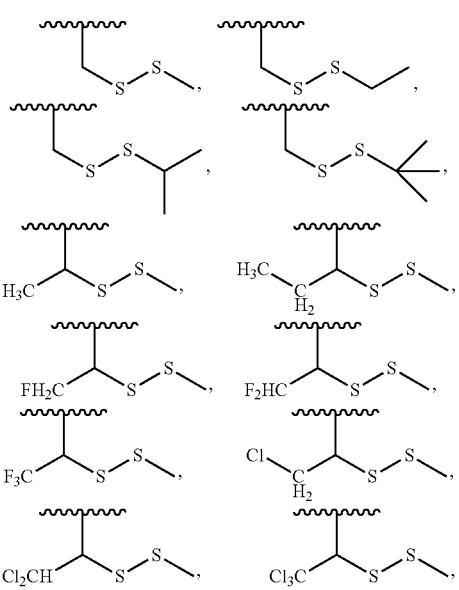

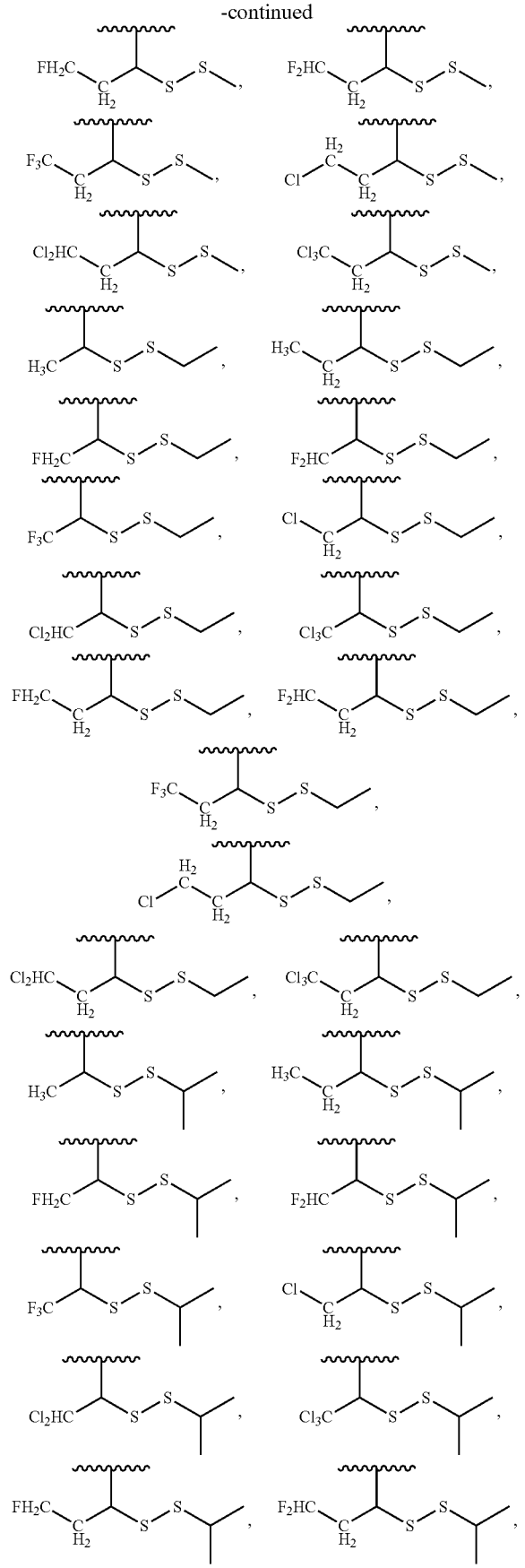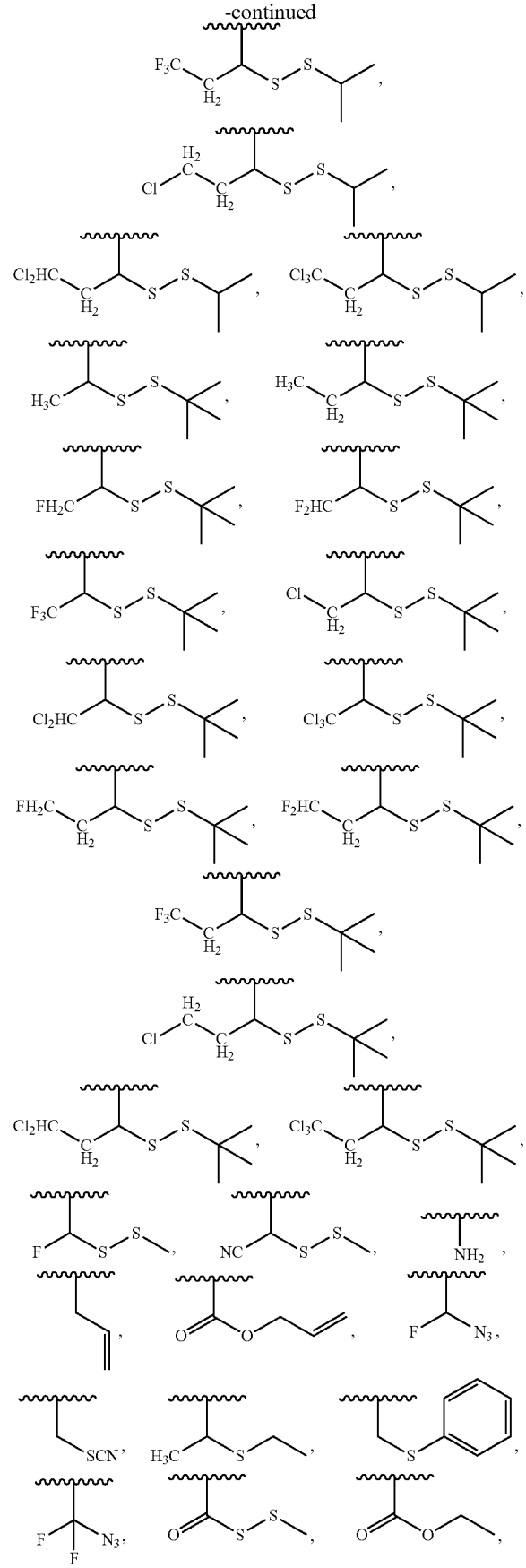

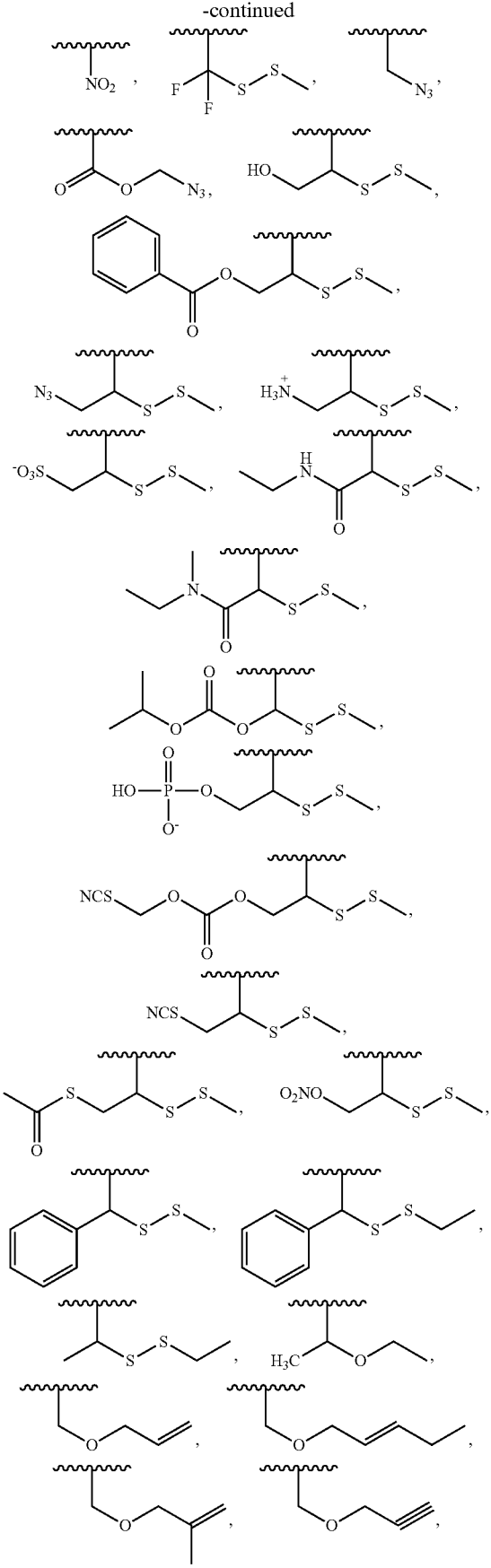

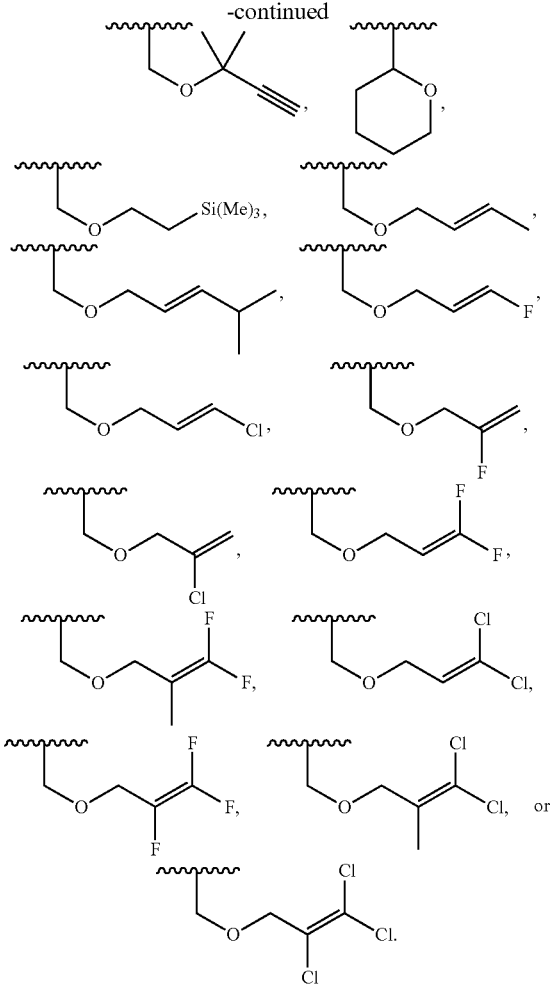

16. A method for sequencing a nucleic acid, comprising:
(i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label;
(ii) detecting said unique detectable label of each incorporated compound, so as to thereby identify each incorporated compound in said extension strand, thereby sequencing the nucleic acid;
wherein each of said four different compounds is independently a compound of claim 1.

17. A method of sequencing nucleic acid comprising:
(i) providing a nucleic acid template hybridized to a primer;
(ii) extending the primer hybridized to said nucleic acid template with a compound of claim 1; and
(iii) identifying the compound, so as to sequence the nucleic acid.

18. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of claim 1.

19. A nucleic acid polymerase complex comprising a nucleic acid polymerase, wherein said nucleic acid polymerase is bound to a compound of claim 1.
20. The compound of claim 1, wherein $L^{100}$ is a divalent linker comprising
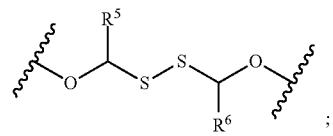
;
wherein $R^5$ and $R^6$ are independently substituted or unsubstituted cycloalkyl.
* * * * *